(12) United States Patent
Weinreb et al.

(10) Patent No.: US 9,598,484 B2
(45) Date of Patent: Mar. 21, 2017

(54) HUMAN ANTI-TAU ANTIBODIES

(71) Applicants: Biogen MA Inc., Cambridge, MA (US);
Biogen International Neuroscience GmbH, Zug (CH)

(72) Inventors: Paul H. Weinreb, Andover, MA (US);
Feng Chen, Zurich (CH); Ellen A. Garber, Cambridge, MA (US); Jan Grimm, Dubendorf (CH); Fabio Montrasio, Schindellegi (CH)

(73) Assignees: Biogen MA Inc., Cambridge, MA (US);
Biogen International Neuroscience GmbH, Zug (CH)

( * ) Notice: Subject to any disclaimer, the term of this patent is extended or adjusted under 35 U.S.C. 154(b) by 0 days.

(21) Appl. No.: 14/654,176

(22) PCT Filed: Dec. 20, 2013

(86) PCT No.: PCT/US2013/076952
§ 371 (c)(1),
(2) Date: Jun. 19, 2015

(87) PCT Pub. No.: WO2014/100600
PCT Pub. Date: Jun. 26, 2014

(65) Prior Publication Data
US 2015/0344553 A1 Dec. 3, 2015

Related U.S. Application Data

(60) Provisional application No. 61/745,410, filed on Dec. 21, 2012.

(51) Int. Cl.
| | | |
|---|---|---|
| C07K 16/18 | (2006.01) |
| A61K 39/00 | (2006.01) |
| G01N 33/68 | (2006.01) |
| A61K 39/395 | (2006.01) |
| A61K 45/06 | (2006.01) |
| A61K 49/00 | (2006.01) |
| A61K 49/16 | (2006.01) |

(52) U.S. Cl.
CPC .......... *C07K 16/18* (2013.01); *A61K 39/3955* (2013.01); *A61K 45/06* (2013.01); *A61K 49/00* (2013.01); *A61K 49/16* (2013.01); *G01N 33/6896* (2013.01); *A61K 2039/505* (2013.01); *C07K 2317/14* (2013.01); *C07K 2317/21* (2013.01); *C07K 2317/24* (2013.01); *C07K 2317/30* (2013.01); *C07K 2317/34* (2013.01); *C07K 2317/41* (2013.01); *C07K 2317/52* (2013.01); *C07K 2317/56* (2013.01); *C07K 2317/565* (2013.01); *C07K 2317/71* (2013.01); *C07K 2317/92* (2013.01); *C07K 2317/94* (2013.01); *G01N 2333/47* (2013.01); *G01N 2800/2814* (2013.01)

(58) Field of Classification Search
None
See application file for complete search history.

(56) References Cited

U.S. PATENT DOCUMENTS

| | | |
|---|---|---|
| 7,442,516 B2 | 10/2008 | Ohno et al. |
| 8,940,272 B2 | 1/2015 | Nitsch et al. |
| 2004/0110938 A1* | 6/2004 | Parekh ................. C07K 14/705 536/23.5 |
| 2006/0122122 A1 | 6/2006 | Kobayashi et al. |
| 2008/0050383 A1 | 2/2008 | Sigurdsson et al. |
| 2010/0316564 A1 | 12/2010 | Sigurdsson et al. |
| 2012/0087861 A1 | 4/2012 | Nitsch et al. |
| 2012/0323214 A1* | 12/2012 | Shantha .................. A61N 1/30 604/501 |
| 2013/0295021 A1 | 11/2013 | Nitsch et al. |
| 2015/0252102 A1 | 9/2015 | Nitsch et al. |

FOREIGN PATENT DOCUMENTS

| | | |
|---|---|---|
| WO | WO 93/08302 | 4/1993 |
| WO | WO 94/13795 | 6/1994 |
| WO | WO 95/17429 | 6/1995 |
| WO | WO 96/04309 | 2/1996 |
| WO | WO 98/22120 | 5/1998 |
| WO | WO 02/062851 | 8/2002 |
| WO | WO 03/014960 | 2/2003 |
| WO | WO 03/017918 | 3/2003 |
| WO | WO 2004/016655 | 2/2004 |
| WO | WO 2005/080986 | 9/2005 |
| WO | WO 2006/122122 | 6/2006 |
| WO | WO 2007/068105 | 6/2007 |
| WO | WO 2008/081008 | 7/2008 |

(Continued)

OTHER PUBLICATIONS

Chen 1995 "enhancement and destruction of antibody function by somatic mutation: unequal occurrence is controlled by v gene combinatorial associations" EMBO 14(12):2784-2794.*
Kussie 1994 "a single engineered amino acid substitution changes antibody fine specificity" J immunol 152(1):146-52.*
Hagemeyer 2007 "Single-chain antibodies as new antithrombic drugs" Seminar Thromb Hemo 33(2):185-195.*
Malpiedi 2013 "Single-chain antibody fragments: purification methodologies" Process Biochem 48:1242-1251.*
"Four New Research Studies Describe Experimental Immunotherapies for Alzheimer's,"p. 2, section "Tau Antibodies Reduce Brain Tangles in Alzheimer-Model Mice," Alzheimer's Association International Conference on Alzheimer's Disease, accessed at http://www.alz.org/icad/201O_release_four_071310_1230pm.asp, accessed on Feb. 28, 2011, 3 pages.
Abou-Doniaa et al. "Autoantibodies against cytoskeletal neuronal proteins in sera of arsenic-exposed subjects correlate with neurological symptoms," Toxicological & Environmental Chemistry 95(5):823-836, abstract only, 3 pages.
Aluise et al., "Peptides and Proteins in Plasma and Cerebrospinal Fluid as Biomarkers for the Prediction, Diagnosis, and Monitoring of Therapeutic Efficacy of Alzheimer's Disease," Biochim Biophys Acta 1782(10):549-558, 2008, 15 pages.

(Continued)

*Primary Examiner* — Adam M Weidner
(74) *Attorney, Agent, or Firm* — Fish & Richardson P.C.

(57) ABSTRACT

Provided are human tau-specific antibodies as well as fragments, derivatives and variants thereof as well as methods related thereto. Assays, kits, and solid supports related to antibodies specific for tau are also disclosed. The antibody, immunoglobulin chain(s), as well as binding fragments, derivatives and variants thereof can be used in pharmaceutical and diagnostic compositions for tau targeted immunotherapy and diagnosis, respectively.

182 Claims, 19 Drawing Sheets

(56) References Cited

FOREIGN PATENT DOCUMENTS

Figure 2:
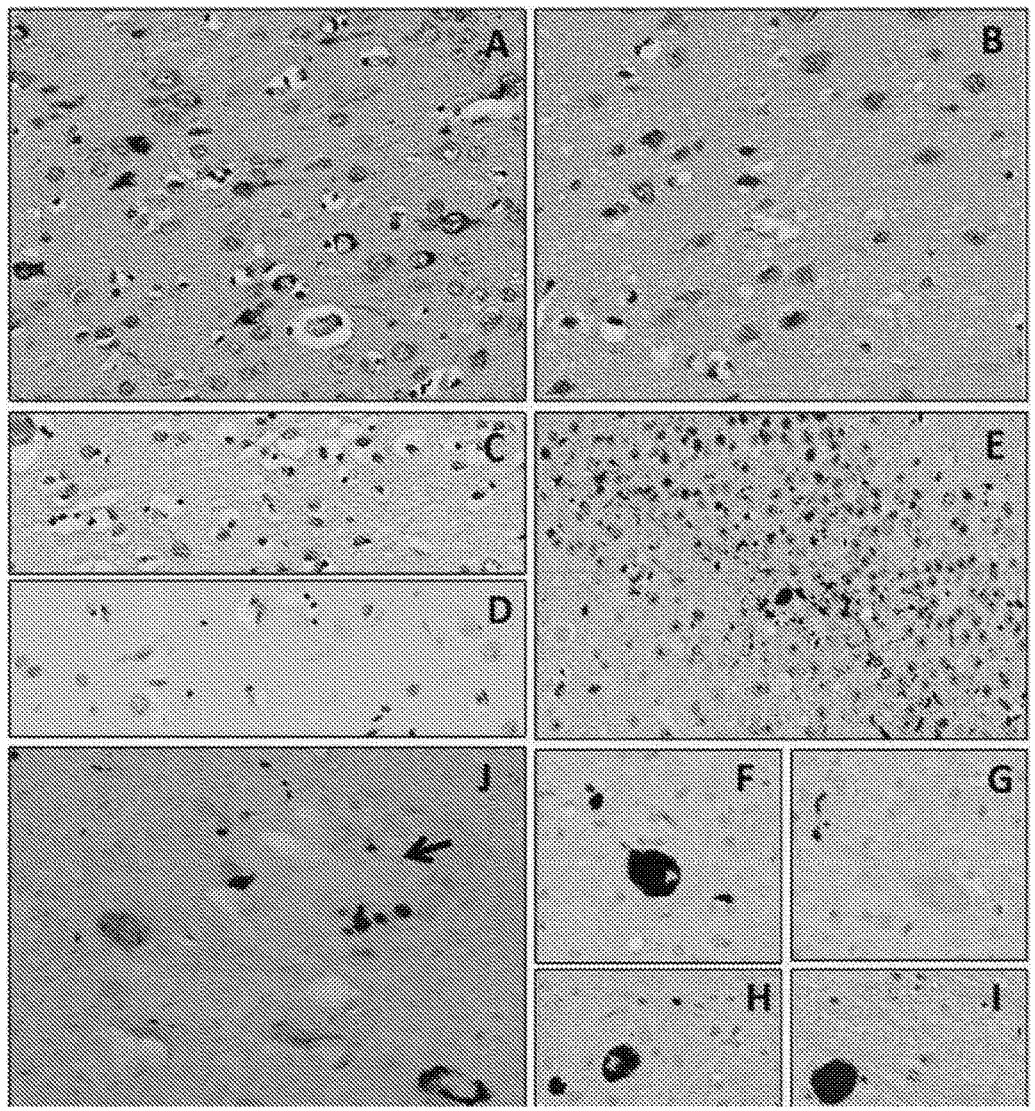

| WO | WO 2010/142423 | 12/2010 |
|---|---|---|
| WO | WO 2010/144711 | 12/2010 |
| WO | WO 2011/053565 | 5/2011 |
| WO | WO 2012/045882 | 4/2012 |
| WO | WO 2012/049570 | 4/2012 |
| WO | WO 2012/106363 | 8/2012 |
| WO | WO 2012/149365 | 11/2012 |

OTHER PUBLICATIONS

Asuni et al., "Immunotherapy Targeting Pathological Tau Conformers in a Tangle Mouse Model Reduces Brain Pathology with Associated Functional Improvements," J Neurosci 27(34):9115-9129, 2007, 15 pages.

Augustinack et al., "Specific tau phosphrylation sites correlate with severity of neuronal cytopathology in Alzheimer's disease," Acta Neuropathol 103:26-35, 2002, Published online Oct. 26, 2001, 10 pages.

Biomel et al., "Efficacy and safety for immunization with phosphorylated tau against neurofibrillary tangles in mice," Exp Neurol 224:472-482, 2010, 14 pages.

Boche et al., "Reduction of aggregated Tau in neuronal processes but not in the cell bodies after Aβ42 immunisation in Alzheimer's disease," Acta Neuropathol 120:13-20, 2010, 1 page.

Boutajangout et at., "Passive immunization targeting pathological phospo-tau protein in a mouse model reduces functional decline and clears tau aggregates from the brain," Journal of Neurochemistry, 118(4): 658-667 (2011), 16 pages.

Cairns et al., "TDP-43 in Familial and Sporadic Frontotemporal Lobar Degeneration with Ubiquitin Inclusions," Am J Pathol 171(1):227-240, 2007, 14 pages.

European Search Report in European Application No. 10013494.9, dated Mar. 28, 2011, 14 pages.

Fischer and Léger, "Bispecific Antibodies: Molecules That Enable Novel Therapeutic Strategies," Pathobiol 74:3-14, 2007, 12 pages.

Frost et al., "Propogation of Tau Misfolding from the Outsie to the Inside of a Cell," J Biol Chem 284(19):12845-12852, 2009, 12 pages.

Gallyas, "A Principle for Silver Staining of Tissue Elements by Physical Development," Acta Morphologica Acad Sci Hung 19(1):57-71, 1971, 15 pages.

Gallyas, "Silver Staining of Alzheimer's Neurofibrillary Changes by Means of Physical Development," Acta Morphologica Acad Sci Hung 19(1):1-8, 1971, 8 pages.

Gendron and Petrucelli, "The role of tau in neurodegeneration," Mol Neurodegen 4(13), 19 pages, 2009.

Goedert and Jakes, "Expression of separate isoforms of human tau protein: correlation with the tau pattern in brain and effects on tubulin polymerization," EMBO J 9(13):4225-4230, 1990, 6 pages.

Goedert et al., "Cloning and Sequencing of the cDNA encoding a core protein of the paired helical filament of Alzheimer disease: Identification as the microtubule-associated protein tau," Proc Natl Acad Sci USA 85:4051-4055, 1988, 5 pages.

Goedert et al., "Cloning and sequencing of the cDNA encoding an isoform of microtubule-associated protein tau containing four tandem repeats: differential expression of tau protein mRNAs in human brain," EMBO J 8(2):393-399, 1989, 7 pages.

Goedert et al., "Tau Proteins of Alzheimer Paired Helical Filaments: Abnormal Phosphorylation of All Six Brain Isoforms," Neuron 8:159-168, 1992, 10 pages.

Götz et al., "Formation of Neurofibrillary Tangles in P301L Tau Transgenic Mice Induced by Aβ42 Fibrils," Sci 293:1491-1495, 2001, 7 pages.

Götz et al., "Tau Filament Formation in Transgenic Mice Expressing P301L Ltau," J Biol Chem 276(1):529-534, 2001, 7 pages.

Götz, "Tau and transgenic animal models," Brain Res Rev 35:266-286, 2001, 22 pages.

Hoffmann et al., "Unique Alzheimer's Disease Paired Helical Filament Specific Epitopes Involve Double Phosphorylation at Specific Sites," Biochem 36:8114-8124, 1997, 12 pages.

Holmes et al., "Long-term effects of Aβ$_{42}$ immunisation in Alzheimer's disease: follow-up of a randomised, placebo-controlled phase I trial," Lancet 372:216-223, 2008, 8 pages.

International Preliminary Report on Patentability in International Application No. PCT/US2013/076952, dated Jun. 23, 2015, 13 pages.

International Search Report and Written Opinion in International Application No. PCT/IB2011/002786, dated Jul. 3, 2012, 17 pages.

International Search Report and Written Opinion in International Application No. PCT/US2013/076952, dated Sep. 7, 2014, 22 pages.

Khlistunova et al., "Inducible Expression of Tau Repeat Domain in Cell Models of Tauopathy: Aggregation is Toxic to Cells But Can be Reversed by Inhibitor Drugs," J of Biol Chem 281(2):1205-1214, 2006, 11 pages.

Lee et al., "Neurodegenerative Tauopathies," Annu. Rev. Neurosci. 24:1121-1159, Annual Reviews, United States (2001), 39 pages.

Miler and Messer, "Intrabody Applications in Neurological Disorders: Progress and Future Prospects," Mol Ther 12(3):394-401, 2005, 8 pages.

Pennanen et al., "Accelerated extinction of conditioned taste aversion in P301L tau transgenic mice," Neurobiol Disease 15:500-509, 2004, 10 pages.

Pennanen et al., "Impaired spatial reference memory and increased exploratory behavior in P301L tau transgenic mice," Genes, Brain and Behavior 5:369-379, 2005, 11 pages.

Robert et al., "Engineered antibody intervention strategies for Alzheimer's disease and related dementias by targeting amyloid and toxic oligomers," Protein Engineering, Design & Selection 22(3):199-208, 2008, 10 pages.

Rosenmann et al., "Taupathy-like Abnormalities and Neurologic Deficits in Mice Immunized With Neuronal Tau Protein," Arch Neurol 63:1459-1467, 2006, 8 pages.

Sergeant et al., "Tau protein as a differential biomarker of tauopathies," Biochemica et Biophysica Acta 1739:179-197 (2005), 19 pages.

Sigurdsson, "Immunotherapy Targeting Pathological Tau Protein in Alzheimer's Disease and Related Tauopathies, "J Alzheimers Dis. 15(2):157-168, 2008, 16 pages.

Talan, "Advances Reported in Targeting Tau Pathology in Alzheimer Disease," Neurology Today 10(16):17-19, Aug. 2010, 3 pages.

van de Nes et al., "β-Protein/A4 deposits are not associated with hyperphosphorylated tau in somatostatin neurons in the hypothalamus of Alzheimer's disease patients," Acta Neuropathol 111:126-138, 2006, 14 pages.

Zheng et al., "Tau as a Potential Novel Therapeutic Target in Ischemic Stroke," Journal Cellular Biochemistry 109:26-29, 2010, published online Nov. 13, 2009, 4 pages.

Colombian Office Action in International Application No. 15-168.271, dated Oct. 14, 2016, 29 pages.

European Examination Report in International Application No. 13818637.4, dated Oct. 10, 2016, 15 pages.

Goedert et al., "Epitope mapping of monoclonal antibodies to the paired helical filaments of Alzheimer's disease: identification of phosphorylation sites in tau protein," Biochemical Journal, 301(3):871-877 (Aug. 1994).

Karu et al., "Recombinant Antibody Technology," ILAR Journal, 37(3):132-41 (Jan. 1995).

Otvos et al., "Monoclonal Antibody PHF4 Recognizes Tau Protein Phosphorylated at Serine Residues 396 and 404," Journal of Neuroscience Research, 39:669-673 (Jan. 1994).

* cited by examiner

Figure 1

A) NI-105.4E4-VH (variable heavy chain sequence VH; SEQ ID NO:9)
```
  --FR1-------------------------CDR1----FR2---------CDR2-------
EVQLVESGGGLVQPGGSLKLSCAASGFNFNISAIHWVRQASGKGLEWVGRIRSKSHNYATLY ---------FR3-------------------------------CDR3------JH-------
AASLKGRFTLSRDDSRNTAYLQMSSLQTEDMAVYYCTVLSANYDTFDYWGQGTLVTVSS
```

NI-105.4E4-VL (variable light chain sequence VL; SEQ ID NO:11)
```
--FR1------------------CDR1-------FR2------------CDR2---FR3--
SYELTQPPSVSVSPGQTARISCFGDTLPKQYTYWYQQKPGQAPVLVIYKDTERPSGIPERFS
LPV
-------------------------CDR3------JK--------
GSSSGTTVTLTISGVQAEDEADYYCLSADNSATWVFGGGTKVTVL
```

B) NI-105.24B2-VH (variable heavy chain sequence VH; SEQ ID NO:13)
```
FR1---------------------------CDR1-FR2-----------CDR2---------
QVQLVQSGAEVKKPGASVKVSCKASGYTFVNYIIHWVRQAPGQGLEWMGIINPNGGNTSYAE
E
----FR3-----------------------------CDR3--JH---------
KFQARVTLTSDTSTSTVYMDLSSLTSEDTAVYYCAVLSPSNPWGQGTTVTVSS
```

NI-105.4E4-VL (variable light chain sequence VL; SEQ ID NO:15)
```
FR1-------------------CDR1-------FR2------------CDR2---FR3----
SYELTQPPSVSVSPGQTAGITCSGDALPKQFVYWYQKKPGQAPVLLIYKDTERPSRIPERFS
V
--------------------------CDR3-------JK--------
GSTSGTTVALTINGVQAEDEADYYCQSADRSGALWVFGGGTKLTVL
```

C) NI-105.4A3-VH (variable heavy chain sequence VH; SEQ ID NO:17)
```
FR1---------------------------CDR1-FR2-----------CDR2---------
QVQLVESGGGAVQPGGSLRLSCAASGFTFSDYAMHWVRQAPGKGLQWVAVISYEGTYKYYAD
E    T
----FR3-----------------------------CDR3-------------JH-------
SVKGRFTISRDNSKNTLNLQMSSLRVEDTAVYFCVKARAFASGQRSTSTVPDYWGQGTLVTV

SS
```

NI-105.4A3-VL (variable light chain sequence VL; SEQ ID NO:19)
```
FR1-------------------CDR1-------FR2------------CDR2---FR3----
SYELTQPPSVSVSPGQTARITCSGDALPKKYAYWYQQKSGQAPVLVIYEDNKRPSGIPERFS -------------------------CDR3-------JK--------
GSSSGTVATLTISGAQVDDEADYYCYSTDISGDLRVFGGGTKLTVL
```

Figure 7A

NI-105.17C1 VH (SEQ ID NO:44)
EVQLVQSGAEVKKPGESLKISCKAF<u>GYSFTNFWIG</u>WVRQVPGKGLEWVG<u>IIYPGDSD
TRYSPSFQGQ</u>VTISADKSIDTAYLQWGHLKASDSAMYFCAR<u>RGFWTGSQIEY</u>WGQG
TQVTVSS

NI-105.17C1 VL (SEQ ID NO:46)
QSALTQPPSASGSPGHSVTISC<u>TGTSSDVGNYSFVS</u>WYQQYPGKAPKVIIY<u>DVSKRS</u>
SGVPDRFFGSKSANTASLTVSGVQEEDEADYFC<u>SSYGGSKYPW</u>VFGGGTKLTVL

Figure 7B

NI-105.6C5 VH (SEQ ID NO:48)
QVQLVESGGGVVQPGRSLRVSCAAS<u>GFTFSSYDMH</u>WVRQAPGKGLEWVA<u>VIWFD
GSNEFYADSVKG</u>RFTISRDNSKNTLFLQMNSLRAEDTAVYYCAR<u>DLGASVTTSNAEN
FHH</u>WGQGTLVTVSS

NI-105.6C5 VL (SEQ ID NO:49)
SYELTQPPSVSVSPGQTARITC<u>SGDALPKRYVY</u>WYQQKSGQAPVLVIY<u>EDSKRPS</u>GI
PETFSGSSSGTMATLTISGAQVEDEADYYC<u>YSTDSNGHHW</u>VFGGGTKLTVL

Figure 7C

NI-105.29G10 VH (SEQ ID NO:50)
EVQLVESGGDLVQPGGSLRLSCAAS<u>GFDFSGYSMA</u>WVRQAPGKGLEWVS<u>YISGTY
VSGGTGTMYYLDSVKG</u>RFFISRDDATSSLYQMDSLRDEDTAVYYCAR<u>VYDYGED</u>W
GQGTLVTVSS

NI-105.29G10 VK (SEQ ID NO:51)
DIVMTQSPDSLAVSLGERATINC<u>KSSRSVLYSSNSKNYLA</u>WYQQKPGQPPKLLIY<u>WA
STRES</u>GVPDRFSGSGSGTEFTLTISSLQAEDVAVYYC<u>QQYYGTPRT</u>FGQGTKVEIK

Figure 7D

NI-105.6L9 VH (SEQ ID NO:52)
EVQLVESGGGLVQPGGSLRLSCAGT<u>RFTFSTYAMG</u>WVRQAPGRGLEWVS<u>AIGGSG DSTSYADSVKG</u>RFTISRDNSKNTLYLQMNSLRAEDTAVYYCAK<u>GVYDYLWGSYRLF DY</u>WGQGTLVTVSS

NI-105.6L9 VL (SEQ ID NO:53)
SYVLTQPPSVSVAPGQTARFTC<u>GGNNIASKSVH</u>WYQQKPGQAPVLVVY<u>DDSDRPS RIPE</u>RFSGSNSGNTATLTISRVEAGDEADYYC<u>QVWDSTSDHVV</u>FGGGTKLTVL

Figure 7E

NI-105.40E8 VH (SEQ ID NO:54)
EVQLVESGGGLVQPGGSLRLSCAAS<u>GFTFPNYVMT</u>WVRQAPGKGLEWVS<u>GISGSG GSTDYADSVKG</u>RFTISRDNSKNTLYLQMNSLRVEDTALYYCAK<u>GSGGIRGQGTMVT</u>VSS

NI-105.40E8 VL (SEQ ID NO:55)
QSALTQPRSVSGSPGQSVTISC<u>TGTSSDVGGYNYVS</u>WHQQHPGKAPKLLIY<u>DVTKR PS</u>GVPDRFSGSKSGNTAALTISGLQAEDEADYYC<u>HSYVGSYTLV</u>FGGGTKLTVL

Figure 7F

NI-105.48E5 VH (SEQ ID NO:56)
EVQLVESGGGLVQPGGSLKLSCAAS<u>GFTFSGSAMH</u>WVRQASGKGLEWVG<u>RIRSKA NSYATAYAASVKG</u>RFTISRDDSKNTAYLQMNSLKTEDTAVYYC<u>TSPTVTTEV</u>WGQG TLVTVSS

NI-105.48E5 VK (SEQ ID NO:57)
DIVMTQSPDSLAVSLGERATINC<u>KSSQSVLYSSNNKDYLA</u>WYQQKPGQPPKLLIY<u>WA STRES</u>GVSDRFSGSGSGTDFTLTISSLQAEDVAVYYC<u>QQYYSTPIT</u>FGQGTRLEIK

Figure 7G
NI-105.6E3 VH (SEQ ID NO:58)
EVQLVESGGGLVQPGGSLRLSCIGS<u>SGMTFSSYAFN</u>WVRQTPGKGLEWVS<u>SISRFG
STVDYTDSVRG</u>RFTISRDDGQRSLYLQMNSLRVEDTAVYYC<u>VRSTASGSRSPGII</u>WG
QGTTVTVSS

NI-105.6E3 VK (SEQ ID NO:59)
DIQMTQSPSSLSASVGDRVTITC<u>RASQGIVNNLA</u>WFQQKPGKAPKSLIY<u>AASSLQG</u>G
VPSKFSGSASGTDFSLTISNLQPEDFATYFC<u>QQYNSYPWT</u>FGQGTKVEIK

Figure 7H
NI-105.22E1 VH (SEQ ID NO:60)
EVQLVQSGAEVKKPGESLKISCKGS<u>GYRFTTYWIG</u>WVRQMPGKGLEWMG<u>IIYPGDS
DTRYSPSYQG</u>QVTISADKSISTAYLQWSSLKASDTGMYYCAR<u>VAGDIGYENYYYYG
MDV</u>WGQGTTVTVSS

NI-105.22E1 VK (SEQ ID NO:61)
DIVMTQSPDSLAVSLGERATINC<u>KSSQSVLYGSNNKNYLA</u>WYQQKLGQSPKLLIY<u>WA
SARES</u>GVPDRFGGSGSGTDFTLTISSLQAEDVAVYYC<u>QQYYSTPWT</u>FGQGTKVEIK

Figure 7I
NI-105.26B12 VH (SEQ ID NO:62)
QVQLVESGGGVVQPGRSLRLSCAAS<u>GFTFTRYGMH</u>WVRQAPGKGLEWVA<u>VIWYD
GTNKYYADSLQG</u>RFTISRDTSTNTLYLQMNGLRVEDRAVYYCAR<u>EGFQGAIDY</u>WGQ
GTLVTVSS

NI-105.26B12 VK (SEQ ID NO:64)
DIVMTQSPDSLAVSLGERATINC<u>KSSQNILYSSDNKNYLA</u>WYQQKPGQPPKLLIY<u>WA
STRES</u>GVPDRFSGSGSGTDFTLTISSLQAEDVAVYYC<u>QQYYSIPRT</u>FGQGTKVEIK

Figure 7J

NI-105.12E12 VH (SEQ ID NO:65)
EVQLVESGGGLVQPGGSLKLSCAA<u>SGFSFSDSAFH</u>WARQASGKGLEWVG<u>RIRSKG
NNYATAYAASVKG</u>RFTVSRDDSKNTTYLQMNSLKTDDTAIYYC<u>TRQGPSYGGIN</u>WG
LGTLVTVSS

NI-105.12E12 VK (SEQ ID NO:66)
DIVMTQSPDSLAVSLGERATINC<u>KSSQTILYSSNNKNYLA</u>WYQQKPGQPPKLLIY<u>WAS
TRES</u>GVPDRFSGSGSGTDFTLTISSLRAEDVAVYYC<u>QQYYSSPQT</u>FGQGTKVEIK

Figure 7K

NI-105.60E7 VH (SEQ ID NO:67)
EVQLVESGGGFVRPGGSITLSCAT<u>SGFTFTKAWMT</u>WVRQAPVKGLEWIG<u>HIKTRIEG
ATTDYAAPVEG</u>RFTISRDDSKNMVYLQMNSLKTEDSGIYYC<u>STDFDY</u>WGQGTLVTV
SS

NI-105.60E7 VK (SEQ ID NO:68)
DVVMTQSPLSLPVTLGQPASISC<u>TSSQSLLYSDGNTYLN</u>WFQQRPGQSPRRLMY<u>KV
SKRDP</u>GVPDRFSGSGSGTDFTLSISRVEAEDVGVYYC<u>MQGSLWPRYT</u>FGQGTKVEI
K

Figure 7L

NI-105.14E2 VH (SEQ ID NO:69)
EVQLVQSGAEVKKPGDSLRISCKAS<u>GYNFPNYWIG</u>WVRQMPGKGLEWMGI<u>IYPGDS
DIRYSPSFQGH</u>VTISSDKSITTAYLQWTSLKVADSAMYYC<u>ARVERPDKGGWFGP</u>WG
QGTLVTVSS

NI-105.14E2 VK (SEQ ID NO:70)
DIVMTQSPDSLAVSLGERATINC<u>KSSQTLLYTSNNQNYLA</u>WYQHKPGQPPKVLIY<u>WA
STREY</u>GVPDRFSGSGSGTDFTLTISSLQPEDVAVYYC<u>QQYYNSPYT</u>FGQGTKLEIK

Figure 7M

NI-105.39E2 VH (SEQ ID NO:71)
EVQLVESGGGLVQPGGSLRLSCAAS<u>GFTFSAYGMN</u>WVRQAPGKGLEWVA<u>HITGSG
TPIFYADSVKG</u>RFTISRDNAKSSLYLQMNSLRNDDTALYFC<u>VRGTVDY</u>WGQGTLVTV
SS

NI-105.39E2 VL (SEQ ID NO:72)
QAGLTQPPSVSKDLRQTATLTC<u>SGNSNNVGNQGAA</u>WLQQFPGHPPKLLFY<u>ENINRP
S</u>GISERFSASRSGNTASLTITGLQPEDEADYYC<u>SAWDGHLNAW</u>FGGGTKLTVL

Figure 7N

NI-105.19C6 VH (SEQ ID NO:73)
EVQLVQSGAEVKKPGESLKISCKAS<u>GYSFISYWVG</u>WVRQMPGKGLEWMG<u>IIYPGDS
DTRYSPSFEGQVSISAD</u>KSISTAYLQWTSLKASDTAMYYCAR<u>HWGPAAVTDSPWFG
P</u>WGQGTLVTVSS

NI-105.19C6 VK (SEQ ID NO:74)
DIVMTQSPDSLAVSLGERATINC<u>KSSQTVLYTSNNKNYLA</u>WYQQKPGQPPKLLIY<u>WA
STRES</u>GVPDRFSGSGSGTDFTLTISSLQAEDVAVYYC<u>QHYYSTPFT</u>FGPGTKVDIK

Figure 7O

NI-105.9C4 VH (after primer-induced mutation corrections) (SEQ ID NO:76)
QVQLVQSGAEVKKPGASVKVSCKAS<u>GYIFTAFFMH</u>WVRQAPGQGLEWMG<u>WINPDS
GATKYAHNFQG</u>RVTMTRDTSISTAFMELSGLKSDDTGVYYCAT<u>GMAVTGNF</u>WGQG
TLVTVSS

NI-105.9C4 VL (after primer-induced mutation corrections) (SEQ ID NO:77)
SYELTQPPSVSVSPGQTARITC<u>SGDVLAETYAR</u>WFQQKPGQAPVLVMY<u>RDRERPAG
I</u>PERFSGSSSGNTVTLTISGAQAEDEAVYHC<u>HSVADNNLDW</u>FGGGTKLTVL Figure 8A-B
A)
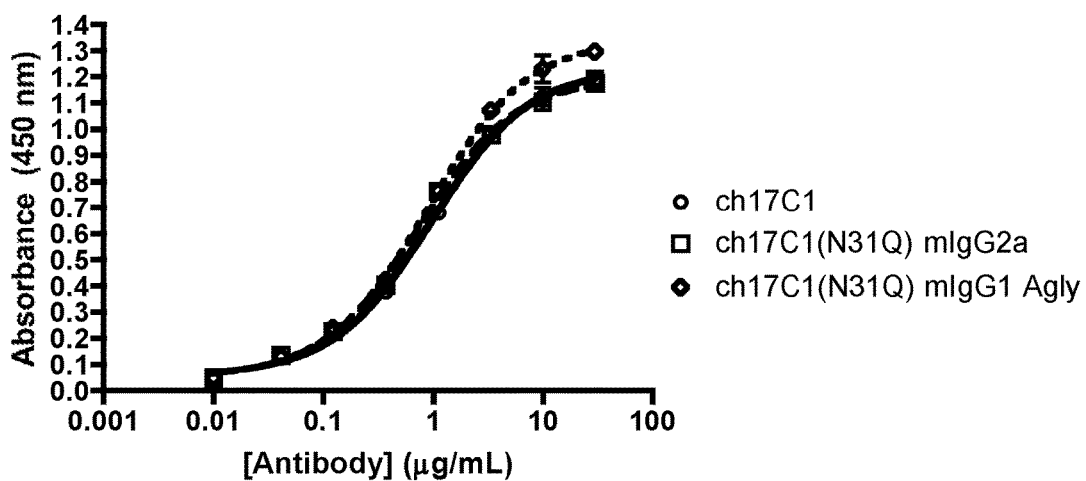
B)
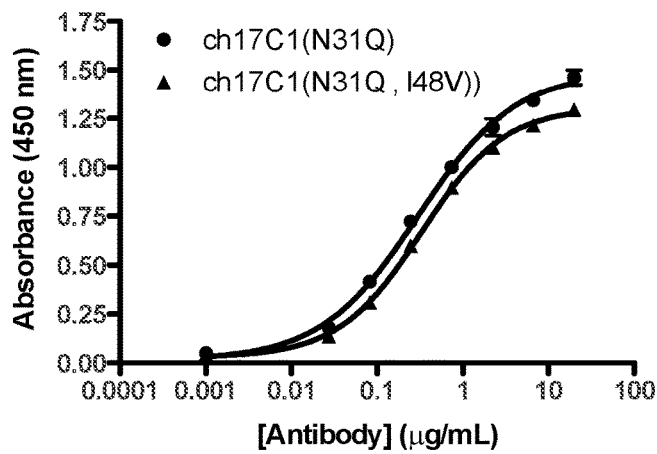

Figure 12D:
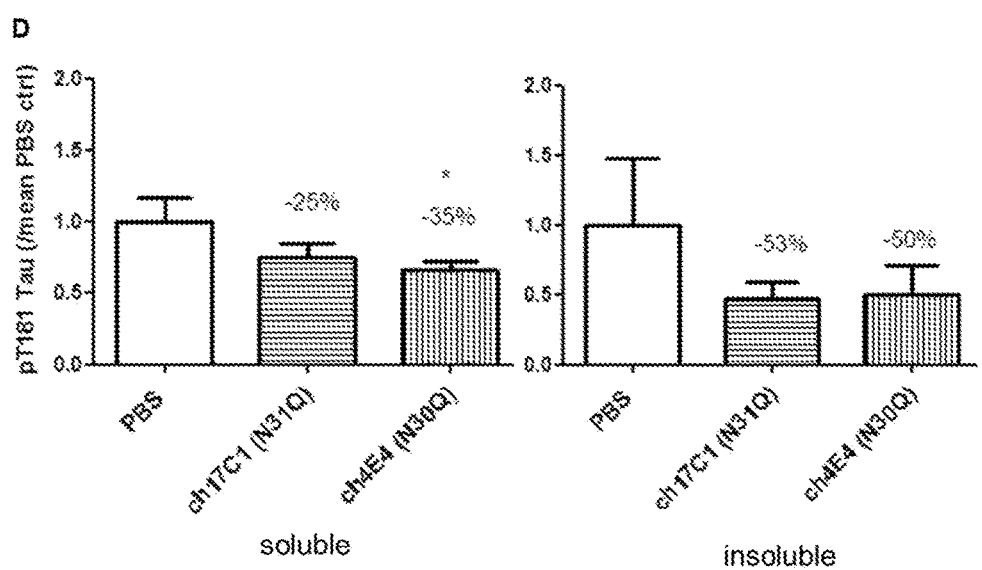

Figure 12A-C
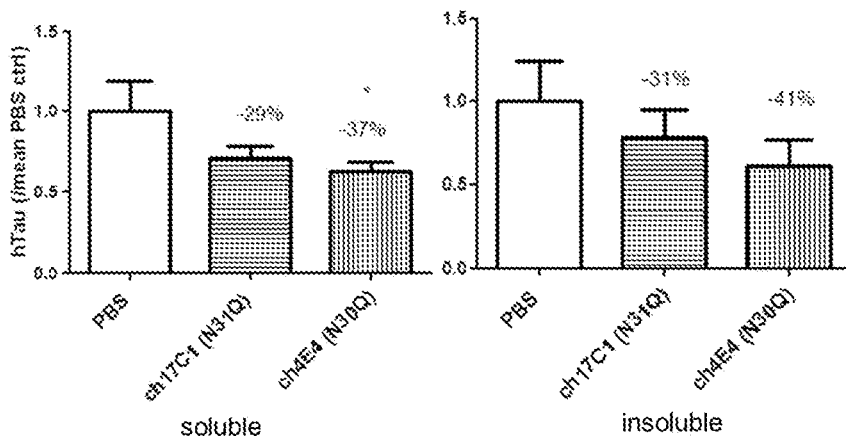
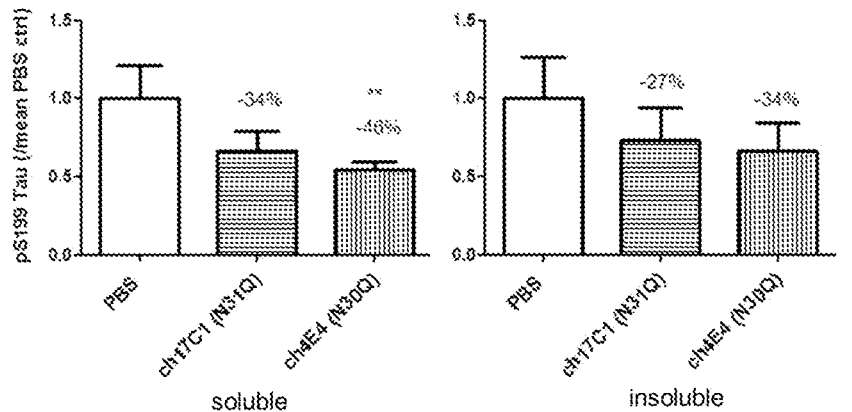
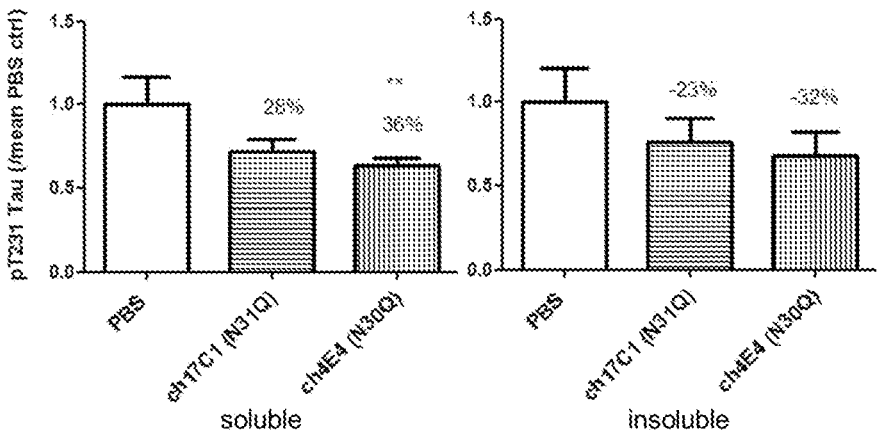

ns application under 35 U.S.C. §371

SEQUENCE LISTING

<160> NUMBER OF SEQ ID NOS: 224

<210> SEQ ID NO 1
<211> LENGTH: 352
<212> TYPE: PRT
<213> ORGANISM: Homo sapiens
<220> FEATURE:
<221> NAME/KEY: PEPTIDE
<222> LOCATION: (1)..(352)
<223> OTHER INFORMATION: Isoform Fetal-Tau
<300> PUBLICATION INFORMATION:
<301> AUTHORS: Goedert M., Wischik C., Crowther R., Walker J., Klug A.
<302> TITLE: Cloning and sequencing of the cDNA encoding a core protein
    of the paired helical filament of Alzheimer disease:
    identification as the microtubule-associated protein tau.
<303> JOURNAL: Proc. Natl. Acad. Sci. U.S.A.
<304> VOLUME: 85
<306> PAGES: 4051-4055
<307> DATE: 1988-06-01
<300> PUBLICATION INFORMATION:
<308> DATABASE ACCESSION NUMBER: P10636-2
<309> DATABASE ENTRY DATE: 2010-10-05
<313> RELEVANT RESIDUES IN SEQ ID NO: (1)..(352)

<400> SEQUENCE: 1

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Val Tyr Lys Pro Val
    210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
            260                 265                 270

His Val Pro Gly Gly Gly Asn Lys Lys Ile Glu Thr His Lys Leu Thr

```
                    275                 280                 285
Phe Arg Glu Asn Ala Lys Ala Lys Thr Asp His Gly Ala Glu Ile Val
    290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
                340                 345                 350

<210> SEQ ID NO 2
<211> LENGTH: 381
<212> TYPE: PRT
<213> ORGANISM: Homo sapiens
<220> FEATURE:
<221> NAME/KEY: PEPTIDE
<222> LOCATION: (1)..(381)
<223> OTHER INFORMATION: Isoform Tau-B
<300> PUBLICATION INFORMATION:
<301> AUTHORS: Goedert M., Spillantini M.G., Jakes R., Rutherford D.,
      Crowther R.A.
<302> TITLE: Multiple isoforms of human microtubule-associated protein
      tau: sequences and localization in neurofibrillary tangles of
      Alzheimer's disease.
<303> JOURNAL: Neuron
<304> VOLUME: 3
<306> PAGES: 519-526
<307> DATE: 1989-10-01
<300> PUBLICATION INFORMATION:
<308> DATABASE ACCESSION NUMBER: P10636-4
<309> DATABASE ENTRY DATE: 2010-10-05
<313> RELEVANT RESIDUES IN SEQ ID NO: (1)..(381)

<400> SEQUENCE: 2

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
                100                 105                 110

Ala Lys Gly Ala Asp Gly Lys Thr Lys Ile Ala Thr Pro Arg Gly Ala
            115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
    195                 200                 205
```

-continued

```
Ser Ala Lys Ser Arg Leu Gln Thr Ala Pro Val Pro Met Pro Asp Leu
    210                 215                 220
Lys Asn Val Lys Ser Lys Ile Gly Ser Thr Glu Asn Leu Lys His Gln
225                 230                 235                 240
Pro Gly Gly Gly Lys Val Gln Ile Val Tyr Lys Pro Val Asp Leu Ser
                245                 250                 255
Lys Val Thr Ser Lys Cys Gly Ser Leu Gly Asn Ile His His Lys Pro
            260                 265                 270
Gly Gly Gly Gln Val Glu Val Lys Ser Glu Lys Leu Asp Phe Lys Asp
            275                 280                 285
Arg Val Gln Ser Lys Ile Gly Ser Leu Asp Asn Ile Thr His Val Pro
290                 295                 300
Gly Gly Gly Asn Lys Lys Ile Glu Thr His Lys Leu Thr Phe Arg Glu
305                 310                 315                 320
Asn Ala Lys Ala Lys Thr Asp His Gly Ala Glu Ile Val Tyr Lys Ser
                325                 330                 335
Pro Val Val Ser Gly Asp Thr Ser Pro Arg His Leu Ser Asn Val Ser
            340                 345                 350
Ser Thr Gly Ser Ile Asp Met Val Asp Ser Pro Gln Leu Ala Thr Leu
            355                 360                 365
Ala Asp Glu Val Ser Ala Ser Leu Ala Lys Gln Gly Leu
370                 375                 380

<210> SEQ ID NO 3
<211> LENGTH: 410
<212> TYPE: PRT
<213> ORGANISM: Homo sapiens
<220> FEATURE:
<221> NAME/KEY: PEPTIDE
<222> LOCATION: (1)..(410)
<223> OTHER INFORMATION: Isoform Tau-C
<300> PUBLICATION INFORMATION:
<301> AUTHORS: Goedert M., Spillantini M.G., Jakes R., Rutherford D.,
      Crowther R.A.
<302> TITLE: Multiple isoforms of human microtubule-associated protein
      tau: sequences and localization in neurofibrillary tangles of
      Alzheimer's disease.
<303> JOURNAL: Neuron
<304> VOLUME: 3
<306> PAGES: 519-526
<307> DATE: 1989-10-01
<300> PUBLICATION INFORMATION:
<308> DATABASE ACCESSION NUMBER: P10636-5
<309> DATABASE ENTRY DATE: 2010-10-05
<313> RELEVANT RESIDUES IN SEQ ID NO: (1)..(410)

<400> SEQUENCE: 3

Met Ala Glu Pro Arg Gln Glu Phe Glu Val Met Glu Asp His Ala Gly
1               5                   10                  15
Thr Tyr Gly Leu Gly Asp Arg Lys Asp Gln Gly Gly Tyr Thr Met His
            20                  25                  30
Gln Asp Gln Glu Gly Asp Thr Asp Ala Gly Leu Lys Glu Ser Pro Leu
        35                  40                  45
Gln Thr Pro Thr Glu Asp Gly Ser Glu Glu Pro Gly Ser Glu Thr Ser
    50                  55                  60
Asp Ala Lys Ser Thr Pro Thr Ala Glu Asp Val Thr Ala Pro Leu Val
65                  70                  75                  80
Asp Glu Gly Ala Pro Gly Lys Gln Ala Ala Gln Pro His Thr Glu
                85                  90                  95
Ile Pro Glu Gly Thr Thr Ala Glu Glu Ala Gly Ile Gly Asp Thr Pro
            100                 105                 110
```

```
Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
                180                 185                 190

Asp Arg Ser Gly Tyr Ser Ser Pro Gly Ser Pro Gly Thr Pro Gly Ser
            195                 200                 205

Arg Ser Arg Thr Pro Ser Leu Pro Thr Pro Pro Thr Arg Glu Pro Lys
        210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Val Tyr Lys Pro Val Asp Leu Ser Lys Val Thr
        275                 280                 285

Ser Lys Cys Gly Ser Leu Gly Asn Ile His His Lys Pro Gly Gly Gly
        290                 295                 300

Gln Val Glu Val Lys Ser Glu Lys Leu Asp Phe Lys Asp Arg Val Gln
305                 310                 315                 320

Ser Lys Ile Gly Ser Leu Asp Asn Ile Thr His Val Pro Gly Gly Gly
                325                 330                 335

Asn Lys Lys Ile Glu Thr His Lys Leu Thr Phe Arg Glu Asn Ala Lys
            340                 345                 350

Ala Lys Thr Asp His Gly Ala Glu Ile Val Tyr Lys Ser Pro Val Val
        355                 360                 365

Ser Gly Asp Thr Ser Pro Arg His Leu Ser Asn Val Ser Ser Thr Gly
    370                 375                 380

Ser Ile Asp Met Val Asp Ser Pro Gln Leu Ala Thr Leu Ala Asp Glu
385                 390                 395                 400

Val Ser Ala Ser Leu Ala Lys Gln Gly Leu
                405                 410

<210> SEQ ID NO 4
<211> LENGTH: 383
<212> TYPE: PRT
<213> ORGANISM: Homo sapiens
<220> FEATURE:
<221> NAME/KEY: PEPTIDE
<222> LOCATION: (1)..(383)
<223> OTHER INFORMATION: Isoform Tau-D
<300> PUBLICATION INFORMATION:
<301> AUTHORS: Goedert M., Spillantini M.G., Potier M.-C., Ulrich J.,
      Crowther R.A.
<302> TITLE: Cloning and sequencing of the cDNA encoding an isoform of
      microtubule-associated protein tau containing four tandem
      repeats: differential expression of tau protein mRNAs in human
      brain.
<303> JOURNAL: EMBO J.
<304> VOLUME: 8
<306> PAGES: 393-399
<307> DATE: 1989-02-01
<300> PUBLICATION INFORMATION:
```

<308> DATABASE ACCESSION NUMBER: P10636-6
<309> DATABASE ENTRY DATE: 2010-10-05
<313> RELEVANT RESIDUES IN SEQ ID NO: (1)..(383)

<400> SEQUENCE: 4

```
Met Ala Glu Pro Arg Gln Glu Phe Glu Val Met Glu Asp His Ala Gly
1               5                  10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
        275                 280                 285

Lys Asp Arg Val Gln Ser Lys Ile Gly Ser Leu Asp Asn Ile Thr His
    290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
        355                 360                 365

Thr Leu Ala Asp Glu Val Ser Ala Ser Leu Ala Lys Gln Gly Leu
    370                 375                 380
```

```
<210> SEQ ID NO 5
<211> LENGTH: 412
<212> TYPE: PRT
<213> ORGANISM: Homo sapiens
<220> FEATURE:
<221> NAME/KEY: PEPTIDE
<222> LOCATION: (1)..(412)
<223> OTHER INFORMATION: Isoform Tau-E
<300> PUBLICATION INFORMATION:
<301> AUTHORS: Goedert M., Spillantini M.G., Jakes R., Rutherford D.,
      Crowther R.A.
<302> TITLE: Multiple isoforms of human microtubule-associated protein
      tau: sequences and localization in neurofibrillary tangles of
      Alzheimer's disease.
<303> JOURNAL: Neuron
<304> VOLUME: 3
<306> PAGES: 519-526
<307> DATE: 1989-10-01
<300> PUBLICATION INFORMATION:
<308> DATABASE ACCESSION NUMBER: P10636-7
<309> DATABASE ENTRY DATE: 2010-10-05
<313> RELEVANT RESIDUES IN SEQ ID NO: (1)..(412)

<400> SEQUENCE: 5

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
                245                 250                 255

Asn Val Gln Ser Lys Cys Gly Ser Lys Asp Asn Ile Lys His Val Pro
            260                 265                 270

Gly Gly Gly Ser Val Gln Ile Val Tyr Lys Pro Val Asp Leu Ser Lys
        275                 280                 285
```

```
Val Thr Ser Lys Cys Gly Ser Leu Gly Asn Ile His His Lys Pro Gly
    290                 295                 300

Gly Gly Gln Val Glu Val Lys Ser Glu Lys Leu Asp Phe Lys Asp Arg
305                 310                 315                 320

Val Gln Ser Lys Ile Gly Ser Leu Asp Asn Ile Thr His Val Pro Gly
                325                 330                 335

Gly Gly Asn Lys Lys Ile Glu Thr His Lys Leu Thr Phe Arg Glu Asn
                340                 345                 350

Ala Lys Ala Lys Thr Asp His Gly Ala Glu Ile Val Tyr Lys Ser Pro
                355                 360                 365

Val Val Ser Gly Asp Thr Ser Pro Arg His Leu Ser Asn Val Ser Ser
370                 375                 380

Thr Gly Ser Ile Asp Met Val Asp Ser Pro Gln Leu Ala Thr Leu Ala
385                 390                 395                 400

Asp Glu Val Ser Ala Ser Leu Ala Lys Gln Gly Leu
                405                 410
```

```
<210> SEQ ID NO 6
<211> LENGTH: 441
<212> TYPE: PRT
<213> ORGANISM: Homo sapiens
<220> FEATURE:
<221> NAME/KEY: PEPTIDE
<222> LOCATION: (1)..(441)
<223> OTHER INFORMATION: Isoform Tau-F
<300> PUBLICATION INFORMATION:
<301> AUTHORS: Goedert M., Spillantini M.G., Jakes R., Rutherford D.,
      Crowther R.A.
<302> TITLE: Multiple isoforms of human microtubule-associated protein
      tau: sequences and localization in neurofibrillary tangles of
      Alzheimer's disease.
<303> JOURNAL: Neuron
<304> VOLUME: 3
<306> PAGES: 519-526
<307> DATE: 1989-10-01
<300> PUBLICATION INFORMATION:
<308> DATABASE ACCESSION NUMBER: P10636-8
<309> DATABASE ENTRY DATE: 2010-10-05
<313> RELEVANT RESIDUES IN SEQ ID NO: (1)..(441)

<400> SEQUENCE: 6

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160
```

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440

<210> SEQ ID NO 7
<211> LENGTH: 7
<212> TYPE: PRT
<213> ORGANISM: artificial sequence
<220> FEATURE:
<223> OTHER INFORMATION: Epitope recognized by NI-105.4E4 antibody
<220> FEATURE:
<221> NAME/KEY: PEPTIDE
<222> LOCATION: (1)..(7)
<223> OTHER INFORMATION: Epitope NI-105.4E4

<400> SEQUENCE: 7

Val Glu Val Lys Ser Glu Lys
1               5

<210> SEQ ID NO 8
<211> LENGTH: 363
<212> TYPE: DNA
<213> ORGANISM: Homo sapiens
<220> FEATURE:
<221> NAME/KEY: CDS

```
<222> LOCATION: (1)..(363)
<223> OTHER INFORMATION: NI-105.4E4-VH variable heavy chain (VH)
      sequence
<220> FEATURE:
<221> NAME/KEY: V_region
<222> LOCATION: (91)..(105)
<223> OTHER INFORMATION: complementarity determining region (CDR) VH-
      CDR1
<220> FEATURE:
<221> NAME/KEY: V_region
<222> LOCATION: (148)..(204)
<223> OTHER INFORMATION: complementarity determining region (CDR) VH-
      CDR2
<220> FEATURE:
<221> NAME/KEY: V_region
<222> LOCATION: (301)..(330)
<223> OTHER INFORMATION: complementarity determining region (CDR) VH-
      CDR3

<400> SEQUENCE: 8 gag gtg cag ctg gtg gag tct ggg gga ggc ttg gtc cag cct ggg gga        48
Glu Val Gln Leu Val Glu Ser Gly Gly Gly Leu Val Gln Pro Gly Gly
1               5                   10                  15 tcc ctg aaa ctc tcc tgt gca gcc tct ggg ttc aat ttc aac atc tct        96
Ser Leu Lys Leu Ser Cys Ala Ala Ser Gly Phe Asn Phe Asn Ile Ser
            20                  25                  30 gct ata cac tgg gtc cgc cag gct tcc ggg aaa ggg ctg gag tgg gtt       144
Ala Ile His Trp Val Arg Gln Ala Ser Gly Lys Gly Leu Glu Trp Val
        35                  40                  45 ggc cga ata aga agt aaa tct cac aat tac gcg act tta tat gct gcg       192
Gly Arg Ile Arg Ser Lys Ser His Asn Tyr Ala Thr Leu Tyr Ala Ala
50                  55                  60 tcc ctg aaa ggc cgg ttc acc ctc tcc aga gat gat tca agg aac acg       240
Ser Leu Lys Gly Arg Phe Thr Leu Ser Arg Asp Asp Ser Arg Asn Thr
65                  70                  75                  80 gcg tat ctg caa atg agc agc ctg caa acc gag gat atg gcc gtc tat       288
Ala Tyr Leu Gln Met Ser Ser Leu Gln Thr Glu Asp Met Ala Val Tyr
                85                  90                  95 tac tgt act gtt ctg agt gcg aat tac gac acc ttt gac tac tgg ggc       336
Tyr Cys Thr Val Leu Ser Ala Asn Tyr Asp Thr Phe Asp Tyr Trp Gly
            100                 105                 110 cag gga acc ctg gtc acc gtc tcc tcg                                   363
Gln Gly Thr Leu Val Thr Val Ser Ser
        115                 120

<210> SEQ ID NO 9
<211> LENGTH: 121
<212> TYPE: PRT
<213> ORGANISM: Homo sapiens

<400> SEQUENCE: 9

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Asn Phe Asn Ile Ser
            20                  25                  30

Ala Ile His Trp Val Arg Gln Ala Ser Gly Lys Gly Leu Glu Trp Val
        35                  40                  45

Gly Arg Ile Arg Ser Lys Ser His Asn Tyr Ala Thr Leu Tyr Ala Ala
50                  55                  60

Ser Leu Lys Gly Arg Phe Thr Leu Ser Arg Asp Asp Ser Arg Asn Thr
65                  70                  75                  80

Ala Tyr Leu Gln Met Ser Ser Leu Gln Thr Glu Asp Met Ala Val Tyr
                85                  90                  95
```

Tyr Cys Thr Val Leu Ser Ala Asn Tyr Asp Thr Phe Asp Tyr Trp Gly
            100                 105                 110

Gln Gly Thr Leu Val Thr Val Ser Ser
        115                 120

<210> SEQ ID NO 10
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-105.4E4-VL variable light chain (VL)
      sequence wherein amino acid sequence Ser-Tyr-Glu at positions 1-3
      may also be Leu-Pro-Val
<220> FEATURE:
<221> NAME/KEY: V_region
<222> LOCATION: (67)..(99)
<223> OTHER INFORMATION: complementarity determining region (CDR) VL-
      CDR1
<220> FEATURE:
<221> NAME/KEY: V_region
<222> LOCATION: (145)..(165)
<223> OTHER INFORMATION: complementarity determining region (CDR) VL-
      CDR2
<220> FEATURE:
<221> NAME/KEY: V_region
<222> LOCATION: (262)..(291)
<223> OTHER INFORMATION: complementarity determining region (CDR) VL-
      CDR3

<400> SEQUENCE: 10 tcc tat gag ctg act cag cca ccc tcg gtg tca gtg tcc cca gga cag        48
Ser Tyr Glu Leu Thr Gln Pro Pro Ser Val Ser Val Ser Pro Gly Gln
1               5                   10                  15 acg gcc agg atc tcc tgc ttt gga gat aca ttg cca aag caa tat act        96
Thr Ala Arg Ile Ser Cys Phe Gly Asp Thr Leu Pro Lys Gln Tyr Thr
            20                  25                  30 tat tgg tat cag cag aag cct ggc cag gcc cct gtg tta gtg att tat       144
Tyr Trp Tyr Gln Gln Lys Pro Gly Gln Ala Pro Val Leu Val Ile Tyr
        35                  40                  45 aaa gac act gag agg ccc tca ggg atc ccc gag cga ttc tct ggc tcc       192
Lys Asp Thr Glu Arg Pro Ser Gly Ile Pro Glu Arg Phe Ser Gly Ser
    50                  55                  60 agc tca ggg aca aca gtc acc ttg acc atc agt gga gtc cag gca gaa       240
Ser Ser Gly Thr Thr Val Thr Leu Thr Ile Ser Gly Val Gln Ala Glu
65                  70                  75                  80 gac gag gct gac tat tac tgt cta tca gct gac aac agt gct act tgg       288
Asp Glu Ala Asp Tyr Tyr Cys Leu Ser Ala Asp Asn Ser Ala Thr Trp
                85                  90                  95 gtg ttc ggc gga ggg acc aag gtg acc gtc cta                           321
Val Phe Gly Gly Gly Thr Lys Val Thr Val Leu
            100                 105

<210> SEQ ID NO 11
<211> LENGTH: 107
<212> TYPE: PRT
<213> ORGANISM: Homo sapiens

<400> SEQUENCE: 11

Ser Tyr Glu Leu Thr Gln Pro Pro Ser Val Ser Val Ser Pro Gly Gln
1               5                   10                  15

Thr Ala Arg Ile Ser Cys Phe Gly Asp Thr Leu Pro Lys Gln Tyr Thr
            20                  25                  30

Tyr Trp Tyr Gln Gln Lys Pro Gly Gln Ala Pro Val Leu Val Ile Tyr
        35                  40                  45

```
Lys Asp Thr Glu Arg Pro Ser Gly Ile Pro Glu Arg Phe Ser Gly Ser
 50                  55                  60

Ser Ser Gly Thr Thr Val Thr Leu Thr Ile Ser Gly Val Gln Ala Glu
 65                  70                  75                  80

Asp Glu Ala Asp Tyr Tyr Cys Leu Ser Ala Asp Asn Ser Ala Thr Trp
                 85                  90                  95

Val Phe Gly Gly Gly Thr Lys Val Thr Val Leu
                100                 105

<210> SEQ ID NO 12
<211> LENGTH: 345
<212> TYPE: DNA
<213> ORGANISM: Homo sapiens
<220> FEATURE:
<221> NAME/KEY: CDS
<222> LOCATION: (1)..(345)
<223> OTHER INFORMATION: NI-105.24B2-VH variable heavy chain (VH)
      sequence wherein Gln at position 1 of the sequence may also be Glu
<220> FEATURE:
<221> NAME/KEY: V_region
<222> LOCATION: (91)..(105)
<223> OTHER INFORMATION: complementarity determining region (CDR) VH-
      CDR1
<220> FEATURE:
<221> NAME/KEY: V_region
<222> LOCATION: (148)..(198)
<223> OTHER INFORMATION: complementarity determining region (CDR) VH-
      CDR2
<220> FEATURE:
<221> NAME/KEY: V_region
<222> LOCATION: (295)..(312)
<223> OTHER INFORMATION: complementarity determining region (CDR) VH-
      CDR3

<400> SEQUENCE: 12 cag gtg cag ctg gtg cag tct ggg gct gag gtg aag aag cct ggg gcc        48
Gln Val Gln Leu Val Gln Ser Gly Ala Glu Val Lys Lys Pro Gly Ala
 1               5                  10                  15 tcg gtg aag gtt tcc tgt aag gca tct gga tac acc ttc gtc aat tac        96
Ser Val Lys Val Ser Cys Lys Ala Ser Gly Tyr Thr Phe Val Asn Tyr
             20                  25                  30 att ata cac tgg gtg cga cag gcc cct gga caa ggg ctt gag tgg atg       144
Ile Ile His Trp Val Arg Gln Ala Pro Gly Gln Gly Leu Glu Trp Met
         35                  40                  45 gga atc atc aat cct aat ggc gga aac aca agt tat gca gag aaa ttc       192
Gly Ile Ile Asn Pro Asn Gly Gly Asn Thr Ser Tyr Ala Glu Lys Phe
     50                  55                  60 cag gcc cga gtc acc ttg acc agc gac acg tct acg agt acg gtg tac       240
Gln Ala Arg Val Thr Leu Thr Ser Asp Thr Ser Thr Ser Thr Val Tyr
 65                  70                  75                  80 atg gac ctg agc agc ctg aca tct gag gac acg gcc gtc tat tac tgt       288
Met Asp Leu Ser Ser Leu Thr Ser Glu Asp Thr Ala Val Tyr Tyr Cys
                 85                  90                  95 gcc gtc ctt tcc cct tcg aat ccc tgg ggc cag ggg acc acg gtc acc       336
Ala Val Leu Ser Pro Ser Asn Pro Trp Gly Gln Gly Thr Thr Val Thr
                100                 105                 110 gtc tcc tcg                                                           345
Val Ser Ser
        115

<210> SEQ ID NO 13
<211> LENGTH: 115
<212> TYPE: PRT
<213> ORGANISM: Homo sapiens
```

<400> SEQUENCE: 13

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Val Asn Tyr
            20                  25                  30

Ile Ile His Trp Val Arg Gln Ala Pro Gly Gln Gly Leu Glu Trp Met
        35                  40                  45

Gly Ile Ile Asn Pro Asn Gly Gly Asn Thr Ser Tyr Ala Glu Lys Phe
50                  55                  60

Gln Ala Arg Val Thr Leu Thr Ser Asp Thr Ser Thr Ser Thr Val Tyr
65                  70                  75                  80

Met Asp Leu Ser Ser Leu Thr Ser Glu Asp Thr Ala Val Tyr Tyr Cys
                85                  90                  95

Ala Val Leu Ser Pro Ser Asn Pro Trp Gly Gln Gly Thr Thr Val Thr
            100                 105                 110

Val Ser Ser
        115
```

<210> SEQ ID NO 14
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: NI-105.24B2-VL variable light chain (VL) sequence wherein Glu at position 3 in the sequence may also be Val
<220> FEATURE:
<221> NAME/KEY: V_region
<222> LOCATION: (67)..(99)
<223> OTHER INFORMATION: complementarity determining region (CDR) VL-CDR1
<220> FEATURE:
<221> NAME/KEY: V_region
<222> LOCATION: (145)..(165)
<223> OTHER INFORMATION: complementarity determining region (CDR) VL-CDR2
<220> FEATURE:
<221> NAME/KEY: V_region
<222> LOCATION: (262)..(294)
<223> OTHER INFORMATION: complementarity determining region (CDR) VL-CDR3

<400> SEQUENCE: 14

```
tcc tat gag ctg act cag cca ccc tcg gtg tca gtg tcc cca gga cag      48
Ser Tyr Glu Leu Thr Gln Pro Pro Ser Val Ser Val Ser Pro Gly Gln
1               5                   10                  15 acg gcc ggg atc acc tgc tct gga gat gct ttg cca aag caa ttt gtt      96
Thr Ala Gly Ile Thr Cys Ser Gly Asp Ala Leu Pro Lys Gln Phe Val
            20                  25                  30 tat tgg tac cag aag aag cca ggc cag gcc cct gtg tta ttg ata tat    144
Tyr Trp Tyr Gln Lys Lys Pro Gly Gln Ala Pro Val Leu Leu Ile Tyr
        35                  40                  45 aaa gac act gag agg ccc tca cga atc cct gag cgc ttc tct ggc tcc    192
Lys Asp Thr Glu Arg Pro Ser Arg Ile Pro Glu Arg Phe Ser Gly Ser
50                  55                  60 acc tca ggg aca aca gtc gcg ttg acc atc aat ggg gtc cag gca gag    240
Thr Ser Gly Thr Thr Val Ala Leu Thr Ile Asn Gly Val Gln Ala Glu
65                  70                  75                  80 gac gag gct gac tat tac tgt caa tca gcc gac cgc agt ggt gct ctt    288
Asp Glu Ala Asp Tyr Tyr Cys Gln Ser Ala Asp Arg Ser Gly Ala Leu
                85                  90                  95 tgg gtg ttc ggc gga ggg acc aag ctg acc gtc cta                     324
```

```
Trp Val Phe Gly Gly Gly Thr Lys Leu Thr Val Leu
            100                 105

<210> SEQ ID NO 15
<211> LENGTH: 108
<212> TYPE: PRT
<213> ORGANISM: Homo sapiens

<400> SEQUENCE: 15

Ser Tyr Glu Leu Thr Gln Pro Pro Ser Val Ser Val Ser Pro Gly Gln
1               5                   10                  15

Thr Ala Gly Ile Thr Cys Ser Gly Asp Ala Leu Pro Lys Gln Phe Val
            20                  25                  30

Tyr Trp Tyr Gln Lys Lys Pro Gly Gln Ala Pro Val Leu Leu Ile Tyr
        35                  40                  45

Lys Asp Thr Glu Arg Pro Ser Arg Ile Pro Glu Arg Phe Ser Gly Ser
50                  55                  60

Thr Ser Gly Thr Thr Val Ala Leu Thr Ile Asn Gly Val Gln Ala Glu
65                  70                  75                  80

Asp Glu Ala Asp Tyr Tyr Cys Gln Ser Ala Asp Arg Ser Gly Ala Leu
                85                  90                  95

Trp Val Phe Gly Gly Gly Thr Lys Leu Thr Val Leu
            100                 105

<210> SEQ ID NO 16
<211> LENGTH: 378
<212> TYPE: DNA
<213> ORGANISM: Homo sapiens
<220> FEATURE:
<221> NAME/KEY: CDS
<222> LOCATION: (1)..(378)
<223> OTHER INFORMATION: NI-105.4A3-VH variable heavy chain (VH)
      sequence wherein Gln at positon 1 of the sequence may also be Glu
      and Ser at position 7 of the sequence may also be Thr
<220> FEATURE:
<221> NAME/KEY: V_region
<222> LOCATION: (91)..(105)
<223> OTHER INFORMATION: complementarity determining region (CDR) VH-
      CDR1
<220> FEATURE:
<221> NAME/KEY: V_region
<222> LOCATION: (148)..(198)
<223> OTHER INFORMATION: complementarity determining region (CDR) VH-
      CDR2
<220> FEATURE:
<221> NAME/KEY: V_region
<222> LOCATION: (295)..(345)
<223> OTHER INFORMATION: complementarity determining region (CDR) VH-
      CDR3

<400> SEQUENCE: 16 cag gtg cag ctg gtg gag tct ggg gga ggc gcg gtc cag cct ggg ggg     48
Gln Val Gln Leu Val Glu Ser Gly Gly Gly Ala Val Gln Pro Gly Gly
1               5                   10                  15 tcc ctg aga ctc tcc tgt gca gcc tct gga ttc acc ttc agt gac tat     96
Ser Leu Arg Leu Ser Cys Ala Ala Ser Gly Phe Thr Phe Ser Asp Tyr
            20                  25                  30 gcc atg cac tgg gtc cgc cag gct cca ggc aag ggg ctg cag tgg gtg    144
Ala Met His Trp Val Arg Gln Ala Pro Gly Lys Gly Leu Gln Trp Val
        35                  40                  45 gca gtt ata tcg tat gag gga act tat aaa tac tat gca gac tcc gtg    192
Ala Val Ile Ser Tyr Glu Gly Thr Tyr Lys Tyr Tyr Ala Asp Ser Val
50                  55                  60 aag ggc cga ttc acc atc tcc aga gac aat tcc aag aac acg ctg aac    240
Lys Gly Arg Phe Thr Ile Ser Arg Asp Asn Ser Lys Asn Thr Leu Asn
```

```
                65                  70                  75                  80
ttg cag atg agc agc ctg aga gtt gaa gac acg gct gtg tat ttc tgt        288
Leu Gln Met Ser Ser Leu Arg Val Glu Asp Thr Ala Val Tyr Phe Cys
                    85                  90                  95 gtg aaa gct cga gcc ttt gcc tcc gga cag cga agc acc tcc acc gta        336
Val Lys Ala Arg Ala Phe Ala Ser Gly Gln Arg Ser Thr Ser Thr Val
            100                 105                 110 cct gac tac tgg ggc cag gga acc ctg gtc acc gtc tcc tcg                378
Pro Asp Tyr Trp Gly Gln Gly Thr Leu Val Thr Val Ser Ser
        115                 120                 125

<210> SEQ ID NO 17
<211> LENGTH: 126
<212> TYPE: PRT
<213> ORGANISM: Homo sapiens

<400> SEQUENCE: 17

Gln Val Gln Leu Val Glu Ser Gly Gly Gly Ala Val Gln Pro Gly Gly
1               5                   10                  15

Ser Leu Arg Leu Ser Cys Ala Ala Ser Gly Phe Thr Phe Ser Asp Tyr
            20                  25                  30

Ala Met His Trp Val Arg Gln Ala Pro Gly Lys Gly Leu Gln Trp Val
        35                  40                  45

Ala Val Ile Ser Tyr Glu Gly Thr Tyr Lys Tyr Tyr Ala Asp Ser Val
    50                  55                  60

Lys Gly Arg Phe Thr Ile Ser Arg Asp Asn Ser Lys Asn Thr Leu Asn
65                  70                  75                  80

Leu Gln Met Ser Ser Leu Arg Val Glu Asp Thr Ala Val Tyr Phe Cys
                85                  90                  95

Val Lys Ala Arg Ala Phe Ala Ser Gly Gln Arg Ser Thr Ser Thr Val
            100                 105                 110

Pro Asp Tyr Trp Gly Gln Gly Thr Leu Val Thr Val Ser Ser
        115                 120                 125

<210> SEQ ID NO 18
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: NI-105.4A3-VL variable light chain (VL)
      sequence
<220> FEATURE:
<221> NAME/KEY: V_region
<222> LOCATION: (67)..(99)
<223> OTHER INFORMATION: complementarity determining region (CDR) VL-
      CDR1
<220> FEATURE:
<221> NAME/KEY: V_region
<222> LOCATION: (145)..(165)
<223> OTHER INFORMATION: complementarity determining region (CDR) VL-
      CDR2
<220> FEATURE:
<221> NAME/KEY: V_region
<222> LOCATION: (262)..(294)
<223> OTHER INFORMATION: complementarity determining region (CDR) VL-
      CDR3

<400> SEQUENCE: 18 tcc tat gag ctg act cag cca ccc tcg gtg tca gtg tcc cca gga caa         48
Ser Tyr Glu Leu Thr Gln Pro Pro Ser Val Ser Val Ser Pro Gly Gln
1               5                   10                  15 acg gcc agg atc acc tgc tct gga gat gca ttg cca aaa aaa tat gct         96
Thr Ala Arg Ile Thr Cys Ser Gly Asp Ala Leu Pro Lys Lys Tyr Ala
```

```
Thr Ala Arg Ile Thr Cys Ser Gly Asp Ala Leu Pro Lys Lys Tyr Ala
            20                  25                  30 tat tgg tac cag cag aag tca ggc cag gcc cct gtg ttg gtc atc tat      144
Tyr Trp Tyr Gln Gln Lys Ser Gly Gln Ala Pro Val Leu Val Ile Tyr
            35                  40                  45 gag gac aac aaa cga ccc tcc ggg atc cct gag aga ttc tct ggc tcc      192
Glu Asp Asn Lys Arg Pro Ser Gly Ile Pro Glu Arg Phe Ser Gly Ser
 50                  55                  60 agc tca ggg aca gtg gcc acc ttg act atc agt ggg gcc cag gtg gac      240
Ser Ser Gly Thr Val Ala Thr Leu Thr Ile Ser Gly Ala Gln Val Asp
 65                  70                  75                  80 gat gaa gct gac tac tac tgc tac tcg aca gac atc agt ggt gac ctt      288
Asp Glu Ala Asp Tyr Tyr Cys Tyr Ser Thr Asp Ile Ser Gly Asp Leu
                 85                  90                  95 cgg gtg ttc ggc gga ggg acc aag ctg acc gtc ctc                      324
Arg Val Phe Gly Gly Gly Thr Lys Leu Thr Val Leu
            100                 105

<210> SEQ ID NO 19
<211> LENGTH: 108
<212> TYPE: PRT
<213> ORGANISM: Homo sapiens

<400> SEQUENCE: 19

Ser Tyr Glu Leu Thr Gln Pro Pro Ser Val Ser Val Ser Pro Gly Gln
 1               5                  10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
            35                  40                  45

Glu Asp Asn Lys Arg Pro Ser Gly Ile Pro Glu Arg Phe Ser Gly Ser
 50                  55                  60

Ser Ser Gly Thr Val Ala Thr Leu Thr Ile Ser Gly Ala Gln Val Asp
 65                  70                  75                  80

Asp Glu Ala Asp Tyr Tyr Cys Tyr Ser Thr Asp Ile Ser Gly Asp Leu
                 85                  90                  95

Arg Val Phe Gly Gly Gly Thr Lys Leu Thr Val Leu
            100                 105

<210> SEQ ID NO 20
<211> LENGTH: 451
<212> TYPE: PRT
<213> ORGANISM: Artificial sequence
<220> FEATURE:
<223> OTHER INFORMATION: mature ch4E4 heavy chain (mouse IgG2a)

<400> SEQUENCE: 20

Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Asn Phe Asn Ile Ser
            20                  25                  30

Ala Ile His Trp Val Arg Gln Ala Ser Gly Lys Gly Leu Glu Trp Val
            35                  40                  45

Gly Arg Ile Arg Ser Lys Ser His Asn Tyr Ala Thr Leu Tyr Ala Ala
 50                  55                  60

Ser Leu Lys Gly Arg Phe Thr Leu Ser Arg Asp Asp Ser Arg Asn Thr
 65                  70                  75                  80

Ala Tyr Leu Gln Met Ser Ser Leu Gln Thr Glu Asp Met Ala Val Tyr
                 85                  90                  95
```

```
Tyr Cys Thr Val Leu Ser Ala Asn Tyr Asp Thr Phe Asp Tyr Trp Gly
            100                 105                 110

Gln Gly Thr Leu Val Thr Val Ser Ala Lys Thr Thr Ala Pro Ser
            115                 120             125

Val Tyr Pro Leu Ala Pro Val Cys Gly Asp Thr Thr Gly Ser Ser Val
            130                 135                 140

Thr Leu Gly Cys Leu Val Lys Gly Tyr Phe Pro Glu Pro Val Thr Leu
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Thr
            180                 185                 190

Ser Ser Thr Trp Pro Ser Gln Ser Ile Thr Cys Asn Val Ala His Pro
            195                 200                 205

Ala Ser Ser Thr Lys Val Asp Lys Lys Ile Glu Pro Arg Gly Pro Thr
            210                 215                 220

Ile Lys Pro Cys Pro Pro Cys Lys Cys Pro Ala Pro Asn Leu Leu Gly
225                 230                 235                 240

Gly Pro Ser Val Phe Ile Phe Pro Pro Lys Ile Lys Asp Val Leu Met
                245                 250                 255

Ile Ser Leu Ser Pro Ile Val Thr Cys Val Val Val Asp Val Ser Glu
            260                 265                 270

Asp Asp Pro Asp Val Gln Ile Ser Trp Phe Val Asn Asn Val Glu Val
            275                 280                 285

His Thr Ala Gln Thr Gln Thr His Arg Glu Asp Tyr Asn Ser Thr Leu
            290                 295                 300

Arg Val Val Ser Ala Leu Pro Ile Gln His Gln Asp Trp Met Ser Gly
305                 310                 315                 320

Lys Glu Phe Lys Cys Lys Val Asn Asn Lys Asp Leu Pro Ala Pro Ile
                325                 330                 335

Glu Arg Thr Ile Ser Lys Pro Lys Gly Ser Val Arg Ala Pro Gln Val
            340                 345                 350

Tyr Val Leu Pro Pro Pro Glu Glu Glu Met Thr Lys Lys Gln Val Thr
            355                 360                 365

Leu Thr Cys Met Val Thr Asp Phe Met Pro Glu Asp Ile Tyr Val Glu
            370                 375                 380

Trp Thr Asn Asn Gly Lys Thr Glu Leu Asn Tyr Lys Asn Thr Glu Pro
385                 390                 395                 400

Val Leu Asp Ser Asp Gly Ser Tyr Phe Met Tyr Ser Lys Leu Arg Val
                405                 410                 415

Glu Lys Lys Asn Trp Val Glu Arg Asn Ser Tyr Ser Cys Ser Val Val
            420                 425                 430

His Glu Gly Leu His Asn His His Thr Thr Lys Ser Phe Ser Arg Thr
            435                 440                 445

Pro Gly Lys
    450
```

<210> SEQ ID NO 21
<211> LENGTH: 213
<212> TYPE: PRT
<213> ORGANISM: Artificial sequence
<220> FEATURE:
<223> OTHER INFORMATION: mature ch4E4 light chain (mouse lambda)

<400> SEQUENCE: 21

```
Ser Tyr Glu Leu Thr Gln Pro Pro Ser Val Ser Val Ser Pro Gly Gln
1               5                   10                  15

Thr Ala Arg Ile Ser Cys Phe Gly Asp Thr Leu Pro Lys Gln Tyr Thr
            20                  25                  30

Tyr Trp Tyr Gln Gln Lys Pro Gly Gln Ala Pro Val Leu Val Ile Tyr
        35                  40                  45

Lys Asp Thr Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Leu Ser Ala Asp Asn Ser Ala Thr Trp
                85                  90                  95

Val Phe Gly Gly Gly Thr Lys Val Thr Val Leu Gly Gln Pro Lys Ser
            100                 105                 110

Ser Pro Ser Val Thr Leu Phe Pro Pro Ser Ser Glu Glu Leu Glu Thr
        115                 120                 125

Asn Lys Ala Thr Leu Val Cys Thr Ile Thr Asp Phe Tyr Pro Gly Val
    130                 135                 140

Val Thr Val Asp Trp Lys Val Asp Gly Thr Pro Val Thr Gln Gly Met
145                 150                 155                 160

Glu Thr Thr Gln Pro Ser Lys Gln Ser Asn Asn Lys Tyr Met Ala Ser
                165                 170                 175

Ser Tyr Leu Thr Leu Thr Ala Arg Ala Trp Glu Arg His Ser Ser Tyr
            180                 185                 190

Ser Cys Gln Val Thr His Glu Gly His Thr Val Glu Lys Ser Leu Ser
        195                 200                 205

Arg Ala Asp Cys Ser
    210

<210> SEQ ID NO 22
<211> LENGTH: 451
<212> TYPE: PRT
<213> ORGANISM: Artificial sequence
<220> FEATURE:
<223> OTHER INFORMATION: mature ch4E4(N30Q) heavy chain (mouse IgG2a)

<400> SEQUENCE: 22

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Asn Phe Gln Ile Ser
            20                  25                  30

Ala Ile His Trp Val Arg Gln Ala Ser Gly Lys Gly Leu Glu Trp Val
        35                  40                  45

Gly Arg Ile Arg Ser Lys Ser His Asn Tyr Ala Thr Leu Tyr Ala Ala
    50                  55                  60

Ser Leu Lys Gly Arg Phe Thr Leu Ser Arg Asp Asp Ser Arg Asn Thr
65                  70                  75                  80

Ala Tyr Leu Gln Met Ser Ser Leu Gln Thr Glu Asp Met Ala Val Tyr
                85                  90                  95

Tyr Cys Thr Val Leu Ser Ala Asn Tyr Asp Thr Phe Asp Tyr Trp Gly
            100                 105                 110

Gln Gly Thr Leu Val Thr Val Ser Ser Ala Lys Thr Thr Ala Pro Ser
        115                 120                 125

Val Tyr Pro Leu Ala Pro Val Cys Gly Asp Thr Thr Gly Ser Ser Val
    130                 135                 140
```

-continued

```
Thr Leu Gly Cys Leu Val Lys Gly Tyr Phe Pro Glu Pro Val Thr Leu
145                 150                 155                 160

Thr Trp Asn Ser Gly Ser Leu Ser Ser Gly Val His Thr Phe Pro Ala
            165                 170                 175

Val Leu Gln Ser Asp Leu Tyr Thr Leu Ser Ser Val Thr Val Thr
        180                 185                 190

Ser Ser Thr Trp Pro Ser Gln Ser Ile Thr Cys Asn Val Ala His Pro
        195                 200                 205

Ala Ser Ser Thr Lys Val Asp Lys Lys Ile Glu Pro Arg Gly Pro Thr
    210                 215                 220

Ile Lys Pro Cys Pro Pro Cys Lys Cys Pro Ala Pro Asn Leu Leu Gly
225                 230                 235                 240

Gly Pro Ser Val Phe Ile Phe Pro Pro Lys Ile Lys Asp Val Leu Met
                245                 250                 255

Ile Ser Leu Ser Pro Ile Val Thr Cys Val Val Asp Val Ser Glu
            260                 265                 270

Asp Asp Pro Asp Val Gln Ile Ser Trp Phe Val Asn Asn Val Glu Val
        275                 280                 285

His Thr Ala Gln Thr Gln Thr His Arg Glu Asp Tyr Asn Ser Thr Leu
    290                 295                 300

Arg Val Val Ser Ala Leu Pro Ile Gln His Gln Asp Trp Met Ser Gly
305                 310                 315                 320

Lys Glu Phe Lys Cys Lys Val Asn Asn Lys Asp Leu Pro Ala Pro Ile
                325                 330                 335

Glu Arg Thr Ile Ser Lys Pro Lys Gly Ser Val Arg Ala Pro Gln Val
            340                 345                 350

Tyr Val Leu Pro Pro Pro Glu Glu Met Thr Lys Lys Gln Val Thr
        355                 360                 365

Leu Thr Cys Met Val Thr Asp Phe Met Pro Glu Asp Ile Tyr Val Glu
    370                 375                 380

Trp Thr Asn Asn Gly Lys Thr Glu Leu Asn Tyr Lys Asn Thr Glu Pro
385                 390                 395                 400

Val Leu Asp Ser Asp Gly Ser Tyr Phe Met Tyr Ser Lys Leu Arg Val
                405                 410                 415

Glu Lys Lys Asn Trp Val Glu Arg Asn Ser Tyr Ser Cys Ser Val Val
            420                 425                 430

His Glu Gly Leu His Asn His Thr Thr Lys Ser Phe Ser Arg Thr
        435                 440                 445

Pro Gly Lys
    450
```

<210> SEQ ID NO 23
<211> LENGTH: 5
<212> TYPE: PRT
<213> ORGANISM: Artificial sequence
<220> FEATURE:
<223> OTHER INFORMATION: NI-105.4E4-VH (variable heavy chain sequence VH) CDR1

<400> SEQUENCE: 23

```
Ile Ser Ala Ile His
1               5
```

<210> SEQ ID NO 24
<211> LENGTH: 19
<212> TYPE: PRT

```
<213> ORGANISM: Artificial sequence
<220> FEATURE:
<223> OTHER INFORMATION: NI-105.4E4-VH (variable heavy chain sequence
      VH) CDR2

<400> SEQUENCE: 24

Arg Ile Arg Ser Lys Ser His Asn Tyr Ala Thr Leu Tyr Ala Ala Ser
1               5                   10                  15

Leu Lys Gly

<210> SEQ ID NO 25
<211> LENGTH: 10
<212> TYPE: PRT
<213> ORGANISM: Artificial sequence
<220> FEATURE:
<223> OTHER INFORMATION: NI-105.4E4-VH (variable heavy chain sequence
      VH) CDR3

<400> SEQUENCE: 25

Leu Ser Ala Asn Tyr Asp Thr Phe Asp Tyr
1               5                   10

<210> SEQ ID NO 26
<211> LENGTH: 11
<212> TYPE: PRT
<213> ORGANISM: Artificial sequence
<220> FEATURE:
<223> OTHER INFORMATION: NI-105.4E4-VL (variable light chain sequence
      VL) CDR1

<400> SEQUENCE: 26

Phe Gly Asp Thr Leu Pro Lys Gln Tyr Thr Tyr
1               5                   10

<210> SEQ ID NO 27
<211> LENGTH: 7
<212> TYPE: PRT
<213> ORGANISM: Artificial sequence
<220> FEATURE:
<223> OTHER INFORMATION: NI-105.4E4-VL (variable light chain sequence
      VL) CDR2

<400> SEQUENCE: 27

Lys Asp Thr Glu Arg Pro Ser
1               5

<210> SEQ ID NO 28
<211> LENGTH: 10
<212> TYPE: PRT
<213> ORGANISM: Artificial sequence
<220> FEATURE:
<223> OTHER INFORMATION: NI-105.4E4-VL (variable light chain sequence
      VL) CD3

<400> SEQUENCE: 28

Leu Ser Ala Asp Asn Ser Ala Thr Trp Val
1               5                   10

<210> SEQ ID NO 29
<211> LENGTH: 5
<212> TYPE: PRT
<213> ORGANISM: Artificial sequence
<220> FEATURE:
<223> OTHER INFORMATION: NI-105.24B2-VH (variable heavy chain sequence
      VH) CDR1

<400> SEQUENCE: 29
```

Asn Tyr Ile Ile His
1               5

<210> SEQ ID NO 30
<211> LENGTH: 17
<212> TYPE: PRT
<213> ORGANISM: Artificial sequence
<220> FEATURE:
<223> OTHER INFORMATION: NI-105.24B2-VH (variable heavy chain sequence
      VH) CD2

<400> SEQUENCE: 30

Ile Ile Asn Pro Asn Gly Gly Asn Thr Ser Tyr Ala Glu Lys Phe Gln
1               5                   10                  15

Ala

<210> SEQ ID NO 31
<211> LENGTH: 6
<212> TYPE: PRT
<213> ORGANISM: Artificial sequence
<220> FEATURE:
<223> OTHER INFORMATION: NI-105.24B2-VH (variable heavy chain sequence
      VH) CDR3

<400> SEQUENCE: 31

Leu Ser Pro Ser Asn Pro
1               5

<210> SEQ ID NO 32
<211> LENGTH: 11
<212> TYPE: PRT
<213> ORGANISM: Artificial sequence
<220> FEATURE:
<223> OTHER INFORMATION: NI-105.24B2-VL (variable light chain sequence
      VL) CDR1

<400> SEQUENCE: 32

Ser Gly Asp Ala Leu Pro Lys Gln Phe Val Tyr
1               5                   10

<210> SEQ ID NO 33
<211> LENGTH: 7
<212> TYPE: PRT
<213> ORGANISM: Artificial sequence
<220> FEATURE:
<223> OTHER INFORMATION: NI-105.24B2-VL (variable light chain sequence
      VL) CDR2

<400> SEQUENCE: 33

Lys Asp Thr Glu Arg Pro Ser
1               5

<210> SEQ ID NO 34
<211> LENGTH: 11
<212> TYPE: PRT
<213> ORGANISM: Artificial sequence
<220> FEATURE:
<223> OTHER INFORMATION: NI-105.24B2-VL (variable light chain sequence
      VL) CDR3

<400> SEQUENCE: 34

Gln Ser Ala Asp Arg Ser Gly Ala Leu Trp Val
1               5                   10

<210> SEQ ID NO 35
<211> LENGTH: 5
<212> TYPE: PRT

```
<213> ORGANISM: Artificial sequence
<220> FEATURE:
<223> OTHER INFORMATION: NI-105.4A3-VH (variable heavy chain sequence
      VH) CDR1

<400> SEQUENCE: 35

Asp Tyr Ala Met His
1               5

<210> SEQ ID NO 36
<211> LENGTH: 17
<212> TYPE: PRT
<213> ORGANISM: Artificial sequence
<220> FEATURE:
<223> OTHER INFORMATION: NI-105.4A3-VH (variable heavy chain sequence
      VH) CDR2

<400> SEQUENCE: 36

Val Ile Ser Tyr Glu Gly Thr Tyr Lys Tyr Tyr Ala Asp Ser Val Lys
1               5                   10                  15
Gly

<210> SEQ ID NO 37
<211> LENGTH: 17
<212> TYPE: PRT
<213> ORGANISM: Artificial sequence
<220> FEATURE:
<223> OTHER INFORMATION: NI-105.4A3-VH (variable heavy chain sequence
      VH) CDR3

<400> SEQUENCE: 37

Ala Arg Ala Phe Ala Ser Gly Gln Arg Ser Thr Ser Thr Val Pro Asp
1               5                   10                  15
Tyr

<210> SEQ ID NO 38
<211> LENGTH: 11
<212> TYPE: PRT
<213> ORGANISM: Artificial sequence
<220> FEATURE:
<223> OTHER INFORMATION: NI-105.4A3-VL (variable light chain sequence
      VL) CDR1

<400> SEQUENCE: 38

Ser Gly Asp Ala Leu Pro Lys Lys Tyr Ala Tyr
1               5                   10

<210> SEQ ID NO 39
<211> LENGTH: 7
<212> TYPE: PRT
<213> ORGANISM: Artificial sequence
<220> FEATURE:
<223> OTHER INFORMATION: NI-105.4A3-VL (variable light chain sequence
      VL) CDR2

<400> SEQUENCE: 39

Glu Asp Asn Lys Arg Pro Ser
1               5

<210> SEQ ID NO 40
<211> LENGTH: 11
<212> TYPE: PRT
<213> ORGANISM: Artificial sequence
<220> FEATURE:
<223> OTHER INFORMATION: NI-105.4A3-VL (variable light chain sequence
      VL) CDR3
```

```
<400> SEQUENCE: 40

Tyr Ser Thr Asp Ile Ser Gly Asp Leu Arg Val
1               5                   10

<210> SEQ ID NO 41
<211> LENGTH: 11
<212> TYPE: PRT
<213> ORGANISM: Artificial sequence
<220> FEATURE:
<223> OTHER INFORMATION: Peptide

<400> SEQUENCE: 41

Asp His Gly Ala Glu Ile Val Tyr Lys Ser Pro
1               5                   10

<210> SEQ ID NO 42
<211> LENGTH: 15
<212> TYPE: PRT
<213> ORGANISM: Artificial sequence
<220> FEATURE:
<223> OTHER INFORMATION: Peptide

<400> SEQUENCE: 42

Gln Glu Gly Asp Thr Asp Ala Gly Leu Lys Glu Ser Pro Leu Gln
1               5                   10                  15

<210> SEQ ID NO 43
<211> LENGTH: 121
<212> TYPE: PRT
<213> ORGANISM: Artificial sequence
<220> FEATURE:
<223> OTHER INFORMATION: VH antibody

<400> SEQUENCE: 43

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Asn Phe Gln Ile Ser
            20                  25                  30

Ala Ile His Trp Val Arg Gln Ala Ser Gly Lys Gly Leu Glu Trp Val
        35                  40                  45

Gly Arg Ile Arg Ser Lys Ser His Asn Tyr Ala Thr Leu Tyr Ala Ala
    50                  55                  60

Ser Leu Lys Gly Arg Phe Thr Leu Ser Arg Asp Asp Ser Arg Asn Thr
65                  70                  75                  80

Ala Tyr Leu Gln Met Ser Ser Leu Gln Thr Glu Asp Met Ala Val Tyr
                85                  90                  95

Tyr Cys Thr Val Leu Ser Ala Asn Tyr Asp Thr Phe Asp Tyr Trp Gly
            100                 105                 110

Gln Gly Thr Leu Val Thr Val Ser Ser
        115                 120

<210> SEQ ID NO 44
<211> LENGTH: 120
<212> TYPE: PRT
<213> ORGANISM: Homo sapiens

<400> SEQUENCE: 44

Glu Val Gln Leu Val Gln Ser Gly Ala Glu Val Lys Lys Pro Gly Glu
1               5                   10                  15

Ser Leu Lys Ile Ser Cys Lys Ala Phe Gly Tyr Ser Phe Thr Asn Phe
            20                  25                  30
```

```
Trp Ile Gly Trp Val Arg Gln Val Pro Gly Lys Gly Leu Glu Trp Val
            35                  40                  45

Gly Ile Ile Tyr Pro Gly Asp Ser Asp Thr Arg Tyr Ser Pro Ser Phe
 50                      55                  60

Gln Gly Gln Val Thr Ile Ser Ala Asp Lys Ser Ile Asp Thr Ala Tyr
65                   70                  75                  80

Leu Gln Trp Gly His Leu Lys Ala Ser Asp Ser Ala Met Tyr Phe Cys
                85                  90                  95

Ala Arg Arg Gly Phe Trp Thr Gly Ser Gln Ile Glu Tyr Trp Gly Gln
               100                 105                 110

Gly Thr Leu Val Thr Val Ser Ser
            115                 120
```

<210> SEQ ID NO 45
<211> LENGTH: 120
<212> TYPE: PRT
<213> ORGANISM: Homo sapiens

<400> SEQUENCE: 45

```
Glu Val Gln Leu Val Gln Ser Gly Ala Glu Val Lys Lys Pro Gly Glu
1               5                   10                  15

Ser Leu Lys Ile Ser Cys Lys Ala Phe Gly Tyr Ser Phe Thr Asn Phe
                20                  25                  30

Trp Ile Gly Trp Val Arg Gln Val Pro Gly Lys Gly Leu Glu Trp Val
            35                  40                  45

Gly Ile Ile Tyr Pro Gly Asp Ser Asp Thr Arg Tyr Ser Pro Ser Phe
 50                      55                  60

Gln Gly Gln Val Thr Ile Ser Ala Asp Lys Ser Ile Asp Thr Ala Tyr
65                   70                  75                  80

Leu Gln Trp Gly His Leu Lys Ala Ser Asp Ser Ala Met Tyr Phe Cys
                85                  90                  95

Ala Arg Arg Gly Phe Trp Thr Gly Ser Gln Ile Glu Tyr Trp Gly Gln
               100                 105                 110

Gly Thr Gln Val Thr Val Ser Ser
            115                 120
```

<210> SEQ ID NO 46
<211> LENGTH: 111
<212> TYPE: PRT
<213> ORGANISM: Homo sapiens

<400> SEQUENCE: 46

```
Gln Ser Ala Leu Thr Gln Pro Pro Ser Ala Ser Gly Ser Pro Gly His
1               5                   10                  15

Ser Val Thr Ile Ser Cys Thr Gly Thr Ser Ser Asp Val Gly Asn Tyr
                20                  25                  30

Ser Phe Val Ser Trp Tyr Gln Gln Tyr Pro Gly Lys Ala Pro Lys Val
            35                  40                  45

Ile Ile Tyr Asp Val Ser Lys Arg Ser Ser Gly Val Pro Asp Arg Phe
 50                      55                  60

Phe Gly Ser Lys Ser Ala Asn Thr Ala Ser Leu Thr Val Ser Gly Val
65                   70                  75                  80

Gln Glu Glu Asp Glu Ala Asp Tyr Phe Cys Ser Ser Tyr Gly Gly Ser
                85                  90                  95

Lys Tyr Pro Trp Val Phe Gly Gly Gly Thr Lys Leu Thr Val Leu
               100                 105                 110
```

<210> SEQ ID NO 47
<211> LENGTH: 125
<212> TYPE: PRT
<213> ORGANISM: Homo sapiens

<400> SEQUENCE: 47

Glu Val Gln Leu Val Glu Ser Gly Gly Gly Val Val Gln Pro Gly Arg
1               5                   10                  15

Ser Leu Arg Val Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Ile Trp Phe Asp Gly Ser Asn Glu Phe Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Asp Leu Gly Ala Ser Val Thr Thr Ser Asn Ala Glu Asn Phe
            100                 105                 110

His His Trp Gly Gln Gly Thr Leu Val Thr Val Ser Ser
            115                 120                 125

<210> SEQ ID NO 48
<211> LENGTH: 125
<212> TYPE: PRT
<213> ORGANISM: Homo sapiens

<400> SEQUENCE: 48

Gln Val Gln Leu Val Glu Ser Gly Gly Gly Val Val Gln Pro Gly Arg
1               5                   10                  15

Ser Leu Arg Val Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Ile Trp Phe Asp Gly Ser Asn Glu Phe Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Asp Leu Gly Ala Ser Val Thr Thr Ser Asn Ala Glu Asn Phe
            100                 105                 110

His His Trp Gly Gln Gly Thr Leu Val Thr Val Ser Ser
            115                 120                 125

<210> SEQ ID NO 49
<211> LENGTH: 108
<212> TYPE: PRT
<213> ORGANISM: Homo sapiens

<400> SEQUENCE: 49

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Arg Tyr Val
            20                  25                  30

Tyr Trp Tyr Gln Gln Lys Ser Gly Gln Ala Pro Val Leu Val Ile Tyr

```
                35                  40                  45
Glu Asp Ser Lys Arg Pro Ser Gly Ile Pro Glu Thr Phe Ser Gly Ser
 50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Ser Asn Gly His His
                85                  90                  95

Trp Val Phe Gly Gly Gly Thr Lys Leu Thr Val Leu
            100                 105

<210> SEQ ID NO 50
<211> LENGTH: 121
<212> TYPE: PRT
<213> ORGANISM: Homo sapiens

<400> SEQUENCE: 50

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Asp Phe Ser Gly Tyr
            20                  25                  30

Ser Met Ala Trp Val Arg Gln Ala Pro Gly Lys Gly Leu Glu Trp Val
        35                  40                  45

Ser Tyr Ile Ser Gly Thr Tyr Val Ser Gly Gly Thr Gly Thr Met Tyr
 50                  55                  60

Tyr Leu Asp Ser Val Lys Gly Arg Phe Phe Ile Ser Arg Asp Asp Ala
65                  70                  75                  80

Thr Ser Ser Leu Tyr Leu Gln Met Asp Ser Leu Arg Asp Glu Asp Thr
                85                  90                  95

Ala Val Tyr Tyr Cys Ala Arg Val Tyr Asp Tyr Gly Leu Asp Trp Gly
            100                 105                 110

Gln Gly Thr Leu Val Thr Val Ser Ser
        115                 120

<210> SEQ ID NO 51
<211> LENGTH: 113
<212> TYPE: PRT
<213> ORGANISM: Homo sapiens

<400> SEQUENCE: 51

Asp Ile Val Met Thr Gln Ser Pro Asp Ser Leu Ala Val Ser Leu Gly
1               5                   10                  15

Glu Arg Ala Thr Ile Asn Cys Lys Ser Ser Arg Ser Val Leu Tyr Ser
            20                  25                  30

Ser Asn Ser Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Glu Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Gly Thr Pro Arg Thr Phe Gly Gln Gly Thr Lys Val Glu Ile
            100                 105                 110

Lys

<210> SEQ ID NO 52
```

<211> LENGTH: 124
<212> TYPE: PRT
<213> ORGANISM: Homo sapiens

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Gly Thr Arg Phe Thr Phe Ser Thr Tyr
            20                  25                  30

Ala Met Gly Trp Val Arg Gln Ala Pro Gly Arg Gly Leu Glu Trp Val
        35                  40                  45

Ser Ala Ile Gly Gly Ser Gly Asp Ser Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Val Tyr Asp Tyr Leu Trp Gly Ser Tyr Arg Leu Phe Asp
            100                 105                 110

Tyr Trp Gly Gln Gly Thr Leu Val Thr Val Ser Ser
        115                 120

<210> SEQ ID NO 53
<211> LENGTH: 108
<212> TYPE: PRT
<213> ORGANISM: Homo sapiens

<400> SEQUENCE: 53

Ser Tyr Val Leu Thr Gln Pro Pro Ser Val Ser Val Ala Pro Gly Gln
1               5                   10                  15

Thr Ala Arg Phe Thr Cys Gly Gly Asn Asn Ile Ala Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Arg Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Thr Asp His
                85                  90                  95

Val Val Phe Gly Gly Gly Thr Lys Leu Thr Val Leu
            100                 105

<210> SEQ ID NO 54
<211> LENGTH: 114
<212> TYPE: PRT
<213> ORGANISM: Homo sapiens

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Pro Asn Tyr
            20                  25                  30

Val Met Thr Trp Val Arg Gln Ala Pro Gly Lys Gly Leu Glu Trp Val
        35                  40                  45

Ser Gly Ile Ser Gly Ser Gly Ser Thr Asp Tyr Ala Asp Ser Val
    50                  55                  60

-continued

```
Lys Gly Arg Phe Thr Ile Ser Arg Asp Asn Ser Lys Asn Thr Leu Tyr
 65                  70                  75                  80

Leu Gln Met Asn Ser Leu Arg Val Glu Asp Thr Ala Leu Tyr Tyr Cys
                 85                  90                  95

Ala Lys Gly Ser Gly Gly Ile Arg Gly Gln Gly Thr Met Val Thr Val
            100                 105                 110

Ser Ser
```

<210> SEQ ID NO 55
<211> LENGTH: 110
<212> TYPE: PRT
<213> ORGANISM: Homo sapiens

<400> SEQUENCE: 55

```
Gln Ser Ala Leu Thr Gln Pro Arg Ser Val Ser Gly Ser Pro Gly Gln
 1               5                   10                  15

Ser Val Thr Ile Ser Cys Thr Gly Thr Ser Ser Asp Val Gly Gly Tyr
                 20                  25                  30

Asn Tyr Val Ser Trp His Gln His Pro Gly Lys Ala Pro Lys Leu
             35                  40                  45

Leu Ile Tyr Asp Val Thr Lys Arg Pro Ser Gly Val Pro Asp Arg Phe
 50                  55                  60

Ser Gly Ser Lys Ser Gly Asn Thr Ala Ala Leu Thr Ile Ser Gly Leu
 65                  70                  75                  80

Gln Ala Glu Asp Glu Ala Asp Tyr Tyr Cys His Ser Tyr Val Gly Ser
                 85                  90                  95

Tyr Thr Leu Val Phe Gly Gly Gly Thr Lys Leu Thr Val Leu
             100                 105                 110
```

<210> SEQ ID NO 56
<211> LENGTH: 118
<212> TYPE: PRT
<213> ORGANISM: Homo sapiens

<400> SEQUENCE: 56

```
Glu Val Gln Leu Val Glu Ser Gly Gly Gly Leu Val Gln Pro Gly Gly
 1               5                   10                  15

Ser Leu Lys Leu Ser Cys Ala Ala Ser Gly Phe Thr Phe Ser Gly Ser
                 20                  25                  30

Ala Met His Trp Val Arg Gln Ala Ser Gly Lys Gly Leu Glu Trp Val
             35                  40                  45

Gly Arg Ile Arg Ser Lys Ala Asn Ser Tyr Ala Thr Ala Tyr Ala Ala
 50                  55                  60

Ser Val Lys Gly Arg Phe Thr Ile Ser Arg Asp Asp Ser Lys Asn Thr
 65                  70                  75                  80

Ala Tyr Leu Gln Met Asn Ser Leu Lys Thr Glu Asp Thr Ala Val Tyr
                 85                  90                  95

Tyr Cys Thr Ser Pro Thr Val Thr Thr Glu Val Trp Gly Gln Gly Thr
            100                 105                 110

Leu Val Thr Val Ser Ser
        115
```

<210> SEQ ID NO 57
<211> LENGTH: 113
<212> TYPE: PRT
<213> ORGANISM: Homo sapiens

<400> SEQUENCE: 57

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asp Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Ser Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Ile Thr Phe Gly Gln Gly Thr Arg Leu Glu Ile
                100                 105                 110

Lys

<210> SEQ ID NO 58
<211> LENGTH: 122
<212> TYPE: PRT
<213> ORGANISM: Homo sapiens

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ile Gly Ser Ser Gly Met Thr Phe Ser Ser
            20                  25                  30

Tyr Ala Phe Asn Trp Val Arg Gln Thr Pro Gly Lys Gly Leu Glu Trp
        35                  40                  45

Val Ser Ser Ile Ser Arg Phe Gly Ser Thr Val Asp Tyr Thr Asp Ser
    50                  55                  60

Val Arg Gly Arg Phe Thr Ile Ser Arg Asp Asp Gly Gln Arg Ser Leu
65                  70                  75                  80

Tyr Leu Gln Met Asn Ser Leu Arg Val Glu Asp Thr Ala Val Tyr Tyr
                85                  90                  95

Cys Val Arg Ser Thr Ala Ser Gly Ser Arg Ser Pro Gly Ile Ile Trp
                100                 105                 110

Gly Gln Gly Thr Thr Val Thr Val Ser Ser
        115                 120

<210> SEQ ID NO 59
<211> LENGTH: 107
<212> TYPE: PRT
<213> ORGANISM: Homo sapiens

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Val Asn Asn
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Gly Gly Val Pro Ser Lys Phe Ser Gly
    50                  55                  60

Ser Ala Ser Gly Thr Asp Phe Ser Leu Thr Ile Ser Asn Leu Gln Pro
65                  70                  75                  80

```
Glu Asp Phe Ala Thr Tyr Phe Cys Gln Gln Tyr Asn Ser Tyr Pro Trp
            85                  90                  95

Thr Phe Gly Gln Gly Thr Lys Val Glu Ile Lys
        100                 105
```

<210> SEQ ID NO 60
<211> LENGTH: 126
<212> TYPE: PRT
<213> ORGANISM: Homo sapiens

<400> SEQUENCE: 60

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Arg Phe Thr Thr Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Tyr
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Gly Met Tyr Tyr Cys
                85                  90                  95

Ala Arg Val Ala Gly Asp Ile Tyr Glu Asn Tyr Tyr Tyr Tyr Gly
            100                 105                 110

Met Asp Val Trp Gly Gln Gly Thr Thr Val Thr Val Ser Ser
            115                 120                 125
```

<210> SEQ ID NO 61
<211> LENGTH: 113
<212> TYPE: PRT
<213> ORGANISM: Homo sapiens

<400> SEQUENCE: 61

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Gly
            20                  25                  30

Ser Asn Asn Lys Asn Tyr Leu Ala Trp Tyr Gln Gln Lys Leu Gly Gln
        35                  40                  45

Ser Pro Lys Leu Leu Ile Tyr Trp Ala Ser Ala Arg Glu Ser Gly Val
    50                  55                  60

Pro Asp Arg Phe Gly Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Trp Thr Phe Gly Gln Gly Thr Lys Val Glu Ile
            100                 105                 110

Lys
```

<210> SEQ ID NO 62
<211> LENGTH: 118
<212> TYPE: PRT
<213> ORGANISM: Homo sapiens

<400> SEQUENCE: 62

```
Gln Val Gln Leu Val Glu Ser Gly Gly Gly Val Val Gln Pro Gly Arg
1               5                   10                  15
```

```
Ser Leu Arg Leu Ser Cys Ala Ala Ser Gly Phe Thr Phe Thr Arg Tyr
            20                  25                  30

Gly Met His Trp Val Arg Gln Ala Pro Gly Lys Gly Leu Glu Trp Val
        35                  40                  45

Ala Val Ile Trp Tyr Asp Gly Thr Asn Lys Tyr Tyr Ala Asp Ser Leu
 50                  55                  60

Gln Gly Arg Phe Thr Ile Ser Arg Asp Thr Ser Thr Asn Thr Leu Tyr
65                  70                  75                  80

Leu Gln Met Asn Gly Leu Arg Val Glu Asp Arg Ala Val Tyr Tyr Cys
                85                  90                  95

Ala Arg Glu Gly Phe Gln Gly Ala Ile Asp Tyr Trp Gly Gln Gly Thr
            100                 105                 110

Leu Val Thr Val Ser Ser
                115

<210> SEQ ID NO 63
<211> LENGTH: 113
<212> TYPE: PRT
<213> ORGANISM: Homo sapiens

<400> SEQUENCE: 63

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Asn Ile Leu Tyr Ser
            20                  25                  30

Ser Asp Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ile Pro Arg Thr Phe Gly Gln Gly Thr Lys Val Glu Ile
            100                 105                 110

Lys

<210> SEQ ID NO 64
<211> LENGTH: 113
<212> TYPE: PRT
<213> ORGANISM: Homo sapiens

<400> SEQUENCE: 64

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Asn Ile Leu Tyr Ser
            20                  25                  30

Ser Asp Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95
```

Tyr Tyr Ser Ile Pro Arg Thr Phe Gly Gln Gly Thr Lys Val Glu Ile
            100                 105                 110
Lys

<210> SEQ ID NO 65
<211> LENGTH: 120
<212> TYPE: PRT
<213> ORGANISM: Homo sapiens

<400> SEQUENCE: 65

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ser Phe Ser Asp Ser
            20                  25                  30

Ala Phe His Trp Ala Arg Gln Ala Ser Gly Lys Gly Leu Glu Trp Val
        35                  40                  45

Gly Arg Ile Arg Ser Lys Gly Asn Asn Tyr Ala Thr Ala Tyr Ala Ala
    50                  55                  60

Ser Val Lys Gly Arg Phe Thr Val Ser Arg Asp Asp Ser Lys Asn Thr
65                  70                  75                  80

Thr Tyr Leu Gln Met Asn Ser Leu Lys Thr Asp Asp Thr Ala Ile Tyr
                85                  90                  95

Tyr Cys Thr Arg Gln Gly Pro Ser Tyr Gly Gly Ile Asn Trp Gly Leu
            100                 105                 110

Gly Thr Leu Val Thr Val Ser Ser
        115                 120

<210> SEQ ID NO 66
<211> LENGTH: 113
<212> TYPE: PRT
<213> ORGANISM: Homo sapiens

<400> SEQUENCE: 66

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Ile Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Arg Ala Glu Asp Val Ala Val Tyr Tyr Cys Gln Gln
                85                  90                  95

Tyr Tyr Ser Ser Pro Gln Thr Phe Gly Gln Gly Thr Lys Val Glu Ile
            100                 105                 110
Lys

<210> SEQ ID NO 67
<211> LENGTH: 115
<212> TYPE: PRT
<213> ORGANISM: Homo sapiens

<400> SEQUENCE: 67

Glu Val Gln Leu Val Glu Ser Gly Gly Gly Phe Val Arg Pro Gly Gly
1               5                   10                  15

```
Ser Ile Thr Leu Ser Cys Ala Thr Ser Gly Phe Thr Phe Thr Lys Ala
            20                  25                  30

Trp Met Thr Trp Val Arg Gln Ala Pro Val Lys Gly Leu Glu Trp Ile
        35                  40                  45

Gly His Ile Lys Thr Arg Ile Glu Gly Ala Thr Thr Asp Tyr Ala Ala
    50                  55                  60

Pro Val Glu Gly Arg Phe Thr Ile Ser Arg Asp Asp Ser Lys Asn Met
65                  70                  75                  80

Val Tyr Leu Gln Met Asn Ser Leu Lys Thr Glu Asp Ser Gly Ile Tyr
                85                  90                  95

Tyr Cys Ser Thr Asp Phe Asp Tyr Trp Gly Gln Gly Thr Leu Val Thr
            100                 105                 110

Val Ser Ser
        115

<210> SEQ ID NO 68
<211> LENGTH: 113
<212> TYPE: PRT
<213> ORGANISM: Homo sapiens

<400> SEQUENCE: 68

Asp Val Val Met Thr Gln Ser Pro Leu Ser Leu Pro Val Thr Leu Gly
1               5                   10                  15

Gln Pro Ala Ser Ile Ser Cys Thr Ser Ser Gln Ser Leu Leu Tyr Ser
            20                  25                  30

Asp Gly Asn Thr Tyr Leu Asn Trp Phe Gln Gln Arg Pro Gly Gln Ser
        35                  40                  45

Pro Arg Arg Leu Met Tyr Lys Val Ser Lys Arg Asp Pro Gly Val Pro
50                  55                  60

Asp Arg Phe Ser Gly Ser Gly Ser Gly Thr Asp Phe Thr Leu Ser Ile
65                  70                  75                  80

Ser Arg Val Glu Ala Glu Asp Val Gly Val Tyr Tyr Cys Met Gln Gly
                85                  90                  95

Ser Leu Trp Pro Arg Tyr Thr Phe Gly Gln Gly Thr Lys Val Glu Ile
            100                 105                 110

Lys

<210> SEQ ID NO 69
<211> LENGTH: 121
<212> TYPE: PRT
<213> ORGANISM: Homo sapiens

<400> SEQUENCE: 69

Glu Val Gln Leu Val Gln Ser Gly Ala Glu Val Lys Lys Pro Gly Asp
1               5                   10                  15

Ser Leu Arg Ile Ser Cys Lys Ala Ser Gly Tyr Asn Phe Pro Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Ile Arg Tyr Ser Pro Ser Phe
    50                  55                  60

Gln Gly His Val Thr Ile Ser Ser Asp Lys Ser Ile Thr Thr Ala Tyr
65                  70                  75                  80

Leu Gln Trp Thr Ser Leu Lys Val Ala Asp Ser Ala Met Tyr Tyr Cys
                85                  90                  95

Ala Arg Val Glu Arg Pro Asp Lys Gly Gly Trp Phe Gly Pro Trp Gly
```

```
                100             105             110
Gln Gly Thr Leu Val Thr Val Ser Ser
        115                 120

<210> SEQ ID NO 70
<211> LENGTH: 113
<212> TYPE: PRT
<213> ORGANISM: Homo sapiens

<400> SEQUENCE: 70

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Leu Leu Tyr Thr
            20                  25                  30

Ser Asn Asn Gln Asn Tyr Leu Ala Trp Tyr Gln His Lys Pro Gly Gln
        35                  40                  45

Pro Pro Lys Val Leu Ile Tyr Trp Ala Ser Thr Arg Glu Tyr Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Pro Glu Asp Val Ala Val Tyr Tyr Cys Gln Gln
                85                  90                  95

Tyr Tyr Asn Ser Pro Tyr Thr Phe Gly Gln Gly Thr Lys Leu Glu Ile
            100                 105                 110

Lys

<210> SEQ ID NO 71
<211> LENGTH: 114
<212> TYPE: PRT
<213> ORGANISM: Homo sapiens

<400> SEQUENCE: 71

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Gly Met Asn Trp Val Arg Gln Ala Pro Gly Lys Gly Leu Glu Trp Val
        35                  40                  45

Ala His Ile Thr Gly Ser Gly Thr Pro Ile Phe Tyr Ala Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Asn Asp Thr Ala Leu Tyr Phe Cys
                85                  90                  95

Val Arg Gly Thr Val Asp Tyr Trp Gly Gln Gly Thr Leu Val Thr Val
            100                 105                 110

Ser Ser

<210> SEQ ID NO 72
<211> LENGTH: 110
<212> TYPE: PRT
<213> ORGANISM: Homo sapiens

<400> SEQUENCE: 72

Gln Ala Gly Leu Thr Gln Pro Pro Ser Val Ser Lys Asp Leu Arg Gln
1               5                   10                  15

Thr Ala Thr Leu Thr Cys Ser Gly Asn Ser Asn Asn Val Gly Asn Gln
```

```
            20                  25                  30

Gly Ala Ala Trp Leu Gln Gln Phe Pro Gly His Pro Pro Lys Leu Leu
            35                  40                  45

Phe Tyr Glu Asn Ile Asn Arg Pro Ser Gly Ile Ser Glu Arg Phe Ser
        50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Ser Ala Trp Asp Gly His Leu
                85                  90                  95

Asn Ala Trp Val Phe Gly Gly Gly Thr Lys Leu Thr Val Leu
            100                 105                 110

<210> SEQ ID NO 73
<211> LENGTH: 124
<212> TYPE: PRT
<213> ORGANISM: Homo sapiens

<400> SEQUENCE: 73

Glu Val Gln Leu Val Gln Ser Gly Ala Glu Val Lys Lys Pro Gly Glu
1               5                   10                  15

Ser Leu Lys Ile Ser Cys Lys Ala Ser Gly Tyr Ser Phe Ile Ser Tyr
            20                  25                  30

Trp Val Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Glu Gly Gln Val Ser Ile Ser Ala Asp Lys Ser Ile Ser Thr Ala Tyr
65                  70                  75                  80

Leu Gln Trp Thr Ser Leu Lys Ala Ser Asp Thr Ala Met Tyr Tyr Cys
                85                  90                  95

Ala Arg His Trp Gly Pro Ala Ala Val Thr Asp Ser Pro Trp Phe Gly
            100                 105                 110

Pro Trp Gly Gln Gly Thr Leu Val Thr Val Ser Ser
            115                 120

<210> SEQ ID NO 74
<211> LENGTH: 113
<212> TYPE: PRT
<213> ORGANISM: Homo sapiens

<400> SEQUENCE: 74

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Leu Tyr Thr
            20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln His
                85                  90                  95

Tyr Tyr Ser Thr Pro Phe Thr Phe Gly Pro Gly Thr Lys Val Asp Ile
            100                 105                 110

Lys
```

<210> SEQ ID NO 75
<211> LENGTH: 117
<212> TYPE: PRT
<213> ORGANISM: Homo sapiens

<400> SEQUENCE: 75

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Ile Phe Thr Ala Phe
                20                  25                  30

Phe Met His Trp Val Arg Gln Ala Pro Gly Gln Gly Leu Glu Trp Met
            35                  40                  45

Gly Trp Ile Asn Pro Asp Ser Gly Ala Thr Lys Tyr Ala His Asn Phe
        50                  55                  60

Gln Gly Arg Val Thr Met Thr Arg Asp Thr Ser Ile Ser Thr Ala Phe
65                  70                  75                  80

Met Glu Leu Ser Gly Leu Lys Ser Asp Asp Thr Gly Val Tyr Tyr Cys
                85                  90                  95

Ala Thr Gly Met Ala Val Thr Gly Asn Phe Trp Gly Gln Gly Thr Leu
                100                 105                 110

Val Thr Val Ser Ser
            115

<210> SEQ ID NO 76
<211> LENGTH: 117
<212> TYPE: PRT
<213> ORGANISM: Homo sapiens

<400> SEQUENCE: 76

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ala Phe
                20                  25                  30

Phe Met His Trp Val Arg Gln Ala Pro Gly Gln Gly Leu Glu Trp Met
            35                  40                  45

Gly Trp Ile Asn Pro Asp Ser Gly Ala Thr Lys Tyr Ala His Asn Phe
        50                  55                  60

Gln Gly Arg Val Thr Met Thr Arg Asp Thr Ser Ile Ser Thr Ala Phe
65                  70                  75                  80

Met Glu Leu Ser Gly Leu Lys Ser Asp Asp Thr Gly Val Tyr Tyr Cys
                85                  90                  95

Ala Thr Gly Met Ala Val Thr Gly Asn Phe Trp Gly Gln Gly Thr Leu
                100                 105                 110

Val Thr Val Ser Ser
            115

<210> SEQ ID NO 77
<211> LENGTH: 108
<212> TYPE: PRT
<213> ORGANISM: Homo sapiens

<400> SEQUENCE: 77

Leu Pro Val Leu Thr Gln Pro Pro Ser Val Ser Val Ser Pro Gly Gln
1               5                   10                  15

Thr Ala Arg Ile Thr Cys Ser Gly Asp Val Leu Ala Glu Thr Tyr Ala
                20                  25                  30

Arg Trp Phe Gln Gln Lys Pro Gly Gln Ala Pro Val Leu Val Met Tyr
            35                  40                  45

Arg Asp Arg Glu Arg Pro Ala Gly Ile Pro Glu Arg Phe Ser Gly Ser
50                      55                  60

Ser Ser Gly Asn Thr Val Thr Leu Thr Ile Ser Gly Ala Gln Ala Glu
65                  70                  75                  80

Asp Glu Ala Val Tyr His Cys His Ser Val Ala Asp Asn Asn Leu Asp
                    85                  90                  95

Trp Val Phe Gly Gly Gly Thr Lys Leu Thr Val Leu
            100                 105

<210> SEQ ID NO 78
<211> LENGTH: 108
<212> TYPE: PRT
<213> ORGANISM: Homo sapiens

<400> SEQUENCE: 78

Ser Tyr Glu Leu Thr Gln Pro Pro Ser Val Ser Val Ser Pro Gly Gln
1               5                   10                  15

Thr Ala Arg Ile Thr Cys Ser Gly Asp Val Leu Ala Glu Thr Tyr Ala
            20                  25                  30

Arg Trp Phe Gln Gln Lys Pro Gly Gln Ala Pro Val Leu Val Met Tyr
            35                  40                  45

Arg Asp Arg Glu Arg Pro Ala Gly Ile Pro Glu Arg Phe Ser Gly Ser
50                      55                  60

Ser Ser Gly Asn Thr Val Thr Leu Thr Ile Ser Gly Ala Gln Ala Glu
65                  70                  75                  80

Asp Glu Ala Val Tyr His Cys His Ser Val Ala Asp Asn Asn Leu Asp
                    85                  90                  95

Trp Val Phe Gly Gly Gly Thr Lys Leu Thr Val Leu
            100                 105

<210> SEQ ID NO 79
<211> LENGTH: 10
<212> TYPE: PRT
<213> ORGANISM: Homo sapiens

<400> SEQUENCE: 79

Gly Tyr Ser Phe Thr Asn Phe Trp Ile Gly
1               5                   10

<210> SEQ ID NO 80
<211> LENGTH: 9
<212> TYPE: PRT
<213> ORGANISM: Homo sapiens

<400> SEQUENCE: 80

Ile Ile Tyr Pro Gly Asp Ser Asp Thr
1               5

<210> SEQ ID NO 81
<211> LENGTH: 11
<212> TYPE: PRT
<213> ORGANISM: Homo sapiens

<400> SEQUENCE: 81

Arg Gly Phe Trp Thr Gly Ser Gln Ile Glu Tyr
1               5                   10

<210> SEQ ID NO 82

```
<211> LENGTH: 14
<212> TYPE: PRT
<213> ORGANISM: Homo sapiens

<400> SEQUENCE: 82

Thr Gly Thr Ser Ser Asp Val Gly Asn Tyr Ser Phe Val Ser
1               5                   10

<210> SEQ ID NO 83
<211> LENGTH: 7
<212> TYPE: PRT
<213> ORGANISM: Homo sapiens

<400> SEQUENCE: 83

Asp Val Ser Lys Arg Ser Ser
1               5

<210> SEQ ID NO 84
<211> LENGTH: 11
<212> TYPE: PRT
<213> ORGANISM: Homo sapiens

<400> SEQUENCE: 84

Ser Ser Tyr Gly Gly Ser Lys Tyr Pro Trp Val
1               5                   10

<210> SEQ ID NO 85
<211> LENGTH: 10
<212> TYPE: PRT
<213> ORGANISM: Homo sapiens

<400> SEQUENCE: 85

Gly Phe Thr Phe Ser Ser Tyr Asp Met His
1               5                   10

<210> SEQ ID NO 86
<211> LENGTH: 17
<212> TYPE: PRT
<213> ORGANISM: Homo sapiens

<400> SEQUENCE: 86

Val Ile Trp Phe Asp Gly Ser Asn Glu Phe Tyr Ala Asp Ser Val Lys
1               5                   10                  15

Gly

<210> SEQ ID NO 87
<211> LENGTH: 16
<212> TYPE: PRT
<213> ORGANISM: Homo sapiens

<400> SEQUENCE: 87

Asp Leu Gly Ala Ser Val Thr Thr Ser Asn Ala Glu Asn Phe His His
1               5                   10                  15

<210> SEQ ID NO 88
<211> LENGTH: 11
<212> TYPE: PRT
<213> ORGANISM: Homo sapiens

<400> SEQUENCE: 88

Ser Gly Asp Ala Leu Pro Lys Arg Tyr Val Tyr
1               5                   10

<210> SEQ ID NO 89
```

-continued

<210> SEQ ID NO 89
<211> LENGTH: 7
<212> TYPE: PRT
<213> ORGANISM: Homo sapiens

<400> SEQUENCE: 89

Glu Asp Ser Lys Arg Pro Ser
1               5

<210> SEQ ID NO 90
<211> LENGTH: 11
<212> TYPE: PRT
<213> ORGANISM: Homo sapiens

<400> SEQUENCE: 90

Tyr Ser Thr Asp Ser Asn Gly His His Trp Val
1               5                   10

<210> SEQ ID NO 91
<211> LENGTH: 10
<212> TYPE: PRT
<213> ORGANISM: Homo sapiens

<400> SEQUENCE: 91

Gly Phe Asp Phe Ser Gly Tyr Ser Met Ala
1               5                   10

<210> SEQ ID NO 92
<211> LENGTH: 22
<212> TYPE: PRT
<213> ORGANISM: Homo sapiens

<400> SEQUENCE: 92

Tyr Ile Ser Gly Thr Tyr Val Ser Gly Gly Thr Gly Thr Met Tyr Tyr
1               5                   10                  15

Leu Asp Ser Val Lys Gly
            20

<210> SEQ ID NO 93
<211> LENGTH: 7
<212> TYPE: PRT
<213> ORGANISM: Homo sapiens

<400> SEQUENCE: 93

Val Tyr Asp Tyr Gly Glu Asp
1               5

<210> SEQ ID NO 94
<211> LENGTH: 17
<212> TYPE: PRT
<213> ORGANISM: Homo sapiens

<400> SEQUENCE: 94

Lys Ser Ser Arg Ser Val Leu Tyr Ser Ser Asn Ser Lys Asn Tyr Leu
1               5                   10                  15

Ala

<210> SEQ ID NO 95
<211> LENGTH: 7
<212> TYPE: PRT
<213> ORGANISM: Homo sapiens

<400> SEQUENCE: 95

Trp Ala Ser Thr Arg Glu Ser
1               5

<210> SEQ ID NO 96
<211> LENGTH: 9
<212> TYPE: PRT
<213> ORGANISM: Homo sapiens

<400> SEQUENCE: 96

Gln Gln Tyr Tyr Gly Thr Pro Arg Thr
1               5

<210> SEQ ID NO 97
<211> LENGTH: 10
<212> TYPE: PRT
<213> ORGANISM: Homo sapiens

<400> SEQUENCE: 97

Arg Phe Thr Phe Ser Thr Tyr Ala Met Gly
1               5                   10

<210> SEQ ID NO 98
<211> LENGTH: 17
<212> TYPE: PRT
<213> ORGANISM: Homo sapiens

<400> SEQUENCE: 98

Ala Ile Gly Gly Ser Gly Asp Ser Thr Ser Tyr Ala Asp Ser Val Lys
1               5                   10                  15

Gly

<210> SEQ ID NO 99
<211> LENGTH: 15
<212> TYPE: PRT
<213> ORGANISM: Homo sapiens

<400> SEQUENCE: 99

Gly Val Tyr Asp Tyr Leu Trp Gly Ser Tyr Arg Leu Phe Asp Tyr
1               5                   10                  15

<210> SEQ ID NO 100
<211> LENGTH: 11
<212> TYPE: PRT
<213> ORGANISM: Homo sapiens

<400> SEQUENCE: 100

Gly Gly Asn Asn Ile Ala Ser Lys Ser Val His
1               5                   10

<210> SEQ ID NO 101
<211> LENGTH: 7
<212> TYPE: PRT
<213> ORGANISM: Homo sapiens

<400> SEQUENCE: 101

Asp Asp Ser Asp Arg Pro Ser
1               5

<210> SEQ ID NO 102
<211> LENGTH: 11
<212> TYPE: PRT
<213> ORGANISM: Homo sapiens

<400> SEQUENCE: 102

Gln Val Trp Asp Ser Thr Ser Asp His Val Val
1               5                   10

```
<210> SEQ ID NO 103
<211> LENGTH: 10
<212> TYPE: PRT
<213> ORGANISM: Homo sapiens

<400> SEQUENCE: 103

Gly Phe Thr Phe Pro Asn Tyr Val Met Thr
1               5                   10

<210> SEQ ID NO 104
<211> LENGTH: 18
<212> TYPE: PRT
<213> ORGANISM: Homo sapiens

<400> SEQUENCE: 104

Ser Gly Ile Ser Gly Ser Gly Gly Ser Thr Asp Tyr Ala Asp Ser Val
1               5                   10                  15

Lys Gly

<210> SEQ ID NO 105
<211> LENGTH: 5
<212> TYPE: PRT
<213> ORGANISM: Homo sapiens

<400> SEQUENCE: 105

Gly Ser Gly Gly Ile
1               5

<210> SEQ ID NO 106
<211> LENGTH: 14
<212> TYPE: PRT
<213> ORGANISM: Homo sapiens

<400> SEQUENCE: 106

Thr Gly Thr Ser Ser Asp Val Gly Gly Tyr Asn Tyr Val Ser
1               5                   10

<210> SEQ ID NO 107
<211> LENGTH: 7
<212> TYPE: PRT
<213> ORGANISM: Homo sapiens

<400> SEQUENCE: 107

Asp Val Thr Lys Arg Pro Ser
1               5

<210> SEQ ID NO 108
<211> LENGTH: 10
<212> TYPE: PRT
<213> ORGANISM: Homo sapiens

<400> SEQUENCE: 108

His Ser Tyr Val Gly Ser Tyr Thr Leu Val
1               5                   10

<210> SEQ ID NO 109
<211> LENGTH: 10
<212> TYPE: PRT
<213> ORGANISM: Homo sapiens

<400> SEQUENCE: 109

Gly Phe Thr Phe Ser Gly Ser Ala Met His
1               5                   10
```

<210> SEQ ID NO 110
<211> LENGTH: 19
<212> TYPE: PRT
<213> ORGANISM: Homo sapiens

<400> SEQUENCE: 110

Arg Ile Arg Ser Lys Ala Asn Ser Tyr Ala Thr Ala Tyr Ala Ala Ser
1               5                   10                  15

Val Lys Gly

<210> SEQ ID NO 111
<211> LENGTH: 9
<212> TYPE: PRT
<213> ORGANISM: Homo sapiens

<400> SEQUENCE: 111

Thr Ser Pro Thr Val Thr Thr Glu Val
1               5

<210> SEQ ID NO 112
<211> LENGTH: 17
<212> TYPE: PRT
<213> ORGANISM: Homo sapiens

<400> SEQUENCE: 112

Lys Ser Ser Gln Ser Val Leu Tyr Ser Ser Asn Asn Lys Asp Tyr Leu
1               5                   10                  15

Ala

<210> SEQ ID NO 113
<211> LENGTH: 7
<212> TYPE: PRT
<213> ORGANISM: Homo sapiens

<400> SEQUENCE: 113

Trp Ala Ser Thr Arg Glu Ser
1               5

<210> SEQ ID NO 114
<211> LENGTH: 9
<212> TYPE: PRT
<213> ORGANISM: Homo sapiens

<400> SEQUENCE: 114

Gln Gln Tyr Tyr Ser Thr Pro Ile Thr
1               5

<210> SEQ ID NO 115
<211> LENGTH: 11
<212> TYPE: PRT
<213> ORGANISM: Homo sapiens

<400> SEQUENCE: 115

Ser Gly Met Thr Phe Ser Ser Tyr Ala Phe Asn
1               5                   10

<210> SEQ ID NO 116
<211> LENGTH: 17
<212> TYPE: PRT
<213> ORGANISM: Homo sapiens

<400> SEQUENCE: 116

Ser Ile Ser Arg Phe Gly Ser Thr Val Asp Tyr Thr Asp Ser Val Arg
1               5                   10                  15

Gly

<210> SEQ ID NO 117
<211> LENGTH: 14
<212> TYPE: PRT
<213> ORGANISM: Homo sapiens

<400> SEQUENCE: 117

Val Arg Ser Thr Ala Ser Gly Ser Arg Ser Pro Gly Ile Ile
1               5                   10

<210> SEQ ID NO 118
<211> LENGTH: 11
<212> TYPE: PRT
<213> ORGANISM: Homo sapiens

<400> SEQUENCE: 118

Arg Ala Ser Gln Gly Ile Val Asn Asn Leu Ala
1               5                   10

<210> SEQ ID NO 119
<211> LENGTH: 7
<212> TYPE: PRT
<213> ORGANISM: Homo sapiens

<400> SEQUENCE: 119

Ala Ala Ser Ser Leu Gln Gly
1               5

<210> SEQ ID NO 120
<211> LENGTH: 9
<212> TYPE: PRT
<213> ORGANISM: Homo sapiens

<400> SEQUENCE: 120

Gln Gln Tyr Asn Ser Tyr Pro Trp Thr
1               5

<210> SEQ ID NO 121
<211> LENGTH: 10
<212> TYPE: PRT
<213> ORGANISM: Homo sapiens

<400> SEQUENCE: 121

Gly Tyr Arg Phe Thr Thr Tyr Trp Ile Gly
1               5                   10

<210> SEQ ID NO 122
<211> LENGTH: 9
<212> TYPE: PRT
<213> ORGANISM: Homo sapiens

<400> SEQUENCE: 122

Ile Ile Tyr Pro Gly Asp Ser Asp Thr
1               5

<210> SEQ ID NO 123
<211> LENGTH: 17
<212> TYPE: PRT
<213> ORGANISM: Homo sapiens

<400> SEQUENCE: 123

Val Ala Gly Asp Ile Gly Tyr Glu Asn Tyr Tyr Tyr Gly Met Asp
1               5                   10                  15
Val

<210> SEQ ID NO 124
<211> LENGTH: 17
<212> TYPE: PRT
<213> ORGANISM: Homo sapiens

<400> SEQUENCE: 124

Lys Ser Ser Gln Ser Val Leu Tyr Gly Ser Asn Asn Lys Asn Tyr Leu
1               5                   10                  15
Ala

<210> SEQ ID NO 125
<211> LENGTH: 7
<212> TYPE: PRT
<213> ORGANISM: Homo sapiens

<400> SEQUENCE: 125

Trp Ala Ser Ala Arg Glu Ser
1               5

<210> SEQ ID NO 126
<211> LENGTH: 9
<212> TYPE: PRT
<213> ORGANISM: Homo sapiens

<400> SEQUENCE: 126

Gln Gln Tyr Tyr Ser Thr Pro Trp Thr
1               5

<210> SEQ ID NO 127
<211> LENGTH: 10
<212> TYPE: PRT
<213> ORGANISM: Homo sapiens

<400> SEQUENCE: 127

Gly Phe Thr Phe Thr Arg Tyr Gly Met His
1               5                   10

<210> SEQ ID NO 128
<211> LENGTH: 17
<212> TYPE: PRT
<213> ORGANISM: Homo sapiens

<400> SEQUENCE: 128

Val Ile Trp Tyr Asp Gly Thr Asn Lys Tyr Tyr Ala Asp Ser Leu Gln
1               5                   10                  15
Gly

<210> SEQ ID NO 129
<211> LENGTH: 9
<212> TYPE: PRT
<213> ORGANISM: Homo sapiens

<400> SEQUENCE: 129

Glu Gly Phe Gln Gly Ala Ile Asp Tyr
1               5

<210> SEQ ID NO 130
<211> LENGTH: 17
<212> TYPE: PRT

<213> ORGANISM: Homo sapiens

<400> SEQUENCE: 130

Lys Ser Ser Gln Asn Ile Leu Tyr Ser Ser Asp Asn Lys Asn Tyr Leu
1               5                   10                  15
Ala

<210> SEQ ID NO 131
<211> LENGTH: 7
<212> TYPE: PRT
<213> ORGANISM: Homo sapiens

<400> SEQUENCE: 131

Trp Ala Ser Thr Arg Glu Ser
1               5

<210> SEQ ID NO 132
<211> LENGTH: 9
<212> TYPE: PRT
<213> ORGANISM: Homo sapiens

<400> SEQUENCE: 132

Gln Gln Tyr Tyr Ser Ile Pro Arg Thr
1               5

<210> SEQ ID NO 133
<211> LENGTH: 11
<212> TYPE: PRT
<213> ORGANISM: Homo sapiens

<400> SEQUENCE: 133

Ser Gly Phe Ser Phe Ser Asp Ser Ala Phe His
1               5                   10

<210> SEQ ID NO 134
<211> LENGTH: 19
<212> TYPE: PRT
<213> ORGANISM: Homo sapiens

<400> SEQUENCE: 134

Arg Ile Arg Ser Lys Gly Asn Asn Tyr Ala Thr Ala Tyr Ala Ala Ser
1               5                   10                  15
Val Lys Gly

<210> SEQ ID NO 135
<211> LENGTH: 11
<212> TYPE: PRT
<213> ORGANISM: Homo sapiens

<400> SEQUENCE: 135

Thr Arg Gln Gly Pro Ser Tyr Gly Gly Ile Asn
1               5                   10

<210> SEQ ID NO 136
<211> LENGTH: 17
<212> TYPE: PRT
<213> ORGANISM: Homo sapiens

<400> SEQUENCE: 136

Lys Ser Ser Gln Thr Ile Leu Tyr Ser Ser Asn Asn Lys Asn Tyr Leu
1               5                   10                  15
Ala

<210> SEQ ID NO 137
<211> LENGTH: 7
<212> TYPE: PRT
<213> ORGANISM: Homo sapiens

<400> SEQUENCE: 137

Trp Ala Ser Thr Arg Glu Ser
1               5

<210> SEQ ID NO 138
<211> LENGTH: 9
<212> TYPE: PRT
<213> ORGANISM: Homo sapiens

<400> SEQUENCE: 138

Gln Gln Tyr Tyr Ser Ser Pro Gln Thr
1               5

<210> SEQ ID NO 139
<211> LENGTH: 11
<212> TYPE: PRT
<213> ORGANISM: Homo sapiens

<400> SEQUENCE: 139

Ser Gly Phe Thr Phe Thr Lys Ala Trp Met Thr
1               5                   10

<210> SEQ ID NO 140
<211> LENGTH: 19
<212> TYPE: PRT
<213> ORGANISM: Homo sapiens

<400> SEQUENCE: 140

His Ile Lys Thr Arg Ile Glu Gly Ala Thr Thr Asp Tyr Ala Ala Pro
1               5                   10                  15

Val Glu Gly

<210> SEQ ID NO 141
<211> LENGTH: 6
<212> TYPE: PRT
<213> ORGANISM: Homo sapiens

<400> SEQUENCE: 141

Ser Thr Asp Phe Asp Tyr
1               5

<210> SEQ ID NO 142
<211> LENGTH: 16
<212> TYPE: PRT
<213> ORGANISM: Homo sapiens

<400> SEQUENCE: 142

Thr Ser Ser Gln Ser Leu Leu Tyr Ser Asp Gly Asn Thr Tyr Leu Asn
1               5                   10                  15

<210> SEQ ID NO 143
<211> LENGTH: 7
<212> TYPE: PRT
<213> ORGANISM: Homo sapiens

<400> SEQUENCE: 143

Lys Val Ser Lys Arg Asp Pro
1               5

<210> SEQ ID NO 144
<211> LENGTH: 10
<212> TYPE: PRT
<213> ORGANISM: Homo sapiens

<400> SEQUENCE: 144

Met Gln Gly Ser Leu Trp Pro Arg Tyr Thr
1               5                   10

<210> SEQ ID NO 145
<211> LENGTH: 10
<212> TYPE: PRT
<213> ORGANISM: Homo sapiens

<400> SEQUENCE: 145

Gly Tyr Asn Phe Pro Asn Tyr Trp Ile Gly
1               5                   10

<210> SEQ ID NO 146
<211> LENGTH: 24
<212> TYPE: PRT
<213> ORGANISM: Homo sapiens

<400> SEQUENCE: 146

Ile Ile Tyr Pro Gly Asp Ser Asp Ile Arg Tyr Ser Pro Ser Phe Gln
1               5                   10                  15

Gly His Val Thr Ile Ser Ser Asp
            20

<210> SEQ ID NO 147
<211> LENGTH: 14
<212> TYPE: PRT
<213> ORGANISM: Homo sapiens

<400> SEQUENCE: 147

Ala Arg Val Glu Arg Pro Asp Lys Gly Gly Trp Phe Gly Pro
1               5                   10

<210> SEQ ID NO 148
<211> LENGTH: 17
<212> TYPE: PRT
<213> ORGANISM: Homo sapiens

<400> SEQUENCE: 148

Lys Ser Ser Gln Thr Leu Leu Tyr Thr Ser Asn Asn Gln Asn Tyr Leu
1               5                   10                  15

Ala

<210> SEQ ID NO 149
<211> LENGTH: 7
<212> TYPE: PRT
<213> ORGANISM: Homo sapiens

<400> SEQUENCE: 149

Trp Ala Ser Thr Arg Glu Tyr
1               5

<210> SEQ ID NO 150
<211> LENGTH: 9
<212> TYPE: PRT
<213> ORGANISM: Homo sapiens

<400> SEQUENCE: 150

Gln Gln Tyr Tyr Asn Ser Pro Tyr Thr
1               5

<210> SEQ ID NO 151
<211> LENGTH: 10
<212> TYPE: PRT
<213> ORGANISM: Homo sapiens

<400> SEQUENCE: 151

Gly Phe Thr Phe Ser Ala Tyr Gly Met Asn
1               5                   10

<210> SEQ ID NO 152
<211> LENGTH: 17
<212> TYPE: PRT
<213> ORGANISM: Homo sapiens

<400> SEQUENCE: 152

His Ile Thr Gly Ser Gly Thr Pro Ile Phe Tyr Ala Asp Ser Val Lys
1               5                   10                  15

Gly

<210> SEQ ID NO 153
<211> LENGTH: 7
<212> TYPE: PRT
<213> ORGANISM: Homo sapiens

<400> SEQUENCE: 153

Val Arg Gly Thr Val Asp Tyr
1               5

<210> SEQ ID NO 154
<211> LENGTH: 13
<212> TYPE: PRT
<213> ORGANISM: Homo sapiens

<400> SEQUENCE: 154

Ser Gly Asn Ser Asn Asn Val Gly Asn Gln Gly Ala Ala
1               5                   10

<210> SEQ ID NO 155
<211> LENGTH: 7
<212> TYPE: PRT
<213> ORGANISM: Homo sapiens

<400> SEQUENCE: 155

Glu Asn Ile Asn Arg Pro Ser
1               5

<210> SEQ ID NO 156
<211> LENGTH: 11
<212> TYPE: PRT
<213> ORGANISM: Homo sapiens

<400> SEQUENCE: 156

Ser Ala Trp Asp Gly His Leu Asn Ala Trp Val
1               5                   10

<210> SEQ ID NO 157
<211> LENGTH: 10
<212> TYPE: PRT
<213> ORGANISM: Homo sapiens

<400> SEQUENCE: 157

```
Gly Tyr Ser Phe Ile Ser Tyr Trp Val Gly
1               5                   10

<210> SEQ ID NO 158
<211> LENGTH: 24
<212> TYPE: PRT
<213> ORGANISM: Homo sapiens

<400> SEQUENCE: 158

Ile Ile Tyr Pro Gly Asp Ser Asp Thr Arg Tyr Ser Pro Ser Phe Glu
1               5                   10                  15

Gly Gln Val Ser Ile Ser Ala Asp
            20

<210> SEQ ID NO 159
<211> LENGTH: 15
<212> TYPE: PRT
<213> ORGANISM: Homo sapiens

<400> SEQUENCE: 159

His Trp Gly Pro Ala Ala Val Thr Asp Ser Pro Trp Phe Gly Pro
1               5                   10                  15

<210> SEQ ID NO 160
<211> LENGTH: 17
<212> TYPE: PRT
<213> ORGANISM: Homo sapiens

<400> SEQUENCE: 160

Lys Ser Ser Gln Thr Val Leu Tyr Thr Ser Asn Asn Lys Asn Tyr Leu
1               5                   10                  15

Ala

<210> SEQ ID NO 161
<211> LENGTH: 7
<212> TYPE: PRT
<213> ORGANISM: Homo sapiens

<400> SEQUENCE: 161

Trp Ala Ser Thr Arg Glu Ser
1               5

<210> SEQ ID NO 162
<211> LENGTH: 9
<212> TYPE: PRT
<213> ORGANISM: Homo sapiens

<400> SEQUENCE: 162

Gln His Tyr Tyr Ser Thr Pro Phe Thr
1               5

<210> SEQ ID NO 163
<211> LENGTH: 10
<212> TYPE: PRT
<213> ORGANISM: Homo sapiens

<400> SEQUENCE: 163

Gly Tyr Ile Phe Thr Ala Phe Phe Met His
1               5                   10

<210> SEQ ID NO 164
<211> LENGTH: 17
<212> TYPE: PRT
<213> ORGANISM: Homo sapiens
```

<400> SEQUENCE: 164

Trp Ile Asn Pro Asp Ser Gly Ala Thr Lys Tyr Ala His Asn Phe Gln
1               5                   10                  15
Gly

<210> SEQ ID NO 165
<211> LENGTH: 8
<212> TYPE: PRT
<213> ORGANISM: Homo sapiens

<400> SEQUENCE: 165

Gly Met Ala Val Thr Gly Asn Phe
1               5

<210> SEQ ID NO 166
<211> LENGTH: 11
<212> TYPE: PRT
<213> ORGANISM: Homo sapiens

<400> SEQUENCE: 166

Ser Gly Asp Val Leu Ala Glu Thr Tyr Ala Arg
1               5                   10

<210> SEQ ID NO 167
<211> LENGTH: 7
<212> TYPE: PRT
<213> ORGANISM: Homo sapiens

<400> SEQUENCE: 167

Arg Asp Arg Glu Arg Pro Ala
1               5

<210> SEQ ID NO 168
<211> LENGTH: 11
<212> TYPE: PRT
<213> ORGANISM: Homo sapiens

<400> SEQUENCE: 168

His Ser Val Ala Asp Asn Asn Leu Asp Trp Val
1               5                   10

<210> SEQ ID NO 169
<211> LENGTH: 360
<212> TYPE: DNA
<213> ORGANISM: Homo sapiens

<400> SEQUENCE: 169
gaggtgcagc tggtgcagtc tggagcagag gtgaagaagc ccggggagtc tctgaagatc      60
tcctgcaagg catttggata cagttttacc aacttctgga tcggctgggt gcgccaggtg     120
cccgggaaag gcctggagtg ggtgggaatc atctatcctg gtgactctga caccagatac     180
agtccgtcct ccaaggcca ggtcaccatt tcagccgaca gtccattga caccgcctac      240 ctacagtggg gccacctgaa ggcctcggac agcgccatgt atttctgtgc cagacggggt     300
ttttggactg gaagtcaaat tgaatactgg ggccagggca ccctggtcac cgtctcctcg     360

<210> SEQ ID NO 170
<211> LENGTH: 360
<212> TYPE: DNA
<213> ORGANISM: Homo sapiens

<400> SEQUENCE: 170

```
gaggtgcagc tggtgcagtc tggagcagag gtgaagaagc ccggggagtc tctgaagatc      60
tcctgcaagg catttggata cagttttacc aacttctgga tcggctgggt gcgccaggtg     120
cccgggaaag gcctggagtg ggtgggaatc atctatcctg gtgactctga caccagatac     180
agtccgtcct tccaaggcca ggtcaccatt tcagccgaca gtccattgac accgcctac      240 ctacagtggg gccacctgaa ggcctcggac agcgccatgt atttctgtgc cagacggggt     300
ttttggactg gaagtcaaat tgaatactgg ggccagggca cccaggtcac cgtctcctcg     360
```

<210> SEQ ID NO 171
<211> LENGTH: 333
<212> TYPE: DNA
<213> ORGANISM: Homo sapiens

<400> SEQUENCE: 171

```
cagtctgccc tgactcagcc tccctccgcg tccgggtctc ctggacactc agtcaccatc      60
tcctgcactg gaactagtag tgacgttggt aattatagtt ttgtctcctg gtatcaacag     120
tatcccggca agccccccaa agtcatcatt tatgacgtca gtaagcggtc ctcagggatc     180
cctgatcgct tctttggctc caagtctgcc aacacggcct ccctgaccgt ctctgggttc     240
caggaagagg atgaggctga ctattttgc agctcatacg gaggcagcaa atatccgtgg     300
gtgtttggcg gagggaccaa gctgaccgtc ctt                                  333
```

<210> SEQ ID NO 172
<211> LENGTH: 375
<212> TYPE: DNA
<213> ORGANISM: Homo sapiens

<400> SEQUENCE: 172

```
gaggtgcagc tggtggagtc tgggggaggc gtggtccagc ctgggaggtc cctgagagtc      60
tcctgtgcag cgtctggatt caccttcagt agttatgaca tgcactgggt ccgccaggct     120
ccaggcaagg ggctggagtg ggtggcggtt atatggtttg atggaagtaa tgaattctat     180
gcagactccg tgaagggccg attcaccatc tccagagaca attccaagaa cacgctgttt     240
ctgcaaatga acagcctgag agccgaggac acggctgtgt attactgtgc gagagaccta     300
ggggcctcag tgactacttc caacgctgaa aacttccacc actggggcca gggcaccctg     360
gtcaccgtct cctcg                                                      375
```

<210> SEQ ID NO 173
<211> LENGTH: 375
<212> TYPE: DNA
<213> ORGANISM: Homo sapiens

<400> SEQUENCE: 173

```
caggtgcagc tggtggagtc tgggggaggc gtggtccagc ctgggaggtc cctgagagtc      60
tcctgtgcag cgtctggatt caccttcagt agttatgaca tgcactgggt ccgccaggct     120
ccaggcaagg ggctggagtg ggtggcggtt atatggtttg atggaagtaa tgaattctat     180
gcagactccg tgaagggccg attcaccatc tccagagaca attccaagaa cacgctgttt     240
ctgcaaatga acagcctgag agccgaggac acggctgtgt attactgtgc gagagaccta     300
ggggcctcag tgactacttc caacgctgaa aacttccacc actggggcca gggcaccctg     360
gtcaccgtct cctcg                                                      375
```

<210> SEQ ID NO 174

```
<211> LENGTH: 324
<212> TYPE: DNA
<213> ORGANISM: Homo sapiens

<400> SEQUENCE: 174
tcctatgagc tgactcagcc accctcggtg tcagtgtccc caggacaaac ggccaggatc    60
acctgctctg gagatgcatt gccaaaaaga tatgtttatt ggtaccagca gaagtcaggc   120
caggcccctg tgctggtcat ctatgaggac agcaaacgac cctccgggat ccctgagaca   180
ttctctggct ccagctcagg gacaatggcc accttgacta tcagtggggc ccaggtagag   240
gatgaagctg actactactg ttactcaaca gacagcaatg gtcatcattg ggtgttcggc   300
ggagggacca agctgaccgt ccta                                          324

<210> SEQ ID NO 175
<211> LENGTH: 363
<212> TYPE: DNA
<213> ORGANISM: Homo sapiens

<400> SEQUENCE: 175
gaggtgcagc tggtggagtc tgggggagac ttggtacagc ctggggggtc cctgagactc    60
tcctgtgcag cctctggatt cgacttcagc ggctatagca tggcctgggt ccgccaggct   120
ccagggaagg ggctggagtg ggtttcgtat attagcggca cttatgttag tggtggtaca   180
ggcacgatgt attatttaga ctctgtgaag ggccgattct tcatctccag agacgatgcc   240
accagttcac tgtatctgca aatggacagc ctgagggacg aggacacggc tgtgtattac   300
tgtgcgagag tttatgacta cggtgaagac tggggccagg gaaccctggt caccgtctcc   360
tcg                                                                 363

<210> SEQ ID NO 176
<211> LENGTH: 339
<212> TYPE: DNA
<213> ORGANISM: Homo sapiens

<400> SEQUENCE: 176
gatattgtga tgactcaatc accagactcc ctggctgtgt ctctgggcga gagggccacc    60
atcaactgca gtccagccg gagtgtctta tacagctcca acagtaagaa ctacttagct   120
tggtatcagc agaaacccgg acagcctcct aagttgctca tttactgggc atctacgcgg   180
gaatccgggg tccctgaccg attcagtggc agcgggtctg ggacagaatt cactctcacc   240
atcagcagcc tgcaggctga agatgtggcg gtttattact gtcagcaata ttatggtact   300
cctcgcacgt tcggccaagg gaccaaggtg gaaatcaaa                          339

<210> SEQ ID NO 177
<211> LENGTH: 372
<212> TYPE: DNA
<213> ORGANISM: Homo sapiens

<400> SEQUENCE: 177
gaggtgcagc tggtggagtc tgggggaggc ttggtacagc ctggggggtc cctgagactc    60
tcctgtgcag gcactagatt caccttagc acctatgcca tggctgggt ccgccaggct   120 ccagggaggg ggctggagtg ggtctcggct attggtggta gtggtgatag cacatcctac   180
gcagactccg tgaagggccg gttcaccatc tccagagaca attccaagaa cacgctgtat   240
ctgcaaatga acagcctgag agccgaggac acggccgtat attattgtgc gaaaggggtt   300
tatgattacc tttgggggag ttatcggctc tttgactact ggggccaggg aaccctggtc   360
```

```
accgtctcct cg                                                          372

<210> SEQ ID NO 178
<211> LENGTH: 324
<212> TYPE: DNA
<213> ORGANISM: Homo sapiens

<400> SEQUENCE: 178
tcctatgtgc tgactcagcc accctcggtg tcagtggccc caggacagac ggccagattt     60
acctgtgggg gaaacaacat tgcaagtaaa agtgtgcact ggtaccagca gaagccaggc    120
caggcccctg tgctggtcgt ctatgatgat agcgaccggc cctcacggat ccctgagcga    180
ttctctggct ccaactctgg gaacacggcc accctgacca tcagcagggt cgaagccggg    240
gatgaggccg actattactg tcaggtgtgg gatagtacta gtgatcatgt ggtattcggc    300
ggagggacca agctgaccgt ccta                                           324

<210> SEQ ID NO 179
<211> LENGTH: 342
<212> TYPE: DNA
<213> ORGANISM: Homo sapiens

<400> SEQUENCE: 179
gaggtgcagc tggtggagtc tgggggaggc ttggtacagc ctgggggggtc cctgagactc     60 tcctgtgcag cctctggatt cacctttccc aactatgtca tgacgtgggt ccgccaggct    120
ccagggaagg gctggagtg gtctcaggt attagtggta gtggtggtag cacagactac    180
gcagactccg tgaagggccg gttcaccatc tccagagaca attccaagaa cacgttgtat    240
ctgcaaatga acagcctgag agtcgaggac acggccttgt attactgtgc gaagggctca    300
ggtggtatcc ggggccaagg gacaatggtc accgtctctt cg                       342

<210> SEQ ID NO 180
<211> LENGTH: 330
<212> TYPE: DNA
<213> ORGANISM: Homo sapiens

<400> SEQUENCE: 180
cagtctgccc tgactcagcc tcgctcagtg tccgggtctc ctggacagtc agtcaccatc     60
tcctgcactg gaaccagcag tgatgttggt ggttataact atgtctcctg gcaccagcag    120
cacccaggca aagcccccaa actcctgatt tatgatgtca ctaagcggcc ctcaggggtc    180
cctgatcgct tctctggctc caagtctggc aacacggccg ccctgaccat ctctggctc    240 caggctgagg atgaggctga ttattactgc cactcatatg taggcagcta cactttggta    300
ttcggcggag ggaccaagct gaccgtcctc                                     330

<210> SEQ ID NO 181
<211> LENGTH: 354
<212> TYPE: DNA
<213> ORGANISM: Homo sapiens

<400> SEQUENCE: 181
gaggtgcagc tggtggagtc tgggggaggc ttggtccagc ctgggggggtc cctgaaactc     60 tcctgtgcag cctctgggtt cacattcagt ggctctgcta tgcactgggt ccgccaggct    120
tccgggaaag gctggagtg ggttggccgt attagaagca aagctaatag ttatgcgaca    180
gcatatgctg cgtcggtgaa aggcaggttc accatctcca gagatgattc aaagaacacg    240
```

```
gcgtatctac aaatgaacag cctgaaaacc gaggacacgg ccgtgtatta ctgtactagc    300
cctacggtga ctaccgaggt ctggggccag ggaaccctgg tcaccgtctc ctcg          354
```

<210> SEQ ID NO 182
<211> LENGTH: 339
<212> TYPE: DNA
<213> ORGANISM: Homo sapiens

<400> SEQUENCE: 182

```
gatattgtga tgactcaatc accagactcc ctggctgtgt ctctgggcga gagggccacc    60
atcaactgca agtccagcca gagtgtttta tacagctcca acaataagga ctacttagct   120
tggtaccagc agaaaccagg acagcctcct aagctgctca tttactgggc atctacccgg   180
gaatccgggg tctctgaccg attcagtggc agcgggtctg ggacagattt cactctcacc   240
atcagcagcc tgcaggctga agatgtggca gtgtattact gtcagcaata ttatagtacc   300
ccgatcacct tcggccaagg gacacgactg gagattaaa                          339
```

<210> SEQ ID NO 183
<211> LENGTH: 366
<212> TYPE: DNA
<213> ORGANISM: Homo sapiens

<400> SEQUENCE: 183

```
gaggtgcagc tggtggagtc tgggggaggc ttggtacagc cggggggtc cctgagactg     60 tcctgtatag gctcctctgg aatgaccttc agtagttatg ccttcaactg gtccgccag    120 actccaggga aggggctgga gtgggtttca tccatcagtc gtttcggttc gaccgtggac   180
tacacagact cggtgcgggg ccgatttacc atctccagag acgatggcca gaggtcactg   240
tatctgcaaa tgaacagcct gagagtcgaa gacacggctg tttattattg tgtcagatcg   300
acggcttctg gttcgcggtc ccccggaatt atctggggcc aggggaccac ggtcaccgtc   360
tcctcg                                                              366
```

<210> SEQ ID NO 184
<211> LENGTH: 321
<212> TYPE: DNA
<213> ORGANISM: Homo sapiens

<400> SEQUENCE: 184

```
gacatccaga tgacccagtc tccatcctca ctgtctgctt ctgtaggaga cagagtcacc    60
atcacttgtc gggcgagtca gggcattgtc aataatttag cctggtttca gcagaagcca   120
gggaaagccc ctaagtccct gatctatgct gcatccagtt tgcaaggtgg ggtcccatca   180
aaattcagcg gcagtgcgtc tgggacagat ttcagtctca ccatcagcaa cctgcagcct   240
gaagactttg caacttattt ctgccaacag tataatagtt acccttggac gttcggccaa   300
gggaccaagg tggagatcaa a                                             321
```

<210> SEQ ID NO 185
<211> LENGTH: 378
<212> TYPE: DNA
<213> ORGANISM: Homo sapiens

<400> SEQUENCE: 185

```
gaggtgcagc tggtgcagtc tggagcagag gtgaaaaagc ccggggagtc tctgaagatc    60
tcctgtaagg gttctggata caggtttacc acctactgga tcggctgggt gcgccagatg   120
cccgggaaag gcctggagtg gatggggatc atctatcctg gtgactctga taccagatac   180
```

```
agcccgtcct accaaggcca ggtcaccatt tcagccgaca agtccatcag taccgcctac    240
ctgcagtgga gcagcctgaa ggcctcggac accggcatgt attactgtgc gagagtggca    300
ggggatattg gctacgagaa ctactactac tacggtatgg acgtctgggg ccaagggacc    360
acggtcaccg tctcctcg                                                  378
```

<210> SEQ ID NO 186
<211> LENGTH: 339
<212> TYPE: DNA
<213> ORGANISM: Homo sapiens

<400> SEQUENCE: 186

```
gatattgtga tgactcaatc accagactcc ctggctgtgt ctctgggcga gagggccacc    60
atcaactgca gtccagcca gagtgtttta tatggctcca acaataagaa ctacttagct    120
tggtaccagc agaaactagg acagtctcct aaactgctca tttactgggc atctgcccgg    180
gaatccgggg tccctgaccg attcggtggc agcgggtctg ggacagattt cactctcacc    240
atcagcagcc tgcaggctga agatgtggca gtctattact gtcagcaata ttacagtact    300
ccgtggacgt tcggccaggg gaccaaggtg gaaatcaaa                           339
```

<210> SEQ ID NO 187
<211> LENGTH: 354
<212> TYPE: DNA
<213> ORGANISM: Homo sapiens

<400> SEQUENCE: 187

```
caggtgcagc tggtggagtc tgggggaggc gtggtccagc ctgggaggtc cctgagactc    60
tcctgtgcag cgtctggatt cacgttcact agatatggca tgcactgggt ccgccaggct    120
ccaggcaagg ggctggagtg ggtggcagtt atatggtatg atggaactaa taaatattat    180
gcagactcac tgcagggccg attcaccatc tccagagaca cttccacgaa cacgctgtat    240
ctgcaaatga acggcctgag agtcgaggac agggctgtat attactgtgc gagagagggg    300
tttcagggag cgatcgacta ctggggccag ggcaccctgg tcaccgtctc ctcg          354
```

<210> SEQ ID NO 188
<211> LENGTH: 339
<212> TYPE: DNA
<213> ORGANISM: Homo sapiens

<400> SEQUENCE: 188

```
gaaattgtga tgactcagtc tccagactcc ctggctgtgt ctctgggcga gagggccacc    60
atcaactgca gtcaagcca gaatatttta tacagctccg acaataagaa ctacttagct    120
tggtaccagc agaaaccagg acagcctcct aaactactca tttactgggc atctacccgg    180
gaatccgggg tccctgaccg attcagtggc agcgggtctg ggacagattt cactctcacc    240
atcagcagcc tgcaggctga agatgtggca gtttattact gtcagcaata ttatagtatt    300
cctcggacgt tcggccaagg gaccaaggtg gagatcaaa                           339
```

<210> SEQ ID NO 189
<211> LENGTH: 360
<212> TYPE: DNA
<213> ORGANISM: Homo sapiens

<400> SEQUENCE: 189

```
gaggtgcagc tggtggagtc tgggggaggc ttggtccagc ctgggggtc cctgaaactc     60
```

-continued

| tcctgtgcag cctctgggtt cagtttcagt gactctgctt tccactgggc ccgccaggct | 120 |
| tccgggaaag ggctggagtg ggttggccgt attagaagta aaggtaataa ttacgcgaca | 180 |
| gcatatgctg cgtcggtgaa aggcaggttc accgtctcca gagatgattc aaagaacacg | 240 |
| acgtatctac agatgaacag cctgaaaacc gacgacacgg ccatatatta ctgtactaga | 300 |
| cagggcccct cctacggtgg tattaattgg ggcctgggca ccctggtcac cgtctcctcg | 360 |

<210> SEQ ID NO 190
<211> LENGTH: 339
<212> TYPE: DNA
<213> ORGANISM: Homo sapiens

<400> SEQUENCE: 190

| gatattgtga tgactcaatc accagactcc ctggctgtgt ctctgggcga gagggccacc | 60 |
| atcaactgca agtccagcca gactatttta tacagttcca acaataagaa ctacttagct | 120 |
| tggtaccagc agaaaccagg acagcctcca aagctgctca tttactgggc atctacccgg | 180 |
| gaatccgggg tccctgaccg attcagtggc agcgggtctg ggacagattt cactctcacc | 240 |
| atcagcagcc tgcgggctga agatgtggca gtttattact gtcagcaata ttatagttct | 300 |
| cctcaaacgt tcggccaggg gaccaaggtg gaaatcaaa | 339 |

<210> SEQ ID NO 191
<211> LENGTH: 345
<212> TYPE: DNA
<213> ORGANISM: Homo sapiens

<400> SEQUENCE: 191

| gaggtgcagc tggtggagtc tgggggaggc ttcgtgaggc cggggggggtc cattacactg | 60 |
| tcctgtgcaa cctctggatt tactttcact aaagcctgga tgacctgggt ccgccaggct | 120 |
| ccagtgaagg ggctggagtg gattggccat attaaaacca gaattgaagg tgcgacaaca | 180 |
| gactacgctg cgcccgtgga aggccgattc accatttcaa gagacgattc aaaaaatatg | 240 |
| gtatatcttc aaatgaacag cctgaagacc gaagactcag gcatttatta ctgttccaca | 300 |
| gactttgact attggggcca gggaaccctg gtcaccgtct cctcg | 345 |

<210> SEQ ID NO 192
<211> LENGTH: 339
<212> TYPE: DNA
<213> ORGANISM: Homo sapiens

<400> SEQUENCE: 192

| gatgttgtga tgactcagtc tccactctcc ctgcccgtca cccttggaca gccggcctcc | 60 |
| atctcctgca cgtctagtca aagcctccta tacagtgatg gaaacaccta cttgaattgg | 120 |
| tttcagcaga ggccaggcca atctccaagg cgcctaatgt ataaggtttc taagcgggac | 180 |
| cctggggtcc cagacagatt cagcggcagt gggtcaggca ctgatttcac actgagcatc | 240 |
| agcagggtgg aggctgagga tgttggcgtt tattactgca tgcaaggttc actctggcct | 300 |
| cggtacactt ttggccaggg gaccaaggtg gagatcaaa | 339 |

<210> SEQ ID NO 193
<211> LENGTH: 363
<212> TYPE: DNA
<213> ORGANISM: Homo sapiens

<400> SEQUENCE: 193

| gaggtgcagc tggtgcagtc tggagcagaa gtgaaaaagc ccggggactc tctgaggatc | 60 |

```
tcctgtaagg cttctggata caactttccc aactactgga tcggctgggt gcgccagatg    120
cccgggaaag gcctggagtg gatgggaatc atctaccctg gtgactctga tatcagatac    180
agcccgtcct tccagggaca cgtcaccatc tccagtgaca agtccatcac caccgcctat    240
ctccagtgga ccagtctgaa ggtcgcggac agcgccatgt attattgtgc gagagtggaa    300
aggcctgaca agggggggctg gttcggcccc tggggccagg gaaccctggt caccgtctcc    360
tcg                                                                  363
```

<210> SEQ ID NO 194
<211> LENGTH: 339
<212> TYPE: DNA
<213> ORGANISM: Homo sapiens

<400> SEQUENCE: 194

```
gatattgtga tgactcaatc accagactcc ctggctgtgt ctctgggcga gagggccacc    60
atcaactgca gtccagcca gactcttttg tacacgtcca ataatcagaa ctatttagct    120
tggtaccaac acaaaccggg acagcctcct aaggtgctca tatactgggc atctacccgg    180
gaatatgggg tccctgaccg attcagtggc agcgggtctg gaacagattt cactctcacc    240
atcagcagcc tgcagcctga agatgtggct gtttattact gtcagcaata ttataatagt    300
ccctacactt ttggccaggg gaccaagctg gagatcaaa                           339
```

<210> SEQ ID NO 195
<211> LENGTH: 342
<212> TYPE: DNA
<213> ORGANISM: Homo sapiens

<400> SEQUENCE: 195

```
gaggtgcagc tggtggagtc tgggggaggc ttggtacagc ctggggggtc cctgagactc    60
tcctgtgcag cctctggatt cacccttcagt gcatatggca tgaactgggt ccgccaggct    120
ccaggaaagg gctggagtg ggttgcacac attactggta gtggcactcc catcttctac    180
gcagactctg tgaagggccg attcaccatt tccagagaca atgccaagag ttccctatat    240
ctgcaaatga acagcctgag aaacgatgac acggctctat atttctgtgt gagaggtacc    300
gttgactact ggggccaggg caccctggtc accgtctcct cg                      342
```

<210> SEQ ID NO 196
<211> LENGTH: 330
<212> TYPE: DNA
<213> ORGANISM: Homo sapiens

<400> SEQUENCE: 196

```
caggctggtc tgactcagcc accctcggtg tccaaggact tgagacagac cgccacactc    60
acctgcagtg ggaacagcaa caatgtcggc aaccaaggag cagcttggct gcagcagttc    120
ccgggccacc ctcccaaact cctcttctac gaaaatatca accggccctc aggaatttca    180
gagagattct ctgcatccag gtcaggaaac acagcttccc tgaccattac tggactccag    240
cctgaggacg aggctgacta ttactgctca gcgtgggacg ccacctcaa tgcttgggtg    300 ttcggcggag ggaccaagct gaccgtccta                                     330
```

<210> SEQ ID NO 197
<211> LENGTH: 372
<212> TYPE: DNA
<213> ORGANISM: Homo sapiens

<400> SEQUENCE: 197

```
gaggtgcagc tggtgcagtc tggagcagag gtgaaaaagc ccggggagtc tctgaagatc        60
tcctgtaagg cttctggata tagttttatc agctactggg tcggctgggt gcgccagatg       120
cccgggaaag gcctggagtg gatgggcatc atctatcccg gtgactctga caccagatac       180
agcccgtcct tcgaaggcca ggtcagcatc tcagccgaca gtccatcag caccgcctac        240
ctccagtgga ccagcctgaa ggcctcggac accgccatgt attactgtgc gagacattgg       300
gggccggcag cagtgacgga ttctccctgg ttcggcccct ggggccaggg aaccctggtc       360
accgtctcct cg                                                            372
```

<210> SEQ ID NO 198
<211> LENGTH: 339
<212> TYPE: DNA
<213> ORGANISM: Homo sapiens

<400> SEQUENCE: 198

```
gatattgtga tgacccagag tccagactcc ctggctgtgt ctctgggcga gagggccacc        60
atcaactgca gtccagcca gactgtttta tatacctcca caataagaa ctacttagct         120
tggtaccagc agaagccagg acagcctcct aagttactat tttactgggc atctacccgg       180
gaatccgggg tccctgaccg attcagtggc agcgggtctg ggacagattt cactctcacc       240
atcagcagcc tgcaggctga agatgtggca gtttattact gtcagcacta ttatagtact       300
ccattcactt tcggccctgg gaccaaagtg gatatcaaa                               339
```

<210> SEQ ID NO 199
<211> LENGTH: 351
<212> TYPE: DNA
<213> ORGANISM: Homo sapiens

<400> SEQUENCE: 199

```
gaggtgcagc tggtggagtc tggggctgag gtgaagaaac ctggggcctc agtgaaggtc        60
tcctgcaagg cttctggata catctttacc gccttcttta tgcactgggt gcgacaggcc       120
cctggacaag gccttgagtg gatgggatgg atcaaccctg acagtggtgc acaaagtat        180
gcacacaact ttcagggcag ggttaccatg accagggaca cgtccatcag cacagccttc       240
atggagctga gtggactgaa gtctgacgac acggcgtat attactgtgc gacgggtatg        300
gcagtgactg gtaacttctg gggccaggga accctggtca ccgtctcctc g                351
```

<210> SEQ ID NO 200
<211> LENGTH: 351
<212> TYPE: DNA
<213> ORGANISM: Homo sapiens

<400> SEQUENCE: 200

```
caggtgcagc tggtgcaatc tggggctgag gtgaagaaac ctggggcctc agtgaaggtc        60
tcctgcaagg cttctggata catctttacc gccttcttta tgcactgggt gcgacaggcc       120
cctggacaag gccttgagtg gatgggatgg atcaaccctg acagtggtgc acaaagtat        180
gcacacaact ttcagggcag ggttaccatg accagggaca cgtccatcag cacagccttc       240
atggagctga gtggactgaa gtctgacgac acggcgtat attactgtgc gacgggtatg        300
gcagtgactg gtaacttctg gggccagggc accctggtca ccgtctcctc g                351
```

<210> SEQ ID NO 201
<211> LENGTH: 324

```
<212> TYPE: DNA
<213> ORGANISM: Homo sapiens

<400> SEQUENCE: 201
ctgcctgtgc tgactcagcc accctcagtg tcagtgtctc cgggacagac agccaggatc    60
acctgctcag gagatgtact ggcagaaaca tatgctcggt ggttccagca aaagccaggc   120
caggcccctg tgttggtgat gtatagagac cgtgagcggc ccgcagggat ccctgagcga   180
ttctccggct ccagctcagg aacacagtc accttgacca tcagcggggc ccaggctgag    240
gatgaggctg tctatcattg tcactctgtg gctgacaaca atctagattg ggtgttcggc   300
ggagggacca aactgaccgt ccta                                          324

<210> SEQ ID NO 202
<211> LENGTH: 324
<212> TYPE: DNA
<213> ORGANISM: Homo sapiens

<400> SEQUENCE: 202
tcctatgagc tgactcagcc accctcagtg tcagtgtctc cgggacagac agccaggatc    60
acctgctcag gagatgtact ggcagaaaca tatgctcggt ggttccagca aaagccaggc   120
caggcccctg tgttggtgat gtatagagac cgtgagcggc ccgcagggat ccctgagcga   180
ttctccggct ccagctcagg aacacagtc accttgacca tcagcggggc ccaggctgag    240
gatgaggctg tctatcattg tcactctgtg gctgacaaca atctagattg ggtgttcggc   300
ggagggacca aactgaccgt ccta                                          324

<210> SEQ ID NO 203
<211> LENGTH: 450
<212> TYPE: PRT
<213> ORGANISM: Artificial Sequence
<220> FEATURE:
<223> OTHER INFORMATION: Chimaera

<400> SEQUENCE: 203

Glu Val Gln Leu Val Gln Ser Gly Ala Glu Val Lys Lys Pro Gly Glu
 1               5                  10                  15

Ser Leu Lys Ile Ser Cys Lys Ala Phe Gly Tyr Ser Phe Thr Asn Phe
                20                  25                  30

Trp Ile Gly Trp Val Arg Gln Val Pro Gly Lys Gly Leu Glu Trp Val
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Asp Thr Ala Tyr
 65                  70                  75                  80

Leu Gln Trp Gly His Leu Lys Ala Ser Asp Ser Ala Met Tyr Phe Cys
                85                  90                  95

Ala Arg Arg Gly Phe Trp Thr Gly Ser Gln Ile Glu Tyr Trp Gly Gln
            100                 105                 110

Gly Thr Gln Val Thr Val Ser Ser Ala Lys Thr Thr Ala Pro Ser Val
        115                 120                 125

Tyr Pro Leu Ala Pro Val Cys Gly Asp Thr Thr Gly Ser Ser Val Thr
    130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175
```

Leu Gln Ser Asp Leu Tyr Thr Leu Ser Ser Val Thr Val Thr Ser
            180                 185                 190

Ser Thr Trp Pro Ser Gln Ser Ile Thr Cys Asn Val Ala His Pro Ala
        195                 200                 205

Ser Ser Thr Lys Val Asp Lys Lys Ile Glu Pro Arg Gly Pro Thr Ile
    210                 215                 220

Lys Pro Cys Pro Pro Cys Lys Cys Pro Ala Pro Asn Leu Leu Gly Gly
225                 230                 235                 240

Pro Ser Val Phe Ile Phe Pro Pro Lys Ile Lys Asp Val Leu Met Ile
                245                 250                 255

Ser Leu Ser Pro Ile Val Thr Cys Val Val Asp Val Ser Glu Asp
            260                 265                 270

Asp Pro Asp Val Gln Ile Ser Trp Phe Val Asn Asn Val Glu Val His
        275                 280                 285

Thr Ala Gln Thr Gln Thr His Arg Glu Asp Tyr Asn Ser Thr Leu Arg
    290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Pro Ala Pro Ile Glu
                325                 330                 335

Arg Thr Ile Ser Lys Pro Lys Gly Ser Val Arg Ala Pro Gln Val Tyr
            340                 345                 350

Val Leu Pro Pro Pro Glu Glu Glu Met Thr Lys Lys Gln Val Thr Leu
        355                 360                 365

Thr Cys Met Val Thr Asp Phe Met Pro Glu Asp Ile Tyr Val Glu Trp
    370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
        435                 440                 445

Gly Lys
    450

<210> SEQ ID NO 204
<211> LENGTH: 217
<212> TYPE: PRT
<213> ORGANISM: Artificial Sequence
<220> FEATURE:
<223> OTHER INFORMATION: Chimaera

<400> SEQUENCE: 204

Gln Ser Ala Leu Thr Gln Pro Pro Ser Ala Ser Gly Ser Pro Gly His
1               5                   10                  15

Ser Val Thr Ile Ser Cys Thr Gly Thr Ser Ser Asp Val Gly Asn Tyr
            20                  25                  30

Ser Phe Val Ser Trp Tyr Gln Gln Tyr Pro Gly Lys Ala Pro Lys Ile
        35                  40                  45

Ile Ile Tyr Asp Val Ser Lys Arg Ser Ser Gly Val Pro Asp Arg Phe
    50                  55                  60

Phe Gly Ser Lys Ser Ala Asn Thr Ala Ser Leu Thr Val Ser Gly Val
65                  70                  75                  80

Gln Glu Glu Asp Glu Ala Asp Tyr Phe Cys Ser Ser Tyr Gly Gly Ser
            85                  90                  95

Lys Tyr Pro Trp Val Phe Gly Gly Gly Thr Lys Leu Thr Val Leu Gly
            100                 105                 110

Gln Pro Lys Ser Ser Pro Ser Val Thr Leu Phe Pro Pro Ser Ser Glu
            115                 120                 125

Glu Leu Glu Thr Asn Lys Ala Thr Leu Val Cys Thr Ile Thr Asp Phe
130                 135                 140

Tyr Pro Gly Val Val Thr Val Asp Trp Lys Val Asp Gly Thr Pro Val
145                 150                 155                 160

Thr Gln Gly Met Glu Thr Thr Gln Pro Ser Lys Gln Ser Asn Asn Lys
                165                 170                 175

Tyr Met Ala Ser Ser Tyr Leu Thr Leu Thr Ala Arg Ala Trp Glu Arg
                180                 185                 190

His Ser Ser Tyr Ser Cys Gln Val Thr His Glu Gly His Thr Val Glu
                195                 200                 205

Lys Ser Leu Ser Arg Ala Asp Cys Ser
            210                 215

<210> SEQ ID NO 205
<211> LENGTH: 455
<212> TYPE: PRT
<213> ORGANISM: Artificial Sequence
<220> FEATURE:
<223> OTHER INFORMATION: Chimaera

<400> SEQUENCE: 205

Gln Val Gln Leu Val Glu Ser Gly Gly Gly Val Val Gln Pro Gly Arg
1               5                   10                  15

Ser Leu Arg Val Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
            35                  40                  45

Ala Val Ile Trp Phe Asp Gly Ser Asn Glu Phe Tyr Ala Asp Ser Val
50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Asp Leu Gly Ala Ser Val Thr Thr Ser Asn Ala Glu Asn Phe
            100                 105                 110

His His Trp Gly Gln Gly Thr Leu Val Thr Val Ser Ser Ala Lys Thr
            115                 120                 125

Thr Ala Pro Ser Val Tyr Pro Leu Ala Pro Val Cys Gly Asp Thr Thr
130                 135                 140

Gly Ser Ser Val Thr Leu Gly Cys Leu Val Lys Gly Tyr Phe Pro Glu
145                 150                 155                 160

Pro Val Thr Leu Thr Trp Asn Ser Gly Ser Leu Ser Ser Gly Val His
                165                 170                 175

Thr Phe Pro Ala Val Leu Gln Ser Asp Leu Tyr Thr Leu Ser Ser Ser
                180                 185                 190

Val Thr Val Thr Ser Ser Thr Trp Pro Ser Gln Ser Ile Thr Cys Asn
            195                 200                 205

Val Ala His Pro Ala Ser Ser Thr Lys Val Asp Lys Lys Ile Glu Pro
210                 215                 220

```
Arg Gly Pro Thr Ile Lys Pro Cys Pro Pro Cys Lys Cys Pro Ala Pro
225                 230                 235                 240

Asn Leu Leu Gly Gly Pro Ser Val Phe Ile Phe Pro Pro Lys Ile Lys
            245                 250                 255

Asp Val Leu Met Ile Ser Leu Ser Pro Ile Val Thr Cys Val Val Val
            260                 265                 270

Asp Val Ser Glu Asp Asp Pro Asp Val Gln Ile Ser Trp Phe Val Asn
            275                 280                 285

Asn Val Glu Val His Thr Ala Gln Thr Gln Thr His Arg Glu Asp Tyr
290                 295                 300

Asn Ser Thr Leu Arg Val Val Ser Ala Leu Pro Ile Gln His Gln Asp
305                 310                 315                 320

Trp Met Ser Gly Lys Glu Phe Lys Cys Lys Val Asn Asn Lys Asp Leu
                325                 330                 335

Pro Ala Pro Ile Glu Arg Thr Ile Ser Lys Pro Lys Gly Ser Val Arg
                340                 345                 350

Ala Pro Gln Val Tyr Val Leu Pro Pro Glu Glu Glu Met Thr Lys
        355                 360                 365

Lys Gln Val Thr Leu Thr Cys Met Val Thr Asp Phe Met Pro Glu Asp
370                 375                 380

Ile Tyr Val Glu Trp Thr Asn Asn Gly Lys Thr Glu Leu Asn Tyr Lys
385                 390                 395                 400

Asn Thr Glu Pro Val Leu Asp Ser Asp Gly Ser Tyr Phe Met Tyr Ser
                405                 410                 415

Lys Leu Arg Val Glu Lys Lys Asn Trp Val Arg Asn Ser Tyr Ser
                420                 425                 430

Cys Ser Val Val His Glu Gly Leu His Asn His His Thr Thr Lys Ser
            435                 440                 445

Phe Ser Arg Thr Pro Gly Lys
    450                 455

<210> SEQ ID NO 206
<211> LENGTH: 213
<212> TYPE: PRT
<213> ORGANISM: Artificial Sequence
<220> FEATURE:
<223> OTHER INFORMATION: Chimaera

<400> SEQUENCE: 206

Tyr Glu Leu Thr Gln Pro Pro Ser Val Ser Val Ser Pro Gly Gln Thr
1               5                   10                  15

Ala Arg Ile Thr Cys Ser Gly Asp Ala Leu Pro Lys Arg Tyr Val Tyr
                20                  25                  30

Trp Tyr Gln Gln Lys Ser Gly Gln Ala Pro Val Leu Val Ile Tyr Glu
            35                  40                  45

Asp Ser Lys Arg Pro Ser Gly Ile Pro Glu Thr Phe Ser Gly Ser Ser
        50                  55                  60

Ser Gly Thr Met Ala Thr Leu Thr Ile Ser Gly Ala Gln Val Glu Asp
65                  70                  75                  80

Glu Ala Asp Tyr Tyr Cys Tyr Ser Thr Asp Ser Asn Gly His His Trp
                85                  90                  95

Val Phe Gly Gly Gly Thr Lys Leu Thr Val Leu Gly Gln Pro Lys Ser
            100                 105                 110

Ser Pro Ser Val Thr Leu Phe Pro Pro Ser Ser Glu Glu Leu Glu Thr
        115                 120                 125
```

```
Asn Lys Ala Thr Leu Val Cys Thr Ile Thr Asp Phe Tyr Pro Gly Val
    130                 135                 140

Val Thr Val Asp Trp Lys Val Asp Gly Thr Pro Val Thr Gln Gly Met
145                 150                 155                 160

Glu Thr Thr Gln Pro Ser Lys Gln Ser Asn Asn Lys Tyr Met Ala Ser
                165                 170                 175

Ser Tyr Leu Thr Leu Thr Ala Arg Ala Trp Glu Arg His Ser Ser Tyr
            180                 185                 190

Ser Cys Gln Val Thr His Glu Gly His Thr Val Glu Lys Ser Leu Ser
        195                 200                 205

Arg Ala Asp Cys Ser
    210

<210> SEQ ID NO 207
<211> LENGTH: 444
<212> TYPE: PRT
<213> ORGANISM: Artificial Sequence
<220> FEATURE:
<223> OTHER INFORMATION: Chimaera

<400> SEQUENCE: 207

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Pro Asn Tyr
            20                  25                  30

Val Met Thr Trp Val Arg Gln Ala Pro Gly Lys Gly Leu Glu Trp Val
        35                  40                  45

Ser Gly Ile Ser Gly Ser Gly Gly Ser Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Leu Tyr Tyr Cys
                85                  90                  95

Ala Lys Gly Ser Gly Gly Ile Arg Gly Gln Gly Thr Met Val Thr Val
            100                 105                 110

Ser Ser Ala Lys Thr Thr Ala Pro Ser Val Tyr Pro Leu Ala Pro Val
        115                 120                 125

Cys Gly Asp Thr Thr Gly Ser Ser Val Thr Leu Gly Cys Leu Val Lys
    130                 135                 140

Gly Tyr Phe Pro Glu Pro Val Thr Leu Thr Trp Asn Ser Gly Ser Leu
145                 150                 155                 160

Ser Ser Gly Val His Thr Phe Pro Ala Val Leu Gln Ser Asp Leu Tyr
                165                 170                 175

Thr Leu Ser Ser Ser Val Thr Val Thr Ser Ser Thr Trp Pro Ser Gln
            180                 185                 190

Ser Ile Thr Cys Asn Val Ala His Pro Ala Ser Ser Thr Lys Val Asp
        195                 200                 205

Lys Lys Ile Glu Pro Arg Gly Pro Thr Ile Lys Pro Cys Pro Pro Cys
    210                 215                 220

Lys Cys Pro Ala Pro Asn Leu Leu Gly Gly Pro Ser Val Phe Ile Phe
225                 230                 235                 240

Pro Pro Lys Ile Lys Asp Val Leu Met Ile Ser Leu Ser Pro Ile Val
                245                 250                 255

Thr Cys Val Val Val Asp Val Ser Glu Asp Asp Pro Asp Val Gln Ile
            260                 265                 270
```

Ser Trp Phe Val Asn Asn Val Glu Val His Thr Ala Gln Thr Gln Thr
        275                 280                 285

His Arg Glu Asp Tyr Asn Ser Thr Leu Arg Val Val Ser Ala Leu Pro
    290                 295                 300

Ile Gln His Gln Asp Trp Met Ser Gly Lys Glu Phe Lys Cys Lys Val
305                 310                 315                 320

Asn Asn Lys Asp Leu Pro Ala Pro Ile Glu Arg Thr Ile Ser Lys Pro
                325                 330                 335

Lys Gly Ser Val Arg Ala Pro Gln Val Tyr Val Leu Pro Pro Pro Glu
            340                 345                 350

Glu Glu Met Thr Lys Lys Gln Val Thr Leu Thr Cys Met Val Thr Asp
                355                 360                 365

Phe Met Pro Glu Asp Ile Tyr Val Glu Trp Thr Asn Asn Gly Lys Thr
370                 375                 380

Glu Leu Asn Tyr Lys Asn Thr Glu Pro Val Leu Asp Ser Asp Gly Ser
385                 390                 395                 400

Tyr Phe Met Tyr Ser Lys Leu Arg Val Glu Lys Lys Asn Trp Val Glu
                405                 410                 415

Arg Asn Ser Tyr Ser Cys Ser Val Val His Glu Gly Leu His Asn His
            420                 425                 430

His Thr Thr Lys Ser Phe Ser Arg Thr Pro Gly Lys
            435                 440

<210> SEQ ID NO 208
<211> LENGTH: 444
<212> TYPE: PRT
<213> ORGANISM: Artificial Sequence
<220> FEATURE:
<223> OTHER INFORMATION: Chimaera

<400> SEQUENCE: 208

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Pro Asn Tyr
            20                  25                  30

Val Met Thr Trp Val Arg Gln Ala Pro Gly Lys Gly Leu Glu Trp Val
        35                  40                  45

Ser Gly Ile Ser Gly Ser Gly Ser Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Leu Tyr Tyr Cys
                85                  90                  95

Ala Lys Gly Ser Gly Gly Ile Trp Gly Gln Gly Thr Met Val Thr Val
            100                 105                 110

Ser Ser Ala Lys Thr Thr Ala Pro Ser Val Tyr Pro Leu Ala Pro Val
        115                 120                 125

Cys Gly Asp Thr Thr Gly Ser Ser Val Thr Leu Gly Cys Leu Val Lys
    130                 135                 140

Gly Tyr Phe Pro Glu Pro Val Thr Leu Thr Trp Asn Ser Gly Ser Leu
145                 150                 155                 160

Ser Ser Gly Val His Thr Phe Pro Ala Val Leu Gln Ser Asp Leu Tyr
                165                 170                 175

Thr Leu Ser Ser Ser Val Thr Val Thr Ser Ser Thr Trp Pro Ser Gln
            180                 185                 190

-continued

```
Ser Ile Thr Cys Asn Val Ala His Pro Ala Ser Ser Thr Lys Val Asp
            195                 200                 205

Lys Lys Ile Glu Pro Arg Gly Pro Thr Ile Lys Pro Cys Pro Pro Cys
210                 215                 220

Lys Cys Pro Ala Pro Asn Leu Leu Gly Gly Pro Ser Val Phe Ile Phe
225                 230                 235                 240

Pro Pro Lys Ile Lys Asp Val Leu Met Ile Ser Leu Ser Pro Ile Val
            245                 250                 255

Thr Cys Val Val Val Asp Val Ser Glu Asp Asp Pro Asp Val Gln Ile
            260                 265                 270

Ser Trp Phe Val Asn Asn Val Glu Val His Thr Ala Gln Thr Gln Thr
            275                 280                 285

His Arg Glu Asp Tyr Asn Ser Thr Leu Arg Val Val Ser Ala Leu Pro
            290                 295                 300

Ile Gln His Gln Asp Trp Met Ser Gly Lys Glu Phe Lys Cys Lys Val
305                 310                 315                 320

Asn Asn Lys Asp Leu Pro Ala Pro Ile Glu Arg Thr Ile Ser Lys Pro
            325                 330                 335

Lys Gly Ser Val Arg Ala Pro Gln Val Tyr Val Leu Pro Pro Pro Glu
            340                 345                 350

Glu Glu Met Thr Lys Lys Gln Val Thr Leu Thr Cys Met Val Thr Asp
            355                 360                 365

Phe Met Pro Glu Asp Ile Tyr Val Glu Trp Thr Asn Asn Gly Lys Thr
            370                 375                 380

Glu Leu Asn Tyr Lys Asn Thr Glu Pro Val Leu Asp Ser Asp Gly Ser
385                 390                 395                 400

Tyr Phe Met Tyr Ser Lys Leu Arg Val Glu Lys Lys Asn Trp Val Glu
            405                 410                 415

Arg Asn Ser Tyr Ser Cys Ser Val Val His Glu Gly Leu His Asn His
            420                 425                 430

His Thr Thr Lys Ser Phe Ser Arg Thr Pro Gly Lys
            435                 440

<210> SEQ ID NO 209
<211> LENGTH: 216
<212> TYPE: PRT
<213> ORGANISM: Artificial Sequence
<220> FEATURE:
<223> OTHER INFORMATION: Chimaera

<400> SEQUENCE: 209

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp His Gln Gln His Pro Gly Lys Ala Pro Lys Leu
        35                  40                  45

Leu Ile Tyr Asp Val Thr Lys Arg Pro Ser Gly Val Pro Asp Arg Phe
    50                  55                  60

Ser Gly Ser Lys Ser Gly Asn Thr Ala Ala Leu Thr Ile Ser Gly Leu
65                  70                  75                  80

Gln Ala Glu Asp Glu Ala Asp Tyr Tyr Cys His Ser Tyr Val Gly Ser
            85                  90                  95

Tyr Thr Leu Val Phe Gly Gly Gly Thr Lys Leu Thr Val Leu Gly Gln
            100                 105                 110
```

```
Pro Lys Ser Ser Pro Ser Val Thr Leu Phe Pro Pro Ser Ser Glu Glu
        115                 120                 125

Leu Glu Thr Asn Lys Ala Thr Leu Val Cys Thr Ile Thr Asp Phe Tyr
130                 135                 140

Pro Gly Val Val Thr Val Asp Trp Lys Val Asp Gly Thr Pro Val Thr
145                 150                 155                 160

Gln Gly Met Glu Thr Thr Gln Pro Ser Lys Gln Ser Asn Asn Lys Tyr
                165                 170                 175

Met Ala Ser Ser Tyr Leu Thr Leu Thr Ala Arg Ala Trp Glu Arg His
            180                 185                 190

Ser Ser Tyr Ser Cys Gln Val Thr His Glu Gly His Thr Val Glu Lys
        195                 200                 205

Ser Leu Ser Arg Ala Asp Cys Ser
    210                 215

<210> SEQ ID NO 210
<211> LENGTH: 452
<212> TYPE: PRT
<213> ORGANISM: Artificial Sequence
<220> FEATURE:
<223> OTHER INFORMATION: Chimaera

<400> SEQUENCE: 210

Glu Val Gln Leu Val Glu Ser Gly Gly Gly Leu Val Gln Pro Gly Gly
1               5                   10                  15

Ser Leu Arg Leu Ser Cys Ile Gly Ser Ser Gly Met Thr Phe Ser Ser
            20                  25                  30

Tyr Ala Phe Asn Trp Val Arg Gln Thr Pro Gly Lys Gly Leu Glu Trp
        35                  40                  45

Val Ser Ser Ile Ser Arg Phe Gly Ser Thr Val Asp Tyr Thr Asp Ser
50                  55                  60

Val Arg Gly Arg Phe Thr Ile Ser Arg Asp Asp Gly Gln Arg Ser Leu
65                  70                  75                  80

Tyr Leu Gln Met Asn Ser Leu Arg Val Glu Asp Thr Ala Val Tyr Tyr
                85                  90                  95

Cys Val Arg Ser Thr Ala Ser Gly Ser Arg Ser Pro Gly Ile Ile Trp
            100                 105                 110

Gly Gln Gly Thr Thr Val Thr Val Ser Ser Ala Lys Thr Thr Ala Pro
        115                 120                 125

Ser Val Tyr Pro Leu Ala Pro Val Cys Gly Asp Thr Thr Gly Ser Ser
    130                 135                 140

Val Thr Leu Gly Cys Leu Val Lys Gly Tyr Phe Pro Glu Pro Val Thr
145                 150                 155                 160

Leu Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
            180                 185                 190

Thr Ser Ser Thr Trp Pro Ser Gln Ser Ile Thr Cys Asn Val Ala His
        195                 200                 205

Pro Ala Ser Ser Thr Lys Val Asp Lys Lys Ile Glu Pro Arg Gly Pro
    210                 215                 220

Thr Ile Lys Pro Cys Pro Pro Cys Lys Cys Pro Ala Pro Asn Leu Leu
225                 230                 235                 240

Gly Gly Pro Ser Val Phe Ile Phe Pro Pro Lys Ile Lys Asp Val Leu
                245                 250                 255
```

```
Met Ile Ser Leu Ser Pro Ile Thr Cys Val Val Asp Val Ser
            260                 265                 270

Glu Asp Asp Pro Asp Val Gln Ile Ser Trp Phe Val Asn Asn Val Glu
        275                 280                 285

Val His Thr Ala Gln Thr Gln Thr His Arg Glu Asp Tyr Asn Ser Thr
    290                 295                 300

Leu Arg Val Val Ser Ala Leu Pro Ile Gln His Gln Asp Trp Met Ser
305                 310                 315                 320

Gly Lys Glu Phe Lys Cys Lys Val Asn Asn Lys Asp Leu Pro Ala Pro
                325                 330                 335

Ile Glu Arg Thr Ile Ser Lys Pro Lys Gly Ser Val Arg Ala Pro Gln
            340                 345                 350

Val Tyr Val Leu Pro Pro Pro Glu Glu Glu Met Thr Lys Lys Gln Val
        355                 360                 365

Thr Leu Thr Cys Met Val Thr Asp Phe Met Pro Glu Asp Ile Tyr Val
    370                 375                 380

Glu Trp Thr Asn Asn Gly Lys Thr Glu Leu Asn Tyr Lys Asn Thr Glu
385                 390                 395                 400

Pro Val Leu Asp Ser Asp Gly Ser Tyr Phe Met Tyr Ser Lys Leu Arg
                405                 410                 415

Val Glu Lys Lys Asn Trp Val Glu Arg Asn Ser Tyr Ser Cys Ser Val
            420                 425                 430

Val His Glu Gly Leu His Asn His His Thr Thr Lys Ser Phe Ser Arg
        435                 440                 445

Thr Pro Gly Lys
        450

<210> SEQ ID NO 211
<211> LENGTH: 214
<212> TYPE: PRT
<213> ORGANISM: Artificial Sequence
<220> FEATURE:
<223> OTHER INFORMATION: Chimaera

<400> SEQUENCE: 211

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Val Asn Asn
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Gly Gly Val Pro Ser Lys Phe Ser Gly
    50                  55                  60

Ser Ala Ser Gly Thr Asp Phe Ser Leu Thr Ile Ser Asn Leu Gln Pro
65                  70                  75                  80

Glu Asp Phe Ala Thr Tyr Phe Cys Gln Gln Tyr Asn Ser Tyr Pro Trp
                85                  90                  95

Thr Phe Gly Gln Gly Thr Lys Val Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160
```

```
Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 212
<211> LENGTH: 217
<212> TYPE: PRT
<213> ORGANISM: Artificial Sequence
<220> FEATURE:
<223> OTHER INFORMATION: Chimaera

<400> SEQUENCE: 212

Gln Ser Ala Leu Thr Gln Pro Pro Ser Ala Ser Gly Ser Pro Gly His
1               5                   10                  15

Ser Val Thr Ile Ser Cys Thr Gly Thr Ser Ser Asp Val Gly Gln Tyr
            20                  25                  30

Ser Phe Val Ser Trp Tyr Gln Gln Tyr Pro Gly Lys Ala Pro Lys Ile
        35                  40                  45

Ile Ile Tyr Asp Val Ser Lys Arg Ser Gly Val Pro Asp Arg Phe
    50                  55                  60

Phe Gly Ser Lys Ser Ala Asn Thr Ala Ser Leu Thr Val Ser Gly Val
65                  70                  75                  80

Gln Glu Glu Asp Glu Ala Asp Tyr Phe Cys Ser Ser Tyr Gly Gly Ser
                85                  90                  95

Lys Tyr Pro Trp Val Phe Gly Gly Gly Thr Lys Leu Thr Val Leu Gly
            100                 105                 110

Gln Pro Lys Ser Ser Pro Ser Val Thr Leu Phe Pro Pro Ser Ser Glu
        115                 120                 125

Glu Leu Glu Thr Asn Lys Ala Thr Leu Val Cys Thr Ile Thr Asp Phe
    130                 135                 140

Tyr Pro Gly Val Val Thr Val Asp Trp Lys Val Asp Gly Thr Pro Val
145                 150                 155                 160

Thr Gln Gly Met Glu Thr Thr Gln Pro Ser Lys Gln Ser Asn Asn Lys
                165                 170                 175

Tyr Met Ala Ser Ser Tyr Leu Thr Leu Thr Ala Arg Ala Trp Glu Arg
            180                 185                 190

His Ser Ser Tyr Ser Cys Gln Val Thr His Glu Gly His Thr Val Glu
        195                 200                 205

Lys Ser Leu Ser Arg Ala Asp Cys Ser
    210                 215

<210> SEQ ID NO 213
<211> LENGTH: 450
<212> TYPE: PRT
<213> ORGANISM: Artificial Sequence
<220> FEATURE:
<223> OTHER INFORMATION: Chimaera

<400> SEQUENCE: 213

Gln Val Gln Leu Val Glu Ser Gly Gly Gly Ala Val Gln Pro Gly Gly
1               5                   10                  15

Ser Leu Arg Leu Ser Cys Ala Ala Ser Gly Phe Thr Phe Ser Asp Tyr
```

-continued

```
                  20                  25                  30
Ala Met His Trp Val Arg Gln Ala Pro Gly Lys Gly Leu Gln Trp Val
                 35                  40                  45
Ala Val Ile Ser Tyr Glu Gly Thr Tyr Lys Tyr Tyr Ala Asp Ser Val
             50                  55                  60
Lys Gly Arg Phe Thr Ile Ser Arg Asp Asn Ser Lys Asn Thr Leu Asn
 65                  70                  75                  80
Leu Gln Met Ser Ser Leu Arg Val Glu Asp Thr Ala Val Tyr Phe Cys
                 85                  90                  95
Val Lys Ala Arg Ala Phe Ala Ser Gly Gln Arg Ser Thr Ser Thr Val
            100                 105                 110
Pro Asp Tyr Trp Gly Gln Gly Thr Leu Val Thr Val Ser Ser Ala Lys
            115                 120                 125
Thr Thr Pro Pro Ser Val Tyr Pro Leu Ala Pro Gly Ser Ala Ala Gln
            130                 135                 140
Thr Asn Ser Met Val Thr Leu Gly Cys Leu Val Lys Gly Tyr Phe Pro
145                 150                 155                 160
Glu Pro Val Thr Val Thr Trp Asn Ser Gly Ser Leu Ser Ser Gly Val
                165                 170                 175
His Thr Phe Pro Ala Val Leu Gln Ser Asp Leu Tyr Thr Leu Ser Ser
            180                 185                 190
Ser Val Thr Val Pro Ser Ser Thr Trp Pro Ser Glu Thr Val Thr Cys
            195                 200                 205
Asn Val Ala His Pro Ala Ser Ser Thr Lys Val Asp Lys Lys Ile Val
            210                 215                 220
Pro Arg Asp Cys Gly Cys Lys Pro Cys Ile Cys Thr Val Pro Glu Val
225                 230                 235                 240
Ser Ser Val Phe Ile Phe Pro Pro Lys Pro Lys Asp Val Leu Thr Ile
                245                 250                 255
Thr Leu Thr Pro Lys Val Thr Cys Val Val Val Asp Ile Ser Lys Asp
                260                 265                 270
Asp Pro Glu Val Gln Phe Ser Trp Phe Val Asp Asp Val Glu Val His
            275                 280                 285
Thr Ala Gln Thr Gln Pro Arg Glu Glu Gln Phe Asn Ser Thr Phe Arg
            290                 295                 300
Ser Val Ser Glu Leu Pro Ile Met His Gln Asp Trp Leu Asn Gly Lys
305                 310                 315                 320
Glu Phe Lys Cys Arg Val Asn Ser Ala Ala Phe Pro Ala Pro Ile Glu
                325                 330                 335
Lys Thr Ile Ser Lys Thr Lys Gly Arg Pro Lys Ala Pro Gln Val Tyr
            340                 345                 350
Thr Ile Pro Pro Pro Lys Glu Gln Met Ala Lys Asp Lys Val Ser Leu
            355                 360                 365
Thr Cys Met Ile Thr Asp Phe Phe Pro Glu Asp Ile Thr Val Glu Trp
            370                 375                 380
Gln Trp Asn Gly Gln Pro Ala Glu Asn Tyr Lys Asn Thr Gln Pro Ile
385                 390                 395                 400
Met Asp Thr Asp Gly Ser Tyr Phe Val Tyr Ser Lys Leu Asn Val Gln
                405                 410                 415
Lys Ser Asn Trp Glu Ala Gly Asn Thr Phe Thr Cys Ser Val Leu His
                420                 425                 430
Glu Gly Leu His Asn His His Thr Glu Lys Ser Leu Ser His Ser Pro
            435                 440                 445
```

```
Gly Lys
    450

<210> SEQ ID NO 214
<211> LENGTH: 445
<212> TYPE: PRT
<213> ORGANISM: Artificial Sequence
<220> FEATURE:
<223> OTHER INFORMATION: Chimaera

<400> SEQUENCE: 214

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Asn Phe Gln Ile Ser
            20                  25                  30

Ala Ile His Trp Val Arg Gln Ala Ser Gly Lys Gly Leu Glu Trp Val
        35                  40                  45

Gly Arg Ile Arg Ser Lys Ser His Asn Tyr Ala Thr Leu Tyr Ala Ala
    50                  55                  60

Ser Leu Lys Gly Arg Phe Thr Leu Ser Arg Asp Asp Ser Arg Asn Thr
65                  70                  75                  80

Ala Tyr Leu Gln Met Ser Ser Leu Gln Thr Glu Asp Met Ala Val Tyr
                85                  90                  95

Tyr Cys Thr Val Leu Ser Ala Asn Tyr Asp Thr Phe Asp Tyr Trp Gly
            100                 105                 110

Gln Gly Thr Leu Val Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
        275                 280                 285

Pro Arg Glu Glu Gln Phe Gln Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350
```

```
Lys Glu Gln Met Ala Lys Asp Lys Val Ser Leu Thr Cys Met Ile Thr
                355                 360                 365

Asp Phe Phe Pro Glu Asp Ile Thr Val Glu Trp Gln Trp Asn Gly Gln
            370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
                435                 440                 445

<210> SEQ ID NO 215
<211> LENGTH: 449
<212> TYPE: PRT
<213> ORGANISM: Artificial Sequence
<220> FEATURE:
<223> OTHER INFORMATION: Chimaera

<400> SEQUENCE: 215

Gln Val Gln Leu Val Glu Ser Gly Gly Gly Val Val Gln Pro Gly Arg
1               5                   10                  15

Ser Leu Arg Val Ser Cys Ala Ala Ser Gly Phe Thr Phe Ser Ser Tyr
                20                  25                  30

Asp Met His Trp Val Arg Gln Ala Pro Gly Lys Gly Leu Glu Trp Val
            35                  40                  45

Ala Val Ile Trp Phe Asp Gly Ser Asn Glu Phe Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Asp Leu Gly Ala Ser Val Thr Thr Ser Asn Ala Glu Asn Phe
            100                 105                 110

His His Trp Gly Gln Gly Thr Leu Val Thr Val Ser Ser Ala Lys Thr
        115                 120                 125

Thr Pro Pro Ser Val Tyr Pro Leu Ala Pro Gly Ser Ala Ala Gln Thr
            130                 135                 140

Asn Ser Met Val Thr Leu Gly Cys Leu Val Lys Gly Tyr Phe Pro Glu
145                 150                 155                 160

Pro Val Thr Val Thr Trp Asn Ser Gly Ser Leu Ser Ser Gly Val His
                165                 170                 175

Thr Phe Pro Ala Val Leu Gln Ser Asp Leu Tyr Thr Leu Ser Ser Ser
            180                 185                 190

Val Thr Val Pro Ser Ser Thr Trp Pro Ser Glu Thr Val Thr Cys Asn
        195                 200                 205

Val Ala His Pro Ala Ser Ser Thr Lys Val Asp Lys Lys Ile Val Pro
    210                 215                 220

Arg Asp Cys Gly Cys Lys Pro Cys Ile Cys Thr Val Pro Glu Val Ser
225                 230                 235                 240

Ser Val Phe Ile Phe Pro Pro Lys Pro Lys Asp Val Leu Thr Ile Thr
                245                 250                 255

Leu Thr Pro Lys Val Thr Cys Val Val Val Asp Ile Ser Lys Asp Asp
            260                 265                 270
```

Pro Glu Val Gln Phe Ser Trp Phe Val Asp Val Glu Val His Thr
            275                 280                 285

Ala Gln Thr Gln Pro Arg Glu Gln Phe Gln Ser Thr Phe Arg Ser
    290                 295                 300

Val Ser Glu Leu Pro Ile Met His Gln Asp Trp Leu Asn Gly Lys Glu
305                 310                 315                 320

Phe Lys Cys Arg Val Asn Ser Ala Ala Phe Pro Ala Pro Ile Glu Lys
                325                 330                 335

Thr Ile Ser Lys Thr Lys Gly Arg Pro Lys Ala Pro Gln Val Tyr Thr
                340                 345                 350

Ile Pro Pro Pro Lys Glu Gln Met Ala Lys Asp Lys Val Ser Leu Thr
                355                 360                 365

Cys Met Ile Thr Asp Phe Phe Pro Glu Asp Ile Thr Val Glu Trp Gln
    370                 375                 380

Trp Asn Gly Gln Pro Ala Glu Asn Tyr Lys Asn Thr Gln Pro Ile Met
385                 390                 395                 400

Asp Thr Asp Gly Ser Tyr Phe Val Tyr Ser Lys Leu Asn Val Gln Lys
                405                 410                 415

Ser Asn Trp Glu Ala Gly Asn Thr Phe Thr Cys Ser Val Leu His Glu
                420                 425                 430

Gly Leu His Asn His His Thr Glu Lys Ser Leu Ser His Ser Pro Gly
                435                 440                 445

Lys

<210> SEQ ID NO 216
<211> LENGTH: 444
<212> TYPE: PRT
<213> ORGANISM: Artificial Sequence
<220> FEATURE:
<223> OTHER INFORMATION: Chimaera

<400> SEQUENCE: 216

Glu Val Gln Leu Val Gln Ser Gly Ala Glu Val Lys Lys Pro Gly Glu
1               5                   10                  15

Ser Leu Lys Ile Ser Cys Lys Ala Phe Gly Tyr Ser Phe Thr Asn Phe
                20                  25                  30

Trp Ile Gly Trp Val Arg Gln Val Pro Gly Lys Gly Leu Glu Trp Val
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Asp Thr Ala Tyr
65                  70                  75                  80

Leu Gln Trp Gly His Leu Lys Ala Ser Asp Ser Ala Met Tyr Phe Cys
                85                  90                  95

Ala Arg Arg Gly Phe Trp Thr Gly Ser Gln Ile Glu Tyr Trp Gly Gln
            100                 105                 110

Gly Thr Gln Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Val Thr Val Pro Ser
                180                 185                 190

Ser Thr Trp Pro Ser Glu Thr Val Thr Cys Asn Val Ala His Pro Ala
            195                 200                 205

Ser Ser Thr Lys Val Asp Lys Lys Ile Val Pro Arg Asp Cys Gly Cys
        210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Gln Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
        355                 360                 365

Phe Phe Pro Glu Asp Ile Thr Val Glu Trp Gln Trp Asn Gly Gln Pro
370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
            420                 425                 430

His Thr Glu Lys Ser Leu Ser His Ser Pro Gly Lys
        435                 440

<210> SEQ ID NO 217
<211> LENGTH: 217
<212> TYPE: PRT
<213> ORGANISM: Artificial Sequence
<220> FEATURE:
<223> OTHER INFORMATION: Chimaera

<400> SEQUENCE: 217

Gln Ser Ala Leu Thr Gln Pro Pro Ser Ala Ser Gly Ser Pro Gly His
1               5                   10                  15

Ser Val Thr Ile Ser Cys Thr Gly Thr Ser Ser Asp Val Gly Gln Tyr
            20                  25                  30

Ser Phe Val Ser Trp Tyr Gln Gln Tyr Pro Gly Lys Ala Pro Lys Val
        35                  40                  45

Ile Ile Tyr Asp Val Ser Lys Arg Ser Ser Gly Val Pro Asp Arg Phe
    50                  55                  60

Phe Gly Ser Lys Ser Ala Asn Thr Ala Ser Leu Thr Val Ser Gly Val
65                  70                  75                  80

Gln Glu Glu Asp Glu Ala Asp Tyr Phe Cys Ser Ser Tyr Gly Gly Ser
                85                  90                  95

```
Lys Tyr Pro Trp Val Phe Gly Gly Gly Thr Lys Leu Thr Val Leu Gly
            100                 105                 110

Gln Pro Lys Ser Ser Pro Ser Val Thr Leu Phe Pro Pro Ser Ser Glu
        115                 120                 125

Glu Leu Glu Thr Asn Lys Ala Thr Leu Val Cys Thr Ile Thr Asp Phe
130                 135                 140

Tyr Pro Gly Val Val Thr Val Asp Trp Lys Val Asp Gly Thr Pro Val
145                 150                 155                 160

Thr Gln Gly Met Glu Thr Thr Gln Pro Ser Lys Gln Ser Asn Asn Lys
                165                 170                 175

Tyr Met Ala Ser Ser Tyr Leu Thr Leu Thr Ala Arg Ala Trp Glu Arg
            180                 185                 190

His Ser Ser Tyr Ser Cys Gln Val Thr His Glu Gly His Thr Val Glu
        195                 200                 205

Lys Ser Leu Ser Arg Ala Asp Cys Ser
        210                 215

<210> SEQ ID NO 218
<211> LENGTH: 458
<212> TYPE: PRT
<213> ORGANISM: Artificial Sequence
<220> FEATURE:
<223> OTHER INFORMATION: Chimaera

<400> SEQUENCE: 218

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Pro Asn Tyr
            20                  25                  30

Val Met Thr Trp Val Arg Gln Ala Pro Gly Lys Gly Leu Glu Trp Val
        35                  40                  45

Ser Gly Ile Ser Gly Ser Gly Gly Ser Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Leu Tyr Tyr Cys
                85                  90                  95

Ala Lys Gly Ser Gly Gly Ile Trp Gly Gln Gly Thr Met Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Arg Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240
```

Pro Pro Lys Pro Lys Asp Thr Leu Met Ile Ser Arg Thr Pro Glu Val
              245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Gln Ser Ala Leu Thr
        435                 440                 445

Gln Pro Arg Ser Val Ser Gly Ser Pro Gly
    450                 455

<210> SEQ ID NO 219
<211> LENGTH: 216
<212> TYPE: PRT
<213> ORGANISM: Artificial Sequence
<220> FEATURE:
<223> OTHER INFORMATION: Chimaera

<400> SEQUENCE: 219

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp His Gln Gln His Pro Gly Lys Ala Pro Lys Leu
        35                  40                  45

Leu Ile Tyr Asp Val Thr Lys Arg Pro Ser Gly Val Pro Asp Arg Phe
    50                  55                  60

Ser Gly Ser Lys Ser Gly Asn Thr Ala Ala Leu Thr Ile Ser Gly Leu
65                  70                  75                  80

Gln Ala Glu Asp Glu Ala Asp Tyr Tyr Cys His Ser Tyr Val Gly Ser
                85                  90                  95

Tyr Thr Leu Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
            165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
            210                 215

<210> SEQ ID NO 220
<211> LENGTH: 114
<212> TYPE: PRT
<213> ORGANISM: Artificial Sequence
<220> FEATURE:
<223> OTHER INFORMATION: Chimaera

<400> SEQUENCE: 220

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Pro Asn Tyr
            20                  25                  30

Val Met Thr Trp Val Arg Gln Ala Pro Gly Lys Gly Leu Glu Trp Val
        35                  40                  45

Ser Gly Ile Ser Gly Ser Gly Ser Thr Asp Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Val Glu Asp Thr Ala Leu Tyr Tyr Cys
            85                  90                  95

Ala Lys Gly Ser Gly Gly Ile Trp Gly Gln Gly Thr Met Val Thr Val
            100                 105                 110

Ser Ser

<210> SEQ ID NO 221
<211> LENGTH: 111
<212> TYPE: PRT
<213> ORGANISM: Artificial Sequence
<220> FEATURE:
<223> OTHER INFORMATION: Chimaera

<400> SEQUENCE: 221

Gln Ser Ala Leu Thr Gln Pro Pro Ser Ala Ser Gly Ser Pro Gly His
1               5                   10                  15

Ser Val Thr Ile Ser Cys Thr Gly Thr Ser Ser Asp Val Gly Gln Tyr
            20                  25                  30

Ser Phe Val Ser Trp Tyr Gln Gln Tyr Pro Gly Lys Ala Pro Lys Ile
        35                  40                  45

Ile Ile Tyr Asp Val Ser Lys Arg Ser Ser Gly Val Pro Asp Arg Phe
    50                  55                  60

Phe Gly Ser Lys Ser Ala Asn Thr Ala Ser Leu Thr Val Ser Gly Val
65                  70                  75                  80

Gln Glu Glu Asp Glu Ala Asp Tyr Phe Cys Ser Ser Tyr Gly Gly Ser
            85                  90                  95

Lys Tyr Pro Trp Val Phe Gly Gly Gly Thr Lys Leu Thr Val Leu
            100                 105                 110

<210> SEQ ID NO 222
<211> LENGTH: 111
<212> TYPE: PRT
<213> ORGANISM: Artificial Sequence
<220> FEATURE:
<223> OTHER INFORMATION: Chimaera

<400> SEQUENCE: 222

Gln Ser Ala Leu Thr Gln Pro Pro Ser Ala Ser Gly Ser Pro Gly His
1               5                   10                  15

Ser Val Thr Ile Ser Cys Thr Gly Thr Ser Ser Asp Val Gly Gln Tyr
            20                  25                  30

Ser Phe Val Ser Trp Tyr Gln Gln Tyr Pro Gly Lys Ala Pro Lys Val
        35                  40                  45

Ile Ile Tyr Asp Val Ser Lys Arg Ser Ser Gly Val Pro Asp Arg Phe
    50                  55                  60

Phe Gly Ser Lys Ser Ala Asn Thr Ala Ser Leu Thr Val Ser Gly Val
65                  70                  75                  80

Gln Glu Glu Asp Glu Ala Asp Tyr Phe Cys Ser Ser Tyr Gly Gly Ser
                85                  90                  95

Lys Tyr Pro Trp Val Phe Gly Gly Thr Lys Leu Thr Val Leu
            100                 105                 110

<210> SEQ ID NO 223
<211> LENGTH: 339
<212> TYPE: DNA
<213> ORGANISM: Homo sapiens

<400> SEQUENCE: 223
gatattgtta tgactcaatc accagactcc ctggctgtgt ctctgggcga gagggccacc      60
atcaactgca agtcaagcca gaatatttta tacagctccg acaataagaa ctacttagct     120
tggtaccagc agaaaccagg acagcctcct aaactactca tttactgggc atctacccgg     180
gaatccgggg tccctgaccg attcagtggc agcgggtctg ggacagattt cactctcacc     240
atcagcagcc tgcaggctga agatgtggca gtttattact gtcagcaata ttatagtatt     300
cctcggacgt tcggccaagg gaccaaggtg gagatcaaa                            339

<210> SEQ ID NO 224
<211> LENGTH: 14
<212> TYPE: PRT
<213> ORGANISM: Homo sapiens

<400> SEQUENCE: 224

Thr Gly Thr Ser Ser Asp Val Gly Gln Tyr Ser Phe Val Ser
1               5                   10

HUMAN ANTI-TAU ANTIBODIES

This is a national stage application under 35 U.S.C. §371 of International Application No. PCT/US2013/076952, filed Dec. 12, 2013, which designated the U.S. and which claims the benefit of U.S. Provisional Application No. 61/745,410 filed Dec. 12, 2012, all of which are incorporated herein by reference.

BACKGROUND OF THE INVENTION

Field of the Invention

The present invention generally relates to novel tau-specific binding molecules, particularly human antibodies as well as fragments, derivatives and variants thereof that recognize the tau protein, including pathologically phosphorylated tau and aggregated forms of tau. In addition, the present invention relates to pharmaceutical and diagnostic compositions comprising such binding molecules, antibodies and mimics thereof valuable both as a diagnostic tool to identify tau and toxic tau species in plasma and CSF and also in passive vaccination strategies for treating neurodegenerative tauopathies such as Alzheimer's disease (AD), amyotrophic lateral sclerosis/parkinsonism-dementia complex (ALS-PDC), argyrophilic grain dementia (AGD), British type amyloid angiopathy, cerebral amyloid angiopathy, corticobasal degeneration (CBD), Creutzfeldt-Jakob disease (CJD), dementia pugilistica, diffuse neurofibrillary tangles with calcification, Down's syndrome, frontotemporal dementia, frontotemporal dementia with parkinsonism linked to chromosome 17 (FTDP-17), frontotemporal lobar degeneration, Gerstmann-Sträussler-Scheinker disease, Hallervorden-Spatz disease, inclusion body myositis, multiple system atrophy, myotonic dystrophy, Niemann-Pick disease type C (NP-C), non-Guamanian motor neuron disease with neurofibrillary tangles, Pick's disease (PiD), postencephalitic parkinsonism, prion protein cerebral amyloid angiopathy, progressive subcortical gliosis, progressive supranuclear palsy (PSP), subacute sclerosing panencephalitis, tangle only dementia, multi-infarct dementia and ischemic stroke.

Background Art

Protein accumulation, modifications and aggregation are pathological aspects of numerous neurodegenerative diseases. Pathologically modified and aggregated tau including hyperphosphorylated tau conformers are an invariant hallmark of tauopathies and correlate with disease severity.

Tau is a microtubule-associated protein expressed in the central nervous system with a primary function to stabilize microtubules. There are six major isoforms of tau expressed mainly in the adult human brain, which are derived from a single gene by alternative splicing. Under pathological conditions, the tau protein becomes hyperphosphorylated, resulting in a loss of tubulin binding and destabilization of microtubules followed by the aggregation and deposition of tau in pathogenic neurofibrillary tangles. Disorders related to tau—collectively referred to as neurodegenerative tauopathies—are part of a group of protein misfolding disorders including Alzheimer's disease (AD), progressive supranuclear palsy, Pick's disease, corticobasal degeneration, FTDP'-17 among others. More than 40 mutations in tau gene have been reported to be associated with hereditary frontotemporal dementia demonstrating that tau gene mutations are sufficient to trigger neurodegeneration (Cairns et al., Am. J. Pathol. 171 (2007), 227-40). Studies in transgenic mice and cell culture indicate that in AD, tau pathology can be caused by a pathological cascade in which Aβ lies upstream of tau (Götz et al., Science 293 (2001), 1491-1495). Other finding however point to a dual-pathway model where both cascades function independently of each other (van de Nes et al., Acta Neuropathol. 111 (2006), 126-138). Immunotherapies targeting the beta-amyloid peptide in AD have produced encouraging, results in animal models and shown promise in clinical trials. More recent autopsy data from a small number of subjects suggests that clearance of beta-amyloid plaques in patients with progressed AD may not be sufficient to halt cognitive deterioration, emphasizing the need for additional therapeutic strategies for AD (Holmes et al., Lancet 372 (2008), 216-223; Boche et at, Acta Neuropathol. 120 (2010), 13-20). In the wake of the success of Abeta-based immunization therapy in transgenic animal models, the concept of active immunotherapy was expanded to the tau protein. Active vaccination of wild type mice using the tau protein was however found to induce the formation of neurofibrillary tangles, axonal damage and mononuclear infiltrates in the central nervous system, accompanied by neurologic deficits (Rosenmann et al., Arch Neurol. 63 (2006), 1459-1467). Subsequent studies in transgenic mouse lines using active vaccination with phosphorylated tau peptides revealed reduced brain levels of tau aggregates in the brain and slowed progression of behavior impairments (Sigurdsson, J. Alzheimers. Dis. 15 (2008), 157-168; Boimel et al., Exp. Neurol. 224 (2010), 472-485). These findings highlight the potential benefit but also the tremendous risks associated with active immunotherapy approaches targeting tau. Novel therapeutic strategies are urgently needed addressing pathological tau proteins with efficacious and safe therapy.

Passive immunization with human antibodies derived from healthy human subjects which are evolutionarily optimized and affinity matured by the human immune system would provide a promising new therapeutic avenue with a high probability for excellent efficacy and safety.

BRIEF SUMMARY OF THE INVENTION

The present invention makes use of the tau-specific immune response of healthy human subjects for the isolation of natural anti-tau specific human monoclonal antibodies. In particular, experiments performed in accordance with the present invention were successful in the isolation of monoclonal tau-specific antibodies from a pool of healthy human subjects with no signs of a neurodegenerative tauopathy.

The present invention is thus directed to human antibodies, antigen-binding fragments and similar antigen-binding molecules which are capable of specifically recognizing tau. By "specifically recognizing tau", "antibody specific to/for tau" and "anti-tau antibody" is meant specifically, generally, and collectively, antibodies to the native form of tau, or aggregated or pathologically modified tau isoforms. Provided herein are human antibodies selective for full-length, pathologically phosphorylated and aggregated forms.

In a particular embodiment of the present invention, the human antibody or antigen-binding fragment thereof demonstrates the immunological binding characteristics of an antibody characterized by the variable regions $V_H$ and/or $V_L$ as set forth in FIG. 7.

The antigen-binding fragment of the antibody can be a single chain Fv fragment, an F(ab') fragment, an F(ab) fragment, and an F(ab)$_2$ fragment, or any other antigen binding fragment. In a specific embodiment, infra, the antibody or fragment thereof is a human IgG isotype antibody. Alternatively, the antibody is a chimeric human-murine or murinized antibody, the latter being particularly useful for diagnostic methods and studies in animals.

Furthermore, the present invention relates to compositions comprising the antibody of the present invention or active fragments thereof, or agonists and cognate molecules, or alternately, antagonists of the same and to immunotherapeutic and immunodiagnostic methods using such compositions in the prevention, diagnosis or treatment of a tauopathy, wherein an effective amount of the composition is administered to a patient in need thereof.

Naturally, the present invention extends to the immortalized human B memory lymphocyte and B cell, respectively, that produces the antibody having the distinct and unique characteristics as defined below.

The present invention also relates to polynucleotides encoding at least a variable region of an immunoglobulin chain of the antibody of the invention. In one embodiment, said variable region comprises at least one complementarity determining region (CDR) of the $V_H$ and/or $V_L$ of the variable region as set forth in FIG. 7.

Accordingly, the present invention also encompasses vectors comprising said polynucleotides and host cells transformed therewith as well as their use for the production of an antibody and equivalent binding, molecules which are specific for tau. Means and methods for the recombinant production of antibodies and mimics thereof as well as methods of screening for competing binding molecules, e.g., antibodies, are known in the art. However, as described herein, in particular with respect to therapeutic applications in human the antibody of the present invention is a human antibody in the sense that application of said antibody is substantially free of an immune response directed against such antibody otherwise observed for chimeric and even humanized antibodies.

Furthermore, disclosed herein are compositions and methods that can be used to identify tau in samples. The disclosed anti-tau antibodies can be used to screen human blood, CSF, and urine for the presence of tau in samples, for example, by using ELISA-based or surface adapted assay. The methods and compositions disclosed herein can aid in neurodegenerative tauopathies such as Alzheimer's disease diagnosis and can be used to monitor disease progression and therapeutic efficacy.

Hence, it is a particular object of the present invention to provide methods for treating, diagnosing or preventing a neurodegenerative tauopathy such as Alzheimer's disease, amyotrophic lateral sclerosis/parkinsonism-dementia complex, argyrophilic gain dementia, British type amyloid angiopathy, cerebral amyloid angiopathy, corticobasal degeneration, Creutzfeldt-Jakob disease, dementia pugilistica, diffuse neurofibrillary tangles with calcification, Down's syndrome, frontotemporal dementia, frontotemporal dementia with parkinsonism linked to chromosome 17, frontotemporal lobar degeneration, Gerstmann-Sträussler-Scheinker disease, Hallervorden-Spatz disease, inclusion body myositis, multiple system atrophy, myotonic dystrophy, Niemann-Pick disease type C, non-Guamanian motor neuron disease with neurofibrillary tangles, Pick's disease, postencephalitic parkinsonism, prion protein cerebral amyloid angiopathy, progressive subcortical gliosis, progressive supranuclear palsy, subacute sclerosing panencephalitis, tangle only dementia, multi-infarct dementia and ischemic stroke. The methods comprise administering, an effective concentration of a human antibody or antibody derivative to the subject where the antibody targets tau.

Further embodiments of the present invention will be apparent from the description and Examples that follow.

BRIEF DESCRIPTION OF THE DRAWINGS/FIGURES

FIG. 1. Amino acid and nucleotide sequences of the variable region, i.e. heavy chain and lambda light chain of human antibodies NI-105.4E4 (A), NI-105.24B2 (B) and NI-105.4A3 (C). Framework (FR) and complementarity determining regions (CDRs) are indicated with the CDRs being underlined. Due to the cloning strategy the amino acid sequence at the N-terminus of the heavy chain and light chain may potentially contain primer-induced alterations in FR1, which however do not substantially affect the biological activity of the antibody. In order to provide a consensus human antibody, the nucleotide and amino acid sequences of the original clone were aligned with and tuned in accordance with the pertinent human germ line variable region sequences in the database; see, e.g., Vbase (http://vbase.mrc-cpe.cam.ac.uk/) hosted by the MRC Centre for Protein Engineering (Cambridge, UK). Those amino acids, which are considered to potentially deviate from the consensus germ line sequence due to the PCR primer and thus have been replaced in the amino acid sequence, are indicated in bold.

FIG. 2. NI-105.4E4 binds to neurofibrillary tangles (NFT), dystrophic neurites and neuropil threads in AD brain and human TauP301L expressing mice. NI-105.4E4 staining identifies NFTs and neuropil threads in AD brain (A), with no significant binding to tau in the brain of healthy control subject (B). In TauP301L transgenic mouse (E-I) NI-105.4E4 binds strongly to the pathological tau resembling NFT (E, and H), neuropil threads (E and G) and dystrophic neurites (E and H). In addition, NI-105.4E4 also identifies tau aggregates at pre-tangle stage (I). NI-105.4E4 binds to NFT, dystrophic neurites and neuropil threads in transgenic mouse expressing human APP with the Swedish and the Arctic mutation and TauP301L; the arrow marks a beta-amyloid plaque, surrounded by dystrophic neurites recognized by NI-105.4E4 (J). Secondary antibody only does not give signal both in human AD (C) and healthy control (D).

Figure 3:
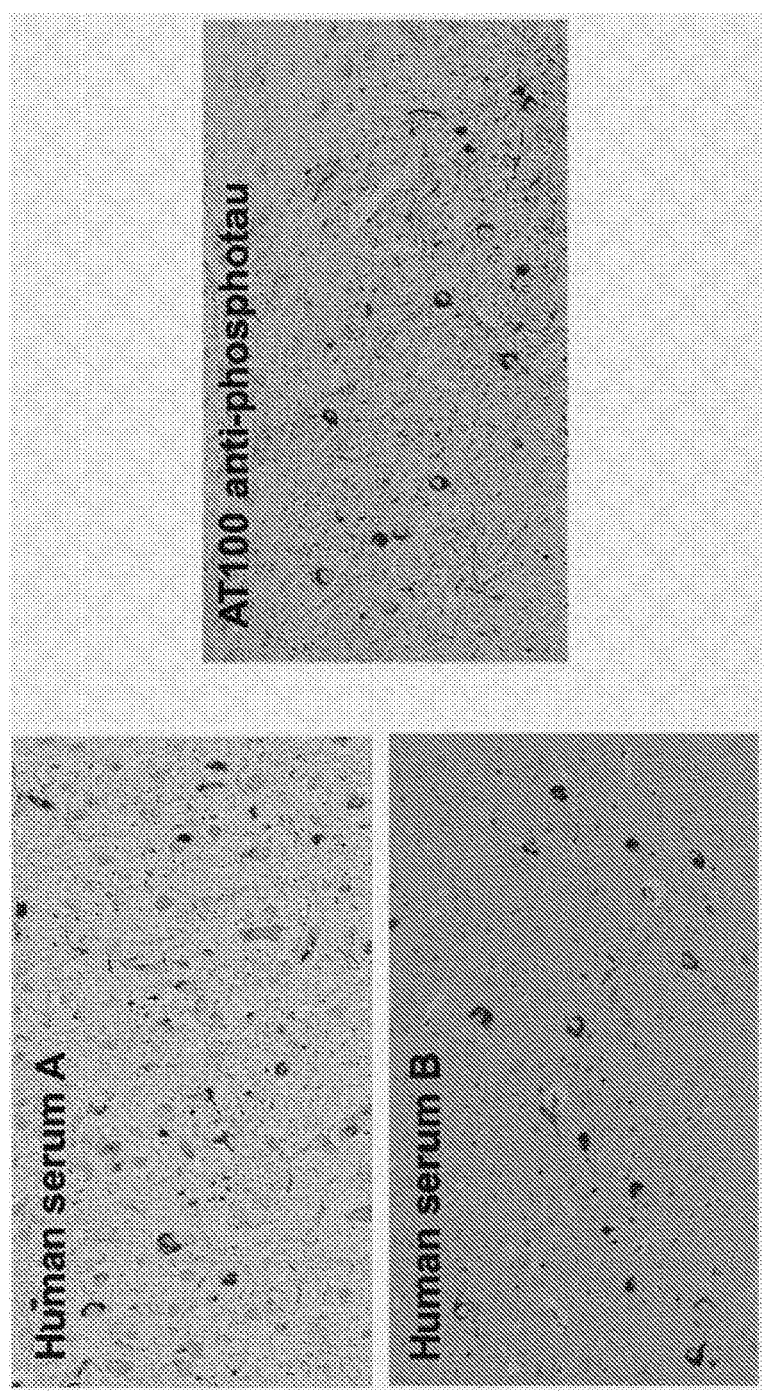

FIG. 3. Tissue amyloid plaque immunoreactivity (TAPIR) assay. Neurofibrillary tangles were stained with either the anti-phospho-tau antibody AT100 or sera isolated from healthy elderly subjects.

Figure 4:
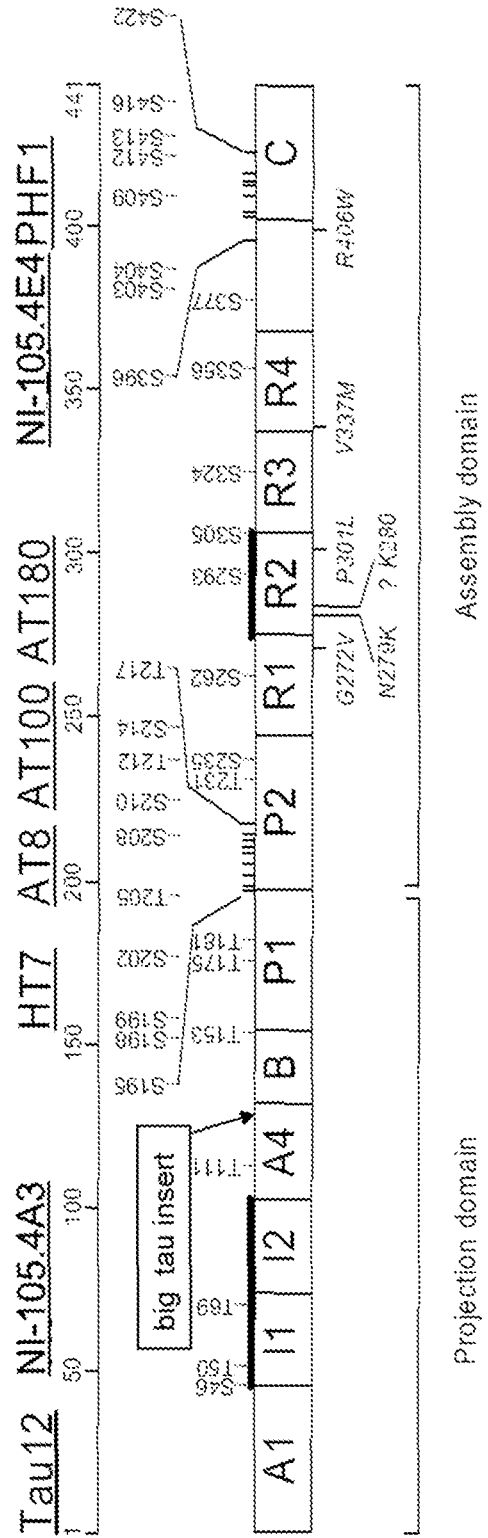

FIG. 4. Schematic representation of the NI-105.4E4 and NI-105.4A3 epitopes and epitopes of commonly used commercially available mouse monoclonal tau antibodies are shown. Human antibody NI-105.4E4 targets a unique epitope that comprises two linear polypeptides, one of which is located in the microtubule binding domain (R4) of tau which is masked in physiological microtubule-associated tau. Tau-12 (Covance, Calif., U.S.A.), HT7, AT8, AT180 (Thermo Scientific, U.S.A.); PHF1 (Lewis et al., Science 293 (2001), 1487-1491).

Figure 5:
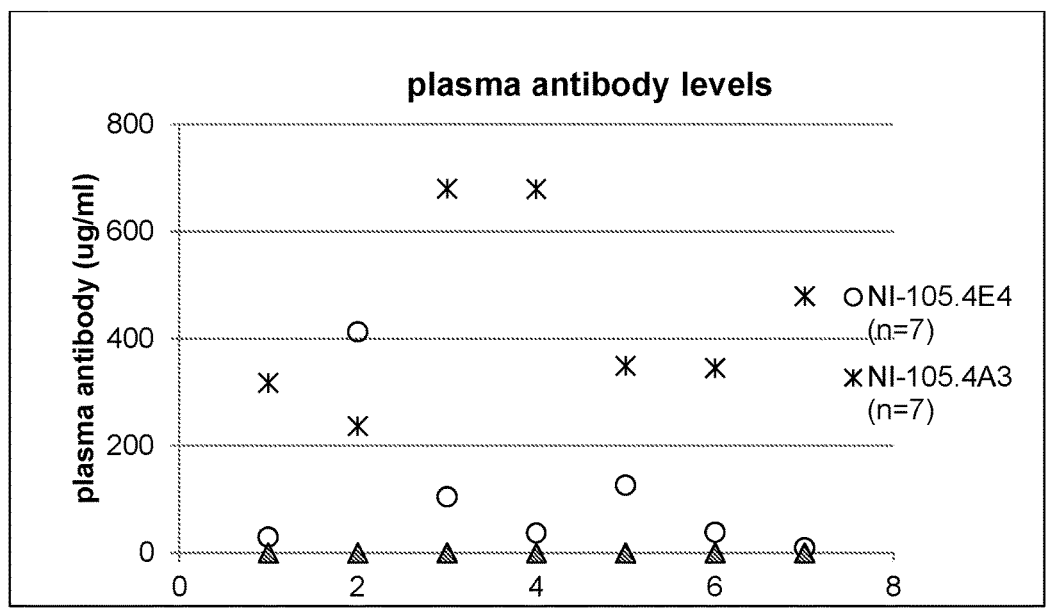

FIG. 5. Human IgG levels in the plasma of mice following intraperitoneal administration of 30 mg/kg NI-105.4E4 or NI-105.4A3 human anti-tau antibody.

Figure 6:
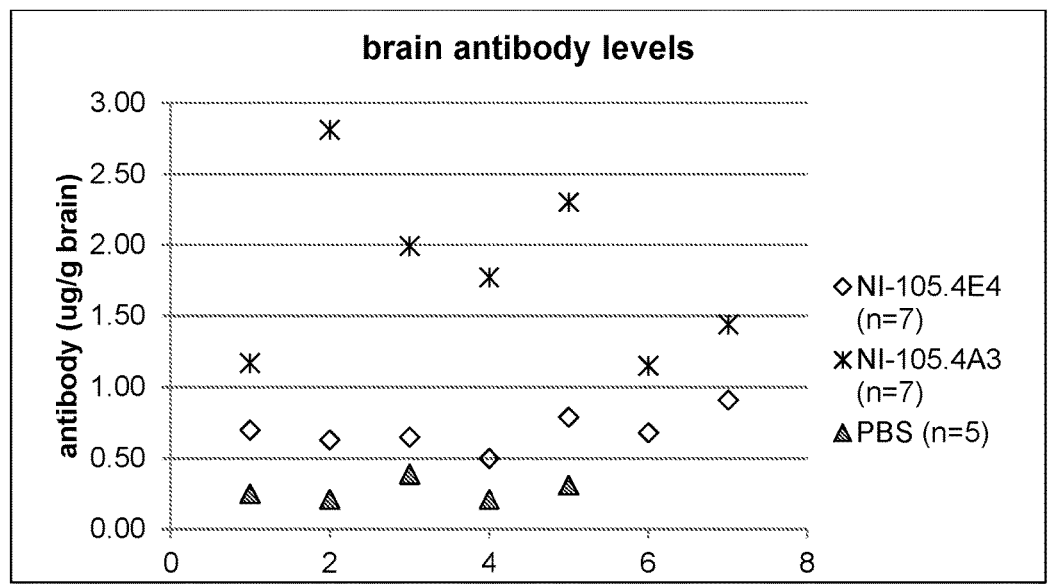

FIG. 6. Human IgG levels in brain homogenate of mice following intraperitoneal administration of 30 mg/kg NI-105.4E4 or NI-105.4A3 human anti-tau antibody.

FIG. 7. Amino acid sequence of heavy chain and light chain variable regions of (A) NI-105.17C1, (B) NI-105.6C5, (C) NI-105.29G10, (D) NI-105.6L9, (E) NI-105.40E8, (F) NI-105.48E5, (G) NI-105.6E3, (H) NI-105.22E1, (I) NI-105.26B12, (J) NI-105.12E12, (K) NI-105.60E7, (L) NI-105.14E2, (M) NI-105.39E2, (N) NI 105.19C6, and (O)

NI-105.9C4 human anti-tau antibodies. Complementarity determining regions (CDRs) are underlined.

FIG. 8. (A) Binding of ch17C1, ch17C1(N31Q) mIgG2a and ch17C1(N31Q) mIgG1 Agly to recombinant Tau in an ELISA assay. (B) Comparison of recombinant Tau binding by ch17C1(N31Q) mIgG2a and ch17C1(N31Q, I48V) mIgG2a in an ELISA assay.

Figure 9:
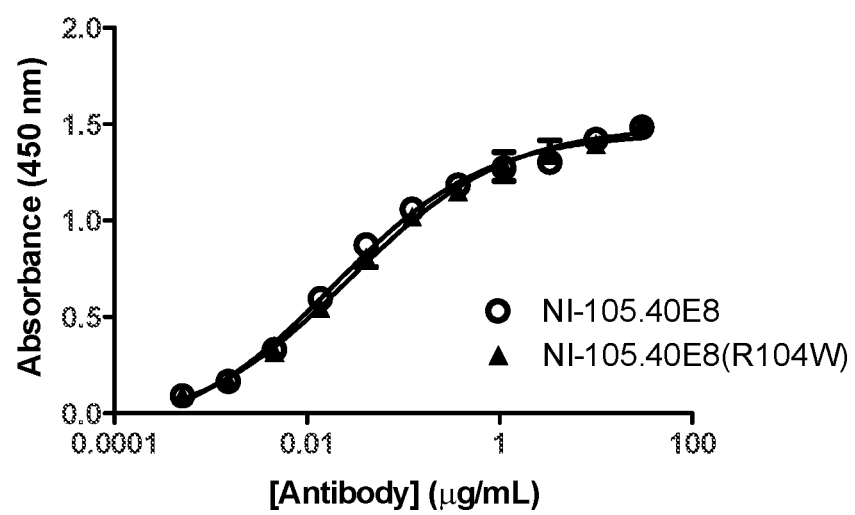

FIG. 9. Comparison of recombinant Tau binding by NI-105.40E8 hIgG1 and NI-105.40E8(R104W) hIgG1 in an ELISA assay.

Figure 10:
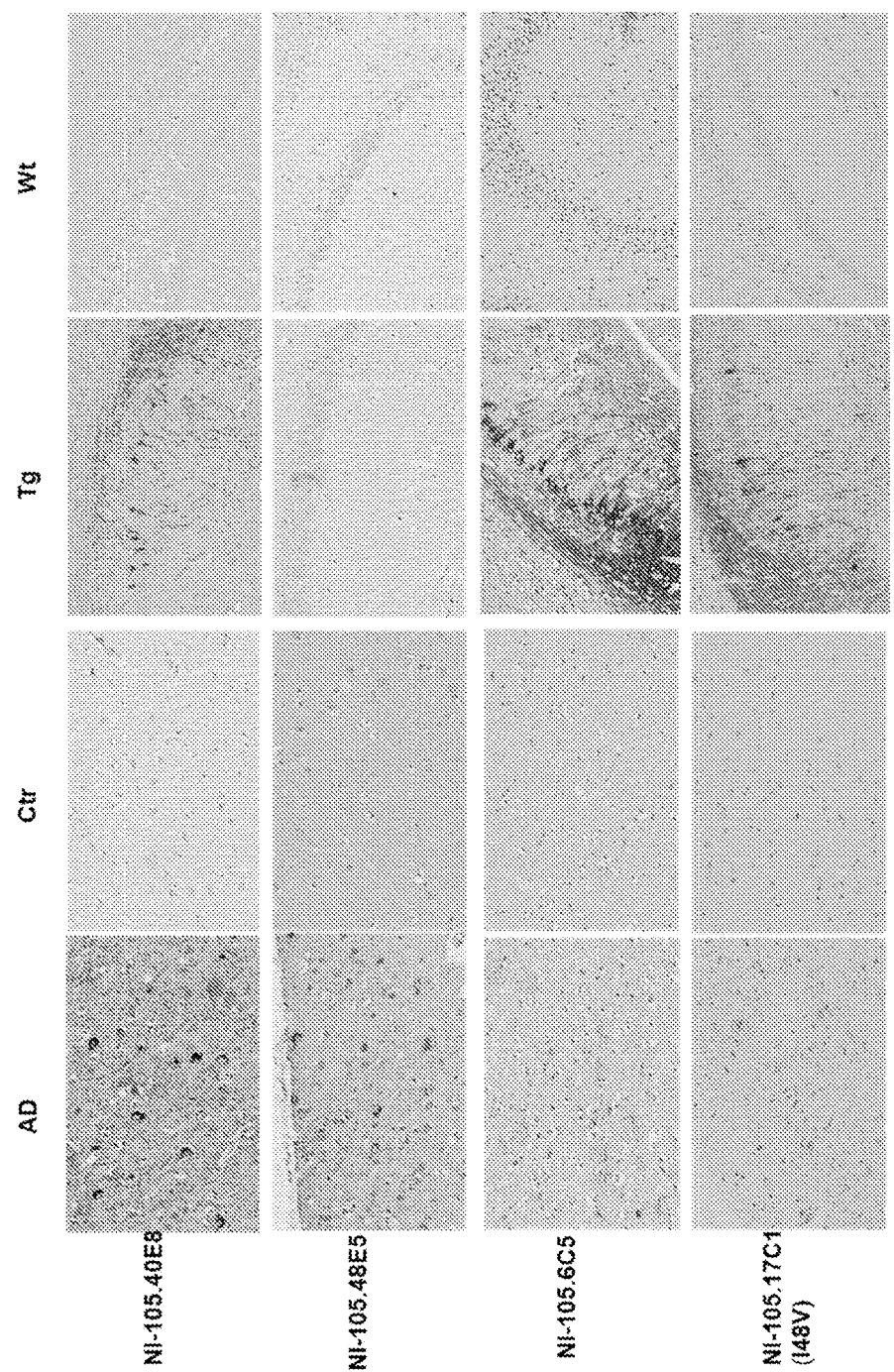

FIG. 10. Binding of NI-105.40E8, NI-105.48E5, NI-105.6C5 and NI-105.17C1(I48V) human anti-tau antibodies to pathologically aggregated tau in AD brain and in the brain of transgenic mouse model of tauopathy. Representative images of human anti-tau antibody binding to pathological tau aggregates in the brain of Alzheimer's disease (AD) and in the brain of transgenic mouse of tauopathy (Tg). Control tissue samples were obtained from mentally healthy subject (Ctr) or wild type mouse brain (Wt).

Figure 11:
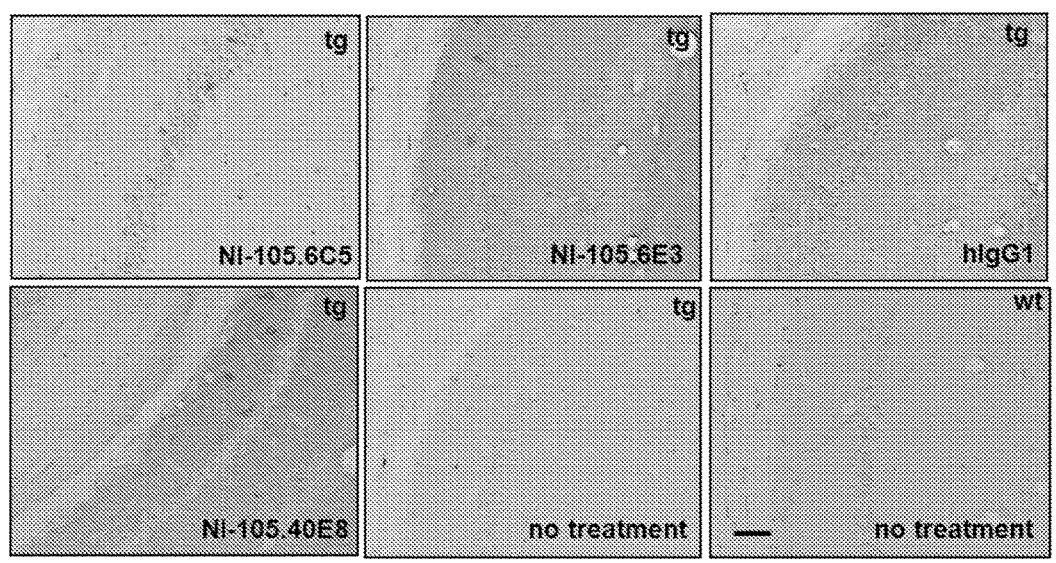

FIG. 11. Brain penetration of NI-105.6C5 or NI-105.6E3 human anti-tau antibodies in TauP301L mice. "tg" indicates representative sections from transgenic animals either treated or untreated, and "wt" indicates an untreated non-transgenic animal. Scale bar: 50 μm.

FIG. 12. Effects of chronic treatment of TauP301L mice with ch4E4(N30Q) and ch17C1(N31Q). Total human tau (A), human pS199 tau (B), human pT231 tau (C) and human pT181 tau (D) levels in soluble, and insoluble fraction of brain protein extracts were quantified with commercial ELISA.

Figure 13:
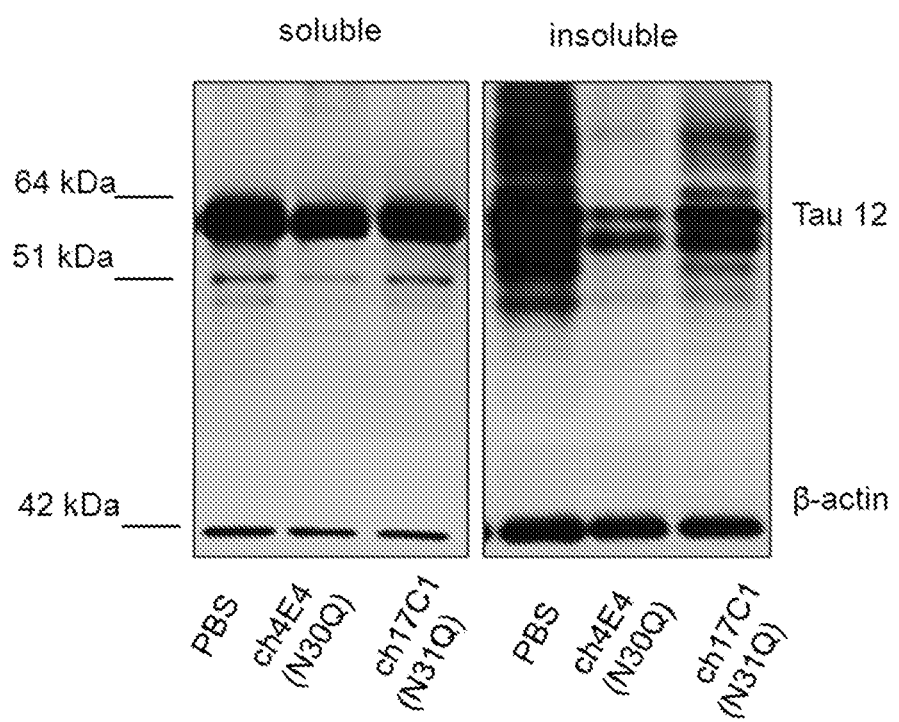

FIG. 13. Soluble and insoluble human tau in TauP301L mice treated with ch17C1(N31Q) and ch4E4(N30Q) detected by Western blots.

Figure 14:
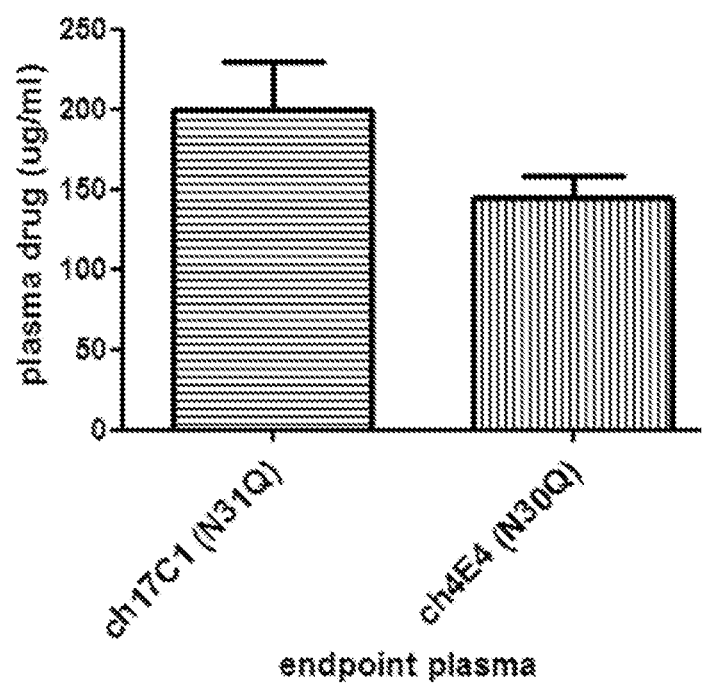

FIG. 14. Average plasma drug concentrations for ch17C1 (N31Q) and ch4E4(N30Q) treated animals 24 h after the i.p. administration of the last dose. Average plasma drug concentrations for ch17C1(N31Q) and ch4E4(N30Q) were 145 and 200 μg/ml, respectively.

Figure 15:
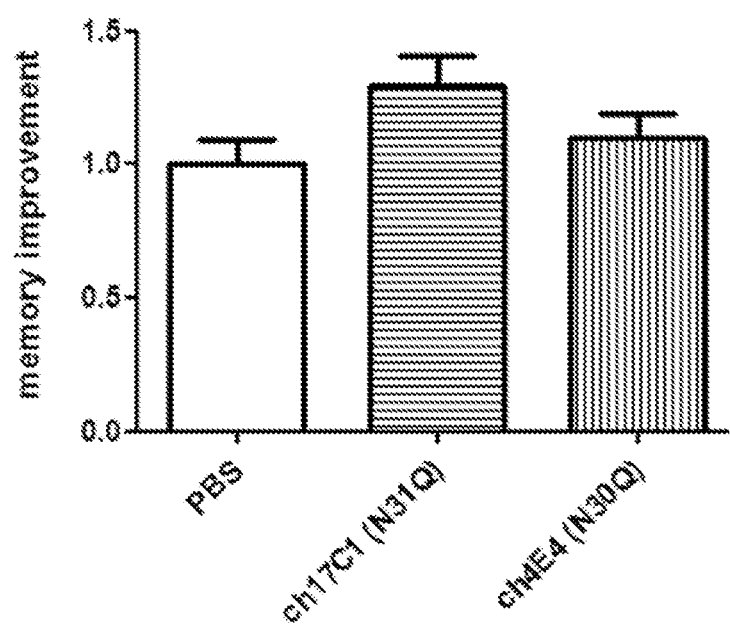

FIG. 15. Spatial working memory in TauP301L mice treated with ch17C1(N31Q) and ch4E4(N30Q) was assessed by two-trial Y-maze.

DETAILED DESCRIPTION OF THE INVENTION

I. Definitions

Neurodegenerative tauopathies are a diverse group of neurodegenerative disorders that share a common pathologic lesion consisting of intracellular aggregates of abnormal filaments that are mainly composed of pathologically hyperphosphorylated tau in neurons and/or glial cells. Clinical features of the tauopathies are heterogeneous and characterized by dementia and/or motor syndromes. The progressive accumulation of filamentous tau inclusions may cause neuronal and glial degeneration in combination with other deposits as, e.g., beta-amyloid in Alzheimer's disease or as a sole pathogenic entity as illustrated by mutations in the tau gene that are associated with familial forms of frontotemporal dementia and parkinsonism linked to chromosome 17 (FTDP-17). Because of the heterogeneity of their clinical manifestations a potentially non-exhaustive list of tauopathic diseases can be provided including Alzheimer's disease, amyotrophic lateral sclerosis/parkinsonism-dementia complex, argyrophilic grain dementia, British type amyloid angiopathy, cerebral amyloid angiopathy, corticobasal degeneration, Creutzfeldt-Jakob disease, dementia pugilistica, diffuse neurofibrillary tangles with calcification, Down's syndrome, frontotemporal dementia, frontotemporal dementia with parkinsonism linked to chromosome 17, frontotemporal lobar degeneration, Gerstmann-Sträussler-Scheinker disease, Hallervorden-Spatz disease, inclusion body myositis, multiple system atrophy, myotonic dystrophy, Niemann-Pick disease type C, non-Guamanian motor neuron disease with neurofibrillary tangles, Pick's disease, postencephalitic parkinsonism, prion protein cerebral amyloid angiopathy, progressive subcortical gliosis, progressive supranuclear palsy, subacute sclerosing panencephalitis, tangle only dementia, multi-infarct dementia and ischemic stroke; see for a review, e.g., Lee et al., Annu. Rev. Neurosci. 24 (2001), 1121-1159 in which Table 1 catalogs the unique members of tauopathies or Sergeant et al, Bioch. Biophy. Acta 1739 (2005), 179-97, with a list in FIG. 2 therein.

In this specification, the terms "tau", is used interchangeable to specifically refer to the native monomer form of tau. The term "tau" is also used to generally identify other conformers of tau, for example, oligomers or aggregates of tau. The term "tau" is also used to refer collectively to all types and forms of tau. Due to alternative splicing 6 tau isoforms are present in the human brain. The protein sequences for these isoforms are:

```
Isothrm Fetal-tau of 352aa
                                                    (SEQ ID NO: 1)
MAEFRQEFEVMEDHAGTYGLGDRKDQGGYTMHQDQEGDTDAGLKAEEAGIGD

TPSLEDEAAGHVTQARIVIVSKSKDGTGSDDKKAKGADGKTKIATPRGAAPPGQK

GQANATRIPAKTPPAPKTPPSSGEPPKSGDRSGYSSPGSPGTYGSRSRTPSLPTPPTR

EPKKVAVVRTPPKSPSSAKSRLQTAPVPMPDLKNVKSKIGSTENLKHQPGGGKV

QIVYKPVDLSKVTSKCGSLGNIHHIKPGGGQVEVKSEKLDFKDRVQSKIGSLDNIT

HVPGGGNKKIETHKLTFRENAKAKTDHGAEIVYKSPVVSGDTSPRHLSNVSSTGS

IDMVDSPQLATLADEVSASLAKQGL

Isoform Tau-B of 381aa
                                                    (SEQ ID NO: 2)
MAEPRQEFEVMEDHAGTYGLGDRKDQGGYTMHQDQEGDTDAGLKESPLQTPT

EDGSEEPGSETSDAKSTPTAEAEEAGIGDTPSLEDEAAGHVTQARMVSKSKDGTG
```

-continued

```
SDDKKAKGADGKTKIATPRGAAPPGQKGQANATRIPAKTPPAPKTPPSSGEPPKS

GDRSGYSSPGSPGTPGSRSRTPSLPTPPTREPKKVAVVRTPPKSPSSAKSRLQTAPV

PMPDLKNVKSKIGSTENLKHQPGGGKVQIVYKPVDLSKVTSKCGSLGNIHHKPG

GGQVEVKSEKLDFKDRVQSKIGSLDNITHVPGGGNKKIETHKLTFRENAKAKTD

HGAEIVYKSPVVSGDTSPRHLSNVSSTGSIDMVDSPQLATLADEVSASLAKQGL

Isoform Tau-C of 410aa
                                                  (SEQ ID NO: 3)
MAEPRQEFEVMEDHAGTYGLGDRKDQGGYTMHQDQEGDTDAGLKESPLQTPT

EDGSEEPGSETSDAKSTPTAEDVTAPLVDEGAPGKQAAAQPHTEIPEGTTAEEAGI

GDTPSLEDEAAGHVTQARMVSKSKDGTGSDDKKAKGADGKTKIATPRGAAPPG

QKGQANATRIPAKTPPAPKTPPSSGEPPKSGDRSGYSSPGSPGTPGSRSRTPSLPTP

PTREPKKVAVVRTPPKSPSSAKSRLQTAPVPMPDLKNVKSKIGSTENLKHQPGGG

KVQIVYKPVDLSKVTSKCGSLGNIHHKPGGGQVEVKSEKLDFKDRVQSKIGSLD

NITHVPGGGNKKIETHKLTFRENAKAKTDHGAEIVYKSPVVSGDTSPRHLSNVSS

TGSIDMVDSPQLATLADEVSASLAKQGL

Isoform Tau-D of 383aa
                                                  (SEQ ID NO: 4)
MAEPRQEFEVMEDHAGTYGLGDRKDQGGYTMHQDQEGDTDAGLKAEEEAGIGD

TPSLEDEAAGHVTQARMVSKSKDGTGSDDKKAKGADGKTKIATPRGAAPPGQK

GQANATRIPAKTPPAPKTPPSSGEPPKSGDRSGYSSPGSPGTPGSRSRTPSLPTPPTR

EPKKVAVVRTPPKSPSSAKSRLQTAPVPMPDLKNVKSKIGSTENLKHQPGGGKV

QIINKKLDLSNVQSKCGSKDNIKHVPGGGSVQIVYKPVDLSKVTSKCGSLGNIHH

KPGGGQVEVKSEKLDFKDRVQSKIGSLDNITHVPGGGNKKIETHKLTFRENAKA

KTDHGAEIVYKSPVVSGDTSPRHLSNVSSTGSIDMVDSPQLATLADEVSASLAKQ

GL

Isoform Tau-E of 412aa
                                                  (SEQ ID NO: 5)
MAEPRQEFEVMEDHAGTYGLGDRKDQGGYTMHQDQEGDTDAGLKESPLQTPT

EDGSEEPGSETSDAKSTPTAEAEEEAGIGDTPSLEDEAAGHVTQARMVSKSKDGTG

SDDKKAKGADGKTKIATPRGAAPPGQKGQANATRIPAKTPPAPKTPPSSGEPPKS

GDRSGYSSPGSPGTPGSRSRTPSLPTPPTREPKKVAVVRTPPKSPSSAKSRLQTAPV

PMPDLKNVKSKIGSTENLKHQPGGGKVQIINKKLDLSNVQSKCGSKDNIKHVPG

GGSVQIVYKPVDLSKVTSKCGSLGNIHHKPGGGQVEVKSEKLDFKDRVQSKIGSL

DNITHVPGGGNKKIETHKLTFRENAKAKTDHGAEIVYKSPVVSGDTSPRHLSNVS

STGSIDMVDSPQLATLADEVSASLAKQGL

Isoform Tau-F of 441aa
                                                  (SEQ ID NO: 6)
MAEPRQEFEVMEDHAGTYGLGDRKDQGGYTMHQDQEGDTDAGLKESPLQTPT

EDGSEEPGSETSDAKSTPTAEDVTAPLVDEGAPGKQAAAQPHTEIPEGTTAEEAGI

GDTPSLEDEAAGHVTQARMVSKSKDGTGSDDKKAKGADGKTKIATPRGAAPPG

QKGQANATRIPAKTPPAPKTPPSSGEPPKSGDRSGYSSPGSPGTPGSRSRTPSLPTP

PTREPKKVAVVRTPPKSPSSAKSRLQTAPVPMPDLKNVKSKIGSTENLKHQPGGG

KVQIINKKLDLSNVQSKCGSKDNIKHVPGGGSVQIVYKPVDLSKVTSKCGSLGNI
```

-continued

```
HHKPGGGQVEVKSEKLDFKDRVQSKIGSLDNITHVPGGGNKKIETHKLTFRENA

KAKTDHGAEIVYKSPVVSGDTSPRHLSNVSSTGSIDMVDSPQLATLADEVSASLA

KQGL
```

The "wild type" tau amino acid sequence is represented by isoform Tau-F of 441aa (SEQ ID NO:6) further also referenced to as "hTau40", "TauF", "Tau-4" or "full-length tau". The amino acid sequence of tau can be retrieved from the literature and pertinent databases; see Goedert et al., Proc. Natl. Acad. Sci. USA 85 (1988), 4051-4055, Goedert et al., EMBO J. 8(1989), 393-399, Goedert et al., EMBO J. 9 (1990), 4225-4230 and GenBank UniProtKB/swissprot: locus TAU_HUMAN, accession numbers P10636-2 (Fetal-tau) and P10636-4 to -8 (Isotorms B to F).

Another striking feature of tau protein is phosphorylation, which occurs at about 30 of 79 potential serine (Ser) and threonine (Thr) phosphorylation sites. Tau is highly phosphorylated during the brain development. The degree of phosphorylation declines it adulthood. Some of the phosphorylation sites are located within the microtubule binding domains of tau, and it has been shown that an increase of tau phosphorylation negatively regulates the binding of microtubules. For example, Ser262 and Ser396, which lie within or adjacent to microtubule binding motifs, are hyperphosphorylated in the tau proteins of the abnormal paired helical filaments (PHFs), a major component of the neurofibrillary tangles (NFTs) in the brain of AD patients. PHFs are filamentous aggregates of tau proteins which are abnormally hyperphosphorylated and can be stained with specific anti-tau antibodies and detected by light microscopy. The same holds true for so called straight tau filaments. PHFs form twisted ribbons consisting of two filaments twisted around one another with a periodicity of about 80 nm. These pathological features are commonly referred to as "tau-pathology", "tauopathology" or "tau-related pathology". For a more detailed description of neuropathological features of tauopathies refer to Lee et al, Annu. Rev. Neurosci. 24 (2001), 1121-1159 and Götz, Brain. Res. Rev. 35 (2001), 266-286, the disclosure content of which is incorporated herein by reference. Physiological tau protein stabilizes microtubules in neurons. Pathological phyosphorylation leads to abnormal tau localization and aggregation, which causes destabilization of microtubules and impaired cellular transport. Aggregated tau is neurotoxic in vitro (Khlistunova et al., J. Biol. Chem. 281 (2006), 1205-1214). The exact neurotoxic species remains unclear, however, as do the mechanism(s) by which they lead to neuronal death. Aggregates of tau can be observed as the main component of neurofibrillary tangles (NFT) in many tauopathies, such as Alzheimer's disease (AD), Frontotemporal dementias, supranuclear palsy, Pick's disease, Argyrophilic grain disease (AGD), corticobasal degeneration, FTDP-17, Parkinson's disease, Dementia pugilistica (Reviewed in Gendron and Petrucelli, Mol. Neurodegener. 4:13 (2009)). Besides these observations, evidence emerges that tau-mediated neuronal death can occur even in the absence of tangle formation. Soluble phospho-tau species are present in CSF (Aluise et al., Biochim. Biophys. Acta. 1782 (2008), 549-558). Tau aggregates can transmit a misfolded state from the outside to the inside of a cell and transfer between co-cultured cells (Frost et al., J. Biol. Chem. 284 (2009), 12845-12852).

In addition to the involvement in neurodegenerative tauopathies, observed alterations in tau phosphorylation during and after ischemia/reperfusion suggest tau playing a crucial role in neuronal damage and clinical pathophysiology of neurovascular disorders such as ischemic stroke (Zheng et al., J. Cell. Biochem. 109 (2010), 26-29).

The human anti-tau antibodies disclosed herein specifically bind tau and epitopes thereof and to various conformations of tau and epitopes thereof. For example, disclosed herein are antibodies that specifically bind tau, tau in its full-length, pathologically modified tau isoforms and tau aggregates. As used herein, reference to an antibody that "specifically binds", "selectively binds", or "preferentially binds" tau refers to an antibody that does not bind other unrelated proteins. In one example, a tau antibody disclosed herein can bind tau or an epitope thereof and show no binding above about 1.5 times background for other proteins. An antibody that "specifically binds" or "selectively binds" a tau conformer refers to an antibody that does not bind all conformations of tau, i.e., does not bind at least one other tau conformer. For example, disclosed herein are antibodies that can preferentially bind to aggregated forms of tau in AD tissue. Since the human anti-tau antibodies of the present invention have been isolated from a pool of healthy human subjects exhibiting an tau-specific immune response the tau antibodies of the present invention can also be called "human auto-antibodies" in order to emphasize that those antibodies were indeed expressed by the subjects and have not been isolated from, for example a human immunoglobulin expressing phage library, which hitherto represented one common method for trying to provide human-like antibodies.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms.

The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide can be derived from a natural biological source or produced by recombinant technology, but is not necessarily translated from a designated nucleic acid sequence. It can be generated in any manner, including by chemical synthesis.

A polypeptide of the invention can be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides can have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for, purposed of the invention, as are native or recombinant polypeptides which have been separated, fractionated, or partially or substantially purified by any suitable technique.

Also included as polypeptides of the present invention are fragments, derivatives, analogs or variants of the foregoing polypeptides, and any combination thereof. The terms "fragment," "variant," "derivative" and "analog" when referring to antibodies or antibody polypeptides of the present invention include any polypeptides which retain at least some of the antigen-binding properties of the corresponding native binding molecule, antibody, or polypeptide. Fragments of polypeptides of the present invention include proteolytic fragments, as well as deletion fragments, in addition to specific antibody fragments discussed elsewhere herein. Variants of antibodies and antibody polypeptides of the present invention include fragments as described above, and also polypeptides with altered amino acid sequences due to amino acid substitutions, deletions, or insertions. Variants can occur naturally or be non-naturally occurring. Non-naturally occurring variants can be produced using art-known mutagenesis techniques. Variant polypeptides can comprise conservative or non-conservative amino acid substitutions, deletions or additions. Derivatives of tau specific binding molecules, e.g., antibodies and antibody polypeptides of the present invention, are polypeptides which have been altered so as to exhibit additional features not found on the native polypeptide. Examples include fusion proteins. Variant polypeptides can also be referred to herein as "polypeptide analogs". As used herein a "derivative" of, a binding molecule or fragment thereof, an antibody, or an antibody polypeptide refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide can comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding an antibody contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, polynucleotide or a nucleic acid can be or can include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector can contain a single coding region, or can comprise two or more coding regions, e.g., a single vector can separately encode an immunoglobulin heavy chain variable region and an immunoglobulin light chain variable region. In addition, a vector, polynucleotide, or nucleic acid of the invention can encode heterologous coding regions, either fused or unfused to a nucleic acid encoding a binding molecule, an antibody, or fragment, variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally can include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" or "operably linked" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter can be a cell-specific promoter that directs substantial transcription of the DNA only in predetermined cells. Other transcription control elements, besides a promoter, for example enhancers, operators, repressors, and transcription termination signals can be operably associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention can be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full-length" polypeptide to produce a secreted or "mature" form of the polypeptide. In certain embodiments, the native signal peptide, e.g., an immunoglobulin heavy chain or light chain signal, peptide is used, or a functional derivative of that sequence that retains the ability to direct the secretion of the polypeptide that is operably associated with it. Alternatively, a heterologous mammalian signal peptide, or a functional derivative thereof, can be used. For example, the wild-type leader sequence can be substituted with the leader sequence of human tissue plasminogen activator (TPA) or mouse β-glucuronidase.

Unless stated otherwise, the terms "disorder" and "disease" are used interchangeably herein.

A "binding molecule" as used in the context of the present invention relates primarily to antibodies, and fragments thereof, but can also refer to other non-antibody molecules that bind to tau including but not limited to hormones, receptors, ligands, major histocompatibility complex (MHC) molecules, chaperones such as heat shock proteins (HSPs) as well as cell-cell adhesion molecules such as members of the cadherin, intergrin, C-type lectin and immunoglobulin (Ig) superfamilies. Thus, for the sake of clarity only and without restricting the scope of the present invention most of the following embodiments are discussed with respect to antibodies and antibody-like molecules which represent a specific embodiment of binding molecules for the development of therapeutic and diagnostic agents.

The terms "antibody" and "immunoglobulin" are used interchangeably herein. An antibody or immunoglobulin is a tau-binding molecule which comprises at least the variable domain of a heavy chain, and normally comprises at least the variable domains of a heavy chain and a light chain. Basic immunoglobulin structures in vertebrate systems are relatively well understood; see, e.g., Harlow et al., Antibodies: A Laboratory Manual, (Cold Spring Harbor Laboratory Press, 2nd ed. 1988).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernible to the skilled artisan in view of the instant disclosure and, accordingly, are within the scope of the instant invention. All immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda (κ, λ). Each heavy chain class can be bound with either a kappa or lambda light chain. In general, the light and heavy chains are covalently bonded to each other, and the "tail" portions of the two heavy chains, are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light ($V_L$) and heavy ($V_H$) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the $V_L$ domain and $V_H$ domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the $V_H$ and $V_L$ chains. Any antibody or immunoglobulin fragment which contains sufficient structure to specifically bind to tau is denoted herein interchangeably as a "binding fragment" or an "immunospecific fragment."

In naturally occurring antibodies, an antibody comprises six hypervariable regions, sometimes called "complementarity determining regions" or "CDRs" present in each antigen-binding domain, which are short, non-contiguous sequences of amino acids that are specifically positioned to form the antigen-binding domain as the antibody assumes its three dimensional configuration in an aqueous environment. The "CDRs" are flanked by four relatively conserved "framework" regions or "FRs" which show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined; see, "Sequences of Proteins of Immunological Interest," Kabat, E, et al., U.S. Department of Health and Human Services, (1983); and Chothia and Lesk, J. Mol. Biol., 196 (1987), 901-917, which are incorporated herein by reference in their entireties.

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia and Lesk, J. Mol. Biol., 196 (1987), 901-917, which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table 1 as a comparison. The exact residue numbers which encompass a particular CDR will vary depending on the sequence and size of the CDR. Those skilled in the art can routinely determine which residues comprise a particular hypervariable region or CDR of the human IgG subtype of antibody given the variable region amino acid sequence of the antibody.

TABLE 1

| CDR Definitions[1] | | |
|---|---|---|
| | Kabat | Chothia |
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody or antigen-binding fragment, variant, or derivative thereof of the present invention are according to the Kabat numbering system, which however is theoretical and may not equally apply every antibody of the present invention. In one embodiment, depending on the position of the first CDR the following CDRs can be shifted in either direction.

Antibodies or antigen-binding fragments, immunospecific fragments, variants, or derivatives thereof of the invention include, but are not limited to, polyclonal, monoclonal, multispecific human, humanized, primatized, murinized or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a $V_L$ or $V_H$ domain, fragments produced by a Fab expression library, and anti-idiotypic (anti-Id) antibodies (including, e.g., anti-Id antibodies to antibodies disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule.

In one embodiment, the antibody of the present invention is not IgM or a derivative thereof with a pentavalent structure. Particular, in specific applications of the present invention, especially therapeutic use, IgMs are less useful than IgG and other bivalent antibodies or corresponding binding molecules since IgMs due to their pentavalent structure and lack of affinity maturation often show unspecific cross-reactivities and very low affinity.

In a particular embodiment, the antibody of the present invention is not a polyclonal antibody, i.e. it substantially consists of one particular antibody species rather than being a mixture obtained from a plasma immunoglobulin sample.

Antibody fragments, including single-chain antibodies, can comprise the variable region(s) alone or in combination with the entirety or a portion of the following: hinge region, CH1, CH2, and CH3 domains. Also included in the invention are tau binding fragments comprising any combination of variable region(s) with a hinge region, CH1, CH2, and CH3 domains. Antibodies or immunospecific fragments thereof of the present invention can be from any animal origin including birds and mammals. In one embodiment, the antibodies are human, murine, donkey, rabbit, goat, guinea pig, camel, llama, horse, or chicken antibodies. In another embodiment, the variable region can be condricthoid in origin (e.g., from sharks).

In one aspect, the antibody of the present invention is a human monoclonal antibody isolated from a human. Optionally, the framework region of the human antibody is aligned and adopted in accordance with the pertinent human germ line variable region sequences in the database; see, e.g., Vbase (http://vbase.mrc-cpe.cam.ac.uk/), hosted by the MRC Centre for Protein Engineering (Cambridge, UK). For example, amino acids considered to potentially deviate from the true germ line sequence could be due to the PCR primer sequences incorporated during the cloning process. Compared to artificially generated human-like antibodies such as single chain antibody fragments (scFvs) from a phage displayed antibody library or xenogeneic mice the human monoclonal antibody of the present invention is characterized by (i) being obtained using the human immune response rather than that of animal surrogates, i.e. the antibody has been generated in response to natural tau in its relevant conformation in the human body, (ii) having protected the individual or is at least significant for the presence of tau, and (iii) since the antibody is of human origin the risks of cross-reactivity against self-antigens is minimized. Thus, in accordance with the present invention the terms "human monoclonal antibody", "human monoclonal autoantibody", "human antibody" and the like are used to denote a tau binding molecule which is of human origin, i.e. which has been isolated from a human cell such as a B cell or hybridoma thereof or the cDNA of which has been directly cloned from mRNA of a human cell, for example a human memory B cell. A human antibody is still "human" even if amino acid substitutions are made in the antibody, e.g., to improve binding characteristics.

Antibodies derived from human immunoglobulin libraries or from animals transgenic for one or more human immunoglobulins and that do not express endogenous immunoglobulins, as described infra and, for example in U.S. Pat. No. 5,939,598 by Kucherlapati et al., are denoted human-like antibodies in order distinguish them from truly human antibodies of the present invention.

For example, the paring of heavy and light chains of human-like antibodies such as synthetic and semi-synthetic antibodies typically isolated from phage display do not necessarily reflect the original paring as it occurred in the original human B cell. Accordingly Fab and scFv fragments obtained from recombinant expression libraries as commonly used in the prior art can be considered as being artificial with all possible associated effects on immunogenicity and stability.

In contrast, the present invention provides isolated affinity-matured antibodies from selected human subjects, which are characterized by their therapeutic utility and their tolerance in man.

As used herein, the term "murinized antibody" or "murinized immunoglobulin" refers to an antibody comprising one or more CDRs from a human antibody of the present invention; and a human framework region that contains amino acid substitutions and/or deletions and/or insertions that are based on a mouse antibody sequence. The human immunoglobulin providing the CDRs is called the "parent" or "acceptor" and the mouse antibody providing the framework changes is called the "donor", Constant regions need not be present, but if they are, they are usually substantially identical to mouse antibody constant regions, i.e. at least about 85-90%, about 95%, about 96%, about 97%, about 98%, about 99% or more identical. Hence, in some embodiments, a full-length murinized human heavy or light chain immunoglobulin contains a mouse constant region, human CDRs, and a substantially human framework that has a number of "murinizing" amino acid substitutions. Typically, a "murinized antibody" is an antibody comprising a murinized variable light chain and/or a murinized variable heavy chain. For example, a murinized antibody would not encompass a typical chimeric antibody, e.g., because the entire variable region of a chimeric antibody is non-mouse. A modified antibody that has been "murinized" by the process of "murinization" binds to the same antigen as the parent antibody that provides the CDRs and is usually less immunogenic in mice, as compared to the parent antibody.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. For example, a binding polypeptide for use in the invention can comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention can lack at least a portion of a CH2 domain (e.g., all or part of a CH2 domain). As set forth above, it will be understood by one of ordinary skill in the art that these domains (e.g., the heavy chain portions) can be modified such that they vary in amino acid sequence from the naturally occurring immunoglobulin molecule.

In certain antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the invention are not identical. For example, each monomer can comprise a different target binding site, forming, for example, a bispecific antibody or diabody.

In another embodiment, the antibodies, or antigen-binding fragments, variants, or derivatives thereof disclosed herein are composed of a single polypeptide chain such as scFvs and are to be expressed intracellularly (intrabodies) for potential in vivo therapeutic and diagnostic applications.

The heavy chain portions of a binding polypeptide for use in the diagnostic and treatment methods disclosed herein can be derived from different immunoglobulin molecules. For example, a heavy chain portion of a polypeptide can comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain. In one embodiment, the light chain portion comprises at least one of a $V_L$ or CL domain.

The minimum size of a peptide or polypeptide epitope for an antibody is thought to be about four to five amino acids. Peptide or polypeptide epitopes can contain at least seven, at least nine or between at least about 15 to about 30 amino acids. Since a CDR can recognize an antigenic peptide or polypeptide in its tertiary form, the amino acids comprising an epitope need not be contiguous, and in some cases, may not even be on the same peptide chain. In the present invention, a peptide or polypeptide epitope recognized by antibodies of the present invention contains a sequence of at least 4, at least 5, at least 6, at least 7, at least 8, at least 9, at least 10, at least 15, at least 20, at least 25, or between about 5 to about 30, about 10 to about 30 or about 15 to about 30 contiguous or non-contiguous amino acids of tau.

By "specifically binding", or "specifically recognizing", used interchangeably herein, it is generally meant that a binding molecule, e.g., an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. A skilled artisan understands that an antibody can specifically bind to, or specifically recognize an isolated polypeptide comprising, or consisting of, amino acid residues corresponding to a linear portion of a non-contiguous epitope. The term "specificity" is used herein to qualify the relative affinity by which a certain antibody binds to a certain epitope. For example, antibody "A" can be deemed to have a higher specificity for a given epitope than antibody "B," or antibody "A" can be said to bind to epitope "C" with a higher specificity than it has for related epitope "D".

Where present, the term "immunological binding characteristics," or other binding characteristics of an antibody with an antigen, in all of its grammatical forms, refers to the specificity, affinity, cross-reactivity, and other binding characteristics of an antibody.

By "preferentially binding", it is meant that the binding molecule, e.g., antibody specifically binds to an epitope more readily than it would bind to a related, similar, homologous, or analogous epitope. Thus, an antibody which "preferentially binds" to a given epitope would more likely bind to that epitope than to a related epitope, even though such an antibody can cross-react with the related epitope.

By way of non-limiting example, a binding molecule, e.g., an antibody can be considered to bind a first epitope preferentially if it binds said first epitope with a dissociation constant ($K_D$) that is less than the antibody's $K_D$ for the second epitope. In another non-limiting example, an antibody can be considered to bind a first antigen preferentially if it binds the first epitope with an affinity that is at least one order of magnitude less than the antibody's $K_D$ for the second epitope. In another non-limiting example, an antibody can be considered to bind a first epitope preferentially if it binds the first epitope with an affinity that is at least two orders of magnitude less than the antibody's $K_D$ for the second epitope.

In another non-limiting example, a binding molecule, e.g., an antibody can be considered to bind a first epitope preferentially if it binds the first epitope with an off rate (k(off)) that is less than the antibody's k(off) for the second epitope. In another non-limiting example, an antibody can be considered to bind a first epitope preferentially if it binds the first epitope with an affinity that is at least one order of magnitude less than the antibody's k(off) for the second epitope. In another non-limiting example, an antibody can be considered to bind a first epitope preferentially if it binds the first epitope with an affinity that is at least two orders of magnitude less than the antibody's k(off) for the second epitope.

A binding molecule, e.g., an antibody or antigen-binding fragment, variant, or derivative disclosed herein can be said to bind a tau or a fragment or variant thereof with an off rate (k(off)) of less than or equal to $5 \times 10^{-2}$ sec$^{-1}$, $10^{-2}$ sec$^{-1}$, $5 \times 10^{-3}$ sec$^{-1}$ or $10^{-3}$ sec$^{-1}$. In one embodiment, an antibody of the invention can be said to bind tau or a fragment or variant thereof with an off rate (k(off)) less than or equal to $5 \times 10^{-4}$ sec$^{-1}$, $10^{-4}$ sec$^{-1}$, $5 \times 10^{-5}$ sec$^{-1}$, or $10^{-5}$ sec$^{-1}$, $5 \times 10^{-6}$ sec$^{-1}$, $10^{-6}$ sec$^{-1}$, $5 \times 10^{-7}$ sec$^{-1}$ or $10^{-7}$ sec$^{-1}$.

A binding molecule, e.g., an antibody or antigen-binding fragment, variant, or derivative disclosed herein can be said to bind tau or a fragment or variant thereof with an on rate (k(on)) of greater than or equal to $10^3$ M$^{-1}$ sec$^{-1}$, $5 \times 10^3$ M$^{-1}$ sec$^{-1}$, $10^4$ M$^{-1}$ sec$^{-1}$ or $5 \times 10^4$ M$^{-1}$ sec$^{-1}$. In one embodiment, an antibody of the invention can be said to bind tau or a fragment or variant thereof with an on rate (k(on)) greater than or equal to $10^5$ M$^{-1}$ sec$^{-1}$, $5 \times 10^5$ M$^{-1}$ sec$^{-1}$, $10^6$ M$^{-1}$ sec$^{-1}$, $5 \times 10^6$ M$^{-1}$ sec$^{-1}$ or $10^7$ M$^{-1}$ sec$^{-1}$.

A binding molecule, e.g., an antibody is said to competitively inhibit binding of a reference antibody to a given epitope if it preferentially binds to that epitope to the extent that it blocks, to some degree, binding of the reference antibody to the epitope. Competitive inhibition can be determined by any method known in the art, for example, competition ELISA assays. An antibody can be said to competitively inhibit binding of the reference antibody to a given epitope by at least 90%, at least 80%, at least 70%, at least 60%, or at least 50%. A skilled artisan understands that the binding of an antibody to its epitope can also be competitively inhibited by a binding molecule that is not an antibody. For example, the specific binding of an antibody described herein to tau, e.g., hTau40, can be competitively inhibited by microtubules.

As used herein, the term "affinity" refers to a measure of the strength of the binding of an individual epitope with the CDR of a binding molecule, e.g., an immunoglobulin molecule; see, e.g., Harlow et al., Antibodies: A Laboratory Manual, Cold Spring Harbor Laboratory Press, 2nd ed. (1988) at pages 27-28. As used herein, the term "avidity" refers to the overall stability of the complex between a population of immunoglobulins and an antigen, that is, the functional combining strength of an immunoglobulin mixture with the antigen; see, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity. The affinity or avidity of an antibody for an antigen can be determined experimentally using any suitable method; see, for example, Berzofsky et al., "Antibody-Antigen Interactions" In *Fundamental Immunology*, Paul, W. E., Ed., Raven Press New York, N Y (1984), Kuby, Janis Immunology, W. H. Freeman and Company New York, N Y (1992), and methods described herein. General techniques for measuring the affinity of an antibody for an antigen include ELISA, RIA, and surface plasmon resonance. The measured affinity of a particular antibody-antigen interaction can vary if measured under different conditions, e.g., salt concentration, pH. Thus, measurements of affinity and other antigen-binding parameters, e.g., $K_D$, IC$_{50}$, are preferably made with standardized solutions of antibody and antigen, and a standardized buffer.

Binding molecules, e.g., antibodies or antigen-binding fragments, variants or derivatives thereof of the invention can also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, can actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody can be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody can be deemed "highly specific" for a certain epitope, if it does not bind any other analog, ortholog, or homolog of that epitope.

Binding molecules, e.g., antibodies or antigen-binding fragments, variants or derivatives thereof of the invention can also be described or specified in terms of their binding affinity to tau. In one embodiment, binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{13}$ M, $10^{-13}$ M, $5\times10^{-14}$ M, $10^{-14}$ M, $5\times10^{-15}$ M, or $10^{-15}$ M.

As previously indicated, the subunit structures and three dimensional configuration of the constant regions of the various immunoglobulin classes are well known. As used herein, the term "$V_H$ domain" includes the amino terminal variable domain of an immunoglobulin heavy chain and the term "CH1 domain" includes the first (most amino terminal) constant region domain of an immunoglobulin heavy chain. The CH1 domain is adjacent to the $V_H$ domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al. op. cit). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains; see Roux et al., J. Immunol. 161 (1998), 4083.

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the terms "linked", "fused" or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature). Although the reading frame is thus made continuous throughout the fused segments, the segments can be physically or spatially separated by, for example, in-frame linker sequence. For example, polynucleotides encoding the CDRs of an immunoglobulin variable region can be fused, in-frame, but be separated by a polynucleotide encoding at least one immunoglobulin framework region or additional CDR regions, as long as the "fused" CDRs are co-translated as part of a continuous polypeptide.

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product, and the translation of such mRNA into polypeptide (s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the term "sample" refers to any biological material obtained from a subject or patient. In one aspect, a sample can comprise blood, cerebrospinal fluid ("CSF"), or urine. In other aspects, a sample can comprise whole blood, plasma, B cells enriched from blood samples, and cultured cells (e.g., B cells from a subject). A sample can also include a biopsy or tissue sample including neural tissue. In still other aspects, a sample can comprise whole cells and/or a lysate of the cells. Blood samples can be collected by methods known in the art. In one aspect, the pellet can be resuspended by vortexing at 4° C. in 200 µl buffer (20 mM Tris, pH. 7.5, 0.5% Nonidet, 1 mM EDTA, 1 mM PMSF, 0.1M NaCl, IX Sigma Protease Inhibitor, and IX Sigma Phosphatase Inhibitors 1 and 2). The suspension can be kept on ice for 20 minutes with intermittent vortexing. After spinning at 15,000×g for 5 minutes at about 4° C., aliquots of supernatant can be stored at about −70° C.

As used herein, the terms "treat" or "treatment" refer to both therapeutic treatment and prophylactic or preventative measures, wherein the object is to prevent or slow down (lessen) an undesired physiological change or disorder, such as the development of Parkinsonism. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the manifestation of the condition or disorder is to be prevented.

By "subject" or "individual" or "animal" or "patient" or "mammal," is meant any subject, particularly a mammalian subject, e.g., a human patient, for whom diagnosis, prognosis, prevention, or therapy is desired.

II. Antibodies

The present invention generally relates to human anti-tau antibodies and antigen-binding fragments thereof. In one embodiment, an antibody of the present invention demonstrates the immunological binding characteristics and/or biological properties as outlined for the antibodies illustrated in the Examples. In accordance with the present invention human monoclonal antibodies specific for tau were cloned from a pool of healthy human subjects.

In the course of the experiments performed in accordance with the present invention initial attempts failed to clone tau specific antibodies but almost always resulted in false-positive clones. In order to circumvent this problem, antibodies in conditioned media of human memory B cell cultures were screened in parallel for binding to recombinant tau protein, PHFTau extracted from AD brain, healthy control brain extracts and bovine serum albumin (BSA). Only B-cell cultures that were positive for recombinant tau and/or PHFTau but not control brain extract or BSA were subjected to antibody cloning.

Initial attempts to isolating to specific antibodies were focused at pools of healthy human subjects with high plasma binding activity to tau, suggestive of elevated levels of circulating tau antibodies plasma. Unexpectedly, these attempts failed to produce tau specific human memory B cells and the antibodies described in the current invention were isolated from pools of healthy human subjects that were not preselected for high tau plasma reactivity or had low plasma reactivity to tau.

Due to this measure, several antibodies could be isolated. Selected antibodies were further analyzed for class and light chain subclass determination. Selected relevant antibody messages from memory B cell cultures are then transcribed by RT-PCR, cloned and combined into expression vectors for recombinant production; see the appended Examples. Recombinant expression of the human antibodies in HEK293 or CHO cells and the subsequent characterization of their binding specificities towards full-length tau, pathologically modified forms thereof on Western Blot and their distinctive binding to pathologically aggregated tau confirmed that for the first time human antibodies have been cloned that are highly specific for tau and recognize distinctive the pathologically modified forms of tau protein.

Thus, the present invention generally relates to an isolated naturally occurring human monoclonal anti-tau antibody and binding fragments, derivatives and variants thereof. In one embodiment of the invention, the antibody is capable of specifically binding full-length recombinant tau and/or the pathologically aggregated and/or phosphorylated form (PH-FTau) isolated from AD brain under denaturing conditions on Western Blot.

In one embodiment, the present invention is directed to an anti-tau antibody, or antigen-binding fragment, variant or derivatives thereof, where the antibody specifically binds to the same epitope of tau as a reference antibody selected from the group consisting of NI-105.17C1, NI-105.6C5, NI-105.29G10, NI-105.6L9, NI-105.40E8, NI-105.48E5, NI-105.6E3, NI-105.22E1, NI-105.26B12, NI-105.12E12, NI-105.60E7, NI-105.14E2, NI-105.39E2, NI-105.19C6, or NI-105.9C4.

Additional human anti-tau antibodies are disclosed in U.S. Patent Application Publication No. 2012/0087861, the content of which is incorporated herein by reference in its entirety.

In one embodiment, an antibody described herein specifically binds to tau at an epitope comprising the amino acid residues selected from the group consisting of: residues corresponding to residues 125-131, 397-441, 226-244, 217-227, 37-55, 387-406, 421-427, 427-439, 1-158, 197-207, 57-67, 355-441, 313-319, 309-319, and 221-231 of hTau40 (SEQ ID NO:6). In a further embodiment, an antibody described herein specifically binds to tau at an epitope comprising the amino acid residues corresponding to residues 37-55 and 387-406 of hTau40 (SEQ ID NO:6). In a specific embodiment, tau is hTau40 (SEQ ID NO:6).

In one embodiment, an antibody described herein binds to tau at an epitope comprising the microtubule binding domain of tau. In a specific embodiment, an antibody described herein binds to tau at an epitope comprising amino acid residues from the R4 region of tau as depicted in FIG. 4. In one embodiment, an antibody described herein competes with microtubules for specific binding to tau. In another embodiment, an antibody described herein has reduced binding affinity to microtubule associated tau compared to the antibodies binding affinity to tau no associated with microtubules. In a further embodiment, an antibody described herein does not bind, or substantially does not bind to tau associated with microtubules. In specific embodiments, the tau protein can be native tau protein or recombinant tau protein. In a specific embodiment, tau is hTau40.

In one embodiment, a human anti-tau antibody of the present invention can specifically bind pathologically aggregated tau and not substantially bind tau in the physiological form in brain tissue. In addition, a human anti-tau antibody of the present invention can be further characterized by its ability to recognize tau at the pre-tangle stage, in neurofibrillary tangles (NFT), neutropil threads and/or dystrophic neurites in the brain. Hence, the present invention provides a set of human tau antibodies with binding specificities, which are thus particularly useful for diagnostic and therapeutic purposes.

In addition, or alternatively, an anti-tau antibody of the present invention preferentially recognizes pathologically aggregated tau rather than physiological forms, in particular when analyzed according to Examples 4 and 18. In addition, or alternatively, an anti-tau antibody of the present invention binds to disease causing mutants of human tau, in particular those described in Example 4. In this context, the binding specificities can be in the range of having half maximal effective concentrations (EC50) of about 100 pM to 100 nM, or an EC50 of about 100 pM to 10 nM for wild-type tau.

Hence, an anti-tau antibody of the present invention binds preferentially to pathological modified forms of tau in brain, e.g. pathological aggregates of tau as exemplified by immunohistochemical staining described in Examples 4 and 18. In another embodiment an anti-tau antibody of the present invention preferentially binds to both recombinant tau and pathologically modified forms of tau as exemplified in Example 2 by Western Blot.

The present invention is also drawn to an antibody, or antigen-binding fragment, variant or derivatives thereof, where the antibody comprises an antigen-binding domain identical to that of an antibody selected from the group consisting of NI-105.17C1, NI-105.17C1(N31Q), NI-105.6C5, NI-105.29G10, NI-105.6L9, NI-105.40E8, NI-105.48E5, NI-105.6E3, NI-105.22E1, NI-105.26B12, NI-105.12E12, NI-105.60E7, NI-105.14E2, NI-105.39E2, NI-105.19C6, and NI-105.9C4.

The present invention further exemplifies several such binding molecules, e.g. antibodies and binding fragments thereof, which can be characterized by comprising in their variable region, e.g, binding domain at least one complementarity determining region (CDR) of the $V_H$ and/or $V_L$ variable region comprising any one of the amino acid sequences depicted in FIG. 7. The corresponding nucleotide sequences encoding the above-identified variable regions are set forth in Table 4 below. An exemplary set of CDRs of the above amino acid sequences of the $V_H$ and/or $V_L$ region as depicted in FIG. 7. However, as discussed in the following the person skilled in the art is well aware of the fact that in addition or alternatively CDRs can be used, which differ in their amino acid sequence from those set forth in FIG. 7 by one, two, three or even more amino acids in case of CDR2 and CDR3.

TABLE 2

Amino acid sequences of the $V_H$ region, $V_H$ CDR1, $V_H$ CDR2, $V_H$ CDR3, $V_L$ region, $V_L$ CDR1, $V_L$ CDR2, and $V_L$ CDR3 of tau specific antibodies.

| Antibody | $V_H/V_L$ | CDR1 | CDR2 | CDR3 |
|---|---|---|---|---|
| NI-105.17C1 | $V_H$ | SEQ ID NO: 45 | SEQ ID NO: 79 | SEQ ID NO: 80 | SEQ ID NO: 81 |
|  | $V_L$ | SEQ ID NO: 46 | SEQ ID NO: 82 | SEQ ID NO: 83 | SEQ ID NO: 84 |
| NI-105.6C5 | $V_H$ | SEQ ID NO: 48 | SEQ ID NO: 85 | SEQ ID NO: 86 | SEQ ID NO: 87 |
|  | $V_L$ | SEQ ID NO: 49 | SEQ ID NO: 88 | SEQ ID NO: 89 | SEQ ID NO: 90 |
| M-105.29G10 | $V_H$ | SEQ ID NO: 50 | SEQ ID NO: 91 | SEQ ID NO: 92 | SEQ ID NO: 93 |
|  | $V_L$ | SEQ ID NO: 51 | SEQ ID NO: 94 | SEQ ID NO: 95 | SEQ ID NO: 96 |
| NI-105.6L9 | $V_H$ | SEQ ID NO: 52 | SEQ ID NO: 97 | SEQ ID NO: 98 | SEQ ID NO: 99 |
|  | $V_L$ | SEQ ID NO: 53 | SEQ ID NO: 100 | SEQ ID NO: 101 | SEQ ID NO: 102 |
| NI-105.40E8 | $V_H$ | SEQ ID NO: 54 | SEQ ID NO: 103 | SEQ ID NO: 104 | SEQ ID NO: 105 |
|  | $V_L$ | SEQ ID NO: 55 | SEQ ID NO: 106 | SEQ ID NO: 107 | SEQ ID NO: 108 |
| NI-105.48E5 | $V_H$ | SEQ ID NO: 56 | SEQ ID NO: 109 | SEQ ID NO: 110 | SEQ ID NO: 111 |
|  | $V_L$ | SEQ ID NO: 57 | SEQ ID NO: 112 | SEQ ID NO: 113 | SEQ ID NO: 114 |
| NI-105.6E3 | $V_H$ | SEQ ID NO: 58 | SEQ ID NO: 115 | SEQ ID NO: 116 | SEQ ID NO: 117 |
|  | $V_L$ | SEQ ID NO: 59 | SEQ ID NO: 118 | SEQ ID NO: 119 | SEQ ID NO: 120 |
| NI-105.22E1 | $V_H$ | SEQ ID NO: 60 | SEQ ID NO: 121 | SEQ ID NO: 122 | SEQ ID NO: 123 |
|  | $V_L$ | SEQ ID NO: 61 | SEQ ID NO: 124 | SEQ ID NO: 125 | SEQ ID NO: 126 |
| NI-105.26B12 | $V_H$ | SEQ ID NO: 62 | SEQ ID NO: 127 | SEQ ID NO: 128 | SEQ ID NO: 129 |
|  | $V_L$ | SEQ ID NO: 64 | SEQ ID NO: 130 | SEQ ID NO: 131 | SEQ ID NO: 132 |
| NI-105.12E12 | $V_H$ | SEQ ID NO: 65 | SEQ ID NO: 133 | SEQ ID NO: 134 | SEQ ID NO: 135 |
|  | $V_L$ | SEQ ID NO: 66 | SEQ ID NO: 136 | SEQ ID NO: 137 | SEQ ID NO: 138 |
| NI-105.60E7 | $V_H$ | SEQ ID NO: 67 | SEQ ID NO: 139 | SEQ ID NO: 140 | SEQ ID NO: 141 |
|  | $V_L$ | SEQ ID NO: 68 | SEQ ID NO: 142 | SEQ ID NO: 143 | SEQ ID NO: 144 |
| NI-105.14E2 | $V_H$ | SEQ ID NO: 69 | SEQ ID NO: 145 | SEQ ID NO: 146 | SEQ ID NO: 147 |
|  | $V_L$ | SEQ ID NO: 70 | SEQ ID NO: 148 | SEQ ID NO: 149 | SEQ ID NO: 150 |
| NI-105.39E2 | $V_H$ | SEQ ID NO: 71 | SEQ ID NO: 151 | SEQ ID NO: 152 | SEQ ID NO: 153 |
|  | $V_L$ | SEQ ID NO: 72 | SEQ ID NO: 154 | SEQ ID NO: 155 | SEQ ID NO: 156 |
| NI-105.19C6 | $V_H$ | SEQ ID NO: 73 | SEQ ID NO: 157 | SEQ ID NO: 158 | SEQ ID NO: 159 |
|  | $V_L$ | SEQ ID NO: 74 | SEQ ID NO: 160 | SEQ ID NO: 161 | SEQ ID NO: 162 |

TABLE 2-continued

Amino acid sequences of the $V_H$ region, $V_H$ CDR1, $V_H$ CDR2, $V_H$ CDR3, $V_L$ region, $V_L$ CDR1, $V_L$ CDR2, and $V_L$ CDR3 of tau specific antibodies.

| Antibody | $V_H/V_L$ | | CDR1 | CDR2 | CDR3 |
|---|---|---|---|---|---|
| NI-105.9C4 | $V_H$ | SEQ ID NO: 75 | SEQ ID NO: 163 | SEQ ID NO: 164 | SEQ ID NO: 165 |
| | $V_L$ | SEQ ID NO: 77 | SEQ ID NO: 166 | SEQ ID NO: 167 | SEQ ID NO: 168 |
| NI-105.17C1 (N31Q) | $V_H$ | SEQ ID NO: 45 | SEQ ID NO: 79 | SEQ ID NO: 80 | SEQ ID NO: 81 |
| | $V_L$ | SEQ ID NO: 221 | SEQ ID NO: 224 | SEQ ID NO: 83 | SEQ ID NO: 84 |

In one embodiment, an antibody of the present invention comprises at least one CDR comprising, or consisting of an amino acid sequence selected from the group consisting of SEQ ID NO: 79-168 and 224.

In one embodiment, an antibody of the present invention comprises one, two, three, four, five or six CDRs comprising, or consisting of an amino acid sequence selected from the group consisting of SEQ ID NO: 79-168 and 224.

In one embodiment, an antibody of the present invention comprises a VH CDR1, VH CDR2, VH CDR3, VL CDR1, VL CDR2, and VL CDR3 comprising the amino acid sequences, respectively SEQ ID NO: 79-84, 85-90, 91-96, 97-102, 103-108, 109-114, 115-120, 121-126, 127-132, 133-138, 139-144, 145-150, 151-156, 157-162, or 163-168. In one embodiment, an antibody of the present invention comprises a VH CDR1, VH CDR2, VH CDR3, VL CDR1, VL CDR2, and VL CDR3 comprising the amino acid sequences, respectively, SEQ ID NOs: 79, 80, 81, 224, 83, and 84.

In one embodiment, an antibody of the invention comprises one, two, or three VH CDRs comprising, or consisting of an amino acid sequence selected from the group consisting of SEQ ID NO: 79-81, 85-87, 91-93, 97-99, 103-105, 109-111, 115-117, 121-123, 127-129, 133-135, 139-141, 145-147, 151-153, 157-159, and 163-165.

In one embodiment, an antibody of the invention comprises a VH CDR1, VH CDR2, and VH CDR3 comprising the amino acid sequences, respectively, SEQ ID NO: 79-81, 85-87, 91-93, 97-99, 103-105, 109-111, 115-117, 121-123, 127-129, 133-135, 139-141, 145-147, 151-153, 157-159, or 163-165.

In one embodiment, an antibody of the invention comprises one, two, or three VL CDRs comprising, or consisting of an amino acid sequence selected from the group consisting of SEQ ID NO: 82-84, 88-90, 94-96, 100-102, 106-108, 112-114, 118-120, 124-126, 130-132, 136-138, 142-144, 148-150, 154-156, 160-162, 166-168, and 224.

In one embodiment, an antibody of the invention comprises a VL CDR1, VL CDR2, and VL CDR3 comprising the amino acid sequences, respectively, SEQ ID NO: 82-84, 88-90, 94-96, 100-102, 106-108, 112-114, 118-120, 124-126, 130-132, 136-138, 142-144, 148-150, 154-156, 160-162, or 166-168. In one embodiment, a VL CDR1, VL CDR2, and VL CDR3 comprising the amino acid sequences, respectively, SEQ ID NO: 83, 84, and 224.

According to one embodiment, an antibody of the invention comprises a heavy chain variable region comprising a VH CDR1 of SEQ ID NO: 79, 85, 91, 97, 103, 109, 115, 121, 127, 133, 139, 145, 151, 157, or 163; a VH CDR2 of SEQ ID NO: 80, 86, 92, 98, 104, 110, 116, 122, 128, 134, 140, 146, 152, 158, or 164; or a VH CDR3 of SEQ ID NO: 81, 87, 93, 99, 105, 111, 117, 123, 129, 135, 141, 147, 153, 159, or 165. According to another embodiment, an antibody comprises a light chain variable region comprising a VL CDR1 of SEQ ID NO: 82, 88, 94, 100, 106, 112, 118, 124, 130, 136, 142, 148, 154, 160, 166 or 224; a VL CDR2 of SEQ ID NO: 83, 89, 95, 101, 107, 113, 119, 125, 131, 137, 143, 149, 155, 161, or 167; or a VL CDR3 of SEQ ID NO: 84, 90, 96, 102, 108, 114, 120, 126, 132, 138, 144, 150, 156, 162, or 168. In another embodiment, the antibody comprises a heavy chain variable region comprising a VH CDR1 of SEQ ID NO: 79, 85, 91, 97, 103, 109, 115, 121, 127, 133, 139, 145, 151, 157, or 163; a VH CDR2 of SEQ ID NO: 80, 86, 92, 98, 104, 110, 116, 122, 128, 134, 140, 146, 152, 158, or 164; or a VH CDR3 of SEQ ID NO: 81, 87, 93, 99, 105, 111, 117, 123, 129, 135, 141, 147, 153, 159, or 165, and further comprises a light chain variable region comprising a VL CDR1 of SEQ ID NO: 82, 88, 94, 100, 106, 112, 118, 124, 130, 136, 142, 148, 154, 160, 166, or 224; a VL CDR2 of SEQ ID NO: 83, 89, 95, 101, 107, 113, 119, 125, 131, 137, 143, 149, 155, 161, or 167; or a VL CDR3 of SEQ ID NO: 84, 90, 96, 102, 108, 114, 120, 126, 132, 138, 144, 150, 156, 162, or 168.

According to one embodiment, an antibody of the invention comprises a heavy chain variable region comprising a VH CDR1 of SEQ ID NO: 79, 85, 91, 97, 103, 109, 115, 121, 127, 133, 139, 145, 151, 157, or 163; a VH CDR2 of SEQ ID NO: 80, 86, 92, 98, 104, 110, 116, 122, 128, 134, 140, 146, 152, 158, or 164; and a VH CDR3 of SEQ ID NO: 81, 87, 93, 99, 105, 111, 117, 123, 129, 135, 141, 147, 153, 159, or 165. According to another embodiment, an antibody comprises a light chain variable region comprising a VL CDR1 of SEQ ID NO: 82, 88, 94, 100, 106, 112, 118, 124, 130, 136, 142, 148, 154, 160, 166, or 224; a VL CDR2 of SEQ ID NO: 83, 89, 95, 101, 107, 113, 119, 125, 131, 137, 143, 149, 155, 161, or 167; and a VL CDR3 of SEQ ID NO: 84, 90, 96, 102, 108, 114, 120, 126, 132, 138, 144, 150, 156, 162, or 168. In another embodiment, the antibody comprises a heavy chain variable region comprising a VH CDR1 of SEQ ID NO: 79, 85, 91, 97, 103, 109, 115, 121, 127, 133, 139, 145, 151, 157, or 163; a VH CDR2 of SEQ ID NO: 80, 86, 92, 98, 104, 110, 116, 122, 128, 134, 140, 146, 152, 158, or 164; and a VH CDR3 of SEQ ID NO: 81, 87, 93, 99, 105, 111, 117, 123, 129, 135, 141, 147, 153, 159, or 165, and further comprises a light chain variable region comprising a VL CDR1 of SEQ ID NO: 82, 88, 94, 100, 106, 112, 118, 124, 130, 136, 142, 148, 154, 160, 166, or 224; a VL CDR2 of SEQ ID NO: 83, 89, 95, 101, 107, 113, 119, 125, 131, 137, 143, 149, 155, 161, or 167; and a VL CDR3 of SEQ ID NO: 84, 90, 96, 102, 108, 114, 120, 126, 132, 138, 144, 150, 156, 162, or 168.

In one embodiment, an antibody of the invention can comprise a heavy chain variable region comprising a VH CDR1 of SEQ ID NO: 79, a VH CDR2 of SEQ ID NO: 80, and VH CDR3 of SEQ ID NO: 81, and can further comprise a light chain variable region comprising a VL CDR1 of SEQ ID NO: 82, a VL CDR2 of SEQ ID NO: 83, and a VL CDR3 of SEQ ID NO: 84.

In one embodiment, an antibody of the invention can comprise a heavy chain variable region comprising a VH CDR1 of SEQ ID NO: 79, a VH CDR2 of SEQ ID NO: 80, and VH CDR3 of SEQ ID NO: 81, and can further comprise a light chain variable region comprising a VL CDR1 of SEQ ID NO: 224, a VL CDR2 of SEQ ID NO: 83, and a VL CDR3 of SEQ ID NO: 84.

In one embodiment, an antibody of the invention can comprise a heavy chain variable region comprising a VH CDR1 of SEQ ID NO: 85, a VH CDR2 of SEQ ID NO: 86, and VH CDR3 of SEQ ID NO: 87, and can further comprise a light chain variable region comprising a VL CDR1 of SEQ ID NO: 88, a VL CDR2 of SEQ ID NO: 89, and a VL CDR3 of SEQ ID NO: 90.

In one embodiment, an antibody of the invention can comprise a heavy chain variable region comprising a VH CDR1 of SEQ ID NO: 91, a VH CDR2 of SEQ ID NO: 92, and VH CDR3 of SEQ ID NO: 93, and can further comprise a light chain variable region comprising a VL CDR1 of SEQ ID NO: 94, a VL CDR2 of SEQ ID NO: 95, and a VL CDR3 of SEQ ID NO: 96.

In one embodiment, an antibody of the invention can comprise a heavy chain variable region comprising a VH CDR1 of SEQ ID NO: 97, a VH CDR2 of SEQ ID NO: 98, and VH CDR3 of SEQ ID NO: 99, and can further comprise a light chain variable region comprising a VL CDR1 of SEQ ID NO: 100, a VL CDR2 of SEQ ID NO: 101, and a VL CDR3 of SEQ ID NO: 102.

In one embodiment, an antibody of the invention can comprise a heavy chain variable region comprising a VH CDR1 of SEQ ID NO: 103, a VH CDR2 of SEQ ID NO: 104, and VH CDR3 of SEQ ID NO: 105, and can further comprise a light chain variable region comprising a VL CDR1 of SEQ ID NO: 106, a VL CDR2 of SEQ ID NO: 107, and a VL CDR3 of SEQ ID NO: 108.

In one embodiment, an antibody of the invention can comprise a heavy chain variable region comprising a VH CDR1 of SEQ ID NO: 109, a VH CDR2 of SEQ ID NO: 110, and VH CDR3 of SEQ ID NO: 111, and can further comprise a light chain variable region comprising a VL CDR1 of SEQ ID NO: 112, a VL CDR2 of SEQ ID NO: 113, and a VL CDR3 of SEQ ID NO: 114.

In one embodiment, an antibody of the invention can comprise a heavy chain variable region comprising a VH CDR1 of SEQ ID NO: 115, a VH CDR2 of SEQ ID NO: 116, and VH CDR3 of SEQ ID NO: 117, and can further comprise a light chain variable region comprising a VL CDR1 of SEQ ID NO: 118, a VL CDR2 of SEQ ID NO: 119, and a VL CDR3 of SEQ ID NO: 120.

In one embodiment, an antibody of the invention can comprise a heavy chain variable region comprising a VH CDR1 of SEQ ID NO: 121, a VH CDR2 of SEQ ID NO: 122, and VH CDR3 of SEQ ID NO: 123, and can further comprise a light chain variable region comprising a VL CDR1 of SEQ ID NO: 124, a VL CDR2 of SEQ ID NO: 125, and a VL CDR3 of SEQ ID NO: 126.

In one embodiment, an antibody of the invention can comprise a heavy chain variable region comprising a VH CDR1 of SEQ ID NO: 127, a VH CDR2 of SEQ ID) NO: 128, and VH CDR3 of SEQ ID NO: 129, and can further comprise a light chain variable region comprising a VL CDR1 of SEQ ID NO: 130, a VL CDR2 of SEQ ID NO: 131, and a VL CDR3 of SEQ ID NO: 132.

In one embodiment, an antibody of the invention can comprise a heavy chain variable region comprising a VH CDR1 of SEQ ID NO: 133, a VH CDR2 of SEQ ID NO: 134, and VH CDR3 of SEQ ID NO: 135, and can further comprise a light chain variable region comprising a VL CDR1 of SEQ ID NO: 136, a VL CDR2 of SEQ ID NO: 137, and a VL CDR3 of SEQ ID NO: 138.

In one embodiment, an antibody of the invention can comprise a heavy chain variable region comprising a VH CDR1 of SEQ ID NO: 139, a VH CDR2 of SEQ ID NO: 140, and VH CDR3 of SEQ ID NO: 141, and can further comprise a light chain variable region comprising a VL CDR1 of SEQ ID NO: 142, a VL CDR2 of SEQ ID NO: 143, and a VL CDR3 of SEQ ID NO: 144.

In one embodiment, an antibody of the invention can comprise a heavy chain variable region comprising a VH CDR1 of SEQ ID NO: 145, a VH CDR2 of SEQ ID NO: 146, and VH CDR3 of SEQ ID NO: 147, and can further comprise a light chain variable region comprising a VL CDR1 of SEQ ID NO: 148, a VL CDR2 of SEQ ID NO: 149, and a VL CDR3 of SEQ ID NO: 150.

In one embodiment, an antibody of the invention can comprise a heavy chain variable region comprising a VH CDR1 of SEQ ID NO: 151, a VH CDR2 of SEQ ID NO: 152, and VH CDR3 of SEQ ID NO: 153, and can further comprise a light chain variable region comprising a VL CDR1 of SEQ ID NO: 154, a VL CDR2 of SEQ ID NO: 155, and a VL CDR3 of SEQ ID NO: 156.

In one embodiment, an antibody of the invention can comprise a heavy chain variable region comprising a VH CDR1 of SEQ ID NO: 157, a VH CDR2 of SEQ ID NO: 158, and VH CDR3 of SEQ ID NO: 159, and can further comprise a light chain variable region comprising a VL CDR1 of SEQ ID NO: 160, a VL CDR2 of SEQ ID NO: 161, and a VL CDR3 of SEQ ID NO: 162.

In one embodiment, an antibody of the invention can comprise a heavy chain variable region comprising a VH CDR1 of SEQ ID NO: 163, a VH CDR2 of SEQ ID NO: 164, and VH CDR3 of SEQ ID NO: 165, and can further comprise a light chain variable region comprising a VL CDR1 of SEQ ID NO: 166, a VL CDR2 of SEQ ID NO: 167, and a VL CDR3 of SEQ ID NO: 168.

In one embodiment, the antibody of the present invention is any one of the antibodies comprising an amino acid sequence of the $V_H$ and/or $V_L$ region as depicted in FIG. 7 and Table 3. In one embodiment, the antibody of the present invention is characterized by the preservation of the cognate pairing of the heavy and light chain as was present in the human B-cell.

TABLE 3

Amino acid sequences of the $V_H$ and $V_L$ region of tau specific antibodies. BG—before germlining

| Antibody | | Amino acid sequences of variable heavy (VH) and variable light (VL) chains |
|---|---|---|
| NI-105.17C1 | BG $V_H$ | SEQ. ID. NO: 44 |
| | $V_H$ | SEQ. ID. NO: 45 |
| | $V_L$ | SEQ. ID. NO: 46 |
| | N31Q $V_L$ | SEQ. ID. NO: 221 |
| | N31Q, I48V $V_L$ | SEQ. ID. NO: 222 |
| NI-105.6C5 | BG $V_H$ | SEQ. ID. NO: 47 |
| | $V_H$ | SEQ. ID. NO: 48 |
| | $V_L$ | SEQ. ID. NO: 49 |
| NI-105.29G10 | $V_H$ | SEQ. ID. NO: 50 |
| | $V_L$ | SEQ. ID. NO: 51 |

TABLE 3-continued

Amino acid sequences of the V$_H$ and V$_L$ region of tau specific antibodies. BG—before germlining

| Antibody | Amino acid sequences of variable heavy (VH) and variable light (VL) chains | |
|---|---|---|
| NI-105.6L9 | V$_H$ | SEQ. ID. NO: 52 |
|  | V$_L$ | SEQ. ID. NO: 53 |
| NI-105.40E8 | V$_H$ | SEQ. ID. NO: 54 |
|  | R104W V$_H$ | SEQ. ID. NO: 220 |
|  | V$_L$ | SEQ. ID. NO: 55 |
| NI-105.48E5 | V$_H$ | SEQ. ID. NO: 56 |
|  | V$_L$ | SEQ. ID. NO: 57 |
| NI-105.6E3 | V$_H$ | SEQ. ID. NO: 58 |
|  | V$_L$ | SEQ. ID. NO: 59 |
| NI-105.22E1 | V$_H$ | SEQ. ID. NO: 60 |
|  | V$_L$ | SEQ. ID. NO: 61 |
| NI-105.26B12 | V$_H$ | SEQ. ID. NO: 62 |
|  | BG V$_L$ | SEQ. ID. NO: 63 |
|  | V$_L$ | SEQ. ID. NO: 64 |
| NI-105.12E12 | V$_H$ | SEQ. ID. NO: 65 |
|  | V$_L$ | SEQ. ID. NO: 66 |
| NI-105.60E7 | V$_H$ | SEQ. ID. NO: 67 |
|  | V$_L$ | SEQ. ID. NO: 68 |
| NI-105.14E2 | V$_H$ | SEQ. ID. NO: 69 |
|  | V$_L$ | SEQ. ID. NO: 70 |
| NI-105.39E2 | V$_H$ | SEQ. ID. NO: 71 |
|  | V$_L$ | SEQ. ID. NO: 72 |
| NI-105.19C6 | V$_H$ | SEQ. ID. NO: 73 |
|  | V$_L$ | SEQ. ID. NO: 74 |
| NI-105.9C4 | BG V$_H$ | SEQ. ID. NO: 75 |
|  | V$_H$ | SEQ. ID. NO: 76 |
|  | BG V$_L$ | SEQ. ID. NO: 77 |
|  | V$_L$ | SEQ. ID. NO: 78 |

In one embodiment, an antibody of the present invention comprises a heavy chain variable region (VH) comprising, or consisting of an amino acid sequence selected from the group consisting of SEQ ID NO: 44, 45, 47, 48, 50, 52, 54, 56, 58, 60, 62, 65, 67, 69, 71, 73, 75, 76, and 220. In one embodiment, an antibody of the present invention comprises a light chain variable region (VL) comprising, or consisting of an amino acid sequence selected from the group consisting of SEQ ID NO: 46, 49, 51, 53, 55, 57, 59, 61, 63, 64, 66, 68, 70, 72, 74, 77, 78, 221, and 222. In one embodiment, an antibody of the present invention comprises a heavy chain variable region (VH) comprising, or consisting of an amino acid sequence selected from the group consisting of SEQ ID NO: 44, 45, 47, 48, 50, 52, 54, 56, 58, 60, 62, 65, 67, 69, 71, 73, 75, 76, and 220, and further comprises a light chain variable region (VL) comprising, or consisting of an amino acid sequence selected from the group consisting of SEQ ID NO: 46, 49, 51, 53, 55, 57, 59, 61, 63, 64, 66, 68, 70, 72, 74, 77, 78, 221, and 222. In a specific embodiment, the antibody comprises a VH of SEQ ID NO: 45 and a VL of SEQ ID NO: 46; or a VH of SEQ ID NO: 45 and a VL of SEQ ID NO: 221; or a VH of SEQ ID NO: 45 and a VL of SEQ ID NO: 222; or a VH of SEQ ID NO: 48 and a VL of SEQ ID NO: 49; or a VH of SEQ ID NO: 50 and a VL of SEQ ID NO: 51; or a VH of SEQ ID NO: 52 and a VL of SEQ ID NO: 53; or a VH of SEQ ID NO: 54 and a VL of SEQ ID NO: 55; or a VH of SEQ ID NO: 220 and a VL of SEQ ID NO: 55; or a VH of SEQ ID NO: 56 and a VL of SEQ ID NO: 57; or a VH of SEQ ID NO: 58 and a VL of SEQ ID NO: 59; or a VH of SEQ ID NO: 60 and a VL of SEQ ID NO: 61; or a VH of SEQ ID NO: 62 and a VL of SEQ ID NO: 64; or a VH of SEQ ID NO: 65 and a VL of SEQ ID NO: 66; or a VH of SEQ ID NO: 67 and a VL of SEQ ID NO: 68; or a VH of SEQ ID NO: 69 and a VL of SEQ ID NO: 70; or a VH of SEQ ID NO: 71 and a VL of SEQ ID NO: 72; or a VH of SEQ ID NO: 73 and a VL of SEQ ID NO: 74; or a VH of SEQ ID NO: 76 and a VL of SEQ ID NO: 78; or a VH of SEQ ID NO: 44 and a VL of SEQ ID NO: 46; or a VH of SEQ ID NO: 47 and a VL of SEQ ID NO: 49; or a VH of SEQ ID NO: 62 and a VL of SEQ ID NO: 63; or a VH of SEQ ID NO: 75 and a VL of SEQ ID NO: 77.

Alternatively, the antibody of the present invention is an antibody or antigen-binding fragment, derivative or variant thereof, which competes for binding to tau, such as, for example, hTau40, with at least one of the antibodies having the V$_H$ and/or V$_L$ region as depicted in FIG. 7 and Table 3. In one embodiment, an antibody of the present invention competes for specific binding to hTau40 with NI-105.17C1, NI-105.6C5, NI-105.29G10, NI-105.6L9, NI-105.40E8, NI-105.48E5, NI-105.6E3, NI-105.22E1, NI-105.26B12, NI-105.12E12, NI-105.60E7, NI-105.14E2, NI-105.39E2, NI-105.19C6, or NI-105.9C4. Those antibodies can be human as well, in particular for therapeutic applications. Alternatively, the antibody is a murine, murinized and chimeric murine-human antibody, which are particularly useful for diagnostic methods and studies in animals.

In one embodiment the antibody of the present invention is provided by cultures of single or oligoclonal B-cells that are cultured and the supernatant of the culture, which contains antibodies produced by said B-cells is screened for presence and affinity of anti-tau antibodies therein. The screening process comprises the steps of a sensitive tissue amyloid plaque immunoreactivity (TAPIR) assay such as described in international application WO2004/095031, the disclosure content of which is incorporated herein by reference; screen on brain sections for binding to PHFTau; screening for binding of a peptide derived from tau of the amino acid sequence represented by SEQ ID NO:6 with phosphate groups on amino acids Ser-202 and Thr-205; on amino acid Thr-231; and/or on amino acids Ser-396 and Ser-404 of said sequence; a screen for binding of recombinant human tau of the amino acid sequence represented by SEQ ID NO:6 and isolating the antibody for which binding is detected or the cell producing said antibody.

As mentioned above, due to its generation upon a human immune response the human monoclonal antibody of the present invention will recognize epitopes which are of particular pathological relevance and which might not be accessible or less immunogenic in case of immunization processes for the generation of, for example, mouse monoclonal antibodies and in vitro screening of phage display libraries, respectively. Accordingly, it is prudent to stipulate that the epitope of the human anti-tau antibody of the present invention is unique and no other antibody which is capable of binding to the epitope recognized by the human monoclonal antibody of the present invention exists. Therefore, the present invention also extends generally to anti-tau antibodies and tau binding molecules which compete with the human monoclonal antibody of the present invention for specific binding to tau. The present invention is more specifically directed to an antibody, or antigen-binding fragment, variant or derivatives thereof, where the antibody specifically binds to the same epitope of tau as a reference antibody selected from the group consisting of NI-105.17C1, NI-105.6C5, NI-105.29G10, NI-105.6L9, NI-105.40E8, NI-105.48E5, NI-105.6E3, NI-105.22E1, NI-105.26B12, NI-105.12E12, NI-105.60E7, NI-105.14E2, NI-105.39E2, NI-105.19C6, and NI-105.9C4.

Competition between antibodies is determined by an assay in which the immunoglobulin under test inhibits specific binding of a reference antibody to a common antigen, such as tau. Numerous types of competitive binding assays are known, for example: solid phase direct or indirect radioimmunoassay (RIA), solid phase direct or indirect enzyme immunoassay (EIA), sandwich competition assay; see Stahli et al., Methods in Enzymology 9 (1983), 242-253; solid phase direct biotin-avidin EIA; see Kirkland et al., J. Immunol. 137 (1986), 3614-3619 and Cheung et al., Virology 176 (1990), 546-552; solid phase direct labeled assay, solid phase direct labeled sandwich assay; see Harlow and Lane, Antibodies, A Laboratory Manual, Cold Spring Harbor Press (1988); solid phase direct label RIA using $I^{125}$ label; see Morel et al, Molec. Immunol. 25 (1988), 7-15 and Moldenhauer et al., Scand. J. Immunol. 32 (1990), 77-82. Typically, such an assay involves the use of purified tau or aggregates thereof bound to a solid surface or cells bearing either of these, an unlabelled test immunoglobulin and a labeled reference immunoglobulin, i.e. the human monoclonal antibody of the present invention. Competitive inhibition is measured by determining the amount of label bound to the solid surface or cells in the presence of the test immunoglobulin. Usually the test immunoglobulin is present in excess. In one embodiment, the competitive binding assay is performed under conditions as described for the ELISA assay in the appended Examples. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50% or 75%. Hence, the present invention is further drawn to an antibody, or antigen-binding fragment, variant or derivatives thereof, where the antibody competitively inhibits a reference antibody selected from the group consisting of NI-105.17C1, NI-105.6C5, NI-105.29G10, NI-105.6L9, NI-105.40E8, NI-105.48E5, NI-105.6E3, NI-105.22E1, NI-105.26B12, NI-105.12E12, NI-105.60E7, NI-105.14E2, NI-105.39E2, NI-105.19C6, or NI-105.9C4 from binding to tau.

In another embodiment, the present invention provides an isolated polypeptide comprising, consisting essentially of, or consisting of an immunoglobulin heavy chain variable region ($V_H$), where at least one of $V_H$-CDRs of the heavy chain variable region or at least two of the $V_H$-CDRs of the heavy chain variable region are at least 80%, 85%, 90%, 95%, 96%, 97%, 98% or 99% identical to reference heavy chain $V_H$-CDR1, $V_H$-CDR2 or $V_H$-CDR3 amino acid sequences from the antibodies disclosed herein. Alternatively, the $V_H$-CDR1, $V_H$-CDR2 and $V_H$-CDR3 regions of the $V_H$ are at least 80%, 85%, 90%, 95%, 96%, 97%, 98% or 99% identical to reference heavy chain $V_H$-CDR1, $V_H$-CDR2 and $V_H$-CDR3 amino acid sequences from the antibodies disclosed herein. Thus, according to this embodiment a heavy chain variable region of the invention has $V_H$-CDR1, $V_H$-CDR2 and $V_H$-CDR3 polypeptide sequences related to the groups shown in FIG. 7. While FIG. 7 shows $V_H$-CDRs defined by the Kabat system, other CDR definitions, e.g., $V_H$-CDRs defined by the Chothia system, are also included in the present invention, and can be easily identified by a person of ordinary skill in the art using the data presented in FIG. 7. In one embodiment, the amino acid sequence of the reference VH CDR1 is SEQ ID NO: 79, 85, 91, 97, 103, 109, 115, 121, 127, 133, 139, 145, 151, 157, or 163; the amino acid sequence of the reference VH CDR2 is SEQ ID NO: 80, 86, 92, 98, 104, 110, 116, 122, 128, 134, 140, 146, 152, 158, or 164; and the amino acid sequence of the reference VH CDR3 is SEQ ID NO: 81, 87, 93, 99, 105, 111, 117, 123, 129, 135, 141, 147, 153, 159, or 165.

In another embodiment, the present invention provides an isolated polypeptide comprising, consisting essentially of, or consisting of an immunoglobulin heavy chain variable region ($V_H$) in which the $V_H$-CDR1, $V_H$-CDR2 and $V_H$-CDR3 regions have polypeptide sequences which are identical to the $V_H$-CDR1, $V_H$-CDR2 and $V_H$-CDR3 groups shown in FIG. 7. In one embodiment, the amino acid sequence of the VH CDR1 is SEQ ID NO: 79, 85, 91, 97, 103, 109, 115, 121, 127, 133, 139, 145, 151, 157, or 163; the amino acid sequence of the VH CDR2 is SEQ ID NO: 80, 86, 92, 98, 104, 110, 116, 122, 128, 134, 140, 146, 152, 158, or 164; and the amino acid sequence of the VH CDR3 is SEQ ID NO: 81, 87, 93, 99, 105, 111, 117, 123, 129, 135, 141, 147, 153, 159, or 165.

In another embodiment, the present invention provides an isolated polypeptide comprising, consisting essentially of, or consisting of an immunoglobulin heavy chain variable region ($V_H$) in which the $V_H$-CDR1, $V_H$-CDR2 and $V_H$-CDR3 regions have polypeptide sequences which are identical to the $V_H$-CDR1, $V_H$-CDR2 and $V_H$-CDR3 groups shown in FIG. 7, except for one, two, three, four, five, six, seven, eight, nine, or ten amino acid substitutions in any one $V_H$-CDR. In certain embodiments the amino acid substitutions are conservative. In one embodiment, the amino acid sequence of the VH CDR1 is SEQ ID NO: 79, 85, 91, 97, 103, 109, 115, 121, 127, 133, 139, 145, 151, 157, or 163; the amino acid sequence of the VH CDR2 is SEQ ID NO: 80, 86, 92, 98, 104, 110, 116, 122, 128, 134, 140, 146, 152, 158, or 164; and the amino acid sequence of the VH CDR3 is SEQ ID NO: 81, 87, 93, 99, 105, 111, 117, 123, 129, 135, 141, 147, 153, 159, or 165.

In another embodiment, the present invention provides an isolated polypeptide comprising, consisting essentially of, or consisting of an immunoglobulin light chain variable region ($V_L$), where at least one of the $V_L$-CDRs of the light chain variable region or at least two of the $V_L$-CDRs of the light chain variable region are at least 80%, 85%, 90%, 95%, 96%, 97%, 98% or 99% identical to reference light chain $V_L$-CDR1, $V_L$-CDR2 or $V_L$-CDR3 amino acid sequences from antibodies disclosed herein. Alternatively, the $V_L$-CDR1, $V_L$-CDR2 and $V_L$-CDR3 regions of the $V_L$ are at least 80%, 85%, 90%, 95%, 96%, 97%, 98% or 99% identical to reference light chain $V_L$-CDR1, $V_L$-CDR2 and $V_L$-CDR3 amino acid sequences from antibodies disclosed herein. Thus, according to this embodiment a light chain variable region of the invention has $V_L$-CDR1, $V_L$-CDR2 and $V_L$-CDR3 polypeptide sequences related to the polypeptides shown in FIG. 7. While FIG. 7 shows $V_L$-CDRs defined by the Kabat system, other CDR definitions, e.g., $V_L$-CDRs defined by the Chothia system, are also included in the present invention. In one embodiment, the amino acid sequence of the reference VL CDR1 is SEQ ID NO: 82, 88, 94, 100, 106, 112, 118, 124, 130, 136, 142, 148, 154, 160, 166, or 224; the amino acid sequence of the reference VL CDR2 is SEQ ID NO: 83, 89, 95, 101, 107, 113, 119, 125, 131, 137, 143, 149, 155, 161, or 167; and the amino acid sequence of the reference VL CDR3 is SEQ ID NO: 84, 90, 96, 102, 108, 114, 120, 126, 132, 138, 144, 150, 156, 162, or 168.

In another embodiment, the present invention provides an isolated polypeptide comprising, consisting essentially of, or consisting of an immunoglobulin light chain variable region ($V_L$) in which the $V_L$-CDR1, $V_L$-CDR2 and $V_L$-CDR3 regions have polypeptide sequences which are identical to the $V_L$-CDR1, $V_L$-CDR2 and $V_L$-CDR3 groups shown in FIG. 7. In one embodiment, the amino acid sequence of the $V_L$ CDR1 is SEQ ID NO: 82, 88, 94, 100, 106, 112, 118, 124, 130, 136, 142, 148, 154, 160, 166, or 224; the amino acid sequence of the VL CDR2 is SEQ ID NO: 83, 89, 95, 101, 107, 113, 119, 125, 131, 137, 143, 149, 155, 161, or 167; and the amino acid sequence of the VL CDR3 is SEQ ID NO: 84, 90, 96, 102, 108, 114, 120, 126, 132, 138, 144, 150, 156, 162, or 168.

In another embodiment, the present invention provides an isolated polypeptide comprising, consisting essentially of, or consisting of an immunoglobulin light chain variable region ($V_L$) in which the $V_L$-CDR1, $V_L$-CDR2 and $V_L$-CDR3 regions have polypeptide sequences which are identical to the $V_L$-CDR1, $V_L$-CDR2 and $V_L$-CDR3 groups shown in FIG. 7, except for one, two, three, four, five, six, seven, eight, nine, or ten amino acid substitutions in any one $V_L$-CDR. In certain embodiments the amino acid substitutions are conservative. In one embodiment, the amino acid sequence of the VL CDR1 is SEQ ID NO: 82, 88, 94, 100, 106, 112, 118, 124, 130, 136, 142, 148, 154, 160, 166, or 224; the amino acid sequence of the VL CDR2 is SEQ ID NO: 83, 89, 95, 101, 107, 113, 119, 125, 131, 137, 143, 149, 155, 161, or 167; and the amino acid sequence of the VL CDR3 is SEQ ID NO: 84, 90, 96, 102, 108, 114, 120, 126, 132, 138, 144, 150, 156, 162, or 168.

In another embodiment, the invention provides an isolated polypeptide comprising, consisting essentially of, or consisting of an immunoglobulin heavy chain variable region ($V_H$) which is identical to a reference heavy chain variable region shown in FIG. 7 and Table 3. In one embodiment, the amino acid sequence of the reference heavy chain variable region comprises SEQ ID NO: 44, 45, 47, 48, 50, 52, 54, 56, 58, 60, 62, 65, 67, 69, 71, 73, 75, 76, or 220.

In another embodiment, the invention provides an isolated polypeptide comprising, consisting essentially of, or consisting of an immunoglobulin heavy chain variable region ($V_H$) having a polypeptide sequence which is identical to a reference heavy chain variable region ($V_H$) sequence shown in FIG. 7 and Table 3, except for one, two, three, four, five, six, seven, eight, nine, or ten amino acid substitutions. In certain embodiments the amino acid substitutions are conservative. In one embodiment, the amino acid sequence of the reference heavy chain variable region sequence comprises SEQ ID NO: 44, 45, 47, 48, 50, 52, 54, 56, 58, 60, 62, 65, 67, 69, 71, 73, 75, 76, or 220.

According to one embodiment, the invention provides an isolated polypeptide comprising, consisting essentially of, or consisting of an immunoglobulin light chain variable region ($V_L$) at least 80%, 85%, 90%, 95%, 96%, 97%, 98% or 99% identical to a reference light chain variable region ($V_L$) amino acid sequence from the antibodies disclosed herein. Thus, according to this embodiment a light chain variable region of the invention has a polypeptide sequence related to the light chain variable regions shown in FIG. 7 and Table 3. In one embodiment, the amino acid sequence of the reference light chain variable region ($V_L$) comprises SEQ ID NO: 46, 49, 51, 53, 55, 57, 59, 61, 63, 64, 66, 68, 70, 72, 74, 77, 78, 221, or 222.

In another embodiment, the invention provides an isolated polypeptide comprising, consisting essentially of, or consisting of an immunoglobulin light chain variable region ($V_L$) which is identical to a reference light chain variable region shown in FIG. 7 and Table 3. In one embodiment, the amino acid sequence of the reference light chain variable region comprises SEQ ID NO: 46, 49, 51, 53, 55, 57, 59, 61, 63, 64, 66, 68, 70, 72, 74, 77, 78, 221, or 222.

In another embodiment, the invention provides an isolated polypeptide comprising, consisting essentially of, or consisting of an immunoglobulin light chain variable region ($V_L$) having a polypeptide sequence which is identical to a reference light chain variable region ($V_L$) sequence shown in FIG. 7 and Table 3, except for one, two, three, four, five, six, seven, eight, nine, or ten amino acid substitutions. In certain embodiments the amino acid substitutions are conservative. In one embodiment, the amino acid sequence of the reference light chain variable region sequence comprises SEQ ID NO: 46, 49, 51, 53, 55, 57, 59, 61, 63, 64, 66, 68, 70, 72, 74, 77, 78, 221, or 222.

An immunoglobulin or its encoding cDNA can be further modified. Thus, in a further embodiment the method of the present invention comprises any one of the step(s) of producing a chimeric antibody, murinized antibody, single-chain antibody, Fab-fragment, bi-specific antibody, fusion antibody, labeled antibody or an analog of any one of those. Corresponding methods are known to the person skilled in the art and are described, e.g., in Harlow and Lane "Antibodies, A Laboratory Manual", CSH Press, Cold Spring Harbor (1988). When derivatives of said antibodies are obtained by the phage display technique, surface plasmon resonance as employed in the BIAcore system can be used to increase the efficiency of phage antibodies which bind to the same epitope as that of any one of the antibodies described herein (Schier, Human Antibodies Hybridomas 7 (1996), 97-105; Malmborg, J. Immunol. Methods 183 (1995), 7-13). The production of chimeric antibodies is described, for example, in international application WO89/09622. Methods for the production of humanized antibodies are described in, e.g., European application EP-A1 0 239 400 and international application WO90/07861. A further source of antibodies to be utilized in accordance with the present invention are so-called xenogeneic antibodies. The general principle for the production of xenogeneic antibodies such as human-like antibodies in mice is described in, e.g., international applications WO91/10741, WO94/02602, WO96/34096 and WO 96/33735. As discussed above, the antibody of the invention can exist in a variety of forms besides complete antibodies; including, for example, Fv, Fab and F(ab)$_2$, as well as in single chains; see e.g. international application WO88/09344.

The antibodies of the present invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, *Molecular Cloning A Laboratory Manual*, Cold Spring Harbor Laboratory (1989) N.Y. and Ausubel, *Current Protocols in Molecular Biology*, Green Publishing Associates and Wiley Interscience, N.Y. (1994). Modifications of the antibody of the invention include chemical and/or enzymatic derivatizations at one or more constituent amino acids, including side chain modifications, backbone modifications, and N- and C-terminal modifications including acetylation, hydroxylation, methylation, amidation, and the attachment of carbohydrate or lipid moieties, cofactors, and the like. Likewise, the present invention encompasses the production of chimeric proteins which comprise the described antibody or some fragment thereof at the amino terminus fused to heterologous molecule such as an immunostimulatory ligand at the carboxyl terminus; see, e.g., international application WO00/30680 for corresponding technical details.

Additionally, the present invention encompasses peptides including those containing a binding molecule as described above, for example containing the CDR3 region of the variable region of any one of the mentioned antibodies, in particular CDR3 of the heavy chain since it has frequently been observed that heavy chain CDR3 (HCDR3) is the region having a greater degree of variability and a predominant participation in antigen-antibody interaction. Such peptides can easily be synthesized or produced by recombinant means to produce a binding agent useful according to the invention. Such methods are well known to those of ordinary skill in the art. Peptides can be synthesized for example, using automated peptide synthesizers which are commercially available. The peptides can also be produced by recombinant techniques by incorporating the DNA expressing the peptide into an expression vector and transforming cells with the expression vector to produce the peptide.

Hence, the present invention relates to any binding molecule, e.g., an antibody or binding fragment thereof which is oriented towards the human anti-tau antibodies of the present invention and display the mentioned properties, i.e. which specifically recognize tau. Such antibodies and binding molecules can be tested for their binding specificity and affinity by ELISA and Western Blot and immunohistochemistry as described herein, see, e.g., the Examples. Furthermore, preliminary results of subsequent experiments performed in accordance with the present invention revealed that in one embodiment, the human ant-tau antibody of the present invention binds primarily to pathologically aggregated tau resembling neurofibrillary tangles (NFT), neuropil threads present on human brain sections of patients who suffered from Alzheimer's disease (AD) in addition. Thus, in a particular preferred embodiment of the present invention, the human antibody or binding fragment, derivative or variant thereof recognizes tau on human AD brain sections.

As an alternative to obtaining immunoglobulins directly from the culture of immortalized B cells or B memory cells, the immortalized cells can be used as a source of rearranged heavy chain and light chain loci for subsequent expression and/or genetic manipulation. Rearranged antibody genes can be reverse transcribed from appropriate mRNAs to produce cDNA. If desired, the heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Once the genetic material is available, design of analogs as described above which retain both their ability to bind the desired target is straightforward. Methods for the cloning of antibody variable regions and generation of recombinant antibodies are known to the person skilled in the art and are described, for example, Gilliland et al., Tissue Antigens 47 (1996), 1-20; Doenecke et al., Leukemia 11 (1997), 1787-1792.

Once the appropriate genetic material is obtained and, if desired, modified to encode an analog, the coding sequences, including those that encode, at a minimum, the variable regions of the heavy and light chain, can be inserted into expression systems contained on vectors which can be transfected into standard recombinant host cells. A variety of such host cells can be used; for efficient processing, however, mammalian cells can be considered. Typical mammalian cell lines useful for this purpose include, but are not limited to, CHO cells, HEK 293 cells, or NS0 cells.

The production of the antibody or analog is then undertaken by culturing the modified recombinant host under culture conditions appropriate for the growth of the host cells and the expression of the coding sequences. The antibodies are then recovered by isolating them from the culture. The expression systems are designed to include signal peptides so that the resulting antibodies are secreted into the medium; however, intracellular production is also possible.

In accordance with the above, the present invention also relates to a polynucleotide encoding the antibody or equivalent binding molecule of the present invention. In one embodiment, the polynucleotide encodes at least a variable region of an immunoglobulin chain of the antibody described above. Typically, said variable region encoded by the polynucleotide comprises at least one complementarity determining region (CDR) of the VH and/or VL of the variable region of the said antibody.

The person skilled in the art will readily appreciate that the variable domain of the antibody having the above-described variable domain can be used for the construction of other polypeptides or antibodies of desired specificity and biological function. Thus, the present invention also encompasses polypeptides and antibodies comprising at least one CDR of the above-described variable domain and which advantageously have substantially the same or similar binding properties as the antibody described in the appended examples. The person skilled in the art knows that binding affinity can be enhanced by making amino acid substitutions within the CDRs or within the hypervariable loops (Chothia and Lesk, J. Mol. Biol. 196 (1987), 901-917) which partially overlap with the CDRs as defined by Kabat; see, e.g., Riechmann, et al, Nature 332 (1988), 323-327. Thus, the present invention also relates to antibodies wherein one or more of the mentioned CDRs comprise one or more, or not more than two amino acid substitutions. In one embodiment, the antibody of the invention comprises in one or both of its immunoglobulin chains two or all three CDRs of the variable regions as set forth in FIG. 1.

Binding molecules, e.g., antibodies, or antigen-binding fragments, variants, or derivatives thereof of the invention, as known by those of ordinary skill in the art, can comprise a constant region which mediates one or more effector functions. For example, binding of the C1 component of complement to an antibody constant region can activate the complement system. Activation of complement is important in the opsonization and lysis of cell pathogens. The activation of complement also stimulates the inflammatory response and can also be involved in autoimmune hypersensitivity. Further, antibodies bind to receptors on various cells via the Fc region, with a Fc receptor binding site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

Accordingly, certain embodiments of the present invention include an antibody, or antigen-binding fragment, variant, or derivative thereof, in which at least a fraction of one or more of the constant region domains has been deleted or otherwise altered so as to provide desired biochemical characteristics such as reduced effector functions, the ability to non-covalently dimerize, increased ability to localize at the site of tau aggregation and deposition, reduced serum half-life, or increased serum half-life when compared with a whole, unaltered antibody of approximately the same immunogenicity. For example, certain antibodies for use in the diagnostic and treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted. In other embodiments, certain antibodies for use in the diagnostic and treatment methods described herein have a constant region, e.g., an IgG heavy chain constant region, which is altered to eliminate glycosylation, referred to elsewhere herein as aglycosylated or "agly" antibodies. Such "agly" antibodies can be prepared enzymatically as well as by engineering the consensus glycosylation site(s) in the constant region. While not being bound by theory, it is believed that "agly" antibodies can have an improved safety and stability profile in vivo. Methods of producing aglycosylated antibodies, having desired effector function are found for example in international application WO2005/018572, which is incorporated by reference in its entirety.

In certain antibodies, or antigen-binding fragments, variants, or derivatives thereof described herein, the Fc portion can be mutated to decrease effector function using techniques known in the art. For example, the deletion or inactivation (through point mutations or other means) of a constant region domain can reduce Fc receptor binding of the circulating modified antibody thereby increasing tau localization. In other cases it can be that constant region modifications consistent with the instant invention moderate complement binding and thus reduce the serum half-life and nonspecific association of a conjugated cytotoxin. Yet other modifications of the constant region can be used to modify disulfide linkages or oligosaccharide moieties that allow for enhanced localization due to increased antigen specificity or antibody flexibility. The resulting physiological profile, bioavailability and other biochemical effects of the modifications, such as tau localization, biodistribution and serum half-life, can easily be measured and quantified using well know immunological techniques without undue experimentation.

In certain antibodies, or antigen-binding fragments, variants, or derivatives thereof described herein, the Fc portion can be mutated or exchanged for alternative protein sequences to increase the cellular uptake of antibodies by way of example by enhancing receptor-mediated endocytosis of antibodies via Fcγ receptors, LRP, or Thy1 receptors or by 'SuperAntibody Technology', which is said to enable antibodies to be shuttled into living cells without harming them (Expert Opin. Biol. Ther. (2005), 237-241). For example, the generation of fusion proteins of the antibody binding region and the cognate protein ligands of cell surface receptors or bi- or multi-specific antibodies with a specific sequences biding to tau as well as a cell surface receptor can be engineered using techniques known in the art.

In certain antibodies, or antigen-binding fragments, variants, or derivatives thereof described herein, the Fc portion can be mutated or exchanged for alternative protein sequences or the antibody can be chemically modified to increase its blood brain barrier penetration.

Modified forms of antibodies, or antigen-binding fragments, variants, or derivatives thereof of the invention can be made from whole precursor or parent antibodies using techniques known in the art. Exemplary techniques are discussed in more detail herein. Antibodies, or antigen-binding fragments, variants, or derivatives thereof of the invention can be made or manufactured using techniques that are known in the art. In certain embodiments, antibody molecules or fragments thereof are "recombinantly produced," i.e., are produced using recombinant DNA technology. Exemplary techniques for making antibody molecules or fragments thereof are discussed in more detail elsewhere herein.

Antibodies, or antigen-binding fragments, variants, or derivatives thereof of the invention also include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of tunicamycin, etc. Additionally, the derivative can contain one or more non-classical amino acids.

In particular embodiments, antibodies, or antigen-binding fragments, variants, or derivatives thereof of the invention will not elicit a deleterious immune response in the animal to be treated, e.g., in a human. In certain embodiments, binding molecules, e.g., antibodies, or antigen-binding fragments thereof of the invention are derived from a patient, e.g., a human patient, and are subsequently used in the same species from which they are derived, e.g., human, alleviating or minimizing the occurrence of deleterious immune responses.

De-immunization can also be used to decrease the immunogenicity of an antibody. As used herein, the term "de-immunization" includes alteration of an antibody to modify T cell epitopes; see, e.g., international applications WO98/52976 and WO00/34317. For example, $V_H$ and $V_L$ sequences from the starting antibody are analyzed and a human T cell epitope "map" from each V region showing the location of epitopes in relation to complementarity determining regions (CDRs) and other key residues within the sequence. Individual T cell epitopes from the T cell epitope map are analyzed in order to identify alternative amino acid substitutions with a low risk of altering activity of the final antibody. A range of alternative $V_H$ and $V_L$ sequences are designed comprising combinations of amino acid substitutions and these sequences are subsequently incorporated into a range of binding polypeptides, e.g., tau-specific antibodies or immunospecific fragments thereof for use in the diagnostic and treatment methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, Cold Spring Harbor Laboratory Press, 2nd ed. (1988); Hammerling et al., in: *Monoclonal Antibodies and T-Cell Hybridomas* Elsevier, N.Y., 563-681 (1981), said references incorporated by reference in their entireties. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology. In certain embodiments, antibodies of the present invention are derived from human B cells which have been immortalized via transformation with Epstein-Barr virus, as described herein.

In the well-known hybridoma process (Kohler et al., Nature 256 (1975), 495) the relatively short-lived, or mortal, lymphocytes from a mammal, e.g., B cells derived from a human subject as described herein, are fused with an immortal tumor cell line (e.g., a myeloma cell line), thus, producing hybrid cells or "hybridomas" which are both immortal and capable of producing the genetically coded antibody of the B cell. The resulting hybrids are segregated into single genetic strains by selection, dilution, and re-growth with each individual strain comprising specific genes for the formation of a single antibody. They produce antibodies, which are homogeneous against a desired antigen and, in reference to their pure genetic parentage, are termed "monoclonal".

Hybridoma cells thus prepared are seeded and grown in a suitable culture medium that contain one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. The binding specificity of the monoclonal antibodies produced by hybridoma cells is determined by in vitro assays such as immunoprecipitation, radioimmunoassay (RIA) or enzyme-linked immunoabsorbent assay (ELISA) as described herein. After hybridoma cells are identified that produce antibodies of the desired specificity, affinity and/or activity, the clones can be subcloned by limiting dilution procedures and grown by standard methods; see, e.g., Goding, *Monoclonal Antibodies: Principles and Practice*, Academic Press, pp 59-103 (1986). It will further be appreciated that the monoclonal antibodies secreted by the subclones can be separated from culture medium, ascites fluid or serum by conventional purification procedures such as, for example, protein-A, hydroxylapatite chromatography, gel electrophoresis, dialysis or affinity chromatography.

In another embodiment, lymphocytes can be selected by micromanipulation and the variable genes isolated. For example, peripheral blood mononuclear cells can be isolated from an immunized or naturally immune mammal, e.g., a human, and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the $V_H$ and $V_L$ genes can be amplified using, e.g., RT-PCR. The $V_H$ and $V_L$ genes can be cloned into an antibody expression vector and transfected into cells (e.g., eukaryotic or prokaryotic cells) for expression.

Alternatively, antibody-producing cell lines can be selected and cultured using techniques well known to the skilled artisan. Such techniques are described in a variety of laboratory manuals and primary publications. In this respect, techniques suitable for use in the invention as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

Antibody fragments that recognize specific epitopes can be generated by known techniques. For example, Fab and F(ab')$_2$ fragments can be produced recombinantly or by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CH1 domain of the heavy chain. Such fragments are sufficient for use, for example, in immunodiagnostic procedures involving coupling the immunospecific portions of immunoglobulins to detecting reagents such as radioisotopes.

Human antibodies, such as described herein, are particularly desirable for therapeutic use in human patients. Human antibodies of the present invention are isolated, e.g., from healthy human subjects who because of their age may be suspected to be at risk of developing a tauopathic disorder, e.g., Alzheimer's disease, or a patient with the disorder but with an unusually stable disease course. However, though it is prudent to expect that elderly healthy and symptom-free subjects, respectively, more regularly will have developed protective anti-tau antibodies than younger subjects, the latter can be used as well as source for obtaining a human antibody of the present invention. This is particularly true for younger patients who are predisposed to develop a familial form of a tauopathic disease but remain symptom-free since their immune system functions more efficiently than that in older adults.

In one embodiment, an antibody of the invention comprises at least one heavy or light chain CDR of an antibody molecule. In another embodiment, an antibody of the invention comprises at least two CDRs from one or more antibody molecules. In another embodiment, an antibody of the invention comprises at least three CDRs from one or more antibody molecules. In another embodiment, an antibody of the invention comprises at least four CDRs from one or more antibody molecules. In another embodiment, an antibody of the invention comprises at least five CDRs from one or more antibody molecules. In another embodiment, an antibody of the invention comprises at least six CDRs from one or more antibody molecules. Exemplary antibody molecules comprising at least one CDR that can be included in the subject antibodies are described herein.

Antibodies of the present invention can be produced by any method known in the art for the synthesis of antibodies, in particular, by chemical synthesis or by recombinant expression techniques as described herein.

In one embodiment, an antibody, or antigen-binding fragment, variant, or derivative thereof of the invention comprises a synthetic constant region wherein one or more domains are partially or entirely deleted ("domain-deleted antibodies"). In certain embodiments compatible modified antibodies will comprise domain deleted constructs or variants wherein the entire CH2 domain has been removed (ΔCH2 constructs). For other embodiments a short connecting peptide can be substituted for the deleted domain to provide flexibility and freedom of movement for the variable region. Those skilled in the art will appreciate that such constructs are particularly preferred due to the regulatory properties of the CH2 domain on the catabolic rate of the antibody. Domain deleted constructs can be derived using a vector encoding an IgG$_1$ human constant domain, see, e.g., international applications WO02/060955 and WO02/096948A2. This vector is engineered to delete the CH2 domain and provide a synthetic vector expressing a domain deleted IgG constant region.

In certain embodiments, antibodies, or antigen-binding fragments, variants, or derivatives thereof of the present invention are minibodies. Minibodies can be made using methods described in the art, see, e.g., U.S. Pat. No. 5,837,821 or international application WO 94/09817.

In one embodiment, an antibody, or antigen-binding fragment, variant, or derivative thereof of the invention comprises an immunoglobulin heavy chain having deletion or substitution of a few or even a single amino acid as long as it permits association between the monomeric subunits. For example, the mutation of a single amino acid in selected areas of the CH2 domain can be enough to substantially reduce Fc binding and thereby increase tau localization. Similarly, it can be desirable to simply delete that part of one or more constant region domains that control the effector function (e.g. complement binding) to be modulated. Such partial deletions of the constant regions can improve selected characteristics of the antibody (serum half-life) while leaving other desirable functions associated with the subject constant region domain intact. Moreover, as alluded to above, the constant regions of the disclosed antibodies can be synthetic through the mutation or substitution of one or more amino acids that enhances the profile of the resulting construct. In this respect, the activity provided by a conserved binding site (e.g. Fc binding) can be disrupted while substantially maintaining the configuration and immunogenic profile of the modified antibody. Yet other embodiments comprise the addition of one or more amino acids to the constant region to enhance desirable characteristics such as effector function or provide for more cytotoxin or carbohydrate attachment. In such embodiments it can be desirable to insert or replicate specific sequences derived from selected constant region domains.

The present invention also provides antibodies that comprise, consist essentially of, or consist of, variants (including derivatives) of antibody molecules (e.g., the $V_H$ regions and/or $V_L$ regions) described herein, which antibodies or fragments thereof immunospecifically bind to tau. Standard techniques known to those of skill in the art can be used to introduce mutations in the nucleotide sequence encoding an antibody, including, but not limited to, site-directed mutagenesis and PCR-mediated mutagenesis which result in amino acid substitutions. In one embodiment, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference $V_H$ region, $V_H$-CDR1, $V_H$-CDR2, $V_H$-CDR3, $V_L$ region, $V_L$-CDR1, $V_L$-CDR2, or $V_L$-CDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind tau).

For example, it is possible to introduce mutations only in framework regions or only in CDR regions of an antibody molecule. Introduced mutations can be silent or neutral missense mutations, e.g., have no, or little, effect on an antibody's ability to bind antigen, indeed some such mutations do not alter the amino acid sequence whatsoever. These types of mutations can be useful to optimize codon usage, or improve a hybridoma's antibody production. Codon-optimized coding regions encoding antibodies of the present invention are disclosed elsewhere herein. Alternatively, non-neutral missense mutations can alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen-binding activity or alteration in binding activity (e.g., improvements in antigen-binding activity or change in antibody specificity). Following mutagenesis, the encoded protein can routinely be expressed and the functional and/or biological activity of the encoded protein, (e.g., ability to immunospecifically bind at least one epitope of tau) can be determined using techniques described herein or by routinely modifying techniques known in the art.

Tau binding agents, for example, but not limited to, tau binding antibodies of the present invention can be characterized using any in vivo or in vitro models of neurodegenerative tauopathies. A skilled artisan readily understands that a tau binding agent (e.g., an antibody) of the invention can be characterized in a mouse model for neurodegenerative tauopathies. for example, but not limited to, any one of the following three different animal models for tauopathies can be used to characterize and validate the tau antibodies (and molecules with the binding specificities thereof) of the present invention.

1. Transgenic TauP301L mice (line183): expressing human Tau40 with P301L mutation under the murine Thy1.2 promoter (Generation of these transgenic animals is described in Götz et al., J. Biol. Chem. 276 (2001), 529-534 and in international application WO 2003/017918, the disclosure content of which is incorporated herein by reference)

2. JNPL3 mice expressing the shortest 4R human tau isoform with P301L mutation under the murine PrP promoter (available from Taconic, Hudson, N.Y., U.S.A).

3. P301STau (line PS19) mice expressing human tau with P301S mutation under the murine PrP promoter (available from the Jackson Laboratory, Bar Harbor, Me., U.S.A).

A skilled artisan understands that an experimental model of neurodegenerative tauopathies can be used in a preventative setting or it can be used in a therapeutic setting. In a preventative setting, the dosing of animals starts prior to the onset of the neurodegenerative tauopathies or symptoms thereof. In preventative settings, a tau binding agent (e.g., antibody) of the invention is evaluated for its ability to prevent, reduce or delay the onset of neurodegenerative tauopathies or symptoms thereof. In a therapeutic setting, the dosing of animals start after the onset of neurodegenerative tauopathies or a symptom thereof. In a therapeutic setting, a tau binding agent (e.g., antibody) of the invention is evaluated for its ability to treat, reduce or alleviate the neurodegenerative tauopathies or a symptom thereof. Symptoms of the neurodegenerative tauopathies include, but are not limited to, accumulation of pathological tau deposits, neurofibrillary tangles (NFT), hyperphosphorylated tau polypeptide, insoluble tau fractions in the neurons, brain, spinal cord, cerebrospinal fluid or serum of the experimental object. A skilled artisan understands that a positive preventative or therapeutic outcome in any animal model of neurodegenerative tauopathies indicates that the particular tau binding agent (e.g., antibody) can be used for preventative or therapeutic purposes in a subject other than the experimental model organism, for example, it can be used to treat neurodegenerative tauopathies in a human subject in need thereof.

In one embodiment, a tau binding agent (e.g., an antibody) of the invention can be administered to a tauopathy mouse model and corresponding control wild type mice. The antibody administered can be a murinized antibody of the present invention or a human-murine chimera of an antibody of the present invention. The tau binding agent (e.g., an antibody) can be administered by any means known in the art, for example, by intraperitoneal, intracranial, intramuscular, intravenous, subcutaneous, oral, and aerosol administration. Experimental animals can be given one, two, three, four, five or more doses of the tau binding agent (e.g., an antibody) or a control composition, such as PBS. In one embodiment, experimental animals will be administered one or two doses of a tau binding agent (e.g., an antibody). See, for example, Example 9. In another embodiment, the animals are chronically dosed with the tau binding agent (e.g., an antibody) over several weeks or months. See, for example, Example 10. A skilled artisan can readily design a dosing regimen that fits the experimental purpose, for example, dosing regimen for acute studies, dosing regimen for chronic studies, dosing regimen for toxicity studies, dosing regimen for preventative or therapeutic studies. The presence of the tau binding agent (e.g., antibody) in a particular tissue compartment of the experimental animals, for example, but not limited to, serum, blood, cerebrospinal fluid, brain tissue, can be established using well know methods of the art. See, for example, Example 9 and 10. In one embodiment, a tau binding agent (e.g., antibody) of the invention is capable to penetrate the blood brain barrier. A skilled artisan understands that by adjusting the tau binding agent (e.g., antibody) dose and the dosing frequency, a desired tau binding agent (e.g., antibody) concentration can be maintained in the experimental animals. Any effect of a tau binding agent (e.g., antibody) of the present invention in the tauopathy models can be assessed by comparing the level, biochemical characteristics or distribution of tau in the treated and control animals. In one example, the neurofibrillary tangles (NFT) are examined using the silver impregnation technique of Gallyas or by immunostaining with monoclonal mouse antibody AT100 and AT180, which recognize pathologically phosphorylated tau in NFT. The number or frequency of Gallyas-positive neurons and/or AT100, AT180 labeled neurons in the brain and spinal cord in antibody treated mice and control animals can be determined to evaluate the effect of antibody treatment. In one embodiment, an antibody of the present invention is capable of reducing the level, amount or concentration of neurofibrillary tangles in the brain or spinal cord in an animal model. The antibody can reduce the level, amount or concentration of neurofibrillary tangles by at least about 5%, 10%, 20%, 30%, 50%, 70%, 90% or more. In another embodiment, an antibody of the present invention is capable of reducing the number or frequency of Gallyas-positive neurons in the brain or spinal cord in an animal model, for example, by at least about 5%, 10%, 20%, 30%, 50%, 70%, 90% or more. In a further embodiment, an antibody of the present invention is capable of reducing the number or frequency of AT100 or AT180 antibody positive neurons in the brain or spinal cord in an animal model, for example, by at least about 5%, 10%, 20%, 30%, 50%, 70%, 90% or more. The effect of an antibody of the present invention can also be assessed by examining the distribution and biochemical properties of tau following antibody administration. In one embodiment, an antibody of the present invention is capable of reducing the amount or concentration of tau protein in the brain or spinal cord of an animal model, for example, by at least about 5%, 10%, 20%, 30%, 50%, 70%, 90% or more. In another embodiment, an antibody of the present invention is capable of reducing the amount or concentration of insoluble tau protein in the brain or spinal cord of an animal model, for example, by at least about 5%, 10%, 20%, 30%, 50%, 70%, 90% or more. Insoluble tau fraction can be prepared as described, for example, in Example 10 or in Goedert M, Spillantini M G, Cairns N J, Crowther R A. Neuron 8, 159 (1992). The amount of tau protein in a biological sample can be determined by any method known to one of skill, for example, as described in Example 10. In a further embodiment, an antibody of the present invention can reduce the amount or concentration of hyperphosphorylated tau protein in the brain or spinal cord in an animal model, for example, by at least about 5%, 10%, 20%, 30%, 50%, 70%, 90% or more. Hyperphosphorylated tau can be detected using antibodies specific for pathologically hyperphosphorylated forms of tau, such as AT100 or AT180. An antibody of the present invention can also alter, for example, reduce or increase, tau concentration in the blood, serum or cerebrospinal fluid or an animal model, for example, by at least about 5%, 10%, 20%, 30%, 50%, 70%, 90% or more. In one embodiment, the % reduction or increase is relative compared to the level, number, frequency, amount or concentration that existed before treatment, or to the level, number, frequency, amount or concentration that exist in an untreated/control treated subject.

In one embodiment, an antibody of the present invention can prevent or delay the onset of at least one symptom of a neurodegenerative tauopathy in a subject. In one embodiment, an antibody of the present invention can reduce or eliminate at least one symptom of a neurodegenerative tauopathy in a subject. The symptom can be the formation of pathological tau deposits, hyperphosphorylated tau deposits, insoluble tau deposits, neurofibrillary fibers, neurofibrillary fibers, pre-tangle phosphor tau aggregates, intraneuronal neurofibrillary tangles or extraneuronal neurofibrillary tangles in the brain or spinal cord of a subject. See, e.g., Augustinack et al, Acta Neuropathol 103:26-35 (2002). The symptom can also be the presence, or elevated concentration or amount, of tau in the serum, blood, urine or cerebrospinal fluid, wherein elevated concentration amount is compared to a healthy subject. The symptom can be a neurological symptom, for example, altered conditioned taste aversion, altered contextual fear conditioning, memory impairment, loss of motor function. In one embodiment, memory impairment is assessed using a two-trial Y-maze task. In a specific embodiment, the two-trial Y-maze task is performed substantially as described in Example 10. In one embodiment, the at least one symptom is reduced by at least about 5%, 10%, 15%, 20%, 30%, 50%, 70%, or 90%. In another embodiment, the two-trial Y-maze task ratio is significantly higher in an antibody treated subject than in a control subject. In a specific embodiment, the two-trial Y-maze task ratio is increased by at least about 5%, 10%, 20%, 30%, 40%, 50%, 60%, 70%, 80%, or 90%. In another embodiment, the two-trial Y-maze task ratio is at least about two times, three times, four times, five times, ten times, or twenty times higher. The present invention also provides a method of preventing or delaying the onset of at least one symptom of a neurodegenerative tauopathy in a subject in need thereof, comprising administering a therapeutically effective amount of a tau antibody described herein. The present invention further provides a method of reducing or eliminating least one symptom of a neurodegenerative tauopathy in a subject in need thereof, comprising administering a therapeutically effective amount of a tau antibody described herein. In one embodiment, the subject is an experimental organism, such as, but not limited to, transgenic mouse. In one embodiment, the subject is a human.

III. Polynucleotides Encoding Antibodies

A polynucleotide encoding an antibody, or antigen-binding fragment, variant, or derivative thereof can be composed of any polyribonucleotide or polydeoxribonucleotide, which can be unmodified RNA or DNA or modified RNA or DNA. For example, a polynucleotide encoding an antibody, or antigen-binding fragment, variant, or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, a polynucleotide encoding an antibody, or antigen-binding fragment, variant, or derivative thereof can be composed of triple-stranded regions comprising RNA or DNA or both RNA and DNA. A polynucleotide encoding an antibody, or antigen-binding fragment, variant, or derivative thereof can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations can be introduced by standard techniques, such as site-directed mutagenesis and PCR-mediated mutagenesis. In one embodiment, conservative amino acid substitutions are made at one or more non-essential amino acid residues.

As is well known, RNA can be isolated from the original B cells, hybridoma cells or from other transformed cells by standard techniques, such as guanidinium isothiocyanate extraction and precipitation followed by centrifugation or chromatography. Where desirable, mRNA can be isolated from total RNA by standard techniques such as chromatography on oligo dT cellulose. Suitable techniques are familiar in the art. In one embodiment, cDNAs that encode the light and the heavy chains of the antibody can be made, either simultaneously or separately, using reverse transcriptase and DNA polymerase in accordance with well-known methods. PCR can be initiated by consensus constant region primers or by more specific primers based on the published heavy and light chain DNA and amino acid sequences. As discussed above, PCR also can be used to isolate DNA clones encoding the antibody light and heavy chains. In this case the libraries can be screened by consensus primers or larger homologous probes, such as human constant region probes.

DNA, typically plasmid DNA, can be isolated from the cells using techniques known in the art, restriction mapped and sequenced in accordance with standard, well known techniques set forth in detail, e.g., in the foregoing references relating to recombinant DNA techniques. Of course, the DNA can be synthetic according to the present invention at any point during the isolation process or subsequent analysis.

In one embodiment, the present invention provides an isolated polynucleotide comprising, consisting essentially of, or consisting of a nucleic acid encoding an immunoglobulin heavy chain variable region ($V_H$), where at least one of the CDRs of the heavy chain variable region or at least two of the $V_H$-CDRs of the heavy chain variable region are at least 80%, 85%, 90%, 95%, 96%, 97%, 98%, or 99% identical to reference heavy chain $V_H$-CDR1, $V_H$-CDR2, or $V_H$-CDR3 amino acid sequences from the antibodies disclosed herein. Alternatively, the $V_H$-CDR1, $V_H$-CDR2, or $V_H$-CDR3 regions of the $V_H$ are at least 80%, 85%, 90%, 95%, 96%, 97%, 98%, or 99% identical to reference heavy chain $V_H$-CDR1, $V_H$-CDR2, and $V_H$-CDR3 amino acid sequences from the antibodies disclosed herein. Thus, according to this embodiment a heavy chain variable region of the invention has $V_H$-CDR1, $V_H$-CDR2, or $V_H$-CDR3 polypeptide sequences related to the polypeptide sequences shown in FIG. 7. In one embodiment, the amino acid sequence of the reference VH CDR1 is SEQ ID NO: 79, 85, 91, 97, 103, 109, 115, 121, 127, 133, 139, 145, 151, 157, or 163; the amino acid sequence of the reference VH CDR2 is SEQ ID NO: 80, 86, 92, 98, 104, 110, 116, 122, 128, 134, 140, 146, 152, 158, or 164; and the amino acid sequence of the reference VH CDR3 is SEQ ID NO: 81, 87, 93, 99, 105, 111, 117, 123, 129, 135, 141, 147, 153, 159, or 165.

In one embodiment, the present invention provides an isolated polynucleotide comprising, consisting essentially of, or consisting of a nucleic acid encoding an immunoglobulin heavy chain variable region ($V_H$), in which the $V_H$-CDR1, $V_H$-CDR2 and $V_H$-CDR3 regions have polypeptide sequences which are identical to the $V_H$-CDR1, $V_H$-CDR2 and $V_H$-CDR3 groups shown in FIG. 7, except for one, two, three, four, five, six, seven, eight, nine, or ten amino acid substitutions in any one $V_H$-CDR. In certain embodiments the amino acid substitutions are conservative. In one embodiment, the amino acid sequence of the VH CDR1 is SEQ ID NO: 79, 85, 91, 97, 103, 109, 115, 121, 127, 133, 139, 145, 151, 157, or 163; the amino acid sequence of the VH CDR2 is SEQ ID NO: 80, 86, 92, 98, 104, 110, 116, 122, 128, 134, 140, 146, 152, 158, or 164; and the amino acid sequence of the VH CDR3 is SEQ ID NO: 81, 87, 93, 99, 105, 111, 117, 123, 129, 135, 141, 147, 153, 159, or 165.

In another embodiment, the present invention provides an isolated polynucleotide comprising, consisting essentially of, or consisting of a nucleic acid encoding an immunoglobulin light chain variable region ($V_L$), where at least one of the $V_L$-CDRs of the light chain variable region or at least two of the $V_L$-CDRs of the light chain variable region are at least 80%, 85%, 90%, 95%, 96%, 97%, 98%, or 99% identical to reference light chain $V_L$-CDR1, $V_L$-CDR2, or $V_L$-CDR3 amino acid sequences from the antibodies disclosed herein. Alternatively, the $V_L$-CDR1, $V_L$-CDR2, or $V_L$-CDR3 regions of the $V_L$ are at least 80%, 85%, 90%, 95%, 96%, 97%, 98%, or 99% identical to reference light chain $V_L$-CDR1, $V_L$-CDR2, and $V_L$-CDR3 amino acid sequences from the antibodies disclosed herein. Thus, according to this embodiment a light chain variable region of the invention has $V_L$-CDR1, $V_L$-CDR2, or $V_L$-CDR3 polypeptide sequences related to the polypeptide sequences shown in FIG. 7. In one embodiment, the amino acid sequence of the reference VL CDR1 is SEQ ID NO: 82, 88, 94, 100, 106, 112, 118, 124, 130, 136, 142, 148, 154, 160, 166, or 224; the amino acid sequence of the reference VL CDR2 is SEQ ID NO: 83, 89, 95, 101, 107, 113, 119, 125, 131, 137, 143, 149, 155, 161, or 167; and the amino acid sequence of the reference VL CDR3 is SEQ ID NO: 84, 90, 96, 102, 108, 114, 120, 126, 132, 138, 144, 150, 156, 162, or 168.

In another embodiment, the present invention provides an isolated polynucleotide comprising, consisting essentially of, or consisting of a nucleic acid encoding an immunoglobulin light chain variable region ($V_L$) in which the $V_L$-CDR1, $V_L$-CDR2 and $V_L$-CDR3 regions have polypeptide sequences which are identical to the $V_L$-CDR1, $V_L$-CDR2 and $V_L$-CDR3 groups shown in FIG. 7, except for one, two, three, four, five, six, seven, eight, nine, or ten amino acid substitutions in any one $V_L$-CDR. In certain embodiments the amino acid substitutions are conservative. In one embodiment, the amino acid sequence of the VL CDR1 is SEQ ID NO: 82, 88, 94, 100, 106, 112, 118, 124, 130, 136, 142, 148, 154, 160, 166, or 224; the amino acid sequence of the VL CDR2 is SEQ ID NO: 83, 89, 95, 101, 107, 113, 119, 125, 131, 137, 143, 149, 155, 161, or 167; and the amino acid sequence of the VL CDR3 is SEQ ID NO: 84, 90, 96, 102, 108, 114, 120, 126, 132, 138, 144, 150, 156, 162, or 168.

In another embodiment, the present invention provides an isolated polynucleotide comprising, consisting essentially of, or consisting of a nucleic acid encoding an immunoglobulin heavy chain variable region ($V_H$) in which the $V_H$-CDR1, $V_H$-CDR2, and $V_H$-CDR3 regions have polypeptide sequences which are identical to the $V_H$-CDR1, $V_H$-CDR2, and $V_H$-CDR3 groups shown in FIG. 7. In one embodiment, the amino acid sequence of the VH CDR1 is SEQ ID NO: 79, 85, 91, 97, 103, 109, 115, 121, 127, 133, 139, 145, 151, 157, or 163; the amino acid sequence of the VH CDR2 is SEQ ID NO: 80, 86, 92, 98, 104, 110, 116, 122, 128, 134, 140, 146, 152, 158, or 164; and the amino acid sequence of the VH CDR3 is SEQ ID NO: 81, 87, 93, 99, 105, 111, 117, 123, 129, 135, 141, 147, 153, 159, or 165.

In another embodiment, the present invention provides an isolated polynucleotide comprising, consisting essentially of, or consisting of a nucleic acid encoding an immunoglobulin light chain variable region ($V_L$) in which the $V_L$-CDR1, $V_L$-CDR2, and $V_L$-CDR3 regions have polypeptide sequences which are identical to the $V_L$-CDR1, $V_L$-CDR2, and $V_L$-CDR3 groups shown in FIG. 7. In one embodiment, the amino acid sequence of the VL CDR1 is SEQ ID NO: 82, 88, 94, 100, 106, 112, 118, 124, 130, 136, 142, 148, 154, 160, 166, or 224; the amino acid sequence of the VL CDR2 is SEQ ID NO: 83, 89, 95, 101, 107, 113, 119, 125, 131, 137, 143, 149, 155, 161, or 167; and the amino acid sequence of the VL CDR3 is SEQ ID NO: 84, 90, 96, 102, 108, 114, 120, 126, 132, 138, 144, 150, 156, 162, or 168.

As known in the art, "sequence identity" between two polypeptides or two polynucleotides is determined by comparing the amino acid or nucleic acid sequence of one polypeptide or polynucleotide to the sequence of a second polypeptide or polynucleotide. When discussed herein, whether any particular polypeptide is at least about 40%, 45%, 50%, 55%, 60%, 65%, 70%, 75%, 80%, 85%, 90% or 95% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2 (1981), 482-489, to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

In one embodiment of the present invention, the polynucleotide comprises, consists essentially of, or consists of a nucleic acid having a polynucleotide sequence of the $V_H$ or $V_L$ region of an anti-tau antibody as depicted in Table 4. In this respect, the person skilled in the art will readily appreciate that the polynucleotides encoding at least the variable domain of the light and/or heavy chain can encode the variable domain of both immunoglobulin chains or only one.

TABLE 4

Nucleotide sequences of the $V_H$ and $V_L$ region of tau specific antibodies. BG—before germlining

| Antibody | | Nucleotide sequence of variable heavy (VH) and variable light (VL) chains |
|---|---|---|
| NI-105.17C1 | BG $V_H$ | SEQ. ID. NO: 169 |
| | $V_H$ | SEQ. ID. NO: 170 |
| | $V_L$ | SEQ. ID. NO: 171 |
| NI-105.6C5 | BG $V_H$ | SEQ. ID. NO: 172 |
| | $V_H$ | SEQ. ID. NO: 173 |
| | $V_L$ | SEQ. ID. NO: 174 |
| NI-105.29G10 | $V_H$ | SEQ. ID. NO: 175 |
| | $V_L$ | SEQ. ID. NO: 176 |
| NI-105.6L9 | $V_H$ | SEQ. ID. NO: 177 |
| | $V_L$ | SEQ. ID. NO: 178 |
| NI-105.40E8 | $V_H$ | SEQ. ID. NO: 179 |
| | $V_L$ | SEQ. ID. NO: 180 |
| NI-105.48E5 | $V_H$ | SEQ. ID. NO: 181 |
| | $V_L$ | SEQ. ID. NO: 182 |
| NI-105.6E3 | $V_H$ | SEQ. ID. NO: 183 |
| | $V_L$ | SEQ. ID. NO: 184 |
| NI-105.22E1 | $V_H$ | SEQ. ID. NO: 185 |
| | $V_L$ | SEQ. ID. NO: 186 |

TABLE 4-continued

Nucleotide sequences of the $V_H$ and $V_L$ region of tau specific antibodies. BG—before germlining

| Antibody | | Nucleotide sequence of variable heavy (VH) and variable light (VL) chains |
|---|---|---|
| NI-105.26B12 | $V_H$ | SEQ. ID. NO: 187 |
| | BG $V_L$ | SEQ. ID. NO: 188 |
| | $V_L$ | SEQ. ID. NO: 223 |
| NI-105.12E12 | $V_H$ | SEQ. ID. NO: 189 |
| | $V_L$ | SEQ. ID. NO: 190 |
| NI-105.60E7 | $V_H$ | SEQ. ID. NO: 191 |
| | $V_L$ | SEQ. ID. NO: 192 |
| NI-105.14E2 | $V_H$ | SEQ. ID. NO: 193 |
| | $V_L$ | SEQ. ID. NO: 194 |
| NI-105.39E2 | $V_H$ | SEQ. ID. NO: 195 |
| | $V_L$ | SEQ. ID. NO: 196 |
| NI-105.19C6 | $V_H$ | SEQ. ID. NO: 197 |
| | $V_L$ | SEQ. ID. NO: 198 |
| NI-105.9C4 | BG $V_H$ | SEQ. ID. NO: 199 |
| | $V_H$ | SEQ. ID. NO: 200 |
| | BG $V_L$ | SEQ. ID. NO: 201 |
| | $V_L$ | SEQ. ID. NO: 202 |

In one embodiment, the present invention provides an isolated polynucleotide comprising, consisting essentially of, or consisting of a nucleic acid encoding an immunoglobulin heavy chain variable region at least 80%, 85%, 90%, 95%, 96%, 97%, 98%, or 99% or 95% identical to reference heavy chain VH. In one embodiment, the amino acid sequence of the reference heavy chain variable region comprises SEQ ID NO: 44, 45, 47, 48, 50, 52, 54, 56, 58, 60, 62, 65, 67, 69, 71, 73, 75, 76, or 220.

In one embodiment, the present invention provides an isolated polynucleotide comprising, consisting essentially of, or consisting of a nucleic acid encoding an immunoglobulin light chain variable region at least 80%, 85%, 90%, 95%, 96%, 97%, 98%, or 99% or 95% identical to reference light chain VL. In one embodiment, the amino acid sequence of the reference light chain variable region comprises SEQ ID NO: 46, 49, 51, 53, 55, 57, 59, 61, 63, 64, 66, 68, 70, 72, 74, 77, 78, 221, or 222.

The present invention also includes fragments of the polynucleotides of the invention, as described elsewhere. Additionally polynucleotides which encode fusion polynucleotides, Fab fragments, and other derivatives, as described herein, are also contemplated by the invention.

The polynucleotides can be produced or manufactured by any method known in the art. For example, if the nucleotide sequence of the antibody is known, a polynucleotide encoding the antibody can be assembled from chemically synthesized oligonucleotides, e.g., as described in Kutmeier et al., BioTechniques 17 (1994), 242, which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody, or antigen-binding fragment, variant, or derivative thereof can be generated from nucleic acid from a suitable source. If a clone containing a nucleic acid encoding a particular antibody is not available, but the sequence of the antibody molecule is known, a nucleic acid encoding the antibody can be chemically synthesized or obtained from a suitable source (e.g., an antibody cDNA library, or a cDNA library generated from, or nucleic acid, preferably polyA+ RNA, isolated from, any tissue or cells expressing the tau-specific antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

Once the nucleotide sequence and corresponding amino acid sequence of the antibody, or antigen-binding fragment, variant, or derivative thereof is determined, its nucleotide sequence can be manipulated using methods well known in the art for the manipulation of nucleotide sequences, e.g., recombinant DNA techniques, site directed mutagenesis, PCR, etc. (see, for example, the techniques described in Sambrook et al., Molecular Cloning, A Laboratory Manual, 2d Ed., Cold Spring Harbor Laboratory, Cold Spring Harbor, N.Y. (1990) and Ausubel et al., eds., Current Protocols in Molecular Biology, John Wiley & Sons, NY (1998), which are both incorporated by reference herein in their entireties), to generate antibodies having a different amino acid sequence, for example to create amino acid substitutions, deletions, and/or insertions.

IV. Expression of Antibody Polypeptides

Following manipulation of the isolated genetic material to provide antibodies, or antigen-binding fragments, variants, or derivatives thereof of the invention, the polynucleotides encoding the antibodies are typically inserted in an expression vector for introduction into host cells that can be used to produce the desired quantity of antibody. Recombinant expression of an antibody, or fragment, derivative or analog thereof, e.g., a heavy or light chain of an antibody which binds to a target molecule is described herein. Once a polynucleotide encoding an antibody molecule or a heavy or light chain of an antibody, or portion thereof (preferably containing the heavy or light chain variable domain), of the invention has been obtained, the vector for the production of the antibody molecule can be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors can include the nucleotide sequence encoding the constant region of the antibody molecule (see, e.g., international applications WO 86/05807 and WO 89/01036; and U.S. Pat. No. 5,122,464) and the variable domain of the antibody can be cloned into such a vector for expression of the entire heavy or light chain.

The term "vector" or "expression vector" is used herein to mean vectors used in accordance with the present invention as a vehicle for introducing into and expressing a desired gene in a host cell. As known to those skilled in the art, such vectors can easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells. For the purposes of this invention, numerous expression vector systems can be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes can be selected by introducing one or more markers which allow selection of transfected host cells. The marker can provide for prototrophy to an auxotrophic host, biocide resistance (e.g., antibiotics) or resistance to heavy metals such as copper. The selectable marker gene can either be directly linked to the DNA sequences to be expressed, or introduced into the same cell by co-transformation. Additional elements can also be needed for optimal synthesis of mRNA. These elements can include signal sequences, splice signals, as well as transcriptional promoters, enhancers, and termination signals.

In particular embodiments the cloned variable region genes are inserted into an expression vector along with the heavy and light chain constant region genes (e.g., human heavy and light chain constant region genes) as discussed above. In one embodiment, this is effected using a proprietary expression vector of Biogen IDEC, Inc., referred to as NEOSPLA, disclosed in U.S. Pat. No. 6,159,730. This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high level expression of antibodies upon incorporation of variable and constant region genes, transfection in CHO cells, followed by selection in G418 containing medium and methotrexate amplification. Of course, any expression vector which is capable of eliciting expression in eukaryotic cells can be used in the present invention. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). In general, screening large numbers of transformed cells for those which express suitably high levels if immunoglobulin heavy and light chains is routine experimentation which can be carried out, for example, by robotic systems. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other embodiments the antibodies, or antigen-binding fragments, variants, or derivatives thereof of the invention can be expressed using polycistronic constructs such as those disclosed in US patent application publication no. 2003-0157641 A1 and incorporated herein in its entirety. In these expression systems, multiple gene products of interest such as heavy and light chains of antibodies can be produced from a single polycistronic construct. These systems advantageously use an internal ribosome entry site (IRES) to provide relatively high levels of antibodies. Compatible IRES sequences are disclosed in U.S. Pat. No. 6,193,980 which is also incorporated herein. Those skilled in the art will appreciate that such expression systems can be used to effectively produce the full range of antibodies disclosed in the instant application.

More generally, once the vector or DNA sequence encoding a monomeric subunit of the antibody has been prepared, the expression vector can be introduced into an appropriate host cell. Introduction of the plasmid into the host cell can be accomplished by various techniques well known to those of skill in the art. These include, but are not limited to, transfection including lipotransfection using, e.g., Fugene® or lipofectamine, protoplast fusion, calcium phosphate precipitation, cell fusion with enveloped DNA, microinjection, and infection with intact virus. Typically, plasmid introduction into the host is via standard calcium phosphate co-precipitation method. The host cells harboring the expression construct are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

The expression vector is transferred to a host cell by conventional techniques and the transfected cells are then cultured by conventional techniques to produce an antibody for use in the methods described herein. Thus, the invention includes host cells containing a polynucleotide encoding an antibody of the invention, or a heavy or light chain thereof, operably linked to a heterologous promoter. In particular embodiments for the expression of double-chained antibodies, vectors encoding both the heavy and light chains can be co-expressed in the host cell for expression of the entire immunoglobulin molecule, as detailed below.

The host cell can be co-transfected with two expression vectors of the invention, the first vector encoding a heavy chain derived polypeptide and the second vector encoding a light chain derived polypeptide. The two vectors can contain identical selectable markers which enable equal expression of heavy and light chain polypeptides. Alternatively, a single vector can be used which encodes both heavy and light chain polypeptides. In such situations, the light chain is advantageously placed before the heavy chain to avoid an excess of toxic free heavy chain; see Proudfoot, Nature 322 (1986), 52; Kohler, Proc. Natl. Acad. Sci. USA 77 (1980), 2197. The coding sequences for the heavy and light chains can comprise cDNA or genomic DNA.

As used herein, "host cells" refers to cells which harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" can mean either from spun down whole cells, or from the cell culture containing both the medium and the suspended cells.

A variety of host-expression vector systems can be utilized to express antibody molecules for use in the methods described herein. Such host-expression systems represent vehicles by which the coding sequences of interest can be produced and subsequently purified, but also represent cells which can, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, NSO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In one embodiment, bacterial cells such as *Escherichia coli*, and more preferably, eukaryotic cells, especially for the expression of whole recombinant antibody molecule, are used for the expression of a recombinant antibody molecule. For example, mammalian cells such as Chinese Hamster Ovary (CHO) cells, in conjunction with a vector such as the major intermediate early gene promoter element from human cytomegalovirus is an effective expression system for antibodies; see, e.g., Foecking et al., Gene 45 (1986), 101; Cockett et al., Bio/Technology 8 (1990), 2.

The host cell line used for protein expression is often of mammalian origin; those skilled in the art are credited with ability to determine particular host cell lines which are best suited for the desired gene product to be expressed therein. Exemplary host cell lines include, but are not limited to, CHO (Chinese Hamster Ovary), DG44 and DUXB11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, W138, R1610 (Chinese hamster fibroblast) BALBC/3T3 (mouse fibroblast), HAK (hamster kidney line), SP2/O (mouse myeloma), P3x63-Ag3.653 (mouse myeloma), BFA-1c1BPT (bovine endothelial cells), RAJI (human lymphocyte) and 293 (human kidney). In a specific embodiment, host cell lines are CHO or 293 cells. Host cell lines are typically available from commercial services, the American Tissue Culture Collection or from published literature.

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used.

For long-term, high-yield production of recombinant proteins, stable expression is preferred. For example, cell lines which stably express the antibody molecule can be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which stably express the antibody molecule.

A number of selection systems can be used, including but not limited to the herpes simplex virus thymidine kinase (Wigler et al., Cell 11 (1977), 223), hypoxanthine-guanine phosphoribosyltransferase (Szybalska & Szybalski, Proc. Natl. Acad. Sci. USA 48 (1992), 202), and adenine phosphoribosyltransferase (Lowy et al., Cell 22 (1980), 817) genes can be employed in tk-, hgprt- or aprt-cells, respectively. Also, anti-metabolite resistance can be used as the basis of selection for the following genes: dhfr, which confers resistance to methotrexate (Wigler et al., Natl. Acad. Sci. USA 77 (1980), 357; O'Hare et al., Proc. Natl. Acad. Sci. USA 78 (1981), 1527); gpt, which confers resistance to mycophenolic acid (Mulligan & Berg, Proc. Natl. Acad. Sci. USA 78 (1981), 2072); neo, which confers resistance to the aminoglycoside G-418 Goldspiel et al., Clinical Pharmacy 12 (1993), 488-505; Wu and Wu, Biotherapy 3 (1991), 87-95; Tolstoshev, Ann. Rev. Pharmacol. Toxicol. 32 (1993), 573-596; Mulligan, Science 260 (1993), 926-932; and Morgan and Anderson, Ann. Rev. Biochem. 62 (1993), 191-217; TIB TECH 11 (1993), 155-215; and hygro, which confers resistance to hygromycin (Santerre et al., Gene 30 (1984), 147. Methods commonly known in the art of recombinant DNA technology which can be used are described in Ausubel et al. (eds.), *Current Protocols in Molecular Biology*, John Wiley & Sons, NY (1993); Kriegler, *Gene Transfer and Expression*, A Laboratory Manual, Stockton Press, NY (1990); and in Chapters 12 and 13, Dracopoli et al. (eds), *Current Protocols in Human Genetics*, John Wiley & Sons, NY (1994); Colberre-Garapin et al., J. Mol. Biol. 150:1 (1981), which are incorporated by reference herein in their entireties.

The expression levels of an antibody molecule can be increased by vector amplification, for a review, see Bebbington and Hentschel, *The use of vectors based on gene amplification for the expression of cloned genes in mammalian cells in DNA cloning*, Academic Press, New York, Vol. 3. (1987). When a marker in the vector system expressing antibody is amplifiable, increase in the level of inhibitor present in culture of host cell will increase the number of copies of the marker gene. Since the amplified region is associated with the antibody gene, production of the antibody will also increase; see Crouse et al., Mol. Cell. Biol. 3 (1983), 257.

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein.

Genes encoding antibodies, or antigen-binding fragments, variants, or derivatives thereof of the invention can also be expressed in non-mammalian cells such as bacteria or insect or yeast or plant cells. Bacteria which readily take up nucleic acids include members of the enterobacteriaceae, such as strains of *Escherichia coli* or *Salmonella*; Bacillaceae, such as *Bacillus subtilis; Pneumococcus; Streptococcus*, and *Haemophilus influenzae*. It will further be appreciated that, when expressed in bacteria, the heterologous polypeptides typically become part of inclusion bodies. The heterologous polypeptides must be isolated, purified and then assembled into functional molecules. Where tetravalent forms of antibodies are desired, the subunits will then self-assemble into tetravalent antibodies; see, e.g., international application WO02/096948.

In bacterial systems, a number of expression vectors can be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruther et al., EMBO J. 2 (1983), 1791), in which the antibody coding sequence can be ligated individually into the vector in frame with the lacZ coding region so that a fusion protein is produced; pIN vectors (Inouye & Inouye, Nucleic Acids Res. 13 (1985), 3101-3109; Van Heeke & Schuster, J. Biol. Chem. 24 (1989), 5503-5509); and the like. pGEX vectors can also be used to express foreign polypeptides as fusion proteins with glutathione S-transferase (GST). In general, such fusion proteins are soluble and can easily be purified from lysed cells by adsorption and binding to a matrix of glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes can also be used. *Saccharomyces cerevisiae*, or common baker's yeast, is the most commonly used among eukaryotic microorganisms although a number of other strains are commonly available, e.g., *Pichia pastoris*. For expression in *Saccharomyces*, the plasmid YRp7, for example, (Stinchcomb et al., Nature 282 (1979), 39; Kingsman et al., Gene 7 (1979), 141; Tschemper et al., Gene 10 (1980), 157) is commonly used. This plasmid already contains the TRP1 gene which provides a selection marker for a mutant strain of yeast lacking the ability to grow in tryptophan, for example ATCC No. 44076 or PEP4-1 (Jones, Genetics 85 (1977), 12). The presence of the trp1 lesion as a characteristic of the yeast host cell genome then provides an effective environment for detecting transformation by growth in the absence of tryptophan.

In an insect system, *Autographa californica* nuclear polyhedrosis virus (AcNPV) is typically used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

Once an antibody molecule of the invention has been recombinantly expressed, the whole antibodies, their dimers, individual light and heavy chains, or other immunoglobulin forms of the present invention, can be purified according to standard procedures of the art, including for example, by chromatography (e.g., ion exchange, affinity, particularly by affinity for the specific antigen after Protein A, and sizing column chromatography), centrifugation, differential solubility, e.g. ammonium sulfate precipitation, or by any other standard technique for the purification of proteins; see, e.g., Scopes, "Protein Purification", Springer Verlag, N.Y. (1982).

Alternatively, another method for increasing the affinity of antibodies of the invention is disclosed in US patent publication 2002-0123057 A1.

V. Fusion Proteins and Conjugates

In certain embodiments, the antibody polypeptide comprises an amino acid sequence or one or more moieties not normally associated with an antibody. Exemplary modifications are described in more detail below. For example, a single-chain Fv antibody fragment of the invention can comprise a flexible linker sequence, or can be modified to add a functional moiety (e.g., PEG, a drug, a toxin, or a label such as a fluorescent, radioactive, enzyme, nuclear magnetic, heavy metal and the like)

An antibody polypeptide of the invention can comprise, consist essentially of, or consist of a fusion protein. Fusion proteins are chimeric molecules which comprise, for example, an immunoglobulin tau-binding domain with at least one target binding site, and at least one heterologous portion, i.e., a portion with which it is not naturally linked in nature. The amino acid sequences can normally exist in separate proteins that are brought together in the fusion polypeptide or they can normally exist in the same protein but are placed in a new arrangement in the fusion polypeptide. Fusion proteins can be created, for example, by chemical synthesis, or by creating and translating a polynucleotide in which the peptide regions are encoded in the desired relationship.

The term "heterologous" as applied to a polynucleotide or a polypeptide, means that the polynucleotide or polypeptide is derived from a distinct entity from that of the rest of the entity to which it is being compared. For instance, as used herein, a "heterologous polypeptide" to be fused to an antibody, or an antigen-binding fragment, variant, or analog thereof is derived from a non-immunoglobulin polypeptide of the same species, or an immunoglobulin or non-immunoglobulin polypeptide of a different species.

As discussed in more detail elsewhere herein, antibodies, or antigen-binding fragments, variants, or derivatives thereof of the invention can further be recombinantly fused to a heterologous polypeptide at the N- or C-terminus or chemically conjugated (including covalent and non-covalent conjugations) to polypeptides or other compositions. For example, antibodies can be recombinantly fused or conjugated to molecules useful as labels in detection assays and effector molecules such as heterologous polypeptides, drugs, radionuclides, or toxins; see, e.g., international applications WO92/08495; WO91/14438; WO89/12624; U.S. Pat. No. 5,314,995; and European patent application EP 0 396 387.

Antibodies, or antigen-binding fragments, variants, or derivatives thereof of the invention can be composed of amino acids joined to each other by peptide bonds or modified peptide bonds, i.e., peptide isosteres, and can contain amino acids other than the 20 gene-encoded amino acids. Antibodies can be modified by natural processes, such as posttranslational processing, or by chemical modification techniques which are well known in the art. Such modifications are well described in basic texts and in more detailed monographs, as well as in a voluminous research literature. Modifications can occur anywhere in the antibody, including the peptide backbone, the amino acid side-chains and the amino or carboxyl termini, or on moieties such as carbohydrates. It will be appreciated that the same type of modification can be present in the same or varying degrees at several sites in a given antibody. Also, a given antibody can contain many types of modifications. Antibodies can be branched, for example, as a result of ubiquitination, and they can be cyclic, with or without branching. Cyclic, branched, and branched cyclic antibodies can result from posttranslation natural processes or can be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination; see, e.g., *Proteins—Structure And Molecular Properties*, T. E. Creighton, W. H. Freeman and Company, New York 2nd Ed., (1993); *Posttranslational Covalent Modification Of Proteins*, B. C. Johnson, Ed., Academic Press, New York, pgs. 1-12 (1983); Seifter et al., Meth. Enzymol. 182 (1990), 626-646; Rattan et al., Ann. NY Acad. Sci. 663 (1992), 48-62).

The present invention also provides for fusion proteins comprising an antibody, or antigen-binding fragment, variant, or derivative thereof, and a heterologous polypeptide. In one embodiment, a fusion protein of the invention comprises, consists essentially of, or consists of, a polypeptide having the amino acid sequence of any one or more of the $V_H$ regions of an antibody of the invention or the amino acid sequence of any one or more of the $V_L$ regions of an antibody of the invention or fragments or variants thereof, and a heterologous polypeptide sequence. In another embodiment, a fusion protein for use in the diagnostic and treatment methods disclosed herein comprises, consists essentially of, or consists of a polypeptide having the amino acid sequence of any one, two, three of the $V_H$-CDRs of an antibody, or fragments, variants, or derivatives thereof, or the amino acid sequence of any one, two, three of the $V_L$-CDRs of an antibody, or fragments, variants, or derivatives thereof, and a heterologous polypeptide sequence. In one embodiment, the fusion protein comprises a polypeptide having the amino acid sequence of a $V_H$-CDR3 of an antibody of the present invention, or fragment, derivative, or variant thereof, and a heterologous polypeptide sequence, which fusion protein specifically binds to tau. In another embodiment, a fusion protein comprises a polypeptide having the amino acid sequence of at least one $V_H$ region of an antibody of the invention and the amino acid sequence of at least one $V_L$ region of an antibody of the invention or fragments, derivatives or variants thereof, and a heterologous polypeptide sequence. In one embodiment, the $V_H$ and $V_L$ regions of the fusion protein correspond to a single source antibody (or scFv or Fab fragment) which specifically binds tau. In yet another embodiment, a fusion protein for use in the diagnostic and treatment methods disclosed herein comprises a polypeptide having the amino acid sequence of any one, two, three or more of the $V_H$ CDRs of an antibody and the amino acid sequence of any one, two, three or more of the $V_L$ CDRs of an antibody, or fragments or variants thereof, and a heterologous polypeptide sequence. In one embodiment, two, three, four, five, six, or more of the $V_H$-CDR(s) or $V_L$-CDR(s) correspond to single source antibody (or scFv or Fab fragment) of the invention. Nucleic acid molecules encoding these fusion proteins are also encompassed by the invention.

Exemplary fusion proteins reported in the literature include fusions of the T cell receptor (Gascoigne et al., Proc. Natl. Acad. Sci. USA 84 (1987), 2936-2940; CD4 (Capon et al., Nature 337 (1989), 525-531; Traunecker et al., Nature 339 (1989), 68-70; Zettmeissl et al., DNA Cell Biol. USA 9 (1990), 347-353; and Byrn et al., Nature 344 (1990), 667-670); L-selectin (homing receptor) (Watson et al., J. Cell. Biol. 110 (1990), 2221-2229; and Watson et al., Nature 349 (1991), 164-167); CD44 (Aruffo et al., Cell 61 (1990), 1303-1313); CD28 and B7 (Linsley et al., J. Exp. Med. 173 (1991), 721-730); CTLA-4 (Lisley et al., J. Exp. Med. 174 (1991), 561-569); CD22 (Stamenkovic et al., Cell 66 (1991), 1133-1144); TNF receptor (Ashkenazi et al., Proc. Natl. Acad. Sci. USA 88 (1991), 10535-10539; Lesslauer et al., Eur. J. Immunol. 27 (1991), 2883-2886; and Peppel et al., J. Exp. Med. 174 (1991), 1483-1489 (1991); and IgE receptor a (Ridgway and Gorman, J. Cell. Biol. 115 (1991), Abstract No. 1448).

As discussed elsewhere herein, antibodies, or antigen-binding fragments, variants, or derivatives thereof of the invention can be fused to heterologous polypeptides to increase the in vivo half-life of the polypeptides or for use in immunoassays using methods known in the art. For example, in one embodiment, PEG can be conjugated to the antibodies of the invention to increase their half-life in vivo; see, e.g., Leong et al., Cytokine 16 (2001), 106-119; Adv. in Drug Deliv. Rev. 54 (2002), 531; or Weir et al., Biochem. Soc. Transactions 30 (2002), 512.

Moreover, antibodies, or antigen-binding fragments, variants, or derivatives thereof of the invention can be fused to marker sequences, such as a peptide to facilitate their purification or detection. In particular embodiments, the marker amino acid sequence is a hexa-histidine peptide (HIS), such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86 (1989), 821-824, for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37 (1984), 767) and the "flag" tag.

Fusion proteins can be prepared using methods that are well known in the art; see for example U.S. Pat. Nos. 5,116,964 and 5,225,538. The precise site at which the fusion is made can be selected empirically to optimize the secretion or binding characteristics of the fusion protein. DNA encoding the fusion protein is then transfected into a host cell for expression.

Antibodies of the present invention can be used in non-conjugated form or can be conjugated to at least one of a variety of molecules, e.g., to improve the therapeutic properties of the molecule, to facilitate target detection, or for imaging or therapy of the patient. Antibodies, or antigen-binding fragments, variants, or derivatives thereof of the invention can be labeled or conjugated either before or after purification, when purification is performed. In particular, antibodies, or antigen-binding fragments, variants, or derivatives thereof of the invention can be conjugated to therapeutic agents, prodrugs, peptides, proteins, enzymes, viruses, lipids, biological response modifiers, pharmaceutical agents, or PEG.

Conjugates that are immunotoxins including conventional antibodies have been widely described in the art. The toxins can be coupled to the antibodies by conventional coupling techniques or immunotoxins containing protein toxin portions can be produced as fusion proteins. The antibodies of the present invention can be used in a corresponding way to obtain such immunotoxins. Illustrative of such immunotoxins are those described by Byers, Seminars Cell. Biol. 2 (1991), 59-70 and by Fanger, Immunol. Today 12 (1991), 51-54.

Those skilled in the art will appreciate that conjugates can also be assembled using a variety of techniques depending on the selected agent to be conjugated. For example, conjugates with biotin are prepared e.g. by reacting a tau binding polypeptide with an activated ester of biotin such as the biotin N-hydroxysuccinimide ester. Similarly, conjugates with a fluorescent marker can be prepared in the presence of a coupling agent, e.g. those listed herein, or by reaction with an isothiocyanate, or fluorescein-isothiocyanate. Conjugates of the antibodies, or antigen-binding fragments, variants or derivatives thereof of the invention are prepared in an analogous manner.

The present invention further encompasses antibodies, or antigen-binding fragments, variants, or derivatives thereof of the invention conjugated to a diagnostic or therapeutic agent. The antibodies can be used diagnostically to, for example, demonstrate presence of a neurological disease, to indicate the risk of getting a neurological disease, to monitor the development or progression of a neurological disease, i.e. tauopathic disease as part of a clinical testing procedure to, e.g., determine the efficacy of a given treatment and/or prevention regimen. Detection can be facilitated by coupling the antibody, or antigen-binding fragment, variant, or derivative thereof to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions; see, e.g., U.S. Pat. No. 4,741,900 for metal ions which can be conjugated to antibodies for use as diagnostics according to the present invention. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, $^{131}$I, $^{111}$In or $^{99}$Tc.

An antibody, or antigen-binding fragment, variant, or derivative thereof also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

One of the ways in which an antibody, or antigen-binding fragment, variant, or derivative thereof can be detectably labeled is by linking the same to an enzyme and using the linked product in an enzyme immunoassay (EIA) (Voller, A., "The Enzyme Linked Immunosorbent Assay (ELISA)" Microbiological Associates Quarterly Publication, Walkersville, Md., Diagnostic Horizons 2 (1978), 1-7); Voller et al., J. Clin. Pathol. 31 (1978), 507-520; Butler, Meth. Enzymol. 73 (1981), 482-523; Maggio, E. (ed.), *Enzyme Immunoassay*, CRC Press, Boca Raton, Fla., (1980); Ishikawa, E. et al., (eds.), *Enzyme Immunoassay*, Kgaku Shoin, Tokyo (1981). The enzyme, which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection can also be accomplished by visual comparison of the extent of enzymatic reaction of a substrate in comparison with similarly prepared standards.

Detection can also be accomplished using any of a variety of other immunoassays. For example, by radioactively labeling the antibody, or antigen-binding fragment, variant, or derivative thereof, it is possible to detect the antibody through the use of a radioimmunoassay (RIA) (see, for example, Weintraub, B., *Principles of Radioimmunoassays, Seventh Training Course on Radioligand Assay Techniques*, The Endocrine Society, (March, 1986)), which is incorporated by reference herein). The radioactive isotope can be detected by means including, but not limited to, a gamma counter, a scintillation counter, or autoradiography.

An antibody, or antigen-binding fragment, variant, or derivative thereof can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

Techniques for conjugating various moieties to an antibody, or antigen-binding fragment, variant, or derivative thereof are well known, see, e.g., Arnon et al., "Monoclonal Antibodies For Immunotargeting Of Drugs In Cancer Therapy", in *Monoclonal Antibodies And Cancer Therapy*, Reisfeld et al. (eds.), pp. 243-56 (Alan R. Liss, Inc. (1985); Hellstrom et al., "Antibodies For Drug Delivery", in *Controlled Drug Delivery* (2nd Ed.), Robinson et al. (eds.), Marcel Dekker, Inc., pp. 623-53 (1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475-506 (1985); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), Academic Press pp. 303-16 (1985), and Thorpe et al., "The Preparation And Cytotoxic Properties Of Antibody-Toxin Conjugates", Immunol. Rev. 62 (1982), 119-158.

As mentioned, in certain embodiments, a moiety that enhances the stability or efficacy of a binding molecule, e.g., a binding polypeptide, e.g., an antibody or immunospecific fragment thereof can be conjugated. For example, in one embodiment, PEG can be conjugated to the binding molecules of the invention to increase their half-life in vivo. Leong et al., Cytokine 16 (2001), 106; Adv. in Drug Deliv. Rev. 54 (2002), 531; or Weir et al., Biochem. Soc. Transactions 30 (2002), 512.

VI. Compositions and Methods of Use

The present invention relates to compositions comprising the aforementioned tau binding molecule, e.g., antibody or antigen-binding fragment thereof of the present invention or derivative or variant thereof, or the polynucleotide, vector or cell of the invention. The composition of the present invention can further comprise a pharmaceutically acceptable carrier. Furthermore, the pharmaceutical composition of the present invention can comprise further agents such as interleukins or interferons depending on the intended use of the pharmaceutical composition. For use in the treatment of a tauopathic disease, e.g., of the Alzheimer's disease the additional agent can be selected from the group consisting of small organic molecules, anti-tau antibodies, and combinations thereof. Hence, in a particular embodiment the present invention relates to the use of the tau binding molecule, e.g., antibody or antigen-binding fragment thereof of the present invention or of a binding molecule having substantially the same binding specificities of any one thereof, the polynucleotide, the vector or the cell of the present invention for the preparation of a pharmaceutical or diagnostic composition for prophylactic and therapeutic treatment of a tauopathic disease, monitoring the progression of a tauopathic disease or a response to a tauopathic disease treatment in a subject or for determining a subject's risk for developing a tauopathic disease.

Hence, in one embodiment the present invention relates to a method of treating a neurological disorder characterized by abnormal accumulation and/or deposition of tau in the brain and the central nervous system, respectively, which method comprises administering to a subject in need thereof a therapeutically effective amount of any one of the afore-described tau binding molecules, antibodies, polynucleotides, vectors or cells of the instant invention. The term "neurological disorder" includes but is not limited to tauopathic diseases such as Alzheimer's disease, amyotrophic lateral sclerosis/parkinsonism-dementia complex, argyrophilic grain dementia, British type amyloid angiopathy, cerebral amyloid angiopathy, corticobasal degeneration, Creutzfeldt-Jakob disease, dementia pugilistica, diffuse neurofibrillary tangles with calcification, Down's syndrome, frontotemporal dementia, frontotemporal dementia with parkinsonism linked to chromosome 17, frontotemporal lobar degeneration, Gerstmann-Sträussler-Scheinker disease, Hallervorden-Spatz disease, inclusion body myositis, multiple system atrophy, myotonic dystrophy, Niemann-Pick disease type C, non-Guamanian motor neuron disease with neurofibrillary tangles, Pick's disease, postencephalitic parkinsonism, prion protein cerebral amyloid angiopathy, progressive subcortical gliosis, progressive supranuclear palsy, subacute sclerosing panencephalitis, tangle only dementia, multi-infarct dementia and ischemic stroke. Unless stated otherwise, the terms neurodegenerative, neurological or neuropsychiatric are used interchangeably herein.

A particular advantage of the therapeutic approach of the present invention lies in the fact that the antibodies of the present invention are derived from B cells or B memory cells from healthy human subjects with no signs of a tauopathic disease and thus are, with a certain probability, capable of preventing a clinically manifest tauopathic disease, or of diminishing the risk of the occurrence of the clinically manifest disease, or of delaying the onset or progression of the clinically manifest disease. Typically, the antibodies of the present invention also have already successfully gone through somatic maturation, i.e. the optimization with respect to selectivity and effectiveness in the high affinity binding to the target tau molecule by means of somatic variation of the variable regions of the antibody.

The knowledge that such cells in vivo, e.g. in a human, have not been activated by means of related or other physiological proteins or cell structures in the sense of an autoimmunological or allergic reaction is also of great medical importance since this signifies a considerably increased chance of successfully living through the clinical test phases. So to speak, efficiency, acceptability and tolerability have already been demonstrated before the preclinical and clinical development of the prophylactic or therapeutic antibody in at least one human subject. It can thus be expected that the human anti-tau antibodies of the present invention, both its target structure-specific efficiency as therapeutic agent and its decreased probability of side effects significantly increase its clinical probability of success.

The present invention also provides a pharmaceutical and diagnostic, respectively, pack or kit comprising one or more containers filled with one or more of the above described ingredients, e.g. ani-tau antibody, binding fragment, derivative or variant thereof, polynucleotide, vector or cell of the present invention. Associated with such container(s) can be a notice in the form prescribed by a governmental agency regulating the manufacture, use or sale of pharmaceuticals or biological products, which notice reflects approval by the agency of manufacture, use or sale for human administration. In addition or alternatively the kit comprises reagents and/or instructions for use in appropriate diagnostic assays. The composition, e.g. kit of the present invention is of course particularly suitable for the risk assessment, diagnosis, prevention and treatment of a disorder which is accompanied with the presence of tau, and in particular applicable for the treatment of Alzheimer's disease (AD), amyotrophic lateral sclerosis/parkinsonism-dementia complex (ALS-PDC), argyrophilic grain dementia (AGD), British type amyloid angiopathy, cerebral amyloid angiopathy, corticobasal degeneration (CBD), Creutzfeldt-Jakob disease (CJD), dementia pugilistica, diffuse neurofibrillary tangles with calcification, Down's syndrome, frontotemporal dementia, frontotemporal dementia with parkinsonism linked to chromosome 17 (FTDP-17), frontotemporal lobar degeneration, Gerstmann-Sträussler-Scheinker disease, Hallervorden-Spatz disease, inclusion body myositis, multiple system atrophy, myotonic dystrophy, Niemann-Pick disease type C (NP-C), non-Guamanian motor neuron disease with neurofibrillary tangles, Pick's disease (PiD), postencephalitic parkinsonism, prion protein cerebral amyloid angiopathy, progressive subcortical gliosis, progressive supranuclear palsy (PSP), subacute sclerosing panencephalitis, tangle only dementia, multi-infarct dementia and ischemic stroke.

The pharmaceutical compositions of the present invention can be formulated according to methods well known in the art; see for example Remington: The Science and Practice of Pharmacy (2000) by the University of Sciences in Philadelphia, ISBN 0-683-306472. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions can be effected by different ways, e.g., by intravenous, intraperitoneal, subcutaneous, intramuscular, intranasal, topical or intradermal administration or spinal or brain delivery. Aerosol formulations such as nasal spray formulations include purified aqueous or other solutions of the active agent with preservative agents and isotonic agents. Such formulations are adjusted to a pH and isotonic state compatible with the nasal mucous membranes. Formulations for rectal or vaginal ad-ministration can be presented as a suppository with a suitable carrier.

Furthermore, whereas the present invention includes the now standard (though fortunately infrequent) procedure of drilling a small hole in the skull to administer a drug of the present invention, in one aspect, the binding molecule, especially antibody or antibody based drug of the present invention can cross the blood-brain barrier, which allows for intravenous or oral administration.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 µg (or of nucleic acid for expression or for inhibition of expression in this range); however, doses below or above this exemplary range are envisioned, especially considering the aforementioned factors. Generally, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, or at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated. Progress can be monitored by periodic assessment. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like. Furthermore, the pharmaceutical composition of the invention can comprise further agents such as dopamine or psychopharmacologic drugs, depending on the intended use of the pharmaceutical composition.

Furthermore, in a particular embodiment of the present invention the pharmaceutical composition can be formulated as a vaccine, for example, if the pharmaceutical composition of the invention comprises an anti-tau antibody or binding fragment, derivative or variant thereof for passive immunization. As mentioned in the background section, phosphor-tau species have been reported extracellularly in plasma and CSF (Aluise et al., Biochim. Biophys. Acta. 1782 (2008), 549-558) and studies in transgenic mouse lines using active vaccination with phosphorylated tau peptides revealed reduced brain levels of tau aggregates in the brain and slowed progression of behavior impairments (Sigurdsson, J. Alzheimers Dis. 15 (2008), 157-168; Boimel et al., Exp Neurol. 224 (2010), 472-485). Accordingly, it is prudent to expect that passive immunization with human anti-tau antibodies and equivalent tau binding molecules of the present invention would help to circumvent several adverse effects of active immunization therapy concepts as already discussed in the background section. Therefore, the present anti-tau antibodies and their equivalents of the present invention will be particularly useful as a vaccine for the prevention or amelioration of tauopathic diseases such as AD, ALS-PDC, AGD, CBD, CJD, FTD, FTDP-17, NP-C, PiD, PSP or other tauopathies as mentioned before.

In one embodiment, it can be beneficial to use recombinant bispecific or multispecific constructs of the antibody of the present invention. For a reference see Fischer and Léger, Pathobiology 74 (2007), 3-14. Such bispecific molecule might be designed to target tau with one binding arm and another pathologic entity such as Aβ or alpha-synuclein or a different pathological conformation of tau with a second binding arm. Alternatively the second binding arm can be designed to target a protein present at the blood-brain-barrier to facilitate antibody penetration into the brain.

In one embodiment, it can be beneficial to use recombinant Fab (rFab) and single chain fragments (scFvs) of the antibody of the present invention, which might more readily penetrate a cell membrane. For example, Robert et al., Protein Eng. Des. Sel. (2008) October 16; S1741-0134, published online ahead, describe the use of chimeric recombinant Fab (rFab) and single chain fragments (scFvs) of monoclonal antibody WO-2 which recognizes an epitope in the N-terminal region of AP. The engineered fragments were able to (i) prevent amyloid fibrillization, (ii) disaggregate preformed Aβ1-42 fibrils and (iii) inhibit Aβ1-42 oligomer-mediated neurotoxicity in vitro as efficiently as the whole IgG molecule. The perceived advantages of using small Fab and scFv engineered antibody formats which lack the effector function include more efficient passage across the blood-brain barrier and minimizing the risk of triggering inflammatory side reactions. Furthermore, besides scFv and single-domain antibodies retain the binding specificity of full-length antibodies, they can be expressed as single genes and intracellularly in mammalian cells as intrabodies, with the potential for alteration of the folding, interactions, modifications, or subcellular localization of their targets; see for review, e.g., Miller and Messer, Molecular Therapy 12 (2005), 394-401.

In a different approach Muller et al., Expert Opin. Biol. Ther. (2005), 237-241, describe a technology platform, so-called 'SuperAntibody Technology', which is said to enable antibodies to be shuttled into living cells without harming them. Such cell-penetrating antibodies open new diagnostic and therapeutic windows. The term 'TransMabs' has been coined for these antibodies.

In a further embodiment, co-administration or sequential administration of other antibodies useful for treating a tauopathic disease can be desirable. In one embodiment, the additional antibody is comprised in the pharmaceutical composition of the present invention. Examples of antibodies which can be used to treat a subject include, but are not limited to, antibodies targeting beta-amyloid, alpha-synuclein, TDP-43 and SOD-1.

In a further embodiment, co-administration or sequential administration of other neuroprotective agents useful for treating a tauopathic disease can be desirable. In one embodiment, the additional agent is comprised in the pharmaceutical composition of the present invention. Examples of neuroprotective agents which can be used to treat a subject include, but are not limited to, an acetylcholinesterase inhibitor, a glutamatergic receptor antagonist, kinase inhibitors, HDAC inhibitors, anti-inflammatory agents, divalproex sodium, or any combination thereof. Examples of other neuroprotective agents that can be used concomitant with pharmaceutical composition of the present invention are described in the art; see, e.g. international application WO2007/011907. In one embodiment, the additional agent is dopamine or a dopamine receptor agonist.

A therapeutically effective dose or amount refers to that amount of the active ingredient sufficient to ameliorate the symptoms or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$. In one embodiment, the therapeutic agent in the composition is present in an amount sufficient to restore or preserve normal behavior and/or cognitive properties in case of AD, ALS-PDC, AGD, CBD, CJD, FTD, FTDP-17, NP-C, PiD, PSP or other tauopathic diseases as mentioned before.

From the foregoing, it is evident that the present invention encompasses any use of a tau binding molecule comprising at least one CDR of the above described antibody, in particular for diagnosing and/or treatment of a tauopathic disease as mentioned above, particularly Alzheimer's disease. In one embodiment, said binding molecule is an antibody of the present invention or an immunoglobulin chain thereof. In addition, the present invention relates to anti-idiotypic antibodies of any one of the mentioned antibodies described hereinbefore. These are antibodies or other binding molecules which bind to the unique antigenic peptide sequence located on an antibody's variable region near the antigen-binding site and are useful, e.g., for the detection of anti-tau antibodies in sample of a subject.

In another embodiment the present invention relates to a diagnostic composition comprising any one of the above described tau binding molecules, antibodies, antigen-binding fragments, polynucleotides, vectors or cells of the invention and optionally suitable means for detection such as reagents conventionally used in immuno or nucleic acid based diagnostic methods. The antibodies of the invention are, for example, suited for use in immunoassays in which they can be utilized in liquid phase or bound to a solid phase carrier. Examples of immunoassays which can utilize the antibody of the invention are competitive and non-competitive immunoassays in either a direct or indirect format. Examples of such immunoassays are the radioimmunoassay (RIA), the sandwich (immunometric assay), flow cytometry and the Western blot assay. The antigens and antibodies of the invention can be bound to many different carriers and used to isolate cells specifically bound thereto. Examples of well known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds; see also the embodiments discussed hereinabove.

By a further embodiment, the tau binding molecules, in particular antibodies of the present invention can also be used in a method for the diagnosis of a disorder in an individual by obtaining a body fluid sample from the tested individual which can be a blood sample, a lymph sample or any other body fluid sample and contacting the body fluid sample with an antibody of the instant invention under conditions enabling the formation of antibody-antigen complexes. The level of such complexes is then determined by methods known in the art, a level significantly higher than that formed in a control sample indicating the disease in the tested individual. In the same manner, the specific antigen bound by the antibodies of the invention can also be used. Thus, the present invention relates to an in vitro immunoassay comprising the binding molecule, e.g., antibody or antigen-binding fragment thereof of the invention.

In this context, the present invention also relates to means specifically designed for this purpose. For example, an antibody-based array can be used, which is for example loaded with antibodies or equivalent antigen-binding molecules of the present invention which specifically recognize tau. Design of microarray immunoassays is summarized in Kusnezow et al., Mol. Cell Proteomics 5 (2006), 1681-1696. Accordingly, the present invention also relates to microarrays loaded with tau binding molecules identified in accordance with the present invention.

In one embodiment, the present invention relates to a method of diagnosing a tauopathic disease in a subject, the method comprising determining the presence of tau and/or pathologically modified and/or aggregated tau in a sample from the subject to be diagnosed with at least one antibody of the present invention, an tau binding fragment thereof or an tau-binding molecule having substantially the same binding specificities of any one thereof, wherein the presence of pathologically modified and/or aggregated tau is indicative of a neurodegenerative tauopathy and an increase of the level of the pathologically modified and/or aggregated tau in comparison to the level of the physiological tau forms is indicative for progression of a neurodegenerative tauopathy in said subject.

The subject to be diagnosed can be asymptomatic or preclinical for the disease. In one embodiment, the control subject has a tauopathic disease, for example, AD, ALS-PDC, AGD, CBD, CJD, FTD, FTDP-17, NP-C, PiD, PSP or other tauopathies as mentioned before, wherein a similarity between the level of pathologically modified and/or aggregated tau and the reference standard indicates that the subject to be diagnosed has a tauopathic disease. Alternatively, or in addition as a second control the control subject does not have a tauopathic disease, wherein a difference between the level tau and/or of pathologically modified and/or aggregated tau and the reference standard indicates that the subject to be diagnosed has a tauopathic disease. In one embodiment, the subject to be diagnosed and the control subject(s) are age-matched. The sample to be analyzed can be any body fluid suspected to contain pathologically modified and/or aggregated tau, for example a blood, CSF, or urine sample.

The level tau and/or of pathologically modified and/or aggregated tau can be assessed by any suitable method known in the art comprising, e.g., analyzing tau by one or more techniques chosen from Western blot, immunoprecipitation, enzyme-linked immunosorbent assay (ELISA), radioimmunoassay (RIA), fluorescent activated cell sorting (FACS), two-dimensional gel electrophoresis, mass spectroscopy (MS), matrix-assisted laser desorption/ionization-time of flight-MS (MALDI-TOF), surface-enhanced laser desorption ionization-time of flight (SELDI-TOF), high performance liquid chromatography (HPLC), fast protein liquid chromatography (FPLC), multidimensional liquid chromatography (LC) followed by tandem mass spectrometry (MS/MS), and laser densitometry. In one embodiment, said in vivo imaging of tau comprises positron emission tomography (PET), single photon emission tomography (SPECT), near infrared (NIR) optical imaging or magnetic resonance imaging (MRI).

Methods of diagnosing a tauopathic disease such as Alzheimer's disease, monitoring a tauopathic disease progression, and monitoring a tauopathic disease treatment using antibodies and related means which can be adapted in accordance with the present invention are also described in international applications WO93/08302, WO94/13795, WO95/17429, WO96/04309, WO2002/062851 and WO2004/016655. Similarly, antibody based detection methods for tau are described in international application WO2005/080986, the disclosure content of all being incorporated herein by reference. Those methods can be applied as described but with a tau specific antibody, binding fragment, derivative or variant of the present invention.

In a further aspect the present invention also relates to peptides having an epitope of tau specifically recognized by any antibody of the present invention. In one embodiment, such peptide comprises, consists of or consists essentially of an amino acid sequence selected from the group consisting of: residues 125-131, 397-441, 226-244, 217-227, 37-55, 387-406, 421-427, 427-439, 1-158, 197-207, 57-67, 355-441, 313-319, 309-319, 221-231 of SEQ ID NO:6, and any combination thereof, and a modified sequence thereof in which one, two, three, four, five, six, seven or more amino acids are substituted, deleted and/or added, wherein the peptide is recognized by any antibody of the present invention.

In one embodiment of this invention such a peptide can be used for diagnosing a neurodegenerative tauopathy in a subject, comprising a step of determining the presence of an antibody that binds to a peptide in a biological sample of said subject, and being used for diagnosis of a tauopathy in said subject by measuring the levels of antibodies which recognize the above described peptide of the present invention and comparing the measurements to the levels which are found in healthy subjects of comparable age and gender. An elevated level of measured antibodies specific for said peptide of the present invention would be indicative for diagnosing a tauopathy in said subject. The peptide of the present invention can be formulated in an array, a kit and composition, respectively, as described hereinbefore.

These and other embodiments are disclosed and encompassed by the description and examples of the present invention. Further literature concerning any one of the materials, methods, uses and compounds to be employed in accordance with the present invention can be retrieved from public libraries and databases, using for example electronic devices. For example the public database "Medline" can be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person skilled in the art and can also be obtained using internet search engines. An overview of patent information in biotechnology and a survey of relevant sources of patent information useful for retrospective searching and for current awareness is given in Berks, TIBTECH 12 (1994), 352-364.

The above disclosure generally describes the present invention. Unless otherwise stated, a term as used herein is given the definition as provided in the Oxford Dictionary of Biochemistry and Molecular Biology, Oxford University Press, 1997, revised 2000 and reprinted 2003, ISBN 0 19 850673 2. Several documents are cited throughout the text of this specification. Full bibliographic citations can be found at the end of the specification immediately preceding the claims. The contents of all cited references (including literature references, issued patents, published patent applications as cited throughout this application and manufacturer's specifications, instructions, etc.) are hereby expressly incorporated by reference; however, there is no admission that any document cited is indeed prior art as to the present invention.

A more complete understanding can be obtained by reference to the following specific examples which are provided herein for purposes of illustration only and are not intended to limit the scope of the invention.

EXAMPLES

The examples which follow further illustrate the invention, but should not be construed to limit the scope of the invention in any way. The experiments in the following Examples are illustrated and described with respect to antibodies NI-105.4E4, NI-105.24B2 and NI-105.4A3 as cloned, i.e. the framework 1 (FR1) Ig-variable regions without being adjusted to the germ line (GL) sequences of human variable heavy and light chains; see FIG. 1.

Material and Methods

Detailed descriptions of conventional methods, such as those employed herein can be found in the cited literature; see also "The Merck Manual of Diagnosis and Therapy" Seventeenth Ed. edited by Beers and Berkow (Merck & Co., Inc. 2003) and U.S. Patent Application Publication No. 2012/0087861, the content of which is incorporated herein by reference in its entirety.

The practice of the present invention will employ, unless otherwise indicated, conventional techniques of cell biology, cell culture, molecular biology, transgenic biology, microbiology, recombinant DNA, and immunology, which are within the skill of the art. For further elaboration of general techniques useful in the practice of this invention, the practitioner can refer to standard textbooks and reviews in cell biology and tissue culture; see also the references cited in the examples. General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); DNA Cloning, Volumes I and II (Glover ed., 1985); Oligonucleotide Synthesis (Gait ed., 1984); Nucleic Acid Hybridization (Hames and Higgins eds. 1984); Transcription And Translation (Hames and Higgins eds. 1984); Culture Of Animal Cells (Freshney and Alan, Liss, Inc., 1987); Gene Transfer Vectors for Mammalian Cells (Miller and Calos, eds.); Current Protocols in Molecular Biology and Short Protocols in Molecular Biology, 3rd Edition (Ausubel et al., eds.); and Recombinant DNA Methodology (Wu, ed., Academic Press). Gene Transfer Vectors For Mammalian Cells (Miller and Calos, eds., 1987, Cold Spring Harbor Laboratory); Methods In Enzymology, Vols. 154 and 155 (Wu et al., eds.); Immobilized Cells And Enzymes (IRL Press, 1986); Perbal, A Practical Guide To Molecular Cloning (1984); the treatise, Methods In Enzymology (Academic Press, Inc., N.Y.); Immunochemical Methods In Cell And Molecular Biology (Mayer and Walker, eds., Academic Press, London, 1987); Handbook Of Experimental Immunology, Volumes I-IV (Weir and Blackwell, eds., 1986). Protein Methods (Bollag et al., John Wiley & Sons 1996); Non-viral Vectors for Gene Therapy (Wagner et al. eds., Academic Press 1999); Viral Vectors (Kaplitt & Loewy eds., Academic Press 1995); Immunology Methods Manual (Lefkovits ed., Academic Press 1997); and Cell and Tissue Culture: Laboratory Procedures in Biotechnology (Doyle & Griffiths, John Wiley & Sons 1998). Reagents, cloning vectors and kits for genetic manipulation referred to in this disclosure are available from commercial vendors such as BioRad, Stratagene, Invitrogen, Sigma-Aldrich, and ClonTech. General techniques in cell culture and media collection are outlined in Large Scale Mammalian Cell Culture (Hu et al., Curr. Opin. Biotechnol. 8 (1997), 148); Serum-free Media (Kitano, Biotechnology 17 (1991), 73); Large Scale Mammalian Cell Culture (Curr. Opin. Biotechnol. 2 (1991), 375); and Suspension Culture of Mammalian Cells (Birch et al., Bioprocess Technol. 19 (1990), 251); Extracting information from cDNA arrays, Herzel et al., CHAOS 11 (2001), 98-107.

Methods of Identification of Tau-Specific B-Cells and Cloning of the Respective Antibodies Unless indicated otherwise below, identification of tau-specific B cells and molecular cloning of anti-tau antibodies displaying specificity of interest as well as their recombinant expression and functional characterization has been or can be generally performed as described in the Examples and Supplementary Methods section of international application PCT/EP2008/000053 published as WO2008/081008, the disclosure content of which is incorporated herein by reference in its entirety. See also U.S. Patent Application Publication No. 2012/0087861, the content of which is incorporated herein by reference in its entirety. A new method for identification of tau-specific B cells and molecular cloning of tau antibodies displaying specificity of interest as well as their recombinant expression and functional characterization is provided within this application. As described above in one embodiment of the present invention cultures of single or oligoclonal B-cells are cultured and the supernatant of the culture, which contains antibodies produced by said B-cells is screened for presence and affinity of new anti-tau antibodies therein. The screening process comprises the steps of a sensitive tissue amyloid plaque immunoreactivity (TAPIR) assay such as described in international application WO 2004/095031, the disclosure content of which is incorporated herein by reference, and shown in FIG. 3; screen on brain extracts for binding to PHFTau as described in Example 2; screening for binding of a peptide derived from tau of the amino acid sequence represented by SEQ ID NO:6 with phosphate groups on amino acids Ser-202 and Ser-205; on amino acid Thr-231; and/or on amino acids Ser-396 and Ser-404 of said sequence as analogously described in Example 3 with non-phosphorylated peptides due to the epitope confirmation experiments for antibody NI-105.4E4; a screen for binding of full-length tau of the amino acid sequence represented by SEQ ID NO:6 and isolating the antibody for which binding is detected or the cell producing said antibody as described in international patent WO2008/081008 and as described in Example 1.

Purification of Antigen

Recombinant human Tau40 was purchased from rPeptide (Bogart, Ga., USA). PHFTau was extracted from AD brain.

Isolation of paired helical filaments containing pathologically phosphorylated tau filaments (PHFTau) was performed following the method by Goedert et al. (Goedert et al., Neuron 8 (1992), 159-168) with modifications. One gram of AD brain tissue was cut into 5 mm pieces with all visible blood vessels removed. The tissue was washed with 40 ml ice cold washing solution (100 mM Tris pH 7.4, 6 mM EGTA, 1 mM $Na_3VO_4$ and 1 mM NaF) for three times followed by homogenization with 20 ml lysis buffer (10 mM Tris pH 7.4, 0.8M NaCl, 1 mM EGTA, 1× protease inhibitor cocktail, 1 mM $Na_3VO_4$, 1 mM NaF, 1 mM AEBSF, 10% sucrose). The homogenate was centrifuged at 4° C. at 20,000×g for 20 min. Supernatant was collected with addition of N-lauroyl sarcosinate (Sigma, Switzerland) to 1% (w/v). After two hours incubation at 37° C. with shaking, the supernatant was then centrifuged at 4° C. at 100,000×g for one hour. The pellet was collected and re-suspended in PBS. After clearing out possible contaminating immunoglobulins with protein A magnetic beads, the PHFTau suspension was stored at −80° C. before use. A control extract from healthy control human brain tissue was prepared accordingly.

Human Tau Antibody Screening

ELISA:

96 well half area microplates (Corning) were coated with recombinant Tau protein (rPeptide, Bogart, USA) at a standard concentration of 1 g/ml in carbonate ELISA coating buffer (pH 9.6) overnight at 4° C. For PHFTau screening, 96 well Immobilizer Microplates (Nunc, Denmark) were coated with PHFTau extracted from human AD brain at 1:100 dilutions in carbonate ELISA coating buffer (pH9.6) overnight at 4° C. Plates were washed in PBS-T pH 7.6 and non-specific binding sites were blocked for 2 hrs at RT with PBS-T containing 2% BSA (Sigma, Buchs, Switzerland). B cell conditioned medium was transferred from memory B cell culture plates to ELISA plates and incubated for one hour at RT. ELISA plates were washed in PBS-T and then incubated with horse radish peroxidase (HRP)-conjugated donkey anti-human IgG (Fcγ fragment specific) polyclonal antibodies (Jackson ImmunoResearch, Newmarket, UK). After washing with PBS-T, binding of human antibodies was determined by measurement of HRP activity in a standard colorimetric assay.

MULTI-ARRAY® Microplate Screening

Standard 96 well 10-Spot MULTI-SPOT plates (Meso Scale Discovery, USA) were coated with 30 µg/ml rTau (rPeptide), PHFTau brain extract and healthy control brain extract in PBS. Non-specific binding sites were blocked for 1 hr at RT with PBS-T containing 3% BSA followed by incubation with B cell conditioned medium for 1 hr at RT. Plates were washed in PBS-T and then incubated with SULFO-Tag conjugated anti-human polyclonal antibody (Meso Scale Discovery, USA). After washing with PBS-T, bound of antibody was detected by electrochemiluminescence measurement using a SECTOR Imager 6000 (Meso Scale Discovery, USA).

Molecular Cloning of Tau Antibodies

Samples containing memory B cells were obtained from healthy human subjects. Living B cells of selected memory B cell cultures are harvested and mRNA is prepared. Immunoglobulin heavy and light chain sequences are then obtained using a nested PCR approach.

A combination of primers representing all sequence families of the human immunoglobulin germline repertoire are used for the amplifications of leader peptides, V-segments and J-segments. The first round amplification is performed using leader peptide-specific primers in 5'-end and constant region-specific primers in 3'-end (Smith et al., Nat Protoc. 4 (2009), 372-384). For heavy chains and kappa light chains, the second round amplification is performed using V-segment-specific primers at the 5'-end and J-segment-specific primers at the 3'end. For lambda light chains, the second round amplification is performed using V-segment-specific primers at the 5'-end and a C-region-specific primer at the 3'end (Marks et al., Mol. Biol. 222 (1991), 581-597; de Haard et al., J. Biol. Chem. 26 (1999), 18218-18230).

Identification of the antibody clone with the desired specificity is performed by re-screening on ELISA upon recombinant expression of complete antibodies. Recombinant expression of complete human IgG1 antibodies or chimeric IgG2a antibodies is achieved upon insertion of the variable heavy and light chain sequences "in the correct reading frame" into expression vectors that complement the variable region sequence with a sequence encoding a leader peptide at the 5'-end and at the 3'-end with a sequence encoding the appropriate constant domain(s). To that end the primers contained restriction sites designed to facilitate cloning of the variable heavy and light chain sequences into antibody expression vectors. Heavy chain immunoglobulins are expressed by inserting the immunoglobulin heavy chain RT-PCR product in frame into a heavy chain expression vector bearing a signal peptide and the constant domains of human immunoglobulin gamma 1 or mouse immunoglobulin gamma 2a. Kappa light chain immunoglobulins are expressed by inserting the kappa light chain RT-PCR-product in frame into a light chain expression vector providing a signal peptide and the constant domain of human kappa light chain immunoglobulin Lambda light chain immunoglobulins are expressed by inserting the lambda light chain RT-PCR-product in frame into a lambda light chain expression vector providing a signal peptide and the constant domain of human or mouse lambda light chain immunoglobulin.

Functional recombinant monoclonal antibodies are obtained upon co-transfection into HEK293 or CHO cells (or any other appropriate recipient cell line of human or mouse origin) of an Ig-heavy-chain expression vector and a kappa or lambda Ig-light-chain expression vector. Recombinant human monoclonal antibody is subsequently purified from the conditioned medium using a standard Protein A column purification. Recombinant human monoclonal antibody can produced in unlimited quantities using either transiently or stably transfected cells. Cell lined producing recombinant human monoclonal antibody can be established either by using the Ig-expression vectors directly or by re-cloning of Ig-variable regions into different expression vectors. Derivatives such as F(ab), F(ab)$_2$ and scFv can also be generated from these Ig-variable regions.

Antibodies

Mouse monoclonal anti-human tau antibody Tau12 (Covance, Calif., U.S.A.) and mouse monoclonal tau antibody AT180 (Thermo Scientific, U.S.A.) were used according to manufacturer's protocol. Recombinant human tau antibodies NI-105.4E4, NI-105.24B2 and NI-105.4A3 are described in U.S. Patent Application Publication No. 2012/0087861, the content of which is incorporated herein by reference in its entirety. Recombinant human tau antibodies NI-105.17C1, NI-105.17C1(N31Q), NI-105.6C5, NI-105.29G10, NI-105.6L9, NI-105.40E8, NI-105.48E5, NI-105.6E3, NI-105.22E1, NI-105.26B12, NI-105.12E12, NI-105.60E7, NI-105.14E2, NI-105.39E2, NI-105.19C6, and NI-105.9C4 are antibodies of this invention. They were expressed in HEK293 or CHO cells, purified from conditioned media and were directly used in subsequent applications unless otherwise stated.

Direct ELISA 96 well microplates (Costar, Corning, USA) were coated with recombinant Tau protein (hTau40, rPeptide, Bogart, USA) diluted to a concentration of 1 µg/ml in carbonate ELISA coating buffer (50 mM, pH9.6) at 4° C. overnight. Non-specific binding sites were blocked for 2 hr at RT with PBS containing 2% BSA (Sigma, Buchs, Switzerland) and 0.5% Tween20. Binding of human antibodies of the present invention was determined using HRP conjugated goat anti-human IgG Fcγ (Jackson immunoResearch, Newmarket, UK), followed by measurement of HRP activity in a standard colorimetric assay. $EC_{50}$ values were estimated by a non-linear regression using GraphPad Prism software (San Diego, USA).

Western Blotting Protein Staining

PHFTau and recombinant hTau40 were resolved by gradient SDS-PAGE (NuPAGE 4-12%; Invitrogen, Basel, Switzerland) followed by electroblotting on nitrocellulose membranes. After blocking the non-specific binding with 2% BSA at room temperature for one hour, blots were incubated overnight with primary human anti-tau antibodies or Tau12 (mouse monoclonal antibody, Covance, Calif., U.S.A.), followed by a HRP-conjugated goat anti-human IgGFcγ (for human primary antibodies) or a HRP-conjugated goat anti-mouse IgG secondary antibody.

Blots were developed using ECL and ImageQuant 350 detection (GE Healthcare, Otelfingen, Switzerland).

PHFTau Extraction from AD Brain

Isolation of paired helical filaments containing pathologically phosphorylated tau filaments (PHFTau) was performed following the method by Goedert et al. (Goedert et al., Neuron 8 (1992), 159-168) with modifications. One gram of AD brain tissue was cut into 5 mm pieces with all visible blood vessels removed. The tissue was washed with 40 ml ice cold washing solution (100 mM Tris pH 7.4, 6 mM EGTA, 1 mM $Na_3VO_4$ and 1 mM NaF) for three times followed by homogenization with 20 ml lysis buffer (10 mM Tris pH 7.4, 0.8M NaCl, 1 mM EGTA, 1× protease inhibitor cocktail, 1 mM $Na_3VO_4$, 1 mM NaF, 1 mM AEBSF, 10% sucrose). The homogenate was centrifuged at 4° C. at 20,000×g for 20 min. Supernatant was collected with addition of N-lauroyl sarcosinate (Sigma, Switzerland) to 1% (w/v). After two hours incubation at 37° C. with shaking, the supernatant was then centrifuged at 4° C. at 100,000×g for one hour. The pellet was collected and resuspended in PBS. After clearing out possible contaminating immunoglobulins with protein A magnetic beads, the PHFTau suspension was stored at −80° C. before use. A control extract from healthy control human brain tissue was prepared accordingly.

Tau Peptides Synthesis

A peptide corresponding to amino acids 333-346 of hTau40 ($_{333}$GGGQVEVKSEKLDF$_{346}$) which includes the epitope of NI-105.4E4 identified by Pepspot mapping (amino acids 337-343) was synthesized by Schafer-N(Copenhagen, Denmark). An additional cysteine was added to the C-terminus to allow for covalent binding to Immobilizer Microplates (Nunc, Denmark). A second peptide corresponding to amino acids 226-239 of human tau ($_{226}$VAVVRpTPPKSPSSA$_{239}$), the cognate epitope of the commercially available mouse monoclonal tau antibody AT180 (Thermo Scientific, USA) was synthesized accordingly and used as control.

Transgenic Mice

Three different animal models for tauopathies are used to validate the tau antibodies (and molecules with the binding specificities thereof) of the present invention.

1. Transgenic TauP301L mice (line183): expressing human Tau40 with P301L mutation under the murine Thy1.2 promoter (Generation of these transgenic animals is described in Gitz et al., J. Biol. Chem. 276 (2001), 529-534 and in international application WO 2003/017918, the disclosure content of which is incorporated herein by reference)

2. JNPL3 mice expressing the shortest 4R human tau isoform with P301L mutation under the murine PrP promoter (available from Taconic, Hudson, N.Y., U.S.A).

3. P301STau (line PS19) mice expressing human tau with P301S mutation under the murine PrP promoter (available from the Jackson Laboratory, Bar Harbor, Me., U.S.A), Tauopathies mouse models and corresponding wild type mice are kept under standard housing conditions on a reversed 12h:12h light/dark cycle with free access to food and water. The treatment groups are balanced for age and gender.

Example 1

Validation of Target and Binding Specificity of Human Tau-Antibodies

To validate tau as a recognized target of isolated antibodies direct ELISA assays were performed as described above. For the exemplary recombinant human NI-105.4A3 antibody 96 well microplates (Costar, Corning, USA) were coated with recombinant human tau (hTau40, rPeptide, Bogart, USA) diluted to a concentration of 3 μg/ml or with BSA in carbonate ELISA coating buffer (pH 9.6) and binding efficiency of the antibody was tested. The exemplary NI-105.4A3 antibody specifically bound to human tau by ELISA. No binding was observed to BSA.

For a determination of the half maximal effective concentration (EC50) of the exemplary antibodies NI-105.4E4 and NI-105.24B2 additional direct ELISA experiments with varying antibody concentrations were performed. 96 well microplates (Costar, Corning, USA) were coated with recombinant human tau (hTau40, rPeptide, Bogart, USA) diluted to a concentration of 1 g/ml (for the assay with NI-105.4E4Antibody), or of 3 μg/ml (for the assay with NI-105.24B2 Antibody) in carbonate ELISA coating buffer and binding efficiency of the antibody was tested. The $EC_{50}$ values were estimated by a non-linear regression using GraphPad Prism software. Recombinant human-derived antibody NI-105.4E4 bound to hTau40 with high affinity in the low nanomolar range at 2.4 nM $EC_{50}$. NI-105.24B2 bound to hTau40 with high affinity in the low nanomolar range at 6.6 nM $EC_{50}$.

The half maximal effective concentration ($EC_{50}$) of the exemplary antibody NI-105.4A3 was also determined using direct ELISA experiments. ELISA plates were coated with recombinant human tau (hTau40, 1 ug/ml), PHFTau (1:100) and control preparation (1:100), and incubated with varying antibody concentrations. NI-105.4A3 bound to rTau with high affinity in the low nanomolar range at 1.4 nM $EC_{50}$. NI-105.4A3 binds to PHFTau with high affinity in the low nanomolar range at 1.2 nM $EC_{50}$.

Example 2

Recombinant Human Antibodies Binding Analysis to Recombinant Tau and Pathological Tau Extracted from AD Brain To determine the binding capacity of NI-105.4E4 and NI-105.24B2 to pathological tau species extracted from AD brain. SDS-PAGE and Western Blot analysis was performed as described in detail above. Blots were incubated overnight with primary antibodies NI-105.4E4 (human), NI-105.24B2 (human) or Tau12 (mouse monoclonal antibody, Covance, Calif., U.S.A.), followed by a HRP-conjugated goat anti-human IgGFcγ (for human antibodies) or a HRP-conjugated goat anti-mouse IgG secondary antibody.

Recombinant antibodies NI-105.4E4 and NI-105.24B2 recognized recombinant hTau40 as well as pathologically modified PHFTau extracted from AD brain on Western blot. The control antibody Tau12 recognized both tau species as well.

Additionally, as discussed in Example 1 above, the half maximal effective concentration ($EC_{50}$) of the exemplary antibody NI-105.4A3 was determined in direct ELISA experiments using PHFTau. NI-105.4A3 bound to PHFTau with high affinity in the low nanomolar range at 1.2 nM $EC_{50}$.

Example 3

Mapping of the NI-105.4E4 and NI-105.4A3 Binding Epitope on hTau40

A peptide array of 118 peptide sequences covering the full-length hTau40 (amino acids 1-441) with an overlap of 11 amino acids between two adjacent peptides was spotted on a nitrocellulose membrane (JPT Peptide Technologies GmbH, Berlin, Germany). Immunolabeling of antibodies as well as membrane regeneration were carried out according to manufacturer's instructions. To rule out non-specific binding of the detection antibody, the membrane was first probed by HRP-conjugated goat anti-human IgG omitting the primary antibody. After regeneration the membrane was probed with 100 nM recombinant NI-105.4E4 antibody. Bound antibody was detected using ECL and ImageQuant 350 detection (GE Healthcare, Otelfingen, Switzerland).

Two groups of adjacent peptide spots (peptide 83, 84 and 85; peptide 96 and 97) were specifically identified by NI105.4E4, when compared to the detection antibody only. The sequences covered by these two groups of peptides correspond to amino acids 329-351 and 387-397 of hTau40. These data suggested that NI-105.4E4 recognized a discontinuous epitope comprising two linear sequences: one within the R4 microtubule binding domain and another in the C-terminal domain.

The sequence shared by peptides 83-85 comprises amino acid residues 337-343 of hTau40. The Pepspot (JPT) data suggested that NI-105.4E4 recognized an epitope in hTau that comprises amino acids 337-343 of human tau. This region is located within the microtubule binding domain of tau and is conserved among all neuronal human tau isoforms as well as across other species including mouse and rat.

As this domain is bound to microtubules in physiological microtubule-associated tau, NI-105.4E4 is expected to preferentially target the pathologically relevant pool of tau that is detached from the microtubules.

To determine key residues within the NI-105.4E4 binding peptides, alanine scanning was performed to substitute each residue with alanine one at a time. The alanine residues in the original sequence (A384 and A390) were substituted to proline and glycine. Spots 35-50 and 51-68 are the original peptides (spot 35 and spot 51) and their alanine substituted variants. Alanine scan suggested V339, E342, D387, E391 and K395 were necessary for NI-105.4E4 binding.

An additional experiment has been performed by testing the binding of NI-105.4E4 to tau peptides. Direct ELISA showed that NI-105.4E4 specifically recognized a peptide corresponding to amino acid 333-346 of hTau40, which contains the amino acid residues 337-343 identified by Pepspot mapping. No cross-reactivity of NI-105.4E4 was observed to the control peptide covering the AT180 epitope. Vice versa, AT180 recognized its cognate epitope containing peptide but failed to bind to the NI-105.4E4 specific peptide. Species-specific secondary antibodies did not bind to any of the peptides. Together, direct ELISA with coated peptides confirmed that NI-105.4E4 specifically recognized a peptide containing the amino acid residues 337-343 of human tau identified by Pepspot mapping.

To grossly map the NI-105.4A3 binding epitope on hTau40, four tau domain polypeptides (Tau domain I, domain II, domain III and domain IV) were produced. DNA fragments, synthesized using GeneArt® (Invitrogen), which encode each Tau domain with 6×His tagged at the N-terminus were cloned into the pRSET-A expression vector (Invitrogen), were transfected into E. Coli BL21 (DE3) (New England Biolabs). The expressions of the His-tagged Tau domains were induced by 0.5 mM IPTG for six hours before bacteria were lysed with lysozyme with sonication. The lysate was boiled for five minutes before being further purified with Ni-NTA Superflow Columns (Qiagen). The eluted His-tagged Tau domains were coated on ELISA plates or loaded on polyacrylamide gel for Western Blot. These sequentially overlapping tau domain polypeptides covered the full length of hTau40. Purified tau domains were coated on ELISA plate and the binding of NI-105.4A3 was tested. NI-105.4A3 binds only to tau domain I and the full length hTau40, indicating the epitope was within the N-terminal part of the hTau40 (aa1-136). Western blot confirmed the specific binding of NI-105.4A3 to tau domain I. NI-105.4A3 epitope mapping with PepSpot (JPT) technology identified amino acids Q35-Q49 of the human Tau40. To determine key residues within the epitope for NI-105.4A3 binding, alanine scanning was performed to substitute each residue with alanine one at a time. The alanine residue in the original sequence (A41) was substituted with glycine or proline. Alanine scan showed that D40, A41 and K44 are key residues for NI-105.4A3 binding.

Example 4

Assessment of the Binding of NI-105.4E4 to Physiological Forms as Well as Pathological Aggregates of Tau AD Brain Tissues and in Human Tau Transgenic Mice Neurofibrillary tangles (NFT) composed of hyperphosphorylated tau filaments are a neuropathological hallmarks of AD. Hyperphosphorylated tau filaments are also the major components of dystrophic neurites and neuropil threads, both of which are common neuropathological features in AD. Overexpression of human tau containing the familial P301L tau mutation in mice induces NFT formation at six months of age (Gotz et al., 2001a).

To assess the binding of recombinant human tau antibody to physiological forms as well as pathological aggregates of tau, immunohistological stainings were performed in AD brain tissues and in TauP301L transgenic mice with the exemplary NI-105.4E4 antibody of this invention.

Mice were perfused with 20 ml 100 mM TrisCl/6 mM EGTA (pH7.4) at room temperature under deep anesthesia. Brains were taken out and immersed in 4% PFA in PBS (pH 7.4) at 4° C. overnight for fixation followed by embedding in paraffin. For human tissue, paraffin blocks of brain tissues from AD and healthy control subjects were used. DAB staining was carried out following standard protocols. As positive control, mouse monoclonal antibody Tau-12 (Covance, Calif., U.S.A.) was used. HRP-conjugated detection antibodies without primary antibodies were also included.

Recombinant human antibody NI-105.4E4 identified numerous NFTs and neuropil threads in AD brain (FIG. 2A), which were absent in healthy control brain (FIG. 2B). Secondary antibody alone did not give signals in both AD (FIG. 2C) and control brain (FIG. 2D). In P301L tau transgenic mouse brain, NI-105.4E4 bound strongly to the pathological tau resembling NFT (FIGS. 2E, F and H), neuropil threads (FIGS. 2E and G) and dystrophic neurites (FIGS. 2E and H). In addition, NI-105.4E4 also identified tau aggregates at pre-tangle stage (FIG. 2I). In the brain of transgenic mice overexpressing both human P301L tau and human APP with Swedish and Arctic mutations, NI-105.4E4 bound specifically to dystrophic neurites surrounding beta-amyloid plaques (FIG. 2J).

Example 5

In Vivo Tests of the Antibodies of the Present Invention

As already described above studies in transgenic mouse lines using active vaccination with phosphorylated tau peptides revealed reduced brain levels of tau aggregates in the brain and slowed progression of behavior impairments (Sigurdsson, J. Alzheimers Dis. 15 (2008), 157-168; Boimel et al., Exp. Neurol. 224 (2010), 472-485). However, active vaccination may not be particularly useable in humans because a significant fraction of the elderly population is expected to be non-responders to vaccination. Furthermore, the potential side effects associated with a tau-directed immune response can be difficult to control. Tau binding molecules of the present invention can be reasonably expected to achieve similar reductions in brain levels of tau aggregates as described above for the mouse antibodies, because of their similar binding specificities against pathologically tau species. However, because of the evolutionarily optimization and affinity maturation within the human immune system antibodies of the present invention provide a valuable therapeutic tool due to being isolated from healthy human subjects with high probability for excellent safety profile and lack of immunogenicity. Confirmation of these expected therapeutic effects can be provided by test methods as described in the above mentioned experiments with mouse antibodies. In particular, the antibodies to be screened can be applied on diverse possible routes to the animals such as intraperitoneal antibody injection, intracranial injection, intraventricular brain infusion and tested for treatment effects. Either of the above mentioned application possibilities can be also used after prior brain injection of beta-amyloid preparations into the brain of tau transgenic mice to evaluate treatment effects on beta amyloid-induced tau pathology.

Evaluation of the treatment effects can be performed by histochemical methods comprising quantification of Gallyas positive cells counts, total human tau staining, brain burden of phosphorylated tau and/or a biochemical determination of brain soluble and insoluble tau and phosphor-tau levels upon sequential brain extraction. Further on, behavior testing of the treated mice can be performed, e.g., conditioned taste aversion or contextual fear conditioning for a confirmation of the therapeutic effects of the antibodies of the present invention (Pennanen, Genes Brain Behav. 5 (2006), 369-79, Pennanen Neurobiol Dis. 15 (2004), 500-9.)

Example 6

Chimerization of Antibodies NI-105.4E4 and NI-105.4A3 with Mouse IgG2a Constant Domains In order to generate antibodies with reduced immunogenicity for use in chronic treatment studies, mouse chimeric versions of antibodies NI-105.4E4 and NI-105.4A3 were generated using recombinant DNA technology. A mouse IgG2a/lambda isotype was selected for these chimeric antibodies, in order to generate a molecule which bound with high affinity to mouse Fc-gamma receptors, and was therefore capable of inducing an immune effector response. The amino acid sequences of the chimeric NI-105.4E4 ("ch4E4") and chimeric NI-105.4A3 ("ch4A3") heavy and light chain constructs are shown below.

TABLE 5

Amino acid sequences of chimeric NI-105.4E4 (ch4E4) and chimeric NI-105.4A3 (ch4A3)

| | |
|---|---|
| mature ch4E4 heavy chain (mouse IgG2a) SEQ ID NO: 20 | EVQLVESGGGLVQPGGSLKLSCAASGFNFNISAIHWVRQASGKGLEWVGR IRSKSHNYATLYAASLKGRFTLSRDDSRNTAYLQMSSLQTEDMAVYYCTV LSANYDTFDYWGQGTLVTVSSAKTTAPSVYPLAPVCGDTTGSSVTLGCLV KGYFPEPVTLTWNSGSLSSGVHTFPAVLQSDLYTLSSSVTVTSSTWPSQS ITCNVAHPASSTKVDKKIEPRGPTIKPCPPCKCPAPNLLGGPSVFIFPPK IKDVLMISLSPIVTCVVVDVSEDDPDVQISWFVNNVEVHTAQTQTHREDY NSTLRVVSALPIQHQDWMSGKEFKCKVNNKDLPAPIERTISKPKGSVRAP QVYVLPPPEEEMTKKQVTLTCMVTDFMPEDIYVEWTNNGKTELNYKNTEP VLDSDGSYFMYSKLRVEKKNWVERNSYSCSVVHEGLHNHHTTKSFSRTPG K |
| mature ch4E4 light chain (mouse lambda) SEQ ID NO: 21 | SYELTQPPVSVSPGQTARISCFGDTLPKQYTYWYQQKPGQAPVLVIYKD TERPSGIPERFSGSSSGTTVTLTISGVQAEDEADYYCLSADNSATWVFGG GTKVTVLGQPKSSPSVTLFPPSSEELETNKATLVCTITDFYPGVVTVDWK VDGTPVTQGMETTQPSKQSNNKYMASSYLTLTARAWERHSSYSCQVTHEG HTVEKSLSRADCS |

Example 7

Removal of Consensus N-Linked Glycosylation Site from ch4E4 Heavy Chain (Mouse IgG2a)

A consensus N-linked glycosylation site was identified in the CDR1 region of the NI-105.4E4 heavy chain. Upon mammalian (CHO) cell expression, the predicted N-glycosylation site (Asn-30) was fully occupied by glycan, as demonstrated by mass spectrometry. In order to eliminate N-glycosylation in this region and reduce product heterogeneity, Asn-30 of the heavy chain of ch4E4 was changed to Gln (Table 4). When produced and purified from CHO cells, the modified antibody bound to recombinant tau with ~4-fold higher apparent binding affinity relative to the original, glycosylated antibody.

TABLE 6

Amino acid sequences of mature ch4E4(N30Q) heavy chain (mouse IgG2a). Substituted Gln residue is in bold, underlined.

| | |
|---|---|
| mature ch4E4(N30Q) heavy chain (mouse IgG2a) SEQ ID NO: 22 | EVQLVESGGGLVQPGGSLKLSCAASGFNFQISAIHWVRQASGKGLEWVGR IRSKSHNYATLYAASLKGRFTLSRDDSRNTAYLQMSSLQTEDMAVYYCTV LSANYDTFDYWGQGTLVTVSSAKTTAPSVYPLAPVCGDTTGSSVTLGCLV KGYFPEPVTLTWNSGSLSSGVHTFPAVLQSDLYTLSSSVTVTSSTWPSQS ITCNVAHPASSTKVDKKIEPRGPTIKPCPPCKCPAPNLLGGPSVFIFPPK IKDVLMISLSPIVTCVVVDVSEDDPDVQISWFVNNVEVHTAQTQTHREDY NSTLRVVSALPIQHQDWMSGKEFKCKVNNKDLPAPIERTISKPKGSVRAP QVYVIPPPEEEMTKKQVTLTCMVTDFMPEDIYVEWTNNGKTELNYKNTEP VLDSDGSYFMYSKLRVEKKNWVERNSYSCSVVHEGLHNHHTTKSFSRTPG K |

Example 8

Production of Aglycosylated Chimeric NI-105.4E4(N30Q) (ch4E4(N30Q) mIgG1 Agly)

A mouse chimeric aglycosylated variant of germlined NI-105.4E4 was produced ("ch4E4(N30Q) IgG1-Agly") in order to evaluate the relationship between antibody effector function and activity. For the heavy chain (SEQ ID 214), the variable domain of NI-105.4E4(N30Q) (SEQ ID NO: 43) was fused to a mouse IgG1 heavy chain constant region containing an Asn to Gln mutation to eliminate the consensus Fc glycosylation site. The heavy chain variable region contained the N30Q change in order to eliminate the consensus N-glycosylation site in CDR1 (Example 7). The light chain was the ch4E4 lambda light chain described above (SEQ ID 21).

Example 9

Acute Brain Penetration Study of Human 4E4 and 4A3

Human NI-105.4E4 and NI-105.4A3 germlined antibodies were produced by transient transfection of CHO cells and purified by affinity purification. The endotoxin levels were controlled and were all bellow 1 EU/mg. TauP301L mice were intraperitoneally injected with 30 mg/kg NI-105.4E4 (n=7), 4A3 (n=7) antibody or equal volume of PBS (n=7) at day 1 and day 4. At day 5, mice were perfused under anesthesia with PBS containing 1 Unit/ml heparin. Blood, brain and spinal cord were collected for analyses. Right hemisphere of the brain was frozen at −80° C., left hemisphere of the brain and the spinal cord were post fixed in 10% neutralized formalin at 4° C. for two days before being embedded in paraffin block and sectioned. Plasma was stored at −80° C. in aliquots.

Brain protein extraction: frozen right hemisphere was weighed and homogenized in 5 volumes (5 mL/g of wet tissue) of a solution containing 50 mM NaCl, 0.2% diethylamine, protease inhibitors (Roche Diagnostics GmbH) and phosphatase inhibitor (Roche Diagnostics GmbH). Samples were then transferred to polycarbonate tubes and added another 5 volume of homogenization solution, and kept on ice for 30 min. Soluble fraction was then collected after centrifugation at 100,000 g, 4° C. for 30 min. This soluble fraction was used in human IgG assay. The pellet was re-suspended in 3 volumes of PBS with protease and phosphatase inhibitor. After centrifugation at 16,000 g, 4° C. for 30 min, supernatants and pellets were stored separately at −80° C. for further insoluble tau extraction. Pellets further extracted with modified sarcosyl extraction (Goedert M, Spillantini M G, Cairns N J, Crowther R A. Neuron 8, 159 (1992)).

Human IgG-specific sandwich ELISA: 2 g/ml of goat anti-human IgG Fab (Jackson) in 50 mM carbonate ELISA coating buffer (pH9.6) was used as capture antibody. Half-area 96-well microtiter plates was coated with 30 μl/well with capture antibody at 4° C. overnight. The plate was then washed 4 times with PBS containing 0.1% Tween 20 before incubating with 50 μl/well PBS containing 2% BSA at room temperature for one hour. Soluble fractions of brain extracts, plasma samples and antibody standard (4A3) were diluted in PBS containing 2% BSA and 0.1% Tween 20. 30 μl of the diluted samples were added into each well and incubated at room temperature for one hour. The plate was then washed with 200 μl/well PBS containing 0.1% Tween 20 for four times before incubated with HRP-conjugated donkey anti-human Fcγ (Jackson, diluted at 1:10,000 in PBS containing 2% BSA and 0.1% Tween 20) at room temperature for one hour. The plate was then washed with 200 μl/well PBS containing 0.1% Tween 20 for four times before adding 20 μl/well TMB (1:20 in 10 mM citrate solution pH=4.1). The reaction was then stopped by adding 10 μl 1M H2SO4 to each well. Antibody standard curve was obtained from serial dilutions of NI-105.4A3. Antibody concentrations in plasma and brain samples were calculated according to the standards. Brain human IgG level was then converted to g antibody/gram fresh brain tissue (assuming 1 g/10 ml) as indicated in FIG. 6.

High levels of human IgG were detected in the plasma of all NI-105.4E4 and NI-105.4A3 treated mice. In contrast, no human IgG was detected in the plasma of PBS treated mice (FIG. 5). Significant amount of human IgG was detected in brain homogenates of 4E4 and 4A3 treated mice (FIG. 6).

Example 10

Chronic Study with Chimeric NI-105.4E4 and NI-105.4A3

Chimeric NI-105.4E4 and NI-105.4A3 containing the variable domains of the original human antibody and the constant regions of mouse IgG2a can be produced by transient transfection of CHO cells and purified by affinity purification. The endotoxin levels in each batch of the antibodies will be controlled and kept below 1 Eu/mg. Gender balanced TauP301L mice at age of 7.5-8 months will be intraperitoneally injected with 10 mg/kg, 3 mg/kg of antibody solution, or equal volume of PBS control. Each treatment group will have 20-25 mice. The treatment will be carried out once a week for 26 weeks. Alternatively, the treatment will be carried out twice a week for 13 weeks. Body weight will be monitored every two weeks. Mice will be perfused under anesthesia at the end of the treatment period. Brain, spinal cord and blood will be collected. Half brain and spinal cord can be post-fixed in 10% formalin for three days before being embedded in paraffin block. 4-6 j m thick sections cut from these tissue blocks can be used for immunohistochemistry studies. The other half brain will be weighted and deep frozen at −80° C. for biochemical analyses.

Drug effects will be evaluated by comparing the level of neurofibrillary tangles (NFT) and the level of tau with different solubility characteristics in treated and control samples. NFT can be visualized by Gallyas silver impregnation (F Gallyas Acta Morphol. Acad. Sci. Hung 19.1 (1971)), or by immunostaining with monoclonal mouse antibody AT100 and AT180, which recognize pathologically phosphorylated tau in NFT. The number or frequency of Gallyas-positive neurons and/or AT100, AT180 labeled neurons in the brain and spinal cord in antibody treated mice and control animals can be determined to evaluate the effect of antibody treatment.

Soluble and insoluble tau can be extracted following the brain protein extraction protocol described herein. Alternatively, soluble and insoluble tau can be extracted with modified sarcosyl extraction (Goedert M, Spillantini M G, Cairns N J, Crowther R A. Neuron 8, 159 (1992)). Briefly, frozen brain is homogenized in 10 volumes (wt/vol) of 10% sucrose homogenate buffer consisting of 10 mM Tris*HCl (pH 7.4), 0.8 M NaCl, 1 mM EGTA, 1 mM Na3VO4, 1 mM NaF, 1 mM AEBSF, protease inhibitors (Roche Diagnostics GmbH) and phosphatase inhibitor (Roche Diagnostics GmbH). The homogenate is spun for 20 min at 20,000 g, and the supernatant retained. The pellet is homogenized in 10 volumes of homogenization buffer and centrifuged for a second time. The supernatants can be pooled together, and N-lauryl-sarkosinate (Sigma) is added to 1% (wt/vol) final concentration, and incubated at 37° C. with 300 rpm rotation for 1.5 hour, followed by centrifugation at 100,000 g for 1 h. The supernatant is collected as sarcosyl soluble fraction and the pellet of 1 g brain tissue is re-suspended in 0.2 ml 50 mM Tris.HCl (pH 7.4) as PHF fraction.

The levels of soluble and insoluble tau will be measured with commercially available Tau ELISA kits (Invitrogen). In addition, brain protein extracts will be separated with 4-12% Bis-Tris SDS-PAGE followed immunoblotting with Tau12 (human tau), AT8 (pS202/pT205), AT100 (pT212/pS214), AT180 (pT231) and E178 (pS396) antibodies. Semi-quantitative analysis will be performed with measuring the integrated density of each sample against standards of known quantities of tau.

Additionally, behavioral tests can be performed as indicated in Example 5, above. For example, improvement of working memory in antibody treated TauP301L mice can be tested using a two-trial Y-maze task (e.g., Pennanen, Genes Brain Behav. 5 (2006), 369-79, which is herein incorporated by reference in its entirety). The three arms of the maze are 22 cm long, 5 cm wide and 15 cm deep. Black and white abstractive clues are placed on a black curtain surrounding the maze. Experiments are conducted with an ambient light level of 6 lux during the dark phase. Each experiment comprises a training session and an observation session. During the training session, a mouse is assigned to two of the three arms (the start arm and the second arm), which can be freely explored during 4 min, with no access to the third arm (the novel arm). The mouse is then removed from the maze and kept in a holding cage for 1.5-5 min, while the maze is thoroughly cleaned with 70% ethanol to remove any olfactory clues. The mouse is then put back again in the maze for observation with all three arms accessible for 4 min. The sequence of entries, the number of entry to each arm and the time spent in each arm is recorded. From that the ratio of time spent in the novel third arm over the average of time spent in the other two arms (start arm and second arm) is calculated and compared among different treatment groups in tauopathy mouse model and corresponding control wild type mice. Rodents typically prefer to investigate a new arm of the maze rather than returning to one that was previously visited. Effects of the antibodies can be monitored in regard of regaining this preference by treated tauopathy model mice in comparison to non-discriminative behavior of untreated mice due to their disorder-related working memory impairment. Therefore, a ratio close to 1 indicates impaired working memory. A higher ratio indicates better working memory. Impaired working memory in TauP301L mice is considered to be due to tau pathology resulting from the overexpression of human tau. Therefore a significantly higher ratio observed in anti-tau antibody treated TauP301L mice than in the control TauP301L mice will indicate that the anti-tau antibody has therapeutic effect on tau pathology.

Example 11

Identification of Human Anti-Tau Antibodies

Recombinant human tau antibodies NI-105.17C1, NI-105.6C5, NI-105.29G10, NI-105.6L9, NI-105.40E8, NI-105.48E5, NI-105.6E3, NI-105.22E1, NI-105.26B12, NI-105.12E12, NI-105.60E7, NI-105.14E2, NI-105.39E2, NI-105.19C6, and NI-105.9C4 were isolated according to the methods described herein. The target and binding specificity of these human tau-antibodies were validated as described above. A summary of the findings is provided in Table 5. All antibodies used except NI-105.17C1 were germlined.

TABLE 7

In vitro characterization of human anti-tau antibodies.

| Antibody | EC$_{50}$ [nM]/rTau ELISA | EC$_{50}$ [nM]/PHFTau ELISA | Binding region (hTau40)* | Phosphorylation required** |
|---|---|---|---|---|
| NI-105.6C5 | 0.033 | 0.04 | 125-131 | No |
| NI-105.17C1 | 3.3 | 4.7 | 397-441 | No |
| NI-105.40E8 | >100 | 0.133 | 226-244 | Yes, pS235 |
| NI-105.6E3 | >100 | 18.7 | ND | Yes |
| NI-105.29G10 | 3.8 | 5.3 | 217-227 | No |
| NI-105.48E5 | >500 | 13.2 | 37-55; 387-406 | pS396, pS46 unconfirmed |
| NI-105.26B12 | 2.9 | >90 | 421-427 | ND |
| NI-105.6L9 | 2.5 | >60 | 427-439 | ND |
| NI-105.12E12 | 28.6 | >150 | 1-158 | ND |
| NI-105.60E7 | 0.18 | — | 197-207 | Phosphorylation at either 198, 199, 202 or 205 disrupts binding |
| NI-105.14E2 | 0.65 | — | 57-67 | No |
| NI-105.39E2 | 0.7 | — | 355-441 | ND |
| NI-105.19C6 | 4.0 | — | 313-319 | No |
| NI-105.22E1 | 1.1 | >200 | 309-319 | No |
| NI-105.9C4 | 5.2 | — | 221-231 | pS231 disrupts binding |

*binding region on hTau40 was identified by combined approaches of PepSPOTs, tau-fragments western blot and ELISA, tau-peptide ELISA and Alanine scanning.
**whether antibody binding requires phosphorylation at certain amino acids on tau protein was verified by comparing the binding of antibody to rTau, PHFTau, PHFTau dephosphorylated by calf intestine phosphatase, rTau in vitro phosphorylated by GSK3β or GSK3β/CDK5/p35, and phosphorylated tau peptides on PepSPOTs and direct ELISA.

Example 12

Chimerization of Human Antibodies with Mouse IgG2a Constant Domains

In order to generate antibodies with reduced immunogenicity for use in chronic treatment studies, mouse chimeric versions of antibodies NI-105.17C1 ("ch17C1"), NI-105.6C5 ("ch6C5"), NI-105.40E8 ("ch40E8"), and NI-105.6E3 ("ch6E3") were generated using recombinant DNA technology. A mouse IgG2a/lambda isotype was selected for these chimeric antibodies, in order to generate a molecule which bound with high affinity to mouse Fc-gamma receptors and was therefore capable of inducing an immune effector response. The amino acid sequences of ch17C1, ch6C5, ch40E8, ch40E8(R104W), and ch6E3 heavy and light chain constructs are shown below.

| | |
|---|---|
| ch17C1 heavy chain (mouse IgG2a) | SEQ ID NO: 203 |
| ch17C1 light chain (mouse lambda) | SEQ ID NO: 204 |
| ch6C5 heavy chain (mouse IgG2a) | SEQ ID NO: 205 |
| ch6C5 light chain (mouse lambda) | SEQ ID NO: 206 |
| ch40E8 heavy chain (mouse IgG2a) | SEQ ID NO: 207 |
| ch40E8(R104W) heavy chain (mouse IgG2a) | SEQ ID NO: 208 |
| ch40E8 light chain (lambda) | SEQ ID NO: 209 |
| ch6E3 heavy chain (mouse IgG2a) | SEQ ID NO: 210 |
| ch6E3 light chain (mouse kappa) | SEQ ID NO: 211 |

Example 13

Elimination of CDR Glycosylation Site in NI-105.17C1 Light Chain

A consensus N-linked glycosylation site was identified in the CDR1 region of the NI-105.17C1 light chain. Upon mammalian (CHO) cell expression, the predicted N-glycosylation site (Asn-31) was fully occupied by glycan, as demonstrated by mass spectrometry. In order to eliminate N-glycosylation in this region and improve product heterogeneity, Asn-31 of the light chain of ch17C1 was changed to Gln (see sequence below). When produced and purified from CHO cells, the modified antibody (ch17C1(N31Q) migG2a) bound to recombinant tau with similar apparent binding affinity relative to the original, glycosylated antibody (see FIG. 8A). The NI-105.17C1(N31Q) light chain variable region comprises the amino acid sequence of SEQ ID NO:221.

| | |
|---|---|
| ch17C1(N31Q) light chain (mouse lambda) | SEQ ID NO: 212 |
| human NI-105.17C1(N31Q) VL | SEQ ID NO: 221 |

Example 14

Production of Antibodies with Reduced Effector Function

Antibody variants containing mutations within the consensus N-glycosylation site in the heavy chain Fc domain were generated. These variants, designated "Agly", were designed to generate anti-tau antibodies with reduced immune effector function. The amino acid sequences of Agly variants of the tau antibodies are provided below.

| | |
|---|---|
| ch4A3-mIgG1-Agly heavy chain | SEQ ID NO: 213 |
| ch4E4(N30Q)-mIgG1-Agly heavy chain | SEQ ID NO: 214 |
| ch6C5-mIgG1-Agly heavy chain | SEQ ID NO: 215 |
| ch17C1-mIgG1-Agly heavy chain | SEQ ID NO: 216 |

Example 15

Comparison of Binding Activity of ch17C1-mIgG2a and ch17C1-mIgG1-Agly

The relationship between antibody effector function and activity was assessed for ch17C1 Agly (FIG. 8A). The ch17C1 antibody comprised the ch17C1 heavy chain (SEQ ID NO:203), and the ch17C1 light chain (SEQ ID NO:204) The ch17C1 (N31Q) mIgG2a antibody comprised the ch17C1 heavy chain (SEQ ID NO:203), and the ch17C1 (N31Q) light chain (SEQ ID NO:212), which incorporates the N31Q mutation in CDR1 to eliminate the CDR glycosylation site. The ch17C1(N31Q) mIgG1 Agly antibody comprised the ch17C1-mIgG1-Agly heavy chain (SEQ ID NO:216), wherein the variable domains of 17C1 are fused to a mouse IgG1 heavy chain containing an Asn to Gln mutation at position 294 (Kabat residue 297) to eliminate the consensus Fc glycosylation site, and the ch17C1(N31Q) light chain (SEQ ID NO:212). When produced and purified from CHO cells, ch17C1(N31Q) mIgG1 Agly bound to recombinant tau with similar apparent binding affinity relative to the original, glycosylated antibody (see FIG. 8A).

Example 16

Comparison of Valine Vs. Isoleucine at Position 48 of the 17C1 Light Chain

In the process of generating the mouse chimeric IgG2a version of germlined antibody NI-105.17C1, residue 48 of the light chain was also changed from valine to isoleucine. To confirm that this substitution did not affect the binding affinity of NI-105.17C1, a mouse chimeric IgG2a version of NI-105.17C1 with valine at position 48 was prepared. When produced and purified from CHO cells, ch17C1(N31Q, I48V) mIgG2a antibody bound to recombinant tau with similar apparent binding affinity relative to the ch17C1 (N31Q) mIgG2a (see FIG. 8B). The ch17C1(N31Q) mIgG2a antibody comprised the ch17C1 heavy chain (SEQ ID NO:203), and the ch17C1(N31Q, I48V) light chain (SEQ ID NO:217).

| | |
|---|---|
| ch17C1(N31Q, I48V) light chain (mouse lambda) | SEQ ID NO: 217 |
| human NI-105.17C1(N31Q, I48V) VL | SEQ ID NO: 222 |

Example 17

Comparison of Arg Vs. Trp at Position 104 of NI-105.40E8

Antibody NI-105.40E8, which is selective for the phosphorylated form of tau found in human paired helical filaments (PHF), contains an unusual arginine residue at position 104 of the NI-105.40E8 VH. Typically this position within the human immunoglobulin repertoire is occupied by a tryptophan residue. A form of the NI-105.40E8 heavy chain, NI-105.40E8(R104W)-hIgG1, was generated in which residue Arg104 was replaced with tryptophan. When produced and purified from CHO cells, NI-105.40E8 (R104W)-hIgG1 antibody bound to human PHF tau with similar apparent binding affinity relative to NI-105.40E8-hIgG1 (see FIG. 9). The light chain of the two antibodies was identical.

| | |
|---|---|
| human NI-105.40E8(R104W)-hIgG1, heavy chain | SEQ ID NO: 218 |
| human NI-105.40E8 light chain (human lambda) | SEQ ID NO: 219 |
| human NI-105.40E8(R104W) VH | SEQ ID NO: 220 |

Example 18

Human Anti-Tau Antibodies Bind to Pathologically Aggregated Tau in AD Brain and in the Brain of Transgenic Mouse Model of Tauopathy Brain tissue samples obtained from Alzheimer's disease and control patients, as well as from the brain of transgenic mouse of tauopathy and wild-type control were stained with the germlined human anti-tau antibodies provided herein. Representative images of germlined human NI-105.40E8, NI-105.48E5, NI-105.6C5 and NI-105.17C1 anti-tau antibodies binding to pathological tau aggregates in the brain of Alzheimer's disease (AD) and in the brain of transgenic mouse of tauopathy (Tg) are shown in FIG. 10. None of these antibodies bind to normal tau in mentally healthy subject (Ctr) or wild type mouse brain (Wt). The different patterns among these antibodies reflected their differences in epitope specificity and binding affinity.

Example 19

Brain Penetration of Antibodies in TauP301L Mice

Animals and Antibody treatments: Human NI-105.6C5, NI-105.40E8 and NI-105.6E3 anti-tau antibodies were produced by transient transfection of CHO cells and purified using standard methods. A humanized antibody with no cross-reactivity to mouse antigens was used as an isotype control (hIgG1). In the first experiment, half of the injected NI-105.6C5, NI-105.6E3 and hIgG1 antibodies were labeled with Cy3 (GE Healthcare, PA13105) with an approximate antibody: Cy3 ratio of 1:3. Cy3-labeling did not change the antibody binding as confirmed by ELISA and immunestaining with TauP301L brain (data not shown). In the second experiment, unlabeled NI-105.6C5 and NI-105.40E8 anti-tau antibodies were used.

TauP301L mice between 18-22 months of age received two doses of 30 mg/kg NI-105.6C5, NI-105.6E3 or human IgG1 isotype control hIgG1 via i.p. injection within seven days. Tissue samples were collected from three mice of each treated group at time points of one day, eight days and 22 days post the second dosing. In the second experiment, TauP301L mice were ip injected with 30 mg/kg h40E8 and h6C5 twice within seven days and tissue samples were collected from those mice one day post the second injection.

For tissue sample collection, mice were deeply anaesthetized with ketamine/xylazine before blood was collected through the right atrium. CSF was then collected by cisterna magna puncture. Brain and spine were subsequently collected following perfusion for 2 min with ice cold PBS, containing 10 UI/ml heparin and five minutes with 10% neutralized formalin through the left ventricle. The brain was fixed in 10% neutralized formalin for another 3 h at 4° C., following immersion in 30% sucrose for 48 h. The brain was then frozen in dry ice and subsequently sectioned into 30 m thick coronal section series. The section series were stored at −20° C. in antifreeze solution containing 1M glucose, 37.5% ethylene glycol in 50 mM sodium phosphate buffer pH7.4 with 0.025% sodium azide before use. The spine was post fixed in 10% neutralized formalin for two days and embedded in paraffin blocks.

Immunohistochemistry: Coronal sections of 30 μm thickness were probed with biotinylated donkey anti-human IgG (H+L) by free floating staining. Free-floating sections were washed in Tris-Triton pH7.4 (50 mM Tris, 150 mM NaCl, 0.05% Triton X-100), incubated in 1% $H_2O_2$ PBS for 30 min, and incubated with a blocking solution containing 2% normal goat- and horse serum in Tris-Triton with additional 0.2% Triton X-100 for 1 h at room temperature. The sections were then incubated with biotinylated donkey anti-human IgG (H+L) (Jackson Immunoresearch Labs, 709-065-149) at 1:200 in blocking solution for 16 h at 4° C. with agitation at 100 rpm to detect neuronal human IgG. The tissue-bound biotinylated antibody was visualized by peroxidase chromogenic reaction using the Vectastain Elite ABC kit (Vector Laboratories, PK6100, 1:100). The enzymatic reaction was stopped with ice cold PBS and the sections were washed in PBS 3 times. The sections were then mounted on glass slides and air dried over night before they were counterstained with hemalum solution to visualize the nuclei (Carl Roth GmbH+Co., T865.1). After dehydration steps, the slides were covered with coverslips before being scanned with the Olympus dotSlide 2.1 virtual microscopy system.

Human antibodies were detected in the brains of TauP301L mice, which had received either human anti-tau antibodies or hIgG1 control antibody via i.p. injection, but not in TauP301L and wild type mice without antibody treatment (FIG. 11). However, neuronal staining was only observed in the hippocampi of NI-105.6C5, NI-105.6E3 and NI-105.40E8 anti-tau antibody treated mice, but not in hIgG1 treated mice. Neuronal staining with anti-tau antibodies was readily detectable one day post injection, less pronounced at eight days post injection, and was undetectable at 22 days post injection (data not shown). TauP301L mice produce high levels of transgenic human tau in the hippocampal formation, and the hippocampus is one of the earliest regions which develop neurofibrillary tangles. Thus, peripherally injected anti-tau antibodies not only entered the brain but also likely entered into neurons which contained high levels of tau.

Example 20

Effects of Chronic Treatment of TauP301L Mice with ch4E4(N30Q) and ch17C1(N31Q)

Animals and Antibody treatments: Chimeric NI-105.4E4 (N30Q) ("ch4E4(N30Q)") and chimeric NI-105.17C1(N31Q) ("ch17C1(N31Q)") containing the variable domains of the human antibody and the constant regions of mouse IgG2a were produced by transient transfection of CHO cells and purified using standard methods.

Gender balanced TauP301L mice at ages of 7.5-8 months were weekly given 10 mg/kg ch17C1(N31Q) (n=20), 10 mg/kg ch4E4(N30Q) (n=20) or an equal volume of PBS (n-20) through intraperitoneal injection. Body weight was monitored every two weeks. No significant weight loss was observed. Two mice from the PBS group and one mouse from the ch17C1(N31Q) treated group died prematurely. Mice were anaesthetized one day after the 25th treatment for tissue collection. Blood was collected through the orbital sinus. Brain and spine were subsequently collected following perfusion for 2 min with ice cold PBS, containing 10 UI/ml heparin, through the left ventricle. The left half brain was then weighed, deep-frozen in dry ice and stored at −80° C. before use. The right half of the brain and the spine were post-fixed in neutralized 10% formalin at 4° C. for two days followed by further storage in PBS before being processed to paraffin embedded brain and spinal cord blocks.

Brain protein extraction: Brain protein was sequentially extracted based on the solubility. The left half brain was first homogenized in 10 times w/v of 50 mM NaCl containing 0.2% diethylamine, 1× protease inhibitor (Roche Diagnostics GmbH) and 1× phosphatase inhibitor (Roche Diagnostics GmbH). After 30 min incubation on ice, the homogenate was centrifuged at 100,000 g at 4° C. for 30 min. Subsequently, the supernatant was collected and defined as the soluble fraction. The remaining pellet was homogenized in 12 times w/v of 10% sucrose lysis buffer containing 10 mM Tris 7.4, 0.8M NaCl, 1 mM EGTA, 1× phosphatase inhibitor, 1× protease inhibitor, mM $Na_3VO_4$, 1 mM NaF and 1 mM AEBSF. After 30 min incubation on ice, the homogenate was centrifuged at 20,500 g at 4° C. for 20 min. 95% of the supernatant was carefully collected for sarcosyl extraction. The pellet was stored at −80° C. N-lauryl-sarcosinate was added to the supernatant (1% (w/v) final concentration). Following 1 h incubation at 37° C. with agitation at 220 rpm, the solution was centrifuged at 100,000 g at 4° C. for one hour. The supernatant was collected and defined as the sarcosyl soluble fraction. The pellet was left to dry at room temperature for 30 min, then dissolved in 50 mM Tris pH 7.4 (20% v/w initial brain weight) and defined as the PHF insoluble fraction, which was stored at −80° C. until use.

ELISA measurements Human total tau and phosphorylated tau in three brain protein fractions were quantified with commercial ELISA kits (Life Technologies) following the manufacturer's protocol. Total human tau, human tau phosphorylated at Threonine 231 (pT231 tau), human tau phosphorylated at Serine 199 (pS199 tau) and human tau phosphorylated at Threonine 181 (pT181) tau were detected. Samples of the soluble fraction were standardized to 1 mg/ml based on the total protein content measured with BCA protein assay (Pierce) with 50 mM Tris pH7.4. Aliquots of the standardized samples were prepared for ELISA measurements and Western blotting. To prepare solubilized PHF insoluble fraction for ELISA, 10 μl PHFTau was incubated with 10 μl 8M guanidine hydrochloride at room temperature for one hour followed by addition of 180 μl 50 mM Tris 7.4. ELISA measurements were carried out following standard protocols. The tau levels in each sample measured by ELISA were normalized to initial brain weight for final analysis.

End point plasma drug levels were measured using a sandwich ELISA. Briefly, 3 μg/ml rTau (rPeptide) (SEQ ID NO:6) in 100 nM carbonate ELISA coating buffer (pH9.6) was incubated in Costar half-area ELISA plates at 4° C. overnight. The plates were blocked with 3% BSA in PBS at room temperature for one hour. Plasma samples were diluted in 3% BSA in PBS containing 0.1% Tween®20 to 1:200, 1:400 and 1:800. Serial dilutions of ch17C1(N31Q) and ch4E4(N30Q) were used to generate standard curves. After one hour incubation, the plates were washed 4 times with PBS containing 0.1% Tween®20 followed by a one hour incubation with donkey anti-mouse IgGFcγ-HRP (1:10, 000). After washing, the bound antibody was further determined by a standard colorimetric assay. Standard curves were generated by sigmoidal curve fit with GraphPad Prism 5.

Western blot: Protein samples of the three fractions were heated at 70° C. for 10 min in 4× NuPAGE® LDS sample buffer (Life Technologies) and an equal amount of total protein from each sample was electrophoresed on a NuPAGE® 4-12% (w/v) gel.

Following semi-dry transfer of protein to PVDF membrane, the membrane was blocked in 3% BSA containing 0.1% Tween-20 in TBS and subsequently probed with different anti-tau antibodies at 4° C. overnight. Peroxidase-conjugated secondary antibodies were then incubated at room temperature for 1 h following 4 washes with TBST. Subsequently, the bound antibodies were detected by enhanced chemiluminescence (ECL) (Pierce). Densitometric analysis of immunoblots was performed with the National Institutes of Health ImageJ program.

Two-trial Y maze: Mice were tested for short-term spatial memory using a two-trial Y-maze test. The arms of the maze were 35 cm long, 5 cm wide and 10 cm deep. Abstractive cues were placed on the curtain surrounding the maze. Experiments were conducted with an ambient light level of 6 lux. During the exposure phase, mice were assigned to two arms (the start arm and one other arm), which can be freely explored during 4 min, without access to the third arm (new arm), blocked by a door made of the same material as the maze. Mice were then removed from the maze and kept in the holding cage for 2 min, when the maze was cleaned with 50% ethanol. During the test phase, mice were placed at the end of the start arm and allowed to freely explore all three arms during 4 min. The test phase was recorded with the TSE videoMot2 software for video tracking and analysis of animal behavior (TSE Systems, Bad Homburg, Germany). The number of arm entries and time spent in the new arm were recorded. The average of number of arm entries and time spent in the other two arms that were open during the training session was calculated. A ratio between the number of arm entries into (or time spent in) the new arm and the average of the other two arms were calculated. Wild type control animals which do not have a deficit in spatial working memory will typically have a ratio between 1.5 and 2 in this test. Pennanen et al., Genes Brain Behav 5(5):369-79 (2006).

Data analysis: ELISA data were log transformed to meet the normality assumption for the two-way analysis of variance. The difference was considered significant when $p<0.05$.

ch4E4(N30Q) significantly reduced soluble human tau in TauP301L mice: Human tau levels in the DEA-soluble, sarcosyl-soluble, and insoluble fractions of brain protein extracts were quantified by ELISA. The majority of the human tau was found in the DEA-soluble fraction (data not shown). Total human tau (hTau) was reduced in the DEA-soluble fraction from ch17C1(N31Q) and ch4E4(N30Q) treated mice compared with that of PBS treated mice (29% reduction on average in ch17C1(N31Q) and 37% in ch4E4(N30Q), FIG. 12A). Reductions were also seen in phosphorylated tau (pT231, pS199 and pT181) in the DEA-soluble fraction (FIGS. 12B, C and D respectively). We have previously observed lower human tau expression in female TauP301L mice than their male counterparts. Therefore, to accurately analyze the data we used two-way ANOVA with gender and treatment as the two variables. A gender effect was confirmed with a $p<0.01$ in all soluble human tau measurements (total human tau, pS199, pT181 and pT231 human tau). There was no interaction between gender and treatment ($0.49<p<0.91$ in all soluble human tau measurements). Importantly, there was a significant treatment effect in DEA-soluble human tau ($p<0.05$ for hTau, pS199 and pT231, and $p=0.06$ for pT181). The treatment effect was predominantly driven by ch4E4(N30Q). When compared with PBS control, ch4E4(N30Q) significantly reduced hTau ($p<0.05$), pS199 ($p<0.01$), pT231 ($p<0.01$) and pT181 ($p<0.05$). ELISA measurements using the sarcosyl-insoluble fraction showed a high variability among animals, and no significant gender effect was observed. No significant treatment effect was observed in the sarcosyl. insoluble fraction. Similarly, no significant treatment effect was observed by ELISA in the sarcosyl-soluble fraction.

Western blots using human tau-specific monoclonal antibody Tau12 showed full length human tau, as a single band at 62 kDa, as the major tau immunoreactive component in the DEA-soluble fraction. A clear reduction of the full length human tau was observed in majority of the mice treated with ch4E4(N30Q) and ch17C1(N31Q). In the sarcosyl insoluble fraction, a 64 kDa band and several other higher molecular weight bands were observed, as well as smaller molecular weight bands presumably corresponding to human tau fragments. Densitometric analysis showed a high degree of variability among individual animals, which prevented any quantitative comparison.

However, there was an overall qualitative reduction in all human tau proteins in the sarcosyl insoluble fraction detected by Tau12 in ch17C1(N31Q) and ch4E4(N30Q) treated mice (representative Western blot shown in FIG. 13).

Plasma drug levels: Mice were treated with ch17C1 (N31Q) and ch4E4(N30Q) at 10 mg/kg weekly through i.p. injection. To assess the drug exposure, plasma samples were collected 24 h after the last treatment. Plasma drug levels were measured with ELISA using rTau as capture agent. The average plasma levels of ch17C1(N31Q) and ch4E4(N30Q) were 200 g/ml and 145 g/ml, respectively, suggesting both antibodies had good blood exposure (FIG. 14).

Antibody treatment and spatial memory: An earlier study suggested deficits in spatial reference memory, which is hippocampus-dependent, in TauP301L mice (Pennanen et al., Genes Brain Behav 5(5):369-79 (2006)). The two-trial Y maze was reported as a sensitive test to detect deficits in short-term spatial memory in tau transgenic mice (Troquier et al., Curr Alzheimer Res. 9(4):397-405 (2012)). During the exposure phase, all groups explored the maze equally, spending a similar amount of time in each available arm (data not shown). No differences were found comparing distance moved. During the test phase, PBS treated TauP301L mice made almost equal number of entries in the new arm as the average of the other two arms explored during the exposure phase, (ratio=1.18), suggesting a poor spatial working memory in PBS treated TauP301L mice. Both ch17C1(N31Q) and ch4E4(N30Q) treated mice showed a preference for the new arm relative to the other two arms, and they made more visits to the new arm than the average of the other two arms (ratio=1.50 for ch17C1 (N31Q) and 1.30 for ch4E4(N30Q)). The ratio of new arm entry in ch17C1(N31Q) and ch4E4(N30Q) treated TauP301L mice compared with that of the PBS treated group is shown in FIG. 15.

The present invention is not to be limited in scope by the specific embodiments described which are intended as single illustrations of individual aspects of the invention, and any compositions or methods which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

What is claimed is:

1. A polynucleotide linked to a heterologous nucleic acid, wherein the polynucleotide is selected from the group consisting of:
   (a) a polynucleotide encoding an immunoglobulin heavy chain or a fragment thereof comprising a heavy chain variable region (VH) comprising complementarity determining regions (CDRs) 1, 2, and 3 with the amino acid sequences set forth in SEQ ID NOs:85, 86, and 87, respectively, wherein the VH when paired with a light chain variable region (VL) comprising the amino acid sequence set forth in SEQ ID NO:49 binds to tau;
   (b) a polynucleotide encoding an immunoglobulin heavy chain or a fragment thereof comprising a VH comprising CDRs 1, 2, and 3 with the amino acid sequences set forth in SEQ ID NOs:103, 104, and 105, respectively, wherein the VH when paired with a VL comprising the amino acid sequence set forth in SEQ ID NO:55 binds to tau;
   (c) a polynucleotide encoding an immunoglobulin light chain or a fragment thereof comprising a VL comprising CDRs 1, 2, and 3 with the amino acid sequences set forth in SEQ ID NOs:88, 89, and 90, respectively, wherein the VL when paired with a VH comprising the amino acid sequence set forth in SEQ ID NO:48 binds to tau;
   (d) a polynucleotide encoding an immunoglobulin light chain or a fragment thereof comprising a VL comprising CDRs 1, 2, and 3 with the amino acid sequences set forth in SEQ ID NOs:106, 107, and 108, respectively, wherein the VL when paired with a VH comprising the amino acid sequence set forth in SEQ ID NO:54 binds to tau;

(e) a polynucleotide encoding (i) an immunoglobulin heavy chain or a fragment thereof comprising a VH comprising CDRs 1, 2, and 3 with the amino acid sequences set forth in SEQ ID NOs:85, 86, and 87, respectively; and (ii) an immunoglobulin light chain or a fragment thereof comprising a VL comprising CDRs 1, 2, and 3 with the amino acid sequences set forth in SEQ ID NOs:88, 89, and 90, respectively, wherein the VH when paired with the VL binds to tau;

(f) a polynucleotide encoding (i) an immunoglobulin heavy chain or a fragment thereof comprising a VH comprising CDRs 1, 2, and 3 with the amino acid sequences set forth in SEQ ID NOs:103, 104, and 105, respectively; and (ii) an immunoglobulin light chain or a fragment thereof comprising a VL comprising CDRs 1, 2, and 3 with the amino acid sequences set forth in SEQ ID NOs:106, 107, and 108, respectively, wherein the VH when paired with the VL binds to tau;

(g) a polynucleotide encoding an immunoglobulin heavy chain or a fragment thereof comprising a VH comprising the amino acid sequence set forth in SEQ ID NO:48, wherein the VH when paired with a VL comprising the amino acid sequence set forth in SEQ ID NO:49 binds to tau;

(h) a polynucleotide encoding an immunoglobulin heavy chain or a fragment thereof comprising a VH comprising the amino acid sequence set forth in SEQ ID NO:47, wherein the VH when paired with a VL comprising the amino acid sequence set forth in SEQ ID NO:49 binds to tau;

(i) a polynucleotide encoding an immunoglobulin light chain or a fragment thereof comprising a VL comprising the amino acid sequence set forth in SEQ ID NO:49, wherein the VL when paired with a VH comprising the amino acid sequence set forth in SEQ ID NO:48 binds to tau;

(j) a polynucleotide encoding an immunoglobulin heavy chain or a fragment thereof comprising a VH comprising the amino acid sequence set forth in SEQ ID NO:54, wherein the VH when paired with a VL comprising the amino acid sequence set forth in SEQ ID NO:55 binds to tau;

(k) a polynucleotide encoding an immunoglobulin heavy chain or a fragment thereof comprising a VH comprising the amino acid sequence set forth in SEQ ID NO:220, wherein the VH when paired with a VL comprising the amino acid sequence set forth in SEQ ID NO:55 binds to tau;

(l) a polynucleotide encoding an immunoglobulin light chain or a fragment thereof comprising a VL comprising the amino acid sequence set forth in SEQ ID NO:55, wherein the VL when paired with a VH comprising the amino acid sequence set forth in SEQ ID NO:54 binds to tau;

(m) a polynucleotide encoding an immunoglobulin heavy chain or a fragment thereof comprising a VH comprising the amino acid sequence set forth in SEQ ID NO:48 and an immunoglobulin light chain or a fragment thereof comprising a VL comprising the amino acid sequence set forth in SEQ ID NO:49;

(n) a polynucleotide encoding an immunoglobulin heavy chain or a fragment thereof comprising a VH comprising the amino acid sequence set forth in SEQ ID NO:47 and an immunoglobulin light chain or a fragment thereof comprising a VL comprising the amino acid sequence set forth in SEQ ID NO:49;

(o) a polynucleotide encoding an immunoglobulin heavy chain or a fragment thereof comprising a VH comprising the amino acid sequence set forth in SEQ ID NO:54 and an immunoglobulin light chain or a fragment thereof comprising a VL comprising the amino acid sequence set forth in SEQ ID NO:55;

(p) a polynucleotide encoding an immunoglobulin heavy chain or a fragment thereof comprising a VH comprising the amino acid sequence set forth in SEQ ID NO:220 and an immunoglobulin light chain or a fragment thereof comprising a VL comprising the amino acid sequence set forth in SEQ ID NO:55;

(q) a polynucleotide encoding an immunoglobulin heavy chain comprising the amino acid sequence set forth in SEQ ID NO:218;

(r) a polynucleotide encoding an immunoglobulin light chain comprising the amino acid sequence set forth in SEQ ID NO:219; and (s) a polynucleotide encoding an immunoglobulin heavy chain comprising the amino acid sequence set forth in SEQ ID NO:218 and an immunoglobulin light chain comprising the amino acid sequence set forth in SEQ ID NO:219.

2. The polynucleotide of claim 1, wherein the heterologous nucleic acid is a regulatory element.

3. The polynucleotide of claim 2, wherein the regulatory element is a promoter, an enhancer, a ribosome binding site, or a transcription terminator.

4. The polynucleotide of claim 1, wherein the heterologous nucleic acid is a secretory signal peptide.

5. The polynucleotide of claim 4, wherein the secretory signal peptide is a mammalian signal peptide.

6. The polynucleotide of claim 5, wherein the mammalian signal peptide is from tissue plasminogen activator.

7. A host cell comprising the polynucleotide of claim 1.

8. The host cell of claim 7, wherein the host cell is a Chinese Hamster Ovary (CHO) cell.

9. A cDNA comprising a polynucleotide encoding a polypeptide comprising:

an immunoglobulin heavy chain or a fragment thereof comprising a heavy chain variable region (VH) comprising complementarity determining regions (CDRs) 1, 2, and 3 with the amino acid sequences set forth in SEQ ID NOs:85, 86, and 87, respectively, wherein the VH when paired with a light chain variable region (VL) comprising the amino acid sequence set forth in SEQ ID NO:49 binds to tau; or an immunoglobulin light chain or a fragment thereof comprising a VL comprising CDRs 1, 2, and 3 with the amino acid sequences set forth in SEQ ID NOs:88, 89, and 90, respectively, wherein the VL when paired with a VH comprising the amino acid sequence set forth in SEQ ID NO:48 binds to tau.

10. The cDNA of claim 9, wherein the polypeptide comprises:

an immunoglobulin heavy chain or fragment thereof comprising a VH with the amino acid sequence set forth in SEQ ID NO:47;

an immunoglobulin heavy chain or fragment thereof comprising a VH with the amino acid sequence set forth in SEQ ID NO:48; or an immunoglobulin light chain or fragment thereof comprising a VL with the amino acid sequence set forth in SEQ ID NO:49.

11. A cDNA comprising a polynucleotide encoding a polypeptide comprising:

an immunoglobulin heavy chain or a fragment thereof comprising a heavy chain variable region (VH) comprising complementarity determining regions (CDRs) 1, 2, and 3 with the amino acid sequences set forth in SEQ ID NOs:103, 104, and 105, respectively, and wherein the VH when paired with a light chain variable region (VL) comprising the amino acid sequence set forth in SEQ ID NO:55 binds to tau; or an immunoglobulin light chain or a fragment thereof comprising a VL comprising CDRs 1, 2, and 3 with the amino acid sequences set forth in SEQ ID NOs:106, 107, and 108, respectively, and wherein the VL when paired with a VH comprising the amino acid sequence set forth in SEQ ID NO:54 binds to tau.

12. The cDNA of claim 11, wherein the polypeptide comprises:

an immunoglobulin heavy chain or fragment thereof comprising a VH with the amino acid sequence set forth in SEQ ID NO:54;

an immunoglobulin heavy chain or fragment thereof comprising a VH with the amino acid sequence set forth in SEQ ID NO:220; or an immunoglobulin light chain or fragment thereof comprising a VL with the amino acid sequence set forth in SEQ ID NO:55.

13. An expression vector comprising a heterologous promoter operably linked to a polynucleotide encoding a polypeptide comprising:

an immunoglobulin heavy chain or a fragment thereof comprising a heavy chain variable region (VH) comprising complementarity determining regions (CDRs) 1, 2, and 3 with the amino acid sequences set forth in SEQ ID NOs:85, 86, and 87, respectively, and wherein the VH when paired with a light chain variable region (VL) comprising the amino acid sequence set forth in SEQ ID NO:49 binds to tau; or an immunoglobulin light chain or a fragment thereof comprising a VL comprising CDRs 1, 2, and 3 with the amino acid sequences set forth in SEQ ID NOs:88, 89, and 90, respectively, and wherein the VL when paired with a VH comprising the amino acid sequence set forth in SEQ ID NO:48 binds to tau.

14. The expression vector of claim 13, wherein the polypeptide comprises:

an immunoglobulin heavy chain or fragment thereof comprising a VH with the amino acid sequence set forth in SEQ ID NO:47;

an immunoglobulin heavy chain or fragment thereof comprising a VH with the amino acid sequence set forth in SEQ ID NO:48; or an immunoglobulin light chain or fragment thereof comprising a VL with the amino acid sequence set forth in SEQ ID NO:49.

15. The expression vector of claim 13, wherein the expression vector is a plasmid, phage, or virus.

16. The expression vector of claim 13, wherein the expression vector is a retrovirus.

17. The expression vector of claim 13, wherein the heterologous promoter is a cytomegalovirus, simian virus 40, or retroviral promoter.

18. The expression vector of claim 13, wherein the heterologous promoter is the cytomegalovirus immediate early promoter.

19. The expression vector of claim 13, wherein the polypeptide comprises a signal peptide.

20. The expression vector of claim 19, wherein the signal peptide is a heterologous signal peptide.

21. An expression vector comprising a heterologous promoter operably linked to a polynucleotide encoding a polypeptide comprising:

an immunoglobulin heavy chain or fragment thereof comprising a heavy chain variable region (VH) comprising complementarity determining regions (CDRs) 1, 2, and 3 with the amino acid sequences set forth in SEQ ID NOs:103, 104, and 105, respectively, and wherein the VH when paired with a light chain variable region (VL) comprising the amino acid sequence set forth in SEQ ID NO:55 binds to tau; or an immunoglobulin light chain or a fragment thereof comprising a VL comprising CDRs 1, 2, and 3 with the amino acid sequences set forth in SEQ ID NOs:106, 107, and 108, respectively, and wherein the VL when paired with a VH comprising the amino acid sequence set forth in SEQ ID NO:54 binds to tau.

22. The expression vector of claim 21, wherein the polypeptide comprises:

an immunoglobulin heavy chain or fragment thereof comprising a VH with the amino acid sequence set forth in SEQ ID NO:54;

an immunoglobulin heavy chain or fragment thereof comprising a VH with the amino acid sequence set forth in SEQ ID NO:220; or an immunoglobulin light chain or fragment thereof comprising a VL with the amino acid sequence set forth in SEQ ID NO:55.

23. The expression vector of claim 21, wherein the expression vector is a plasmid, phage, or virus.

24. The expression vector of claim 21, wherein the expression vector is a retrovirus.

25. The expression vector of claim 21, wherein the heterologous promoter is a cytomegalovirus, simian virus 40, or retroviral promoter.

26. The expression vector of claim 21, wherein the heterologous promoter is the cytomegalovirus immediate early promoter.

27. The expression vector of claim 21, wherein the polypeptide comprises a signal peptide.

28. The expression vector of claim 27, wherein the signal peptide is a heterologous signal peptide.

29. An expression vector comprising:

a first polynucleotide encoding a first polypeptide comprising an immunoglobulin heavy chain or a fragment thereof comprising a heavy chain variable region (VH) comprising VH complementarity determining regions (CDRs) 1, 2, and 3 with the amino acid sequences set forth in SEQ ID NOs:85, 86, and 87, respectively; and a second polynucleotide encoding a second polypeptide comprising an immunoglobulin light chain or a fragment thereof comprising a light chain variable region (VL) comprising VL CDRs 1, 2, and 3 with the amino acid sequences set forth in SEQ ID NOs:88, 89, and 90, respectively, wherein the immunoglobulin heavy chain or fragment thereof when paired with the immunoglobulin light chain or fragment thereof forms an anti-human tau antibody or human tau-binding fragment thereof, and wherein the expression vector is a plasmid, phage, or virus.

30. The expression vector of claim 29, wherein the expression vector is a retrovirus.

31. The expression vector of claim 29, wherein:

the VH consists of the amino acid sequence set forth in SEQ ID NO:48; and the VL consists of the amino acid sequence set forth in SEQ ID NO:49.

32. The expression vector of claim 31, wherein the first polypeptide comprises a human IgG1 heavy chain constant region and the second polypeptide comprises a human lambda light chain constant region.

33. The expression vector of claim 29, wherein:

the first polynucleotide comprises the nucleic acid sequence set forth in SEQ ID NO:173; and the second polynucleotide comprises the nucleic acid sequence set forth in SEQ ID NO:174.

34. A host cell comprising:
a first expression vector comprising a first heterologous promoter operably linked to a first polynucleotide encoding a first polypeptide comprising an immunoglobulin heavy chain or a fragment thereof comprising a heavy chain variable region (VH) comprising VH complementarity determining regions (CDRs) 1, 2, and 3 with the amino acid sequences set forth in SEQ ID NOs:85, 86, and 87, respectively; and
a second expression vector comprising a second heterologous promoter operably linked to a second polynucleotide encoding a second polypeptide comprising an immunoglobulin light chain or a fragment thereof comprising a light chain variable region (VL) comprising VL CDRs 1, 2, and 3 with the amino acid sequences set forth in SEQ ID NOs:88, 89, and 90, respectively,
wherein the immunoglobulin heavy chain or fragment thereof when paired with the immunoglobulin light chain or fragment thereof forms an anti-human tau antibody or human tau-binding fragment thereof.

35. The host cell of claim 34, wherein the first heterologous promoter is a cytomegalovirus, simian virus 40, or retroviral promoter and the second heterologous promoter is a cytomegalovirus, simian virus 40, or retroviral promoter.

36. The host cell of claim 34, wherein the first heterologous promoter is the cytomegalovirus immediate early promoter and the second heterologous promoter is the cytomegalovirus immediate early promoter.

37. The host cell of claim 34, wherein the first expression vector is a plasmid, phage, or virus and the second expression vector is a plasmid, phage, or virus.

38. The host cell of claim 34, wherein the first expression vector is a retrovirus and the second expression vector is a retrovirus.

39. The host cell of claim 34, wherein:
the VH consists of the amino acid sequence set forth in SEQ ID NO:48; and
the VL consists of the amino acid sequence set forth in SEQ ID NO:49.

40. The host cell of claim 39, wherein the first polypeptide comprises a human IgG1 heavy chain constant region and the second polypeptide comprises a human lambda light chain constant region.

41. The host cell of claim 34, wherein the host cell is a mammalian host cell.

42. The host cell of claim 34, wherein the host cell is a Chinese Hamster Ovary (CHO) cell, a HEK 293 cell, or a NSO cell.

43. A host cell comprising an expression vector comprising:
a first polynucleotide encoding a first polypeptide comprising an immunoglobulin heavy chain or a fragment thereof comprising a heavy chain variable region (VH) comprising VH complementarity determining regions (CDRs) 1, 2, and 3 with the amino acid sequences set forth in SEQ ID NOs:85, 86, and 87, respectively; and
a second polynucleotide encoding a second polypeptide comprising an immunoglobulin light chain or a fragment thereof comprising a light chain variable region (VL) comprising VL CDRs 1, 2, and 3 with the amino acid sequences set forth in SEQ ID NOs:88, 89, and 90, respectively,
wherein the immunoglobulin heavy chain or fragment thereof when paired with the immunoglobulin light chain or fragment thereof forms an anti-human tau antibody or human tau-binding fragment thereof, and
wherein the expression vector is a plasmid, phage, or virus.

44. The host cell of claim 43, wherein the expression vector is a retrovirus.

45. The host cell of claim 43, wherein:
the VH consists of the amino acid sequence set forth in SEQ ID NO:48; and
the VL consists of the amino acid sequence set forth in SEQ ID NO:49.

46. The host cell of claim 45, wherein the first polypeptide comprises a human IgG1 heavy chain constant region and the second polypeptide comprises a human lambda light chain constant region.

47. The host cell of claim 43, wherein the host cell is a mammalian host cell.

48. The host cell of claim 43, wherein the host cell is a Chinese Hamster Ovary (CHO) cell, a HEK 293 cell, or a NSO cell.

49. A method for preparing an anti-human tau antibody or human tau-binding fragment thereof, the method comprising:
culturing the host cell of claim 34 in a cell culture; and
isolating the anti-human tau antibody or human tau-binding fragment thereof from the cell culture.

50. The method of claim 49, further comprising formulating the anti-human tau antibody or human tau-binding fragment thereof into a sterile pharmaceutical composition suitable for administration to a human subject.

51. The method of claim 50, wherein the pharmaceutical composition is suitable for intravenous or subcutaneous administration.

52. The method of claim 50, wherein:
the VH consists of the amino acid sequence set forth in SEQ ID NO:48; and
the VL consists of the amino acid sequence set forth in SEQ ID NO:49.

53. The method of claim 52, wherein the first polypeptide comprises a human IgG1 heavy chain constant region and the second polypeptide comprises a human lambda light chain constant region.

54. A method for preparing an anti-human tau antibody or human tau-binding fragment thereof, the method comprising:
culturing the host cell of claim 43 in a cell culture; and
isolating the anti-human tau antibody or human tau-binding fragment thereof from the cell culture.

55. The method of claim 54, further comprising formulating the anti-human tau antibody or human tau-binding fragment thereof into a sterile pharmaceutical composition suitable for administration to a human subject.

56. The method of claim 55, wherein the pharmaceutical composition is suitable for intravenous or subcutaneous administration.

57. The method of claim 55, wherein:
the VH consists of the amino acid sequence set forth in SEQ ID NO:48; and
the VL consists of the amino acid sequence set forth in SEQ ID NO:49.

58. The method of claim 57, wherein the first polypeptide comprises a human IgG1 heavy chain constant region and the second polypeptide comprises a human lambda light chain constant region.

59. An expression vector comprising:
a first polynucleotide encoding a first polypeptide comprising an immunoglobulin heavy chain or a fragment thereof comprising a heavy chain variable region (VH) comprising VH complementarity determining regions (CDRs) 1, 2, and 3 with the amino acid sequences set forth in SEQ ID NOs:103, 104, and 105, respectively; and
a second polynucleotide encoding a second polypeptide comprising an immunoglobulin light chain or a fragment thereof comprising a light chain variable region (VL) comprising VL CDRs 1, 2, and 3 with the amino acid sequences set forth in SEQ ID NOs:106, 107, and 108, respectively,
wherein the immunoglobulin heavy chain or fragment thereof when paired with the immunoglobulin light chain or fragment thereof forms an anti-human tau antibody or human tau-binding fragment thereof, and
wherein the expression vector is a plasmid, phage, or virus.

60. The expression vector of claim 59, wherein the expression vector is a retrovirus.

61. The expression vector of claim 59, wherein:
the VH consists of the amino acid sequence set forth in SEQ ID NO:220; and
the VL consists of the amino acid sequence set forth in SEQ ID NO:55.

62. The expression vector of claim 61, wherein the first polypeptide comprises a human IgG1 heavy chain constant region and the second polypeptide comprises a human lambda light chain constant region.

63. The expression vector of claim 59, wherein:
the first polynucleotide comprises the nucleic acid sequence set forth in SEQ ID NO:179; and
the second polynucleotide comprises the nucleic acid sequence set forth in SEQ ID NO:180.

64. A host cell comprising:
a first expression vector comprising a first heterologous promoter operably linked to a first polynucleotide encoding a first polypeptide comprising an immunoglobulin heavy chain or a fragment thereof comprising a heavy chain variable region (VH) comprising VH complementarity determining regions (CDRs) 1, 2, and 3 with the amino acid sequences set forth in SEQ ID NOs:103, 104, and 105, respectively; and
a second expression vector comprising a second heterologous promoter operably linked to a second polynucleotide encoding a second polypeptide comprising an immunoglobulin light chain or a fragment thereof comprising a light chain variable region (VL) comprising VL CDRs 1, 2, and 3 with the amino acid sequences set forth in SEQ ID NOs:106, 107, and 108, respectively,
wherein the immunoglobulin heavy chain or fragment thereof when paired with the immunoglobulin light chain or fragment thereof forms an anti-human tau antibody or human tau-binding fragment thereof.

65. The host cell of claim 64, wherein the first heterologous promoter is a cytomegalovirus, simian virus 40, or retroviral promoter and the second heterologous promoter is a cytomegalovirus, simian virus 40, or retroviral promoter.

66. The host cell of claim 64, wherein the first heterologous promoter is the cytomegalovirus immediate early promoter and the second heterologous promoter is the cytomegalovirus immediate early promoter.

67. The host cell of claim 64, wherein the first expression vector is a plasmid, phage, or virus and the second expression vector is a plasmid, phage, or virus.

68. The host cell of claim 64, wherein the first expression vector is a retrovirus and the second expression vector is a retrovirus.

69. The host cell of claim 64, wherein:
the VH consists of the amino acid sequence set forth in SEQ ID NO:220; and
the VL consists of the amino acid sequence set forth in SEQ ID NO:55.

70. The host cell of claim 69, wherein the first polypeptide comprises a human IgG1 heavy chain constant region and the second polypeptide comprises a human lambda light chain constant region.

71. The host cell of claim 64, wherein the host cell is a mammalian host cell.

72. The host cell of claim 64, wherein the host cell is a Chinese Hamster Ovary (CHO) cell, a HEK 293 cell, or a NSO cell.

73. A host cell comprising an expression vector comprising:
a first polynucleotide encoding a first polypeptide comprising an immunoglobulin heavy chain or a fragment thereof comprising a heavy chain variable region (VH) comprising VH complementarity determining regions (CDRs) 1, 2, and 3 with the amino acid sequences set forth in SEQ ID NOs:103, 104, and 105, respectively; and
a second polynucleotide encoding a second polypeptide comprising an immunoglobulin light chain or a fragment thereof comprising a light chain variable region (VL) comprising VL CDRs 1, 2, and 3 with the amino acid sequences set forth in SEQ ID NOs:106, 107, and 108, respectively,
wherein the immunoglobulin heavy chain or fragment thereof when paired with the immunoglobulin light chain or fragment thereof forms an anti-human tau antibody or human tau-binding fragment thereof, and
wherein the expression vector is a plasmid, phage, or virus.

74. The host cell of claim 73, wherein the expression vector is a retrovirus.

75. The host cell of claim 73, wherein:
the VH consists of the amino acid sequence set forth in SEQ ID NO:220; and
the VL consists of the amino acid sequence set forth in SEQ ID NO:55.

76. The host cell of claim 75, wherein the first polypeptide comprises a human IgG1 heavy chain constant region and the second polypeptide comprises a human lambda light chain constant region.

77. The host cell of claim 73, wherein the host cell is a mammalian host cell.

78. The host cell of claim 73, wherein the host cell is a Chinese Hamster Ovary (CHO) cell, a HEK 293 cell, or a NSO cell.

79. A method for preparing an anti-human tau antibody or human tau-binding fragment thereof, the method comprising:
culturing the host cell of claim 64 in a cell culture; and
isolating the anti-human tau antibody or human tau-binding fragment thereof from the cell culture.

80. The method of claim 79, further comprising formulating the anti-human tau antibody or human tau-binding fragment thereof into a sterile pharmaceutical composition suitable for administration to a human subject.

81. The method of claim 80, wherein the pharmaceutical composition is suitable for intravenous or subcutaneous administration.

82. The method of claim 80, wherein:
the VH consists of the amino acid sequence set forth in SEQ ID NO:220; and
the VL consists of the amino acid sequence set forth in SEQ ID NO:55.

83. The method of claim 82, wherein the first polypeptide comprises a human IgG1 heavy chain constant region and the second polypeptide comprises a human lambda light chain constant region.

84. A method for preparing an anti-human tau antibody or human tau-binding fragment thereof, the method comprising:
culturing the host cell of claim 73 in a cell culture; and
isolating the anti-human tau antibody or human tau-binding fragment thereof from the cell culture.

85. The method of claim 84, further comprising formulating the anti-human tau antibody or human tau-binding fragment thereof into a sterile pharmaceutical composition suitable for administration to a human subject.

86. The method of claim 85, wherein the pharmaceutical composition is suitable for intravenous or subcutaneous administration.

87. The method of claim 85, wherein:
the VH consists of the amino acid sequence set forth in SEQ ID NO:220; and
the VL consists of the amino acid sequence set forth in SEQ ID NO:55.

88. The method of claim 87, wherein the first polypeptide comprises a human IgG1 heavy chain constant region and the second polypeptide comprises a human lambda light chain constant region.

89. A method of treating a neurodegenerative tauopathy in a human subject in need thereof, the method comprising administering to the human subject a therapeutically effective amount of an anti-tau antibody or tau-binding fragment thereof, wherein the anti-tau antibody or tau-binding fragment thereof comprises:
a heavy chain variable region (VH) comprising VH complementarity determining regions 1, 2, and 3 with the amino acid sequences set forth in SEQ ID NO:85, SEQ ID NO:86, and SEQ ID NO:87, respectively; and
a light chain variable region (VL) comprising VL complementarity determining regions 1, 2, and 3 with the amino acid sequences set forth in SEQ ID NO:88, SEQ ID NO:89, and SEQ ID NO:90, respectively.

90. The method of claim 89, wherein the neurodegenerative tauopathy is selected from the group consisting of Alzheimer's disease, amyotrophic lateral sclerosis/parkinsonismdementia complex, argyrophilic grain dementia, British type amyloid angiopathy, cerebral amyloid angiopathy, corticobasal degeneration, Creutzfeldt-Jakob disease, dementia pugilistica, diffuse neurofibrillary tangles with calcification, Down's syndrome, frontotemporal dementia, frontotemporal dementia with parkinsonism linked to chromosome 17, frontotemporal lobar degeneration, Gerstmann-Strussler-Scheinker disease, Hallervorden-Spatz disease, inclusion body myositis, multiple system atrophy, myotonic dystrophy, Niemann-Pick disease type C, non-Guamanian motor neuron disease with neurofibrillary tangles, Pick's disease, postencephalitic parkinsonism, prion protein cerebral amyloid angiopathy, progressive subcortical gliosis, progressive supranuclear palsy, subacute sclerosing panencephalitis, Tangle only dementia, multi-infarct dementia, and ischemic stroke.

91. The method of claim 89, wherein the neurodegenerative tauopathy is Alzheimer's disease.

92. The method of claim 89, wherein:
the VH consists of the amino acid sequence set forth in SEQ ID NO:47; and
the VL consists of the amino acid sequence set forth in SEQ ID NO:49.

93. The method of claim 89, wherein:
the VH consists of the amino acid sequence set forth in SEQ ID NO:48; and
the VL consists of the amino acid sequence set forth in SEQ ID NO:49.

94. The method of claim 92, wherein the antibody or antigen-binding fragment thereof comprises a human IgG1 heavy chain constant region and a human lambda light chain constant region.

95. The method of claim 93, wherein the antibody or antigen-binding fragment thereof comprises a human IgG1 heavy chain constant region and a human lambda light chain constant region.

96. The method of claim 92, wherein the neurodegenerative tauopathy is Alzheimer's disease.

97. The method of claim 93, wherein the neurodegenerative tauopathy is Alzheimer's disease.

98. The method of claim 94, wherein the neurodegenerative tauopathy is Alzheimer's disease.

99. The method of claim 95, wherein the neurodegenerative tauopathy is Alzheimer's disease.

100. A method of treating abnormal accumulation or deposition of tau in the central nervous system in a human subject in need thereof, the method comprising administering to the human subject a therapeutically effective amount of an anti-tau antibody or tau-binding fragment thereof, wherein the anti-tau antibody or tau-binding fragment thereof comprises:
a heavy chain variable region (VH) comprising VH complementarity determining regions 1, 2, and 3 with the amino acid sequences set forth in SEQ ID NO:85, SEQ ID NO:86, and SEQ ID NO:87, respectively; and
a light chain variable region (VL) comprising VL complementarity determining regions 1, 2, and 3 with the amino acid sequences set forth in SEQ ID NO:88, SEQ ID NO:89, and SEQ ID NO:90, respectively.

101. The method of claim 100, wherein:
the VH consists of the amino acid sequence set forth in SEQ ID NO:47; and
the VL consists of the amino acid sequence set forth in SEQ ID NO:49.

102. The method of claim 100, wherein:
the VH consists of the amino acid sequence set forth in SEQ ID NO:48; and
the VL consists of the amino acid sequence set forth in SEQ ID NO:49.

103. The method of claim 101, wherein the antibody or antigen-binding fragment thereof comprises a human IgG1 heavy chain constant region and a human lambda light chain constant region.

104. The method of claim 102, wherein the antibody or antigen-binding fragment thereof comprises a human IgG1 heavy chain constant region and a human lambda light chain constant region.

105. A method of treating a neurodegenerative tauopathy in a human subject in need thereof, the method comprising administering to the human subject a therapeutically effective amount of an anti-tau antibody or tau-binding fragment thereof, wherein the anti-tau antibody or tau-binding fragment thereof comprises:
a heavy chain variable region (VH) comprising VH complementarity determining regions 1, 2, and 3 with the amino acid sequences set forth in SEQ ID NO:103, SEQ ID NO:104, and SEQ ID NO:105, respectively; and
a light chain variable region (VL) comprising VL complementarity determining regions 1, 2, and 3 with the amino acid sequences set forth in SEQ ID NO:106, SEQ ID NO:107, and SEQ ID NO:108, respectively.

106. The method of claim 105, wherein the neurodegenerative tauopathy is selected from the group consisting of Alzheimer's disease, amyotrophic lateral sclerosis/parkinsonism-dementia complex, argyrophilic grain dementia, British type amyloid angiopathy, cerebral amyloid angiopathy, corticobasal degeneration, Creutzfeldt-Jakob disease, dementia pugilistica, diffuse neurofibrillary tangles with calcification, Down's syndrome, frontotemporal dementia, frontotemporal dementia with parkinsonism linked to chromosome 17, frontotemporal lobar degeneration, Gerstmann-Sträussler-Scheinker disease, Hallervorden-Spatz disease, inclusion body myositis, multiple system atrophy, myotonic dystrophy, Niemann-Pick disease type C, non-Guamanian motor neuron disease with neurofibrillary tangles, Pick's disease, postencephalitic parkinsonism, prion protein cerebral amyloid angiopathy, progressive subcortical gliosis, progressive supranuclear palsy, subacute sclerosing panencephalitis, Tangle only dementia, multi-infarct dementia, and ischemic stroke.

107. The method of claim 105, wherein the neurodegenerative tauopathy is Alzheimer's disease.

108. The method of claim 105, wherein:
the VH consists of the amino acid sequence set forth in SEQ ID NO:54; and
the VL consists of the amino acid sequence set forth in SEQ ID NO:55.

109. The method of claim 105, wherein:
the VH consists of the amino acid sequence set forth in SEQ ID NO:220; and
the VL consists of the amino acid sequence set forth in SEQ ID NO:55.

110. The method of claim 108, wherein the antibody or antigen-binding fragment thereof comprises a human IgG1 heavy chain constant region and a human lambda light chain constant region.

111. The method of claim 109, wherein the antibody or antigen-binding fragment thereof comprises a human IgG1 heavy chain constant region and a human lambda light chain constant region.

112. The method of claim 108, wherein the neurodegenerative tauopathy is Alzheimer's disease.

113. The method of claim 109, wherein the neurodegenerative tauopathy is Alzheimer's disease.

114. The method of claim 110, wherein the neurodegenerative tauopathy is Alzheimer's disease.

115. The method of claim 111, wherein the neurodegenerative tauopathy is Alzheimer's disease.

116. A method of treating abnormal accumulation or deposition of tau in the central nervous system in a human subject in need thereof, the method comprising administering to the human subject a therapeutically effective amount of an anti-tau antibody or tau-binding fragment thereof, wherein the anti-tau antibody or tau-binding fragment thereof comprises:
a heavy chain variable region (VH) comprising VH complementarity determining regions 1, 2, and 3 with the amino acid sequences set forth in SEQ ID NO:103, SEQ ID NO:104, and SEQ ID NO:105, respectively; and
a light chain variable region (VL) comprising VL complementarity determining regions 1, 2, and 3 with the amino acid sequences set forth in SEQ ID NO:106, SEQ ID NO:107, and SEQ ID NO:108, respectively.

117. The method of claim 116, wherein:
the VH consists of the amino acid sequence set forth in SEQ ID NO:54; and
the VL consists of the amino acid sequence set forth in SEQ ID NO:55.

118. The method of claim 116, wherein:
the VH consists of the amino acid sequence set forth in SEQ ID NO:220; and
the VL consists of the amino acid sequence set forth in SEQ ID NO:55.

119. The method of claim 117, wherein the antibody or antigen-binding fragment thereof comprises a human IgG1 heavy chain constant region and a human lambda light chain constant region.

120. The method of claim 118, wherein the antibody or antigen-binding fragment thereof comprises a human IgG1 heavy chain constant region and a human lambda light chain constant region.

121. A method for in vivo detection of tau deposition in the brain, the method comprising:
administering to a human subject an antibody or antigen-binding fragment thereof that specifically binds to tau, wherein the antibody or antigen-binding fragment thereof comprises: a heavy chain variable region (VH) comprising VH complementarity determining regions 1, 2, and 3 with the amino acid sequences set forth in SEQ ID NO:85, SEQ ID NO:86, and SEQ ID NO:87, respectively; and a light chain variable region (VL) comprising VL complementarity determining regions 1, 2, and 3 with the amino acid sequences set forth in SEQ ID NO:88, SEQ ID NO:89, and SEQ ID NO:90, respectively, wherein the antibody or antigen-binding fragment thereof is attached to a detectable label; and
detecting the detectable label in the brain of the human subject, to thereby detect tau deposition in the brain of the human subject.

122. The method of claim 121, wherein:
the VH consists of the amino acid sequence set forth in SEQ ID NO:48; and
the VL consists of the amino acid sequence set forth in SEQ ID NO:49.

123. The method of claim 121, wherein:
the VH consists of the amino acid sequence set forth in SEQ ID NO:47; and
the VL consists of the amino acid sequence set forth in SEQ ID NO:49.

124. The method of claim 121, wherein the detectable label is an enzyme, prosthetic group, fluorescent material, luminescent material, bioluminescent material, radioactive material, positron emitting metal, or nonradioactive paramagnetic metal ion.

125. The method of claim 122, wherein the detectable label is an enzyme, prosthetic group, fluorescent material, luminescent material, bioluminescent material, radioactive material, positron emitting metal, or nonradioactive paramagnetic metal ion.

126. The method of claim 123, wherein the detectable label is an enzyme, prosthetic group, fluorescent material, luminescent material, bioluminescent material, radioactive material, positron emitting metal, or nonradioactive paramagnetic metal ion.

127. The method of claim 124, wherein the detectable label is detected by a positron emission tomography.

128. The method of claim 125, wherein the detectable label is detected by a positron emission tomography.

129. The method of claim 126, wherein the detectable label is detected by a positron emission tomography.

130. The method of claim 121, wherein the antibody or antigen-binding fragment is selected from the group consisting of an Fab, an Fab', an F(ab')2, an Fd, an Fv, a single-chain Fv (scFv), a single-chain antibody, and a disulfide-linked Fv (sdFv).

131. The method of claim 122, wherein the antibody or antigen-binding fragment is selected from the group consisting of an Fab, an Fab', an F(ab')2, an Fd, an Fv, a single-chain Fv (scFv), a single-chain antibody, and a disulfide-linked Fv (sdFv).

132. The method of claim 123, wherein the antibody or antigen-binding fragment is selected from the group consisting of an Fab, an Fab', an F(ab')2, an Fd, an Fv, a single-chain Fv (scFv), a single-chain antibody, and a disulfide-linked Fv (sdFv).

133. The method of claim 121, wherein the antibody or antigen-binding fragment thereof comprises a human IgG1 heavy chain constant region and a human lambda light chain constant region.

134. The method of claim 122, wherein the antibody or antigen-binding fragment thereof comprises a human IgG1 heavy chain constant region and a human lambda light chain constant region.

135. The method of claim 123, wherein the antibody or antigen-binding fragment thereof comprises a human IgG1 heavy chain constant region and a human lambda light chain constant region.

136. A method of diagnosing or monitoring the progression of a neurodegenerative tauopathy, the method comprising:
measuring the level of pathologically modified or aggregated tau in a sample from a human subject with an anti-tau antibody or tau-binding fragment thereof, wherein the anti-tau antibody or tau-binding fragment thereof comprises a heavy chain variable region (VH) comprising VH complementarity determining regions 1, 2, and 3 with the amino acid sequences set forth in SEQ ID NO:85, SEQ ID NO:86, and SEQ ID NO:87, respectively, and a light chain variable region (VL) comprising VL complementarity determining regions 1, 2, and 3 with the amino acid sequences set forth in SEQ ID NO:88, SEQ ID NO:89, and SEQ ID NO:90, respectively; and
comparing the level of modified or aggregated tau to a reference standard that indicates the level of the pathologically modified or aggregated tau in one or more control subjects,
wherein a difference or similarity between the level of pathologically modified or aggregated tau and the reference standard indicates that the human subject has a neurodegenerative tauopathy.

137. The method of claim 136, wherein:
the VH consists of the amino acid sequence set forth in SEQ ID NO:48; and
the VL consists of the amino acid sequence set forth in SEQ ID NO:49.

138. The method of claim 136, wherein:
the VH consists of the amino acid sequence set forth in SEQ ID NO:47; and
the VL consists of the amino acid sequence set forth in SEQ ID NO:49.

139. The method of claim 136, wherein the neurodegenerative tauopathy is Alzheimer's disease.

140. The method of claim 137, wherein the neurodegenerative tauopathy is Alzheimer's disease.

141. The method of claim 138, wherein the neurodegenerative tauopathy is Alzheimer's disease.

142. A method for in vivo detection of tau deposition in the brain, the method comprising:
administering to a human subject an antibody or antigen-binding fragment thereof that specifically binds to tau, wherein the antibody or antigen-binding fragment thereof comprises: a heavy chain variable region (VH) comprising VH complementarity determining regions 1, 2, and 3 with the amino acid sequences set forth in SEQ ID NO:103, SEQ ID NO:104, and SEQ ID NO:105, respectively; and a light chain variable region (VL) comprising VL complementarity determining regions 1, 2, and 3 with the amino acid sequences set forth in SEQ ID NO:106, SEQ ID NO:107, and SEQ ID NO:108, respectively, wherein the antibody or antigen-binding fragment thereof is attached to a detectable label; and
detecting the detectable label in the brain of the human subject, to thereby detect tau deposition in the brain of the human subject.

143. The method of claim 142, wherein:
the VH consists of the amino acid sequence set forth in SEQ ID NO:54; and
the VL consists of the amino acid sequence set forth in SEQ ID NO:55.

144. The method of claim 142, wherein:
the VH consists of the amino acid sequence set forth in SEQ ID NO:220; and
the VL consists of the amino acid sequence set forth in SEQ ID NO:55.

145. The method of claim 142, wherein the detectable label is an enzyme, prosthetic group, fluorescent material, luminescent material, bioluminescent material, radioactive material, positron emitting metal, or nonradioactive paramagnetic metal ion.

146. The method of claim 143, wherein the detectable label is an enzyme, prosthetic group, fluorescent material, luminescent material, bioluminescent material, radioactive material, positron emitting metal, or nonradioactive paramagnetic metal ion.

147. The method of claim 144, wherein the detectable label is an enzyme, prosthetic group, fluorescent material, luminescent material, bioluminescent material, radioactive material, positron emitting metal, or nonradioactive paramagnetic metal ion.

148. The method of claim 145, wherein the detectable label is detected by positron emission tomography.

149. The method of claim 146, wherein the detectable label is detected by positron emission tomography.

150. The method of claim 147, wherein the detectable label is detected by positron emission tomography.

151. The method of claim 142, wherein the antibody or antigen-binding fragment is selected from the group consisting of an Fab, an Fab', an F(ab')2, an Fd, an Fv, a single-chain Fv (scFv), a single-chain antibody, and a disulfide-linked Fv (sdFv).

152. The method of claim 143, wherein the antibody or antigen-binding fragment is selected from the group consisting of an Fab, an Fab', an F(ab')2, an Fd, an Fv, a single-chain Fv (scFv), a single-chain antibody, and a disulfide-linked Fv (sdFv).

153. The method of claim 144, wherein the antibody or antigen-binding fragment is selected from the group consisting of an Fab, an Fab', an F(ab')2, an Fd, an Fv, a single-chain Fv (scFv), a single-chain antibody, and a disulfide-linked Fv (sdFv).

154. The method of claim 142, wherein the antibody or antigen-binding fragment thereof comprises a human IgG1 heavy chain constant region and a human lambda light chain constant region.

155. The method of claim 143, wherein the antibody or antigen-binding fragment thereof comprises a human IgG1 heavy chain constant region and a human lambda light chain constant region.

156. The method of claim 144, wherein the antibody or antigen-binding fragment thereof comprises a human IgG1 heavy chain constant region and a human lambda light chain constant region.

157. A method of diagnosing or monitoring the progression of a neurodegenerative tauopathy, the method comprising:
measuring the level of pathologically modified or aggregated tau in a sample from a human subject with an anti-tau antibody or tau-binding fragment thereof, wherein the anti-tau antibody or tau-binding fragment thereof comprises a heavy chain variable region (VH) comprising VH complementarity determining regions 1, 2, and 3 with the amino acid sequences set forth in SEQ ID NO:103, SEQ ID NO:104, and SEQ ID NO:105, respectively, and a light chain variable region (VL) comprising VL complementarity determining regions 1, 2, and 3 with the amino acid sequences set forth in SEQ ID NO:106, SEQ ID NO:107, and SEQ ID NO:108, respectively; and comparing the level of modified or aggregated tau to a reference standard that indicates the level of the pathologically modified or aggregated tau in one or more control subjects, wherein a difference or similarity between the level of pathologically modified or aggregated tau and the reference standard indicates that the human subject has a neurodegenerative tauopathy.

158. The method of claim 157, wherein:
the VH consists of the amino acid sequence set forth in SEQ ID NO:54; and
the VL consists of the amino acid sequence set forth in SEQ ID NO:55.

159. The method of claim 157, wherein:
the VH consists of the amino acid sequence set forth in SEQ ID NO:220; and
the VL consists of the amino acid sequence set forth in SEQ ID NO:55.

160. The method of claim 157, wherein the neurodegenerative tauopathy is Alzheimer's disease.

161. The method of claim 158, wherein the neurodegenerative tauopathy is Alzheimer's disease.

162. The method of claim 159, wherein the neurodegenerative tauopathy is Alzheimer's disease.

163. An antibody or antigen-binding fragment thereof that binds to human tau and comprises:
a heavy chain variable region (VH) comprising VH complementarity determining regions 1, 2, and 3 with the amino acid sequences set forth in SEQ ID NO:85, SEQ ID NO:86, and SEQ ID NO:87, respectively; and
a light chain variable region (VL) comprising VL complementarity determining regions 1, 2, and 3 with the amino acid sequences set forth in SEQ ID NO:88, SEQ ID NO:89, and SEQ ID NO:90, respectively,
wherein the antibody or antigen-binding fragment thereof comprises polyethylene glycol or a detectable label selected from the group consisting of an enzyme, a radioisotope, a fluorescent compound, a chemiluminescent compound, a bioluminescent compound, and a heavy metal.

164. The antibody or antigen-binding fragment thereof of claim 163, wherein:
the VH consists of the amino acid sequence set forth in SEQ ID NO:48; and
the VL consists of the amino acid sequence set forth in SEQ ID NO:49.

165. The antibody or antigen-binding fragment thereof of claim 163, wherein:
the VH consists of the amino acid sequence set forth in SEQ ID NO:47; and
the VL consists of the amino acid sequence set forth in SEQ ID NO:49.

166. The antibody or antigen-binding fragment thereof of claim 163, wherein the antibody or antigen-binding fragment is selected from the group consisting of an Fab, an Fab', an F(ab')2, an Fd, an Fv, a single-chain Fv (scFv), a single-chain antibody, and a disulfide-linked Fv (sdFv).

167. The antibody or antigen-binding fragment thereof of claim 164, wherein the antibody or antigen-binding fragment is selected from the group consisting of an Fab, an Fab', an F(ab')2, an Fd, an Fv, a single-chain Fv (scFv), a single-chain antibody, and a disulfide-linked Fv (sdFv).

168. The antibody or antigen-binding fragment thereof of claim 165, wherein the antibody or antigen-binding fragment is selected from the group consisting of an Fab, an Fab', an F(ab')2, an Fd, an Fv, a single-chain Fv (scFv), a single-chain antibody, and a disulfide-linked Fv (sdFv).

169. The antibody or antigen-binding fragment thereof of claim 163, wherein the antibody or antigen-binding fragment thereof comprises a human IgG1 heavy chain constant region and a human lambda light chain constant region.

170. The antibody or antigen-binding fragment thereof of claim 164, wherein the antibody or antigen-binding fragment thereof comprises a human IgG1 heavy chain constant region and a human lambda light chain constant region.

171. The antibody or antigen-binding fragment thereof of claim 165, wherein the antibody or antigen-binding fragment thereof comprises a human IgG1 heavy chain constant region and a human lambda light chain constant region.

172. An antibody or antigen-binding fragment thereof that binds to human tau and comprises:
a heavy chain variable region (VH) comprising VH complementarity determining regions 1, 2, and 3 with the amino acid sequences set forth in SEQ ID NO:103, SEQ ID NO:104, and SEQ ID NO:105, respectively; and
a light chain variable region (VL) comprising VL complementarity determining regions 1, 2, and 3 with the amino acid sequences set forth in SEQ ID NO:106, SEQ ID NO:107, and SEQ ID NO:108, respectively,
wherein the antibody or antigen-binding fragment thereof comprises polyethylene glycol or a detectable label selected from the group consisting of an enzyme, a radioisotope, a fluorescent compound, a chemiluminescent compound, a bioluminescent compound, and a heavy metal.

173. The antibody or antigen-binding fragment thereof of claim 172, wherein:
the VH consists of the amino acid sequence set forth in SEQ ID NO:54; and
the VL consists of the amino acid sequence set forth in SEQ ID NO:55.

174. The antibody or antigen-binding fragment thereof of claim 172, wherein:
the VH consists of the amino acid sequence set forth in SEQ ID NO:220; and
the VL consists of the amino acid sequence set forth in SEQ ID NO:55.

175. The antibody or antigen-binding fragment thereof of claim 172, wherein the antibody or antigen-binding fragment is selected from the group consisting of an Fab, an Fab', an F(ab')2, an Fd, an Fv, a single-chain Fv (scFv), a single-chain antibody, and a disulfide-linked Fv (sdFv).

176. The antibody or antigen-binding fragment thereof of claim 173, wherein the antibody or antigen-binding fragment is selected from the group consisting of an Fab, an Fab', an F(ab')2, an Fd, an Fv, a single-chain Fv (scFv), a single-chain antibody, and a disulfide-linked Fv (sdFv).

177. The antibody or antigen-binding fragment thereof of claim 174, wherein the antibody or antigen-binding fragment is selected from the group consisting of an Fab, an Fab', an F(ab')2, an Fd, an Fv, a single-chain Fv (scFv), a single-chain antibody, and a disulfide-linked Fv (sdFv).

178. The antibody or antigen-binding fragment thereof of claim 172, wherein the antibody or antigen-binding fragment thereof comprises a human IgG1 heavy chain constant region and a human lambda light chain constant region.

179. The antibody or antigen-binding fragment thereof of claim 173, wherein the antibody or antigen-binding fragment thereof comprises a human IgG1 heavy chain constant region and a human lambda light chain constant region.

180. The antibody or antigen-binding fragment thereof of claim 174, wherein the antibody or antigen-binding fragment thereof comprises a human IgG1 heavy chain constant region and a human lambda light chain constant region.

181. An anti-tau single chain antibody or scFv antibody comprising:
a heavy chain variable region (VH) comprising VH complementarity determining regions 1, 2, and 3 with the amino acid sequences set forth in SEQ ID NO:85, SEQ ID NO:86, and SEQ ID NO:87, respectively; and a light chain variable region (VL) comprising VL complementarity determining regions 1, 2, and 3 with the amino acid sequences set forth in SEQ ID NO:88, SEQ ID NO:89, and SEQ ID NO:90, respectively.

182. An anti-tau single chain antibody or scFv antibody comprising:

a heavy chain variable region (VH) comprising VH complementarity determining regions 1, 2, and 3 with the amino acid sequences set forth in SEQ ID NO:103, SEQ ID NO:104, and SEQ ID NO:105, respectively; and a light chain variable region (VL) comprising VL complementarity determining regions 1, 2, and 3 with the amino acid sequences set forth in SEQ ID NO:106, SEQ ID NO:107, and SEQ ID NO:108, respectively.

* * * * *

UNITED STATES PATENT AND TRADEMARK OFFICE
CERTIFICATE OF CORRECTION

PATENT NO. : 9,598,484 B2  
APPLICATION NO. : 14/654176  
DATED : March 21, 2017  
INVENTOR(S) : Paul H. Weinreb et al.

Page 1 of 1

It is certified that error appears in the above-identified patent and that said Letters Patent is hereby corrected as shown below:

In the Claims

Column 251  
Claim 90, Lines 33-34, delete "sclerosis/parkinsonismdementia" and insert -- sclerosis/parkinsonism-dementia --.

Column 251  
Claim 90, Line 41, delete "Strussler-" and insert -- Sträussler --.

Signed and Sealed this  
Ninth Day of May, 2017

Michelle K. Lee  
*Director of the United States Patent and Trademark Office*